US012486332B2

(12) United States Patent
Vincent et al.

(10) Patent No.: US 12,486,332 B2
(45) **Date of Patent: *Dec. 2, 2025**

(54) ANTI-ERBB3 ANTIBODIES

(71) Applicant: AVEO Pharmaceuticals, Inc., Cambridge, MA (US)

(72) Inventors: Sylvie Vincent, Somerville, MA (US); William M. Winston, Jr., Marlborough, MA (US); Fang Wang, Belmont, MA (US); Solly Weiler, Newton, MA (US); Kristan Meetze, Lexington, MA (US); Lyne Breault, Roslindale, MA (US); Steve Bottega, Cambridge, MA (US); Ting Chen, Acton, MA (US); Michael DePrima, Somerville, MA (US); Christina Fleet, Melrose, MA (US); Steven Tyler, Boston, MA (US); Jin-Kyeung Woo, Newton, MA (US); Jeno Gyuris, Lincoln, MA (US)

(73) Assignee: AVEO Pharmaceuticals, Inc., Boston, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 18/307,638

(22) Filed: Apr. 26, 2023

(65) Prior Publication Data

US 2023/0365710 A1 Nov. 16, 2023

Related U.S. Application Data

(60) Division of application No. 16/667,056, filed on Oct. 29, 2019, now Pat. No. 11,680,108, which is a continuation of application No. 15/448,164, filed on Mar. 2, 2017, now Pat. No. 10,494,441, which is a division of application No. 14/987,374, filed on Jan. 4, 2016, now Pat. No. 9,598,498, which is a division of application No. 13/919,582, filed on Jun. 17, 2013, now Pat. No. 9,228,021, which is a division of application No. 13/082,852, filed on Apr. 8, 2011, now Pat. No. 8,481,687.

(60) Provisional application No. 61/322,712, filed on Apr. 9, 2010.

(51) Int. Cl.

| | |
|---|---|
| ***C07K 16/30*** | (2006.01) |
| ***A61K 39/395*** | (2006.01) |
| ***C07K 16/32*** | (2006.01) |
| ***C12N 15/00*** | (2006.01) |
| ***C12N 15/13*** | (2006.01) |
| *A61K 39/00* | (2006.01) |
| *C12N 5/10* | (2006.01) |
| *C12N 15/63* | (2006.01) |

(52) U.S. Cl.

CPC .............. *C07K 16/32* (2013.01); *C07K 16/30* (2013.01); *A61K 39/39558* (2013.01); *A61K 2039/505* (2013.01); *C07K 2317/24* (2013.01); *C07K 2317/51* (2013.01); *C07K 2317/515* (2013.01); *C07K 2317/565* (2013.01); *C07K 2317/73* (2013.01); *C07K 2317/76* (2013.01); *C07K 2317/92* (2013.01); *C12N 5/10* (2013.01); *C12N 15/00* (2013.01); *C12N 15/63* (2013.01)

(58) Field of Classification Search

CPC ............ A61K 2039/505; A61K 39/395; A61K 39/39558; A61K 49/16; C07K 16/18; C07K 16/22; C07K 16/28; C07K 16/30; C07K 16/32; C07K 2317/24; C07K 2317/51; C07K 2317/515; C07K 2317/56; C07K 2317/565; C07K 2317/73; C07K 2317/76; C07K 2317/92

See application file for complete search history.

(56) References Cited

U.S. PATENT DOCUMENTS

| | | | | |
|---|---|---|---|---|
| 5,183,884 | A | 2/1993 | Kraus et al. | |
| 5,480,968 | A | 1/1996 | Kraus et al. | |
| 5,820,859 | A | 10/1998 | Kraus et al. | |
| 5,916,755 | A | 6/1999 | Kraus et al. | |
| 5,968,511 | A | 10/1999 | Akita et al. | |
| 6,639,060 | B1 | 10/2003 | Kraus et al. | |
| 7,285,649 | B2 | 10/2007 | Akita et al. | |
| 7,705,130 | B2 | 4/2010 | Rothe et al. | |
| 7,846,440 | B2 | 12/2010 | Schoeberl et al. | |
| 8,481,687 | B2 | 7/2013 | Vincent et al. | |
| 9,228,021 | B2 | 1/2016 | Vincent et al. | |
| 9,598,498 | B2 | 3/2017 | Vincent et al. | |
| 9,828,635 | B2 * | 11/2017 | Vincent | G01N 33/574 |
| 10,494,441 | B2 | 12/2019 | Vincent et al. | |

(Continued)

FOREIGN PATENT DOCUMENTS

| | | | |
|---|---|---|---|
| WO | WO-2007/077028 | A2 | 7/2007 |
| WO | WO-2008/100624 | A2 | 8/2008 |

(Continued)

OTHER PUBLICATIONS

Chen et al. (1996) "An Immunological Approach Reveals Biological Differences between the Two NDF/Heregulin Receptors, ErbB-3 and ErbB-4" J. Biol. Chem. 271: 7620-7629.

(Continued)

*Primary Examiner* — Hong Sang
(74) *Attorney, Agent, or Firm* — Dechert LLP

(57) ABSTRACT

Monoclonal antibodies that bind and inhibit activation of epidermal growth factor receptor related member ErbB3/HER3 are disclosed. The antibodies can be used to treat cell proliferative diseases and disorders, including certain forms of cancer, associated with activation of ErbB3/HER3.

15 Claims, 26 Drawing Sheets

Specification includes a Sequence Listing.

(56) References Cited

U.S. PATENT DOCUMENTS

| | | | | |
|---|---|---|---|---|
| 2004/0197332 | A1 | 10/2004 | Ullrich et al. | |
| 2007/0009972 | A1 | 1/2007 | Chao et al. | |
| 2007/0122407 | A1 | 5/2007 | Akita et al. | |
| 2008/0124345 | A1 | 5/2008 | Rothe et al. | |
| 2009/0291085 | A1 * | 11/2009 | Schoeberl ............... | A61P 11/00 530/388.1 |
| 2010/0266584 | A1 | 10/2010 | Schoeberl et al. | |
| 2010/0310557 | A1 | 12/2010 | Keyt et al. | |
| 2011/0171222 | A1 | 7/2011 | Bossenmaier et al. | |

FOREIGN PATENT DOCUMENTS

| | | | |
|---|---|---|---|
| WO | WO-2010/127181 | A1 | 11/2010 |
| WO | WO-2011/022727 | A2 | 2/2011 |
| WO | WO-2011/044311 | A2 | 4/2011 |

OTHER PUBLICATIONS

International Search Report and Written Opinion, International Patent Application No. PCT/US2011/031829, mailed on Dec. 19, 2011 (17 pages).

Sithanandam et al. (2008) "The ERBB3 receptor in cancer and cancer gene therapyERBB3 in cancer" Cancer Gene Therapy 15:413-448.

Schoeberl et al. (2010) "An ErbB3 Antibody, MM-121, Is Active in Cancers with Ligand-Dependent Activation" Cancer Res. 70(6):2485-2494.

Schoeberl et al. (2009) "Therapeutically Targeting ErbB3: A Key Node in Ligand-Induced Activation of the ErbB Receptor-PI3K Axis" Science Signaling 2:1-14 (from www.SCIENCESIGNALING.org).

Sheng et al. (2010) "An activated ErbB3/NRG1 autocrine loop supports in vivo proliferation in ovarian cancer cells" Cancer Cell. 17(3):298-310.

* cited by examiner

FIG. 2

Complete Heavy Chain Variable Region Amino Acid Alignments

| Antibody | | | CDR1 | | CDR2 | |
|---|---|---|---|---|---|---|
| 04D01 | (1) | QVQLQQPGAELVRPGTSVKLSCKASGYTFT | SH--WLH | WVKQRPGQGLEWIG | VLDPSDFYSNYNQNFKG | KA |
| 09D03 | (1) | QVTLKESGPGILRPSQTLSLTCSFSGFSLS | TFGLSVG | WIRQPSGKGLEWLA | HIWWDDDK-YYNPALKS | RL |
| 11G01 | (1) | QVQLQQSDAELVKPGASVKISCKVSGYTFT | DH--IIH | WMKQRPEQGLEWIG | YIYPRDGYIKYNEKFKG | KA |
| 12A07 | (1) | QVQLLQPGAELVRPGTSVKLSCKTSGYTFS | SY--WMH | WVKQRPGQGLEWIG | MIDPSDVYTNYNPKFKG | KA |
| 18H02 | (1) | QIQLVQSGPELKKPGEAVKISCKSSGYTFT | TY--GMS | WVKQAPGRALKWMG | WINTYSGVPTYADDFKG | RF |
| 22A02 | (1) | QVQLQQPGAELVRPGTSVKLSCKASGYTFT | NY--WMH | WVKQRPGQGLEWIG | MIDPSDSYTNYNPKFKG | KA |
| 24C05 | (1) | EVQLVESGGGLVKPGGSLKLSCAASGFTFS | DY--AMS | WVRQTPEKRLEWVA | TISDGGTYTYYPDNVKG | RF |

| Antibody | | | CDR3 | | |
|---|---|---|---|---|---|
| 04D01 | (69) | TLTVDTSSSTAYMQLSSLTSEDSAVYYCAR | GLL-SGDYAMDY | WGQGTSVTVSS | (SEQ ID NO: 2) |
| 09D03 | (70) | TISKDTSKNQVFLKIANVDTADTATYYCAR | IG--ADALPFDY | WGQGTTLTVSS | (SEQ ID NO: 12) |
| 11G01 | (69) | TLTADKSSSTAYMQVNSLTSEDSAVYFCAR | G----YYYAMDY | WGQGTSVTVSS | (SEQ ID NO: 22) |
| 12A07 | (69) | TLTVDTSSSTAYMQLSSLTSEDSAVYYCAR | ------NYSGDY | WGQGTTLTVSS | (SEQ ID NO: 31) |
| 18H02 | (69) | AFSLESSASTAYLQINNLKNEDTATYFCAR | GRDGYQVAWFAY | WGQGTLVTVSA | (SEQ ID NO: 38) |
| 22A02 | (69) | TLTVDTSSSTAYMQLSSLTSEDSAVYYCAR | ------NYSGDY | WGQGTTLTVSS | (SEQ ID NO: 48) |
| 24C05 | (69) | TISRDNAKNNLYLQMSHLKSEDTAMYYCAR | EWG--DYDGFDY | WGQGTTLTVSS | (SEQ ID NO: 54) |

FIG. 3

Heavy Chain CDR Amino Acid Alignments

| Antibody | CDR1 | | CDR2 | | CDR3 | |
|---|---|---|---|---|---|---|
| 04D01 | SH--WLH | (SEQ ID NO: 5) | VLDPSDFYSNYNQNFKG | (SEQ ID NO: 6) | GLL-SGDYAMDY | (SEQ ID NO: 7) |
| 09D03 | TFGLSVG | (SEQ ID NO: 15) | HIWWDDD-KYYNPALKS | (SEQ ID NO: 16) | IG--ADALPFDY | (SEQ ID NO: 17) |
| 11G01 | DH--IIH | (SEQ ID NO: 25) | YIYPRDGYIKYNEKFKG | (SEQ ID NO: 26) | G----YYYAMDY | (SEQ ID NO: 27) |
| 12A07 | SY--WMH | (SEQ ID NO: 34) | MIDPSDVYTNYNPKFKG | (SEQ ID NO: 35) | ------NYSGDY | (SEQ ID NO: 36) |
| 18H02 | TY--GMS | (SEQ ID NO: 41) | WINTYSGVPTYADDFKG | (SEQ ID NO: 42) | GRDGYQVAWFAY | (SEQ ID NO: 43) |
| 22A02 | NY--WMH | (SEQ ID NO: 51) | MIDPSDSYTNYNPKFKG | (SEQ ID NO: 52) | ------NYSGDY | (SEQ ID NO: 36) |
| 24C05 | DY--AMS | (SEQ ID NO: 57) | TISDGGTYTYYPDNVKG | (SEQ ID NO: 58) | EWG--DYDGFDY | (SEQ ID NO: 59) |

FIG. 4

Complete Light (Kappa) Chain Variable Region Amino Acid Alignments

```
                                                CDR1                               CDR2
Antibody
04D01   (1)  DVLMTQIPLSLPVSLGDQASISC RSSQSIVHSNGNTYLE WYLQKPGQSPKSLIY KVSNRFS GVPDRFSGS
09D03   (1)  DIVLTQTAPSVPVTPGESVSISC RSSKSLLHSNGNTYLY WFLQRPGQSPQLLIY RMSNLAS GVPDRFSGS
11G01   (1)  DVLMTQTPLSLPVSLGDQASISC RSSQSIVHSIGNTYLE WYLQKPGQSPKLLIY KVSNRFS GVPERFSGS
12A07   (1)  DVLMTQIPLSLPVSLGDQASISC RSSQSIVHSNGNTYLE WYLQKPGQSPKLLIY KVSNRFS GVPDRFSGS
18H02   (1)  ETTVTQSPASLSMAIGDKVTIRC ITSTDIDDD-----MN WFQQKPGEPPKLLIS EGNTLRP GVPSRFSGS
22A02   (1)  DVLMTQTPLSLPVSLGDQASISC RSSQSIVHSNGNTYLE WYLQKPGQSPKLLIY KVSNRFS GVPDRFSGS
24C05   (1)  DIQMTQSPSSLSASLGERVSLTC RASQEISG-----YLS WLQQKPDGTIKRLIY AASTLDS GVPKRFSGS

                                        CDR3
04D01  (71)  GSGTDFTLKISRVEAEDLGVYYC FQGSYVPWT FGGGTKLEIK  (SEQ ID NO: 4)
09D03  (71)  GSGTAFTLRISRVEAEDVGVYYC MQHLEYPFT FGSGTKLEIK  (SEQ ID NO: 14)
11G01  (71)  GSGTDFTLKISRVEAEDLGVYYC FQGSHVPFT FGSGTKLEIK  (SEQ ID NO: 24)
12A07  (71)  GSGTDFTLKISRVEAEDLGVYYC FQGSYVPWT FGGGTKLEIK  (SEQ ID NO: 33)
18H02  (66)  GYGTDFIFTIENMLSEDVADYYC LQSDNLPYT FGGGTKLEIK  (SEQ ID NO: 40)
22A02  (71)  GSGTDFTLKISRVEAEDLGVYYC FQGSYVPWT FGGGTKLEIK  (SEQ ID NO: 50)
24C05  (66)  RSGSDYSLTIGSLESEDLADYYC LQYDSYPYT FGGGTKLEIK  (SEQ ID NO: 56)
```

FIG. 5

Light (Kappa) Chain CDR Amino Acid Alignments

| Antibody | CDR1 | CDR2 | CDR3 |
|---|---|---|---|
| 04D01 | RSSQSIVHSNGNTYLE (SEQ ID NO: 8) | KVSNRFS (SEQ ID NO: 9) | FQGSYVPWT (SEQ ID NO: 10) |
| 09D03 | RSSKSLLHSNGNTYLY (SEQ ID NO: 18) | RMSNLAS (SEQ ID NO: 19) | MQHLEYPFT (SEQ ID NO: 20) |
| 11G01 | RSSQSIVHSIGNTYLE (SEQ ID NO: 28) | KVSNRFS (SEQ ID NO: 9) | FQGSHVPFT (SEQ ID NO: 29) |
| 12A07 | RSSQSIVHSNGNTYLE (SEQ ID NO: 8) | KVSNRFS (SEQ ID NO: 9) | FQGSYVPWT (SEQ ID NO: 10) |
| 18H02 | ITSTDIDDD-----MN (SEQ ID NO: 44) | EGNTLRP (SEQ ID NO: 45) | LQSDNLPYT (SEQ ID NO: 46) |
| 22A02 | RSSQSIVHSNGNTYLE (SEQ ID NO: 8) | KVSNRFS (SEQ ID NO: 9) | FQGSYVPWT (SEQ ID NO: 10) |
| 24C05 | RASQEISG-----YLS (SEQ ID NO: 60) | AASTLDS (SEQ ID NO: 61) | LQYDSYPYT (SEQ ID NO: 62) |

FIG. 15

Complete Humanized Heavy Chain Variable Region Amino Acid Alignments

| Heavy Chain | | | CDR1 | | CDR2 | |
|---|---|---|---|---|---|---|
| 24C05 | (1) | EVQLVESGGGLVKPGGSLKLSCAASGFTFS | DYAMS | WVRQTPEKRLEWVA | TISDGGTYTYYPDNVKG | RFTI |
| Sh24C05 Hv3-7 | (1) | EVQLVESGGGLVQPGGSLRLSCAASGFTFS | DYAMS | WVRQAPGKGLEWVA | TISDGGTYTYYPDNVKG | RFTI |
| Sh24C05 Hv3-11 | (1) | QVQLVESGGGLVKPGGSLRLSCAASGFTFS | DYAMS | WIRQAPGKGLEWVS | TISDGGTYTYYPDNVKG | RFTI |
| Sh24C05 Hv3-11 N62S | (1) | QVQLVESGGGLVKPGGSLRLSCAASGFTFS | DYAMS | WIRQAPGKGLEWVS | TISDGGTYTYYPDSVKG | RFTI |
| Sh24C05 Hv3-21 | (1) | EVQLVESGGGLVKPGGSLRLSCAASGFTFS | DYAMS | WVRQAPGKGLEWVS | TISDGGTYTYYPDNVKG | RFTI |
| Sh24C05 Hv3-23 | (1) | EVQLLESGGGLVQPGGSLRLSCAASGFTFS | DYAMS | WVRQAPGKGLEWVS | TISDGGTYTYYPDNVKG | RFTI |
| Sh24C05 Hv3-30 | (1) | QVQLVESGGGVVQPGRSLRLSCAASGFTFS | DYAMS | WVRQAPGKGLEWVA | TISDGGTYTYYPDNVKG | RFTI |
| Hu24C05 HvA | (1) | EVQLVESGGGLVKPGGSLRLSCAASGFTFS | DYAMS | WVRQAPGKGLEWVA | TISDGGTYTYYPDNVKG | RFTI |

| | | | CDR3 | | |
|---|---|---|---|---|---|
| 24C05 | (71) | SRDNAKNNLYLQMSHLKSEDTAMYYCAR | EWGDYDGFDY | WGQGTTLTVSS | (SEQ ID NO: 54) |
| Sh24C05 Hv3-7 | (71) | SRDNAKNSLYLQMNSLRAEDTAVYYCAR | EWGDYDGFDY | WGQGTLVTVSS | (SEQ ID NO: 150) |
| Sh24C05 Hv3-11 | (71) | SRDNAKNSLYLQMNSLRAEDTAVYYCAR | EWGDYDGFDY | WGQGTLVTVSS | (SEQ ID NO: 152) |
| Sh24C05 Hv3-11 N62S | (71) | SRDNAKNSLYLQMNSLRAEDTAVYYCAR | EWGDYDGFDY | WGQGTLVTVSS | (SEQ ID NO: 154) |
| Sh24C05 Hv3-21 | (71) | SRDNAKNSLYLQMNSLRAEDTAVYYCAR | EWGDYDGFDY | WGQGTLVTVSS | (SEQ ID NO: 156) |
| Sh24C05 Hv3-23 | (71) | SRDNSKNTLYLQMNSLRAEDTAVYYCAR | EWGDYDGFDY | WGQGTLVTVSS | (SEQ ID NO: 158) |
| Sh24C05 Hv3-30 | (71) | SRDNSKNTLYLQMSSLRAEDTAVYYCAR | EWGDYDGFDY | WGQGTLVTVSS | (SEQ ID NO: 160) |
| Hu24C05 HvA | (71) | SRDNAKNSLYLQMNSLRAEDTAVYYCAR | EWGDYDGFDY | WGQGTLVTVSS | (SEQ ID NO: 162) |

FIG. 16

Complete Humanized Light (Kappa) Chain Variable Region Amino Acid Alignments

```
Light Chain                                    CDR1                      CDR2
          24C05  (1) DIQMTQSPSSLSASLGERVSLTC RASQEISGYLS WLQQKPDGTIKRLIY AASTLDS GVPKRFSGSRSGSD
   Sh24C05 Kv1-9 (1) DIQLTQSPSFLSASVGDRVTITC RASQEISGYLS WYQQKPGKAPKLLIY AASTLDS GVPSRFSGSGSGTE
  Sh24C05 Kv1-16 (1) DIQMTQSPSSLSASVGDRVTITC RASQEISGYLS WFQQKPGKAPKSLIY AASTLDS GVPSRFSGSGSGTD
  Sh24C05 Kv1-17 (1) DIQMTQSPSSLSASVGDRVTITC RASQEISGYLS WYQQKPGKAPKRLIY AASTLDS GVPSRFSGSGSGTE
  Sh24C05 Kv1-33 (1) DIQMTQSPSSLSASVGDRVTITC RASQEISGYLS WYQQKPGKAPKLLIY AASTLDS GVPSRFSGSGSGTD
  Sh24C05 Kv1-39 (1) DIQMTQSPSSLSASVGDRVTITC RASQEISGYLS WYQQKPGKAPKLLIY AASTLDS GVPSRFSGSGSGTD
    Hu24C05 KvA (1) DIQMTQSPSSLSASVGDRVTITC RASQEISGYLS WLQQKPGGAIKRLIY AASTLDS GVPSRFSGSGSGSD

                                           CDR3
          24C05  (71) YSLTIGSLESEDLADYYC LQYDSYPYT FGGGTKLEIK (SEQ ID NO: 56)
   Sh24C05 Kv1-9 (71) FTLTISSLQPEDFATYYC LQYDSYPYT FGQGTKLEIK (SEQ ID NO: 164)
  Sh24C05 Kv1-16 (71) FTLTISSLQPEDFATYYC LQYDSYPYT FGQGTKLEIK (SEQ ID NO: 166)
  Sh24C05 Kv1-17 (71) FTLTISSLQPEDFATYYC LQYDSYPYT FGQGTKLEIK (SEQ ID NO: 168)
  Sh24C05 Kv1-33 (71) FTFTISSLQPEDIATYYC LQYDSYPYT FGQGTKLEIK (SEQ ID NO: 170)
  Sh24C05 Kv1-39 (71) FTLTISSLQPEDFATYYC LQYDSYPYT FGQGTKLEIK (SEQ ID NO: 172)
    Hu24C05 KvA (71) YTLTISSLQPEDFATYYC LQYDSYPYT FGQGTKLEIK (SEQ ID NO: 174)
```

| ka (1/Ms) | kd (1/s) | KD (M) | n |
|---|---|---|---|
| 3.5E+06 | 2.7E-04 | 7.6E-11 | 6 |

| ka (1/Ms) | kd (1/s) | KD (M) | n |
|---|---|---|---|
| 9.3E+05 | 1.9E-04 | 2.3E-10 | 3 |

| ka (1/Ms) | kd (1/s) | KD (M) | n |
|---|---|---|---|
| 1.8E+06 | 9.4E-04 | 5.3E-10 | 3 |

POOR DATA FIT

SEQUENCE LISTING

```
Sequence total quantity: 212
SEQ ID NO: 1            moltype = DNA  length = 360
FEATURE                 Location/Qualifiers
misc_feature            1..360
                        note = Description of Artificial Sequence:
                         Syntheticpolynucleotide
source                  1..360
                        mol_type = other DNA
                        organism = synthetic construct
SEQUENCE: 1
caggtccaac tgcagcagcc tggggctgaa ctggtgaggc ctgggacttc agtgaagttg  60
tcctgcaagg cttctggcta caccttcacc agccactggt tgcactgggt gaagcagagg  120
cctggacaag gccttgagtg gatcggagtg cttgatcctt ctgattttta tagtaactac  180
aatcaaaact tcaagggcaa ggccacattg actgtagaca catcctccag cacagcctac  240
atgcagctca gcagcctgac atctgaggac tctgcggtct attactgtgc acgaggccta  300
ctatccgggg actatgctat ggactactgg ggtcaaggaa cctcagtcac cgtctcctca  360

SEQ ID NO: 2            moltype = AA  length = 120
FEATURE                 Location/Qualifiers
REGION                  1..120
                        note = Description of Artificial Sequence:
                         Syntheticpolypeptide
source                  1..120
                        mol_type = protein
                        organism = synthetic construct
SEQUENCE: 2
QVQLQQPGAE LVRPGTSVKL SCKASGYTFT SHWLHWVKQR PGQGLEWIGV LDPSDFYSNY  60
NQNFKGKATL TVDTSSSTAY MQLSSLTSED SAVYYCARGL LSGDYAMDYW GQGTSVTVSS  120

SEQ ID NO: 3            moltype = DNA  length = 336
FEATURE                 Location/Qualifiers
misc_feature            1..336
```

```
                      note = Description of Artificial Sequence:
                       Syntheticpolynucleotide
source                1..336
                      mol_type = other DNA
                      organism = synthetic construct
SEQUENCE: 3
gatgttttga tgacccaaat tccactctcc ctgcctgtca gtcttggaga tcaagcctcc  60
atctcttgca gatctagtca gagcattgta catagtaatg gaaacaccta tttagaatgg  120
tacctgcaga aaccaggcca gtctccaaag tccctgatct acaaagtttc taaccgattt  180
tctggggtcc cagacaggtt cagtggcagt ggatcaggga cagatttcac actcaagatc  240
agcagagtgg aggctgagga tctgggagtt tattactgct ttcaaggttc atatgttccg  300
tggacgttcg gtggaggcac caagctggaa atcaaa                            336

SEQ ID NO: 4          moltype = AA  length = 112
FEATURE               Location/Qualifiers
REGION                1..112
                      note = Description of Artificial Sequence:
                       Syntheticpolypeptide
source                1..112
                      mol_type = protein
                      organism = synthetic construct
SEQUENCE: 4
DVLMTQIPLS LPVSLGDQAS ISCRSSQSIV HSNGNTYLEW YLQKPGQSPK SLIYKVSNRF  60
SGVPDRFSGS GSGTDFTLKI SRVEAEDLGV YYCFQGSYVP WTFGGGTKLE IK          112

SEQ ID NO: 5          moltype = AA  length = 5
FEATURE               Location/Qualifiers
REGION                1..5
                      note = Description of Artificial Sequence: Syntheticpeptide
source                1..5
                      mol_type = protein
                      organism = synthetic construct
SEQUENCE: 5
SHWLH                                                              5

SEQ ID NO: 6          moltype = AA  length = 17
FEATURE               Location/Qualifiers
REGION                1..17
                      note = Description of Artificial Sequence: Syntheticpeptide
source                1..17
                      mol_type = protein
                      organism = synthetic construct
SEQUENCE: 6
VLDPSDFYSN YNQNFKG                                                 17

SEQ ID NO: 7          moltype = AA  length = 11
FEATURE               Location/Qualifiers
REGION                1..11
                      note = Description of Artificial Sequence: Syntheticpeptide
source                1..11
                      mol_type = protein
                      organism = synthetic construct
SEQUENCE: 7
GLLSGDYAMD Y                                                       11

SEQ ID NO: 8          moltype = AA  length = 16
FEATURE               Location/Qualifiers
REGION                1..16
                      note = Description of Artificial Sequence: Syntheticpeptide
source                1..16
                      mol_type = protein
                      organism = synthetic construct
SEQUENCE: 8
RSSQSIVHSN GNTYLE                                                  16

SEQ ID NO: 9          moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 9
KVSNRFS                                                            7

SEQ ID NO: 10         moltype = AA  length = 9
FEATURE               Location/Qualifiers
REGION                1..9
                      note = Description of Artificial Sequence: Syntheticpeptide
```

```
source                 1..9
                       mol_type = protein
                       organism = synthetic construct
SEQUENCE: 10
FQGSYVPWT                                                          9

SEQ ID NO: 11          moltype = DNA  length = 360
FEATURE                Location/Qualifiers
misc_feature           1..360
                       note = Description of Artificial Sequence:
                        Syntheticpolynucleotide
source                 1..360
                       mol_type = other DNA
                       organism = synthetic construct
SEQUENCE: 11
caggttactc taaaagagtc tggccctggg atattgcggc cctcccagac cctcagtctg  60
acttgttctt tctctgggtt ttcactgagc acttttggtt tgagtgtagg ctggattcgt  120
cagccttcag ggaagggtct ggagtggctg gcacacattt ggtgggatga tgataagtac  180
tataacccag cccttaagag tcggctcaca atctccaagg atacctccaa aaaccaggta  240
ttcctcaaga tcgccaatgt ggacactgca gatactgcca catactactg tgctcgaata  300
ggggcggacg cccttccttt tgactactgg ggccaaggca ccactctcac agtctcctca  360

SEQ ID NO: 12          moltype = AA  length = 120
FEATURE                Location/Qualifiers
REGION                 1..120
                       note = Description of Artificial Sequence:
                        Syntheticpolypeptide
source                 1..120
                       mol_type = protein
                       organism = synthetic construct
SEQUENCE: 12
QVTLKESGPG ILRPSQTLSL TCSFSGFSLS TFGLSVGWIR QPSGKGLEWL AHIWWDDDKY  60
YNPALKSRLT ISKDTSKNQV FLKIANVDTA DTATYYCARI GADALPFDYW GQGTTLTVSS  120

SEQ ID NO: 13          moltype = DNA  length = 336
FEATURE                Location/Qualifiers
misc_feature           1..336
                       note = Description of Artificial Sequence:
                        Syntheticpolynucleotide
source                 1..336
                       mol_type = other DNA
                       organism = synthetic construct
SEQUENCE: 13
gatattgtgt tgactcagac tgcaccctct gtacctgtca ctcctggaga gtcagtatcc  60
atctcctgca ggtctagtaa gagtctcctg catagtaatg gcaacactta cttgtattgg  120
ttcctgcaga ggccaggcca gtctcctcag ctcctgatat atcggatgtc caaccttgcc  180
tcaggagtcc cagacaggtt cagtggcagt gggtcaggaa ctgctttcac actgagaatc  240
agtagagtgg aggctgagga tgtgggtgtt tattactgta tgcaacatct agaatatcct  300
ttcacgttcg gctcggggac aaagttggaa ataaaa                            336

SEQ ID NO: 14          moltype = AA  length = 112
FEATURE                Location/Qualifiers
REGION                 1..112
                       note = Description of Artificial Sequence:
                        Syntheticpolypeptide
source                 1..112
                       mol_type = protein
                       organism = synthetic construct
SEQUENCE: 14
DIVLTQTAPS VPVTPGESVS ISCRSSKSLL HSNGNTYLYW FLQRPGQSPQ LLIYRMSNLA  60
SGVPDRFSGS GSGTAFTLRI SRVEAEDVGV YYCMQHLEYP FTFGSGTKLE IK          112

SEQ ID NO: 15          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 15
TFGLSVG                                                            7

SEQ ID NO: 16          moltype = AA  length = 16
FEATURE                Location/Qualifiers
REGION                 1..16
                       note = Description of Artificial Sequence: Syntheticpeptide
source                 1..16
                       mol_type = protein
                       organism = synthetic construct
```

```
SEQUENCE: 16
HIWWDDDKYY NPALKS                                                 16

SEQ ID NO: 17          moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 17
IGADALPFDY                                                        10

SEQ ID NO: 18          moltype = AA  length = 16
FEATURE                Location/Qualifiers
REGION                 1..16
                       note = Description of Artificial Sequence: Syntheticpeptide
source                 1..16
                       mol_type = protein
                       organism = synthetic construct
SEQUENCE: 18
RSSKSLLHSN GNTYLY                                                 16

SEQ ID NO: 19          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 19
RMSNLAS                                                           7

SEQ ID NO: 20          moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 20
MQHLEYPFT                                                         9

SEQ ID NO: 21          moltype = DNA  length = 351
FEATURE                Location/Qualifiers
misc_feature           1..351
                       note = Description of Artificial Sequence:
                        Syntheticpolynucleotide
source                 1..351
                       mol_type = other DNA
                       organism = synthetic construct
SEQUENCE: 21
caggttcagc tgcaacagtc tgacgctgag ttggtgaaac ctggagcttc agtgaagata  60
tcctgcaagg tttctggcta caccttcact gaccatatta ttcactggat gaagcagagg  120
cctgaacagg gcctggaatg gattggatat atttatccta gagatggtta tattaagtac  180
aatgagaagt tcaagggcaa ggccacattg actgcagaca aatcctccag cacagcctac  240
atgcaggtca acagcctgac atctgaggac tctgcagtct atttctgtgc aaggggttac  300
tattatgcta tggactactg gggtcaagga acctcagtca ccgtctcctc a           351

SEQ ID NO: 22          moltype = AA  length = 117
FEATURE                Location/Qualifiers
REGION                 1..117
                       note = Description of Artificial Sequence:
                        Syntheticpolypeptide
source                 1..117
                       mol_type = protein
                       organism = synthetic construct
SEQUENCE: 22
QVQLQQSDAE LVKPGASVKI SCKVSGYTFT DHIIHWMKQR PEQGLEWIGY IYPRDGYIKY  60
NEKFKGKATL TADKSSSTAY MQVNSLTSED SAVYFCARGY YYAMDYWGQG TSVTVSS     117

SEQ ID NO: 23          moltype = DNA  length = 336
FEATURE                Location/Qualifiers
misc_feature           1..336
                       note = Description of Artificial Sequence:
                        Syntheticpolynucleotide
source                 1..336
                       mol_type = other DNA
                       organism = synthetic construct
```

```
SEQUENCE: 23
gatgttttga tgacccaaac tccactctcc ctgcctgtca gtcttggaga tcaagcctcc  60
atctcttgca gatctagtca gagcattgta catagtattg gaaacaccta tttagaatgg  120
tacctgcaga aaccaggcca gtctccaaag ctcctgatct acaaagtttc caaccgattt  180
tctggggtcc cagagaggtt cagtggcagt ggatcaggga cagatttcac actcaagatc  240
agcagagtgg aggctgagga tctgggagtt tattactgct ttcaaggttc acatgttcca  300
ttcacgttcg gctcggggac aaagttggaa ataaaa                            336

SEQ ID NO: 24          moltype = AA  length = 112
FEATURE                Location/Qualifiers
REGION                 1..112
                       note = Description of Artificial Sequence:
                        Syntheticpolypeptide
source                 1..112
                       mol_type = protein
                       organism = synthetic construct
SEQUENCE: 24
DVLMTQTPLS LPVSLGDQAS ISCRSSQSIV HSIGNTYLEW YLQKPGQSPK LLIYKVSNRF  60
SGVPERFSGS GSGTDFTLKI SRVEAEDLGV YYCFQGSHVP FTFGSGTKLE IK          112

SEQ ID NO: 25          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 25
DHIIH                                                              5

SEQ ID NO: 26          moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
SEQUENCE: 26
YIYPRDGYIK YNEKFKG                                                 17

SEQ ID NO: 27          moltype = AA  length = 8
FEATURE                Location/Qualifiers
REGION                 1..8
                       note = Description of Artificial Sequence: Syntheticpeptide
source                 1..8
                       mol_type = protein
                       organism = synthetic construct
SEQUENCE: 27
GYYYAMDY                                                           8

SEQ ID NO: 28          moltype = AA  length = 16
FEATURE                Location/Qualifiers
REGION                 1..16
                       note = Description of Artificial Sequence: Syntheticpeptide
source                 1..16
                       mol_type = protein
                       organism = synthetic construct
SEQUENCE: 28
RSSQSIVHSI GNTYLE                                                  16

SEQ ID NO: 29          moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 29
FQGSHVPFT                                                          9

SEQ ID NO: 30          moltype = DNA  length = 345
FEATURE                Location/Qualifiers
misc_feature           1..345
                       note = Description of Artificial Sequence:
                        Syntheticpolynucleotide
source                 1..345
                       mol_type = other DNA
                       organism = synthetic construct
SEQUENCE: 30
```

```
caggtccaac tgctgcagcc tggggctgag ctggtgaggc ctgggacttc agtgaagttg  60
tcctgcaaga cttctggcta caccttctcc agctactgga tgcactgggt aaagcagagg  120
cctggacaag gccttgagtg gatcggaatg attgatcctt ctgatgttta tactaactac  180
aatccaaagt tcaagggcaa ggccacattg actgttgaca catcctccag cacagcctac  240
atgcagctca gcagcctgac atctgaggac tctgcggtct attactgtgc aagaaactac  300
tctggggact actggggcca aggcaccact ctcacagtct cctca                  345

SEQ ID NO: 31          moltype = AA  length = 115
FEATURE                Location/Qualifiers
REGION                 1..115
                       note = Description of Artificial Sequence:
                        Syntheticpolypeptide
source                 1..115
                       mol_type = protein
                       organism = synthetic construct
SEQUENCE: 31
QVQLLQPGAE LVRPGTSVKL SCKTSGYTFS SYWMHWVKQR PGQGLEWIGM IDPSDVYTNY  60
NPKFKGKATL TVDTSSSTAY MQLSSLTSED SAVYYCARNY SGDYWGQGTT LTVSS       115

SEQ ID NO: 32          moltype = DNA  length = 336
FEATURE                Location/Qualifiers
misc_feature           1..336
                       note = Description of Artificial Sequence:
                        Syntheticpolynucleotide
source                 1..336
                       mol_type = other DNA
                       organism = synthetic construct
SEQUENCE: 32
gatgttttga tgacccaaat tccactctcc ctgcctgtca gtcttggaga tcaagcctcc  60
atctcttgta gatctagtca gagcattgtc catagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tattactgct ttcaaggttc atatgttccg  300
tggacgttcg gtggaggcac caagctggaa atcaaa                            336

SEQ ID NO: 33          moltype = AA  length = 112
FEATURE                Location/Qualifiers
REGION                 1..112
                       note = Description of Artificial Sequence:
                        Syntheticpolypeptide
source                 1..112
                       mol_type = protein
                       organism = synthetic construct
SEQUENCE: 33
DVLMTQIPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSYVP WTFGGGTKLE IK          112

SEQ ID NO: 34          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 34
SYWMH                                                              5

SEQ ID NO: 35          moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
SEQUENCE: 35
MIDPSDVYTN YNPKFKG                                                 17

SEQ ID NO: 36          moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 36
NYSGDY                                                             6

SEQ ID NO: 37          moltype = DNA  length = 363
FEATURE                Location/Qualifiers
```

```
misc_feature           1..363
                       note = Description of Artificial Sequence:
                        Syntheticpolynucleotide
source                 1..363
                       mol_type = other DNA
                       organism = synthetic construct
SEQUENCE: 37
cagatccagt tggtacagtc tggacctgaa ctgaagaagc ctggagaggc agtcaagatc  60
tcctgcaagt cttctgggta taccttcaca acctatggaa tgagctgggt gaaacaggct  120
ccaggaaggg ctttaaagtg gatgggctgg ataaacacct actctggagt gccaacatat  180
gctgatgact tcaagggacg gtttgccttc tctttggaat cctctgccag cactgcctat  240
ttgcagatca acaacctcaa aaatgaggac acggctacat atttctgtgc aagagggagg  300
gatggttacc aagtggcctg gtttgcttac tggggccaag ggacgctggt cactgtctct  360
gca                                                                363

SEQ ID NO: 38          moltype = AA  length = 121
FEATURE                Location/Qualifiers
REGION                 1..121
                       note = Description of Artificial Sequence:
                        Syntheticpolypeptide
source                 1..121
                       mol_type = protein
                       organism = synthetic construct
SEQUENCE: 38
QIQLVQSGPE LKKPGEAVKI SCKSSGYTFT TYGMSWVKQA PGRALKWMGW INTYSGVPTY  60
ADDFKGRFAF SLESSASTAY LQINNLKNED TATYFCARGR DGYQVAWFAY WGQGTLVTVS  120
A                                                                  121

SEQ ID NO: 39          moltype = DNA  length = 321
FEATURE                Location/Qualifiers
misc_feature           1..321
                       note = Description of Artificial Sequence:
                        Syntheticpolynucleotide
source                 1..321
                       mol_type = other DNA
                       organism = synthetic construct
SEQUENCE: 39
gaaacaactg tgacccagtc tccagcatcc ctgtccatgg ctataggaga taaagtcacc  60
atcagatgca taaccagcac tgatattgat gatgatatga actggttcca gcagaagcca  120
ggggaacctc ctaagctcct tatttcagaa ggcaatactc ttcgtcctgg agtcccatcc  180
cgattctccg gcagtggcta tggtacagat tttatttta caattgaaaa catgctctct  240
gaagatgttg cagattacta ctgtttgcaa agtgataact tgccgtacac gttcggaggg  300
gggaccaagc tggaaataaa a                                            321

SEQ ID NO: 40          moltype = AA  length = 107
FEATURE                Location/Qualifiers
REGION                 1..107
                       note = Description of Artificial Sequence:
                        Syntheticpolypeptide
source                 1..107
                       mol_type = protein
                       organism = synthetic construct
SEQUENCE: 40
ETTVTQSPAS LSMAIGDKVT IRCITSTDID DDMNWFQQKP GEPPKLLISE GNTLRPGVPS  60
RFSGSGYGTD FIFTIENMLS EDVADYYCLQ SDNLPYTFGG GTKLEIK                107

SEQ ID NO: 41          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 41
TYGMS                                                              5

SEQ ID NO: 42          moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
SEQUENCE: 42
WINTYSGVPT YADDFKG                                                 17

SEQ ID NO: 43          moltype = AA  length = 12
FEATURE                Location/Qualifiers
REGION                 1..12
```

```
                        note = Description of Artificial Sequence: Syntheticpeptide
source                  1..12
                        mol_type = protein
                        organism = synthetic construct
SEQUENCE: 43
GRDGYQVAWF AY                                                     12

SEQ ID NO: 44           moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 44
ITSTDIDDDM N                                                      11

SEQ ID NO: 45           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 45
EGNTLRP                                                           7

SEQ ID NO: 46           moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 46
LQSDNLPYT                                                         9

SEQ ID NO: 47           moltype = DNA  length = 345
FEATURE                 Location/Qualifiers
misc_feature            1..345
                        note = Description of Artificial Sequence:
                         Syntheticpolynucleotide
source                  1..345
                        mol_type = other DNA
                        organism = synthetic construct
SEQUENCE: 47
caggtccaac tgcagcagcc tggggctgag ctggtgaggc ctgggacttc agtgaagttg  60
tcctgcaagg cttctggcta caccttcacc aactactgga tgcactgggt aaagcagagg  120
cctggacaag gccttgagtg gatcggaatg attgatcctt ctgatagtta tactaactac  180
aatccaaagt tcaagggtaa ggccacattg actgtagaca catcctccag cacagcctac  240
atgcagctca gcagcctgac atctgaggac tctgcggtct attactgtgc aagaaactac  300
tctggggact actggggcca aggcaccact ctcacagtct cctca                  345

SEQ ID NO: 48           moltype = AA  length = 115
FEATURE                 Location/Qualifiers
REGION                  1..115
                        note = Description of Artificial Sequence:
                         Syntheticpolypeptide
source                  1..115
                        mol_type = protein
                        organism = synthetic construct
SEQUENCE: 48
QVQLQQPGAE LVRPGTSVKL SCKASGYTFT NYWMHWVKQR PGQGLEWIGM IDPSDSYTNY  60
NPKFKGKATL TVDTSSSTAY MQLSSLTSED SAVYYCARNY SGDYWGQGTT LTVSS       115

SEQ ID NO: 49           moltype = DNA  length = 336
FEATURE                 Location/Qualifiers
misc_feature            1..336
                        note = Description of Artificial Sequence:
                         Syntheticpolynucleotide
source                  1..336
                        mol_type = other DNA
                        organism = synthetic construct
SEQUENCE: 49
gatgttttga tgacccaaac tccactctcc ctgcctgtca gtcttggaga tcaagcctcc  60
atctcttgca gatctagtca gagcattgta catagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tattattgct ttcaaggttc atatgttccg  300
```

```
tggacgttcg gtggaggcac caagctggaa atcaaa                     336

SEQ ID NO: 50          moltype = AA  length = 112
FEATURE                Location/Qualifiers
REGION                 1..112
                       note = Description of Artificial Sequence:
                        Syntheticpolypeptide
source                 1..112
                       mol_type = protein
                       organism = synthetic construct
SEQUENCE: 50
DVLMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSYVP WTFGGGTKLE IK          112

SEQ ID NO: 51          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 51
NYWMH                                                              5

SEQ ID NO: 52          moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
SEQUENCE: 52
MIDPSDSYTN YNPKFKG                                                 17

SEQ ID NO: 53          moltype = DNA  length = 357
FEATURE                Location/Qualifiers
misc_feature           1..357
                       note = Description of Artificial Sequence:
                        Syntheticpolynucleotide
source                 1..357
                       mol_type = other DNA
                       organism = synthetic construct
SEQUENCE: 53
gaggtgcagc tggtggaatc tgggggaggc ttagtgaagc ctggagggtc cctgaaactc  60
tcctgtgcag cctctggatt cactttcagt gactatgcca tgtcttgggt tcgccagact  120
ccggaaaaga ggctggagtg ggtcgcaacc attagtgatg gtggtactta cacctactat  180
ccagacaatg taaagggccg attcaccatc tccagagaca atgccaagaa caacctgtac  240
ctgcaaatga gccatctgaa gtctgaggac acagccatgt attactgtgc aagagaatgg  300
ggtgattacg acggatttga ctactggggc caaggcacca ctctcacagt ctcctcg     357

SEQ ID NO: 54          moltype = AA  length = 119
FEATURE                Location/Qualifiers
REGION                 1..119
                       note = Description of Artificial Sequence:
                        Syntheticpolypeptide
source                 1..119
                       mol_type = protein
                       organism = synthetic construct
SEQUENCE: 54
EVQLVESGGG LVKPGGSLKL SCAASGFTFS DYAMSWVRQT PEKRLEWVAT ISDGGTYTYY  60
PDNVKGRFTI SRDNAKNNLY LQMSHLKSED TAMYYCAREW GDYDGFDYWG QGTTLTVSS   119

SEQ ID NO: 55          moltype = DNA  length = 321
FEATURE                Location/Qualifiers
misc_feature           1..321
                       note = Description of Artificial Sequence:
                        Syntheticpolynucleotide
source                 1..321
                       mol_type = other DNA
                       organism = synthetic construct
SEQUENCE: 55
gacatccaga tgacccagtc tccatcctcc ttatctgcct ctctgggaga aagagtcagt  60
ctcacttgtc gggcaagtca ggaaattagt ggttacttaa gctggcttca gcagaaacca  120
gatggaacta ttaaacgcct gatctacgcc gcatccactt tagattctgg tgtcccaaaa  180
aggttcagtg gcagtaggtc tgggtcagat tattctctca ccatcggcag ccttgagtct  240
gaagatcttg cagactatta ctgtctacaa tatgatagtt atccgtacac gttcggaggg  300
gggaccaagc tggaaataaa a                                            321

SEQ ID NO: 56          moltype = AA  length = 107
```

```
FEATURE                Location/Qualifiers
REGION                 1..107
                       note = Description of Artificial Sequence:
                        Syntheticpolypeptide
source                 1..107
                       mol_type = protein
                       organism = synthetic construct
SEQUENCE: 56
DIQMTQSPSS LSASLGERVS LTCRASQEIS GYLSWLQQKP DGTIKRLIYA ASTLDSGVPK  60
RFSGSRSGSD YSLTIGSLES EDLADYYCLQ YDSYPYTFGG GTKLEIK                107

SEQ ID NO: 57          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 57
DYAMS                                                              5

SEQ ID NO: 58          moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
SEQUENCE: 58
TISDGGTYTY YPDNVKG                                                 17

SEQ ID NO: 59          moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 59
EWGDYDGFDY                                                         10

SEQ ID NO: 60          moltype = AA  length = 11
FEATURE                Location/Qualifiers
REGION                 1..11
                       note = Description of Artificial Sequence: Syntheticpeptide
source                 1..11
                       mol_type = protein
                       organism = synthetic construct
SEQUENCE: 60
RASQEISGYL S                                                       11

SEQ ID NO: 61          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 61
AASTLDS                                                            7

SEQ ID NO: 62          moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 62
LQYDSYPYT                                                          9

SEQ ID NO: 63          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 63
```

```
GYTFTSH                                                         7

SEQ ID NO: 64          moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 64
DPSDFY                                                          6

SEQ ID NO: 65          moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 65
GFSLSTFGL                                                       9

SEQ ID NO: 66          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 66
WWDDD                                                           5

SEQ ID NO: 67          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 67
GYTFTDH                                                         7

SEQ ID NO: 68          moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 68
YPRDGY                                                          6

SEQ ID NO: 69          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 69
GYTFSSY                                                         7

SEQ ID NO: 70          moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 70
DPSDVY                                                          6

SEQ ID NO: 71          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
```

```
SEQUENCE: 71
GYTFTTY                                                         7

SEQ ID NO: 72           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 72
NTYSGV                                                          6

SEQ ID NO: 73           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 73
GYTFTNY                                                         7

SEQ ID NO: 74           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 74
DPSDSY                                                          6

SEQ ID NO: 75           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 75
GFTFSDY                                                         7

SEQ ID NO: 76           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 76
SDGGTY                                                          6

SEQ ID NO: 77           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 77
GYTFTSHW                                                        8

SEQ ID NO: 78           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 78
LDPSDFYS                                                        8

SEQ ID NO: 79           moltype = AA  length = 13
FEATURE                 Location/Qualifiers
REGION                  1..13
                        note = Description of Artificial Sequence: Syntheticpeptide
source                  1..13
                        mol_type = protein
```

```
                        organism = synthetic construct
SEQUENCE: 79
ARGLLSGDYA MDY                                              13

SEQ ID NO: 80           moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 80
GFSLSTFGLS                                                  10

SEQ ID NO: 81           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 81
IWWDDDK                                                     7

SEQ ID NO: 82           moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 82
ARIGADALPF DY                                               12

SEQ ID NO: 83           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 83
GYTFTDHI                                                    8

SEQ ID NO: 84           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 84
IYPRDGYI                                                    8

SEQ ID NO: 85           moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 85
ARGYYYAMDY                                                  10

SEQ ID NO: 86           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 86
GYTFSSYW                                                    8

SEQ ID NO: 87           moltype = AA  length = 8
FEATURE                 Location/Qualifiers
REGION                  1..8
                        note = Description of Artificial Sequence: Syntheticpeptide
source                  1..8
```

```
                        mol_type = protein
                        organism = synthetic construct
SEQUENCE: 87
IDPSDVYT                                                8

SEQ ID NO: 88           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 88
ARNYSGDY                                                8

SEQ ID NO: 89           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 89
GYTFTTYG                                                8

SEQ ID NO: 90           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 90
INTYSGVP                                                8

SEQ ID NO: 91           moltype = AA  length = 14
FEATURE                 Location/Qualifiers
REGION                  1..14
                        note = Description of Artificial Sequence: Syntheticpeptide
source                  1..14
                        mol_type = protein
                        organism = synthetic construct
SEQUENCE: 91
ARGRDGYQVA WFAY                                         14

SEQ ID NO: 92           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 92
GYTFTNYW                                                8

SEQ ID NO: 93           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 93
IDPSDSYT                                                8

SEQ ID NO: 94           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 94
GFTFSDYA                                                8

SEQ ID NO: 95           moltype = AA  length = 8
FEATURE                 Location/Qualifiers
REGION                  1..8
                        note = Description of Artificial Sequence: Syntheticpeptide
```

```
source                  1..8
                        mol_type = protein
                        organism = synthetic construct
SEQUENCE: 95
ISDGGTYT                                                                  8

SEQ ID NO: 96           moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 96
AREWGDYDGF DY                                                             12

SEQ ID NO: 97           moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 97
QSIVHSNGNT Y                                                              11

SEQ ID NO: 98           moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 98
KSLLHSNGNT Y                                                              11

SEQ ID NO: 99           moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 99
QSIVHSIGNT Y                                                              11

SEQ ID NO: 100          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 100
TDIDDD                                                                    6

SEQ ID NO: 101          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 101
QEISGY                                                                    6

SEQ ID NO: 102          moltype = DNA  length = 972
FEATURE                 Location/Qualifiers
misc_feature            1..972
                        note = Description of Artificial Sequence:
                         Syntheticpolynucleotide
source                  1..972
                        mol_type = other DNA
                        organism = synthetic construct
SEQUENCE: 102
gccaaaacga cacccccatc tgtctatcca ctggcccctg gatctgctgc ccaaactaac  60
tccatggtga ccctgggatg cctggtcaag ggctatttcc ctgagccagt gacagtgacc  120
tggaactctg gatccctgtc cagcggtgtg cacaccttcc cagctgtcct gcagtctgac  180
ctctacactc tgagcagctc agtgactgtc ccctccagca cctggcccag ccagaccgtc  240
```

```
acctgcaacg ttgcccaccc ggccagcagc accaaggtgg acaagaaaat tgtgcccagg  300
gattgtggtt gtaagccttg catatgtaca gtcccagaag tatcatctgt cttcatcttc  360
cccccaaagc ccaaggatgt gctcaccatt actctgactc ctaaggtcac gtgtgttgtg  420
gtagacatca gcaaggatga tcccgaggtc cagttcagct ggtttgtaga tgatgtggag  480
gtgcacacag ctcagacgca accccgggag gagcagttca acagcacttt ccgctcagtc  540
agtgaacttc ccatcatgca ccaggactgg ctcaatggca aggagttcaa atgcagggtc  600
aacagtgcag ctttccctgc ccccatcgag aaaaccatct ccaaaaccaa aggcagaccg  660
aaggctccac aggtgtacac cattccacct cccaaggagc agatggccaa ggataaagtc  720
agtctgacct gcatgataac agacttcttc cctgaagaca ttactgtgga gtggcagtgg  780
aatgggcagc cagcggagaa ctacaagaac actcagccca tcatggacac agatggctct  840
tacttcgtct acagcaagct caatgtgcag aagagcaact gggaggcagg aaatactttc  900
acctgctctg tgttacatga gggcctgcac aaccaccata ctgagaagag cctctcccac  960
tctcctggta aa                                                      972

SEQ ID NO: 103         moltype = AA  length = 324
FEATURE                Location/Qualifiers
REGION                 1..324
                       note = Description of Artificial Sequence:
                        Syntheticpolypeptide
source                 1..324
                       mol_type = protein
                       organism = synthetic construct
SEQUENCE: 103
AKTTPPSVYP LAPGSAAQTN SMVTLGCLVK GYFPEPVTVT WNSGSLSSGV HTFPAVLQSD  60
LYTLSSSVTV PSSTWPSQTV TCNVAHPASS TKVDKKIVPR DCGCKPCICT VPEVSSVFIF  120
PPKPKDVLTI TLTPKVTCVV VDISKDDPEV QFSWFVDDVE VHTAQTQPRE EQFNSTFRSV  180
SELPIMHQDW LNGKEFKCRV NSAAFPAPIE KTISKTKGRP KAPQVYTIPP PKEQMAKDKV  240
SLTCMITDFF PEDITVEWQW NGQPAENYKN TQPIMDTDGS YFVYSKLNVQ KSNWEAGNTF  300
TCSVLHEGLH NHHTEKSLSH SPGK                                         324

SEQ ID NO: 104         moltype = DNA  length = 1008
FEATURE                Location/Qualifiers
misc_feature           1..1008
                       note = Description of Artificial Sequence:
                        Syntheticpolynucleotide
source                 1..1008
                       mol_type = other DNA
                       organism = synthetic construct
SEQUENCE: 104
gccaaaacaa cacccccatc agtctatcca ctggcccctg ggtgtggaga tacaactggt  60
tcctctgtga ctctgggatg cctggtcaag ggctacttcc ctgagtcagt gactgtgact  120
tggaactctg gatccctgtc cagcagtgtg cacaccttcc cagctctcct gcagtctgga  180
ctctacacta tgagcagctc agtgactgtc ccctccagca cctggccaag tcagaccgtc  240
acctgcagcg ttgctcaccc agccagcagc accacggtgg acaaaaaact tgagcccagc  300
gggcccattt caacaatcaa cccctgtcct ccatgcaagg agtgtcacaa atgcccagct  360
cctaacctcg agggtggacc atccgtcttc atcttccctc caaatatcaa ggatgtactc  420
atgatctccc tgacacccaa ggtcacgtgt gtggtggtgg atgtgagcga ggatgaccca  480
gacgtccaga tcagctggtt tgtgaacaac gtggaagtac acacagctca gacacaaacc  540
catagagagg attacaacag tactatccgg gtggtcagca ccctccccat ccagcaccag  600
gactggatga gtggcaagga gttcaaatgc aaggtcaaca acaaagacct cccatcaccc  660
atcgagagaa ccatctcaaa aattaaaggg ctagtcagag ctccacaagt atacatcttg  720
ccgccaccag cagagcagtt gtccaggaaa gatgtcagtc tcacttgcct ggtcgtgggc  780
ttcaaccctg gagacatcag tgtggagtgg accagcaatg ggcatacaga ggagaactac  840
aaggacaccg caccagtcct agactctgac ggttcttact tcatatatag caagctcaat  900
atgaaaacaa gcaagtggga gaaaacagat tccttctcat gcaacgtgag acacgagggt  960
ctgaaaaatt actacctgaa gaagaccatc tcccggtctc cgggtaaa               1008

SEQ ID NO: 105         moltype = AA  length = 336
FEATURE                Location/Qualifiers
REGION                 1..336
                       note = Description of Artificial Sequence:
                        Syntheticpolypeptide
source                 1..336
                       mol_type = protein
                       organism = synthetic construct
SEQUENCE: 105
AKTTPPSVYP LAPGCGDTTG SSVTLGCLVK GYFPESVTVT WNSGSLSSSV HTFPALLQSG  60
LYTMSSSVTV PSSTWPSQTV TCSVAHPASS TTVDKKLEPS GPISTINPCP PCKECHKCPA  120
PNLEGGPSVF IFPPNIKDVL MISLTPKVTC VVVDVSEDDP DVQISWFVNN VEVHTAQTQT  180
HREDYNSTIR VVSTLPIQHQ DWMSGKEFKC KVNNKDLPSP IERTISKIKG LVRAPQVYIL  240
PPPAEQLSRK DVSLTCLVVG FNPGDISVEW TSNGHTEENY KDTAPVLDSD GSYFIYSKLN  300
MKTSKWEKTD SFSCNVRHEG LKNYYLKKTI SRSPGK                             336

SEQ ID NO: 106         moltype = DNA  length = 321
FEATURE                Location/Qualifiers
misc_feature           1..321
                       note = Description of Artificial Sequence:
                        Syntheticpolynucleotide
source                 1..321
```

```
                        mol_type = other DNA
                        organism = synthetic construct
SEQUENCE: 106
cgggctgatg ctgcaccaac tgtatccatc ttcccaccat ccagtgagca gttaacatct  60
ggaggtgcct cagtcgtgtg cttcttgaac aacttctacc ccagagacat caatgtcaag  120
tggaagattg atggcagtga acgacaaaat ggtgtcctga acagttggac tgatcaggac  180
agcaaagaca gcacctacag catgagcagc accctcacat tgaccaagga cgagtatgaa  240
cgacataaca gctatacctg tgaggccact cacaagacat caacttcacc cattgtcaag  300
agcttcaaca ggaatgagtg t                                           321

SEQ ID NO: 107          moltype = AA  length = 107
FEATURE                 Location/Qualifiers
REGION                  1..107
                        note = Description of Artificial Sequence:
                         Syntheticpolypeptide
source                  1..107
                        mol_type = protein
                        organism = synthetic construct
SEQUENCE: 107
RADAAPTVSI FPPSSEQLTS GGASVVCFLN NFYPRDINVK WKIDGSERQN GVLNSWTDQD  60
SKDSTYSMSS TLTLTKDEYE RHNSYTCEAT HKTSTSPIVK SFNRNEC                107

SEQ ID NO: 108          moltype = DNA  length = 1389
FEATURE                 Location/Qualifiers
misc_feature            1..1389
                        note = Description of Artificial Sequence:
                         Syntheticpolynucleotide
source                  1..1389
                        mol_type = other DNA
                        organism = synthetic construct
SEQUENCE: 108
atgggatgga gctgtatcat tgtcctcttg gtatcaacag ctacaggtgt ccactcccag  60
gtccaactgc agcagcctgg ggctgaactg gtgaggcctg ggacttcagt gaagttgtcc  120
tgcaaggctt ctggctacac cttcaccagc cactggttgc actgggtgaa gcagaggcct  180
ggacaaggcc ttgagtggat cggagtgctt gatccttctg atttttatag taactacaat  240
caaaacttca agggcaaggc cacattgact gtagacacat cctccagcac agcctacatg  300
cagctcagca gcctgacatc tgaggactct gcggtctatt actgtgcacg aggcctacta  360
tccggggact atgctatgga ctactggggt caaggaacct cagtcaccgt ctcctcagcc  420
aaaacgacac ccccatctgt ctatccactg gcccctggat ctgctgccca aactaactcc  480
atggtgaccc tgggatgcct ggtcaagggc tatttccctg agccagtgac agtgacctgg  540
aactctggat ccctgtccag cggtgtgcac accttcccag ctgtcctgca gtctgacctc  600
tacactctga gcagctcagt gactgtcccc tccagcacct ggcccagcca gaccgtcacc  660
tgcaacgttg cccacccggc cagcagcacc aaggtggaca agaaaattgt gcccagggat  720
tgtggttgta agccttgcat atgtacagtc ccagaagtat catctgtctt catcttcccc  780
ccaaagccca aggatgtgct caccattact ctgactccta aggtcacgtg tgttgtggta  840
gacatcagca aggatgatcc cgaggtccag ttcagctggt ttgtagatga tgtggaggtg  900
cacacagctc agacgcaacc ccgggaggag cagttcaaca gcactttccg ctcagtcagt  960
gaacttccca tcatgcacca ggactggctc aatggcaagg agttcaaatg cagggtcaac  1020
agtgcagctt tccctgcccc catcgagaaa accatctcca aaaccaaagg cagaccgaag  1080
gctccacagg tgtacaccat tccacctccc aaggagcaga tggccaagga taaagtcagt  1140
ctgacctgca tgataacaga cttcttccct gaagacatta ctgtggagtg gcagtggaat  1200
gggcagccag cggagaacta caagaacact cagcccatca tggacacaga tggctcttac  1260
ttcgtctaca gcaagctcaa tgtgcagaag agcaactggg aggcaggaaa tactttcacc  1320
tgctctgtgt tacatgaggg cctgcacaac caccatactg agaagagcct ctcccactct  1380
cctggtaaa                                                         1389

SEQ ID NO: 109          moltype = AA  length = 463
FEATURE                 Location/Qualifiers
REGION                  1..463
                        note = Description of Artificial Sequence:
                         Syntheticpolypeptide
source                  1..463
                        mol_type = protein
                        organism = synthetic construct
SEQUENCE: 109
MGWSCIIVLL VSTATGVHSQ VQLQQPGAEL VRPGTSVKLS CKASGYTFTS HWLHWVKQRP  60
GQGLEWIGVL DPSDFYSNYN QNFKGKATLT VDTSSSTAYM QLSSLTSEDS AVYYCARGLL  120
SGDYAMDYWG QGTSVTVSSA KTTPPSVYPL APGSAAQTNS MVTLGCLVKG YFPEPVTVTW  180
NSGSLSSGVH TFPAVLQSDL YTLSSSVTVP SSTWPSQTVT CNVAHPASST KVDKKIVPRD  240
CGCKPCICTV PEVSSVFIFP PKPKDVLTIT LTPKVTCVVV DISKDDPEVQ FSWFVDDVEV  300
HTAQTQPREE QFNSTFRSVS ELPIMHQDWL NGKEFKCRVN SAAFPAPIEK TISKTKGRPK  360
APQVYTIPPP KEQMAKDKVS LTCMITDFFP EDITVEWQWN GQPAENYKNT QPIMDTDGSY  420
FVYSKLNVQK SNWEAGNTFT CSVLHEGLHN HHTEKSLSHS PGK                    463

SEQ ID NO: 110          moltype = DNA  length = 714
FEATURE                 Location/Qualifiers
misc_feature            1..714
                        note = Description of Artificial Sequence:
                         Syntheticpolynucleotide
```

```
source                  1..714
                        mol_type = other DNA
                        organism = synthetic construct
SEQUENCE: 110
atgaagttgc ctgttaggct gttggtgctg atgttctgga ttcctgcttc cagcagtgat  60
gttttgatga cccaaattcc actctccctg cctgtcagtc ttggagatca agcctccatc  120
tcttgcagat ctagtcagag cattgtacat agtaatggaa acacctattt agaatggtac  180
ctgcagaaac caggccagtc tccaaagtcc ctgatctaca aagtttctaa ccgattttct  240
ggggtcccag acaggttcag tggcagtgga tcagggacag atttcacact caagatcagc  300
agagtggagg ctgaggatct gggagtttat tactgcttc aaggttcata tgttccgtgg  360
acgttcggtg gaggcaccaa gctggaaatc aaacgggctg atgctgcacc aactgtatcc  420
atcttcccac catccagtga gcagttaaca tctggaggtg cctcagtcgt gtgcttcttg  480
aacaacttct accccagaga catcaatgtc aagtggaaga ttgatggcag tgaacgacaa  540
aatggtgtcc tgaacagttg gactgatcag gacagcaaag acagcaccta cagcatgagc  600
agcaccctca cattgaccaa ggacgagtat gaacgacata acagctatac ctgtgaggcc  660
actcacaaga catcaacttc acccattgtc aagagcttca acaggaatga gtgt        714

SEQ ID NO: 111          moltype = AA  length = 238
FEATURE                 Location/Qualifiers
REGION                  1..238
                        note = Description of Artificial Sequence:
                         Syntheticpolypeptide
source                  1..238
                        mol_type = protein
                        organism = synthetic construct
SEQUENCE: 111
MKLPVRLLVL MFWIPASSSD VLMTQIPLSL PVSLGDQASI SCRSSQSIVH SNGNTYLEWY  60
LQKPGQSPKS LIYKVSNRFS GVPDRFSGSG SGTDFTLKIS RVEAEDLGVY YCFQGSYVPW  120
TFGGGTKLEI KRADAAPTVS IFPPSSEQLT SGGASVVCFL NNFYPRDINV KWKIDGSERQ  180
NGVLNSWTDQ DSKDSTYSMS STLTLTKDEY ERHNSYTCEA THKTSTSPIV KSFNRNEC    238

SEQ ID NO: 112          moltype = DNA  length = 1425
FEATURE                 Location/Qualifiers
misc_feature            1..1425
                        note = Description of Artificial Sequence:
                         Syntheticpolynucleotide
source                  1..1425
                        mol_type = other DNA
                        organism = synthetic construct
SEQUENCE: 112
atgggcaggc ttacttcttc attcctgtta ctgattgtcc ctgcatatgt cctgtcccag  60
gttactctaa aagagtctgg ccctgggata ttgcggccct cccagaccct cagtctgact  120
tgttctttct ctgggttttc actgagcact tttggtttga gtgtaggctg gattcgtcag  180
ccttcaggga agggtctgga gtggctggca cacatttggt gggatgatga taagtactat  240
aacccagccc ttaagagtcg gctcacaatc tccaaggata cctccaaaaa ccaggtattc  300
ctcaagatcg ccaatgtgga cactgcagat actgccacat actactgtgc tcgaataggg  360
gcggacgccc ttcctttga ctactggggc caaggcacca ctctcacagt ctcctcagcc  420
aaaacaacac ccccatcagt ctatccactg gcccctgggt gtggagatac aactggttcc  480
tccgtgacct ctgggtgcct ggtcaagggg tacttccctg agccagtgac tgtgacttgg  540
aactctggat ccctgtccag cagtgtgcac accttcccag ctctcctgca gtctggactc  600
tacactatga gcagctcagt gactgtcccc tccagcacct ggccaagtca gaccgtcacc  660
tgcagcgttg ctcacccagc cagcagcacc acggtggaca aaaaacttga gcccagcggg  720
cccatttcaa caatcaaccc ctgtcctcca tgcaaggagt gtcacaaatg cccagctcct  780
aacctcgagg gtggaccatc cgtcttcatc ttccctccaa atatcaagga tgtactcatg  840
atctccctga cacccaaggt cacgtgtgtg gtggtggatg tgagcgagga tgacccagac  900
gtccagatca gctggtttgt gaacaacgtg gaagtacaca cagctcagac acaaacccat  960
agagaggatt acaacagtac tatccgggtg gtcagcaccc tccccatcca gcaccaggac  1020
tggatgagtg gcaaggagtt caaatgcaag gtgaacaaca aagacctccc atcacccatc  1080
gagagaacca tctcaaaaat taaagggcta gtcagagctc cacaagtata cactttgccg  1140
ccaccagcag agcagttgtc caggaaagat gtcagtctca cttgcctggt cgtgggcttc  1200
aaccctggag acatcagtgt ggagtggacc agcaatgggc atacagagga gaactacaag  1260
gacaccgcac cagttcttga ctctgacggt tcttacttca tatatagcaa gctcaatatg  1320
aaaacaagca agtgggagaa aacagattcc ttctcatgca acgtgagaca cgagggtctg  1380
aaaaattact acctgaagaa gaccatctcc cggtctccgg gtaaa                  1425

SEQ ID NO: 113          moltype = AA  length = 475
FEATURE                 Location/Qualifiers
REGION                  1..475
                        note = Description of Artificial Sequence:
                         Syntheticpolypeptide
source                  1..475
                        mol_type = protein
                        organism = synthetic construct
SEQUENCE: 113
MGRLTSSFLL LIVPAYVLSQ VTLKESGPGI LRPSQTLSLT CSFSGFSLST FGLSVGWIRQ  60
PSGKGLEWLA HIWWDDDKYY NPALKSRLTI SKDTSKNQVF LKIANVDTAD TATYYCARIG  120
ADALPFDYWG QGTTLTVSSA KTTPPSVYPL APGCGDTTGS SVTSGCLVKG YFPEPVTVTW  180
NSGSLSSSVH TFPALLQSGL YTMSSSVTVP SSTWPSQTVT CSVAHPASST TVDKKLEPSG  240
PISTINPCPP CKECHKCPAP NLEGGPSVFI FPPNIKDVLM ISLTPKVTCV VVDVSEDDPD  300
```

```
VQISWFVNNV EVHTAQTQTH REDYNSTIRV VSTLPIQHQD WMSGKEFKCK VNNKDLPSPI  360
ERTISKIKGL VRAPQVYTLP PPAEQLSRKD VSLTCLVVGF NPGDISVEWT SNGHTEENYK  420
DTAPVLDSDG SYFIYSKLNM KTSKWEKTDS FSCNVRHEGL KNYYLKKTIS RSPGK       475

SEQ ID NO: 114         moltype = DNA  length = 717
FEATURE                Location/Qualifiers
misc_feature           1..717
                       note = Description of Artificial Sequence:
                        Syntheticpolynucleotide
source                 1..717
                       mol_type = other DNA
                       organism = synthetic construct
SEQUENCE: 114
atgaggtgcc tagctgagtt cctggggctg cttgtgctct ggatccctgg agccattggg  60
gatattgtgt tgactcagac tgcaccctct gtacctgtca ctcctggaga gtcagtatcc  120
atctcctgca ggtctagtaa gagtctcctg catagtaatg gcaacactta cttgtattgg  180
ttcctgcaga ggccaggcca gtctcctcag ctcctgatat atcggatgtc caaccttgcc  240
tcaggagtcc cagacaggtt cagtggcagt gggtcaggaa ctgctttcac actgagaatc  300
agtagagtgg aggctgagga tgtgggtgtt tattactgta tgcaacatct agaatatcct  360
ttcacgttcg gctcggggac aaagttggaa ataaaacggg ctgatgctgc accaactgta  420
tccatcttcc caccatccag tgagcagtta acatctggag gtgcctcagt cgtgtgcttc  480
ttgaacaact tctaccccag agacatcaat gtcaagtgga agattgatgg cagtgaacga  540
caaaatggtg tcctgaacag ttggactgat caggacagca aagacagcac ctacagcatg  600
agcagcaccc tcacattgac caaggacgag tatgaacgac ataacagcta tacctgtgag  660
gccactcaca agacatcaac ttcacccatt gtcaagagct tcaacaggaa tgagtgt     717

SEQ ID NO: 115         moltype = AA  length = 239
FEATURE                Location/Qualifiers
REGION                 1..239
                       note = Description of Artificial Sequence:
                        Syntheticpolypeptide
source                 1..239
                       mol_type = protein
                       organism = synthetic construct
SEQUENCE: 115
MRCLAEFLGL LVLWIPGAIG DIVLTQTAPS VPVTPGESVS ISCRSSKSLL HSNGNTYLYW  60
FLQRPGQSPQ LLIYRMSNLA SGVPDRFSGS GSGTAFTLRI SRVEAEDVGV YYCMQHLEYP  120
FTFGSGTKLE IKRADAAPTV SIFPPSSEQL TSGGASVVCF LNNFYPRDIN VKWKIDGSER  180
QNGVLNSWTD QDSKDSTYSM SSTLTLTKDE YERHNSYTCE ATHKTSTSPI VKSFNRNEC   239

SEQ ID NO: 116         moltype = DNA  length = 1380
FEATURE                Location/Qualifiers
misc_feature           1..1380
                       note = Description of Artificial Sequence:
                        Syntheticpolynucleotide
source                 1..1380
                       mol_type = other DNA
                       organism = synthetic construct
SEQUENCE: 116
atggaatgga gctgggtctc tctcttcttc ctgtcagtaa ctacaggtgt ccactcccag  60
gttcagctgc aacagtctga cgctgagttg gtgaaacctg gagcttcagt gaagatatcc  120
tgcaaggttt ctggctacac cttcactgac catattattc actggatgaa gcagaggcct  180
gaacagggcc tggaatggat tggatatatt tatcctagag atggttatat taagtacaat  240
gagaagttca agggcaaggc cacattgact gcagacaaat cctccagcac agcctacatg  300
caggtcaaca gcctgacatc tgaggactct gcagtctatt tctgtgcaag gggttactat  360
tatgctatgg actactgggg tcaaggaacc tcagtcaccg tctcctcagc caaaacgaca  420
cccccatctg tctatccact ggcccctgga tctgctgccc aaactaactc catggtgacc  480
ctgggatgcc tggtcaaggg ctatttccct gagccagtga cagtgacctg gaactctgga  540
tccctgtcca gcggtgtgca caccttccca gctgtcctgc agtctgacct ctacactctg  600
agcagctcag tgactgtccc ctccagcacc tggcccagcc agaccgtcac ctgcaacgtt  660
gcccacccgg ccagcagcac caaggtggac aagaaaattg tgcccaggga ttgtggttgt  720
aagccttgca tatgtacagt cccagaagta tcatctgtct tcatcttccc cccaaagccc  780
aaggatgtgc tcaccattac tctgactcct aaggtcacgt gtgttgtggt agacatcagc  840
aaggatgatc ccgaggtcca gttcagctgg tttgtagatg atgtggaggt gcacacagct  900
cagacgcaac cccgggagga gcagttcaac agcactttcc gctcagtcag tgaacttccc  960
atcatgcacc aggactggct caatggcaag gagttcaaat gcagggtcaa cagtgcagct  1020
ttccctgccc ccatcgagaa aaccatctcc aaaaccaaag gcagaccgaa ggctccacag  1080
gtgtacacca ttccacctcc caaggagcag atggccaagg ataaagtcag tctgacctgc  1140
atgataacag acttcttccc tgaagacatt actgtggagt ggcagtggaa tgggcagcca  1200
gcggagaact acaagaacac tcagcccatc atggacacag atggctctta cttcgtctac  1260
agcaagctca atgtgcagaa gagcaactgg gaggcaggaa atactttcac ctgctctgtg  1320
ttacatgagg gcctgcacaa ccaccatact gagaagagcc tctcccactc tcctggtaaa  1380

SEQ ID NO: 117         moltype = AA  length = 460
FEATURE                Location/Qualifiers
REGION                 1..460
                       note = Description of Artificial Sequence:
                        Syntheticpolypeptide
source                 1..460
```

```
                         mol_type = protein
                         organism = synthetic construct
SEQUENCE: 117
MEWSWVSLFF LSVTTGVHSQ VQLQQSDAEL VKPGASVKIS CKVSGYTFTD HIIHWMKQRP  60
EQGLEWIGYI YPRDGYIKYN EKFKGKATLT ADKSSSTAYM QVNSLTSEDS AVYFCARGYY  120
YAMDYWGQGT SVTVSSAKTT PPSVYPLAPG SAAQTNSMVT LGCLVKGYFP EPVTVTWNSG  180
SLSSGVHTFP AVLQSDLYTL SSSVTVPSST WPSQTVTCNV AHPASSTKVD KKIVPRDCGC  240
KPCICTVPEV SSVFIFPPKP KDVLTITLTP KVTCVVVDIS KDDPEVQFSW FVDDVEVHTA  300
QTQPREEQFN STFRSVSELP IMHQDWLNGK EFKCRVNSAA FPAPIEKTIS KTKGRPKAPQ  360
VYTIPPPKEQ MAKDKVSLTC MITDFFPEDI TVEWQWNGQP AENYKNTQPI MDTDGSYFVY  420
SKLNVQKSNW EAGNTFTCSV LHEGLHNHHT EKSLSHSPGK                      460

SEQ ID NO: 118           moltype = DNA  length = 714
FEATURE                  Location/Qualifiers
misc_feature             1..714
                         note = Description of Artificial Sequence:
                          Syntheticpolynucleotide
source                   1..714
                         mol_type = other DNA
                         organism = synthetic construct
SEQUENCE: 118
atgaagttgc ctgttaggct gttggtgctg atgttctgga ttcctgcttc cagaagtgat  60
gttttgatga cccaaactcc actctccctg cctgtcagtc ttggagatca agcctccatc  120
tcttgcagat ctagtcagag cattgtacat agtattggaa acacctattt agaatggtac  180
ctgcagaaac caggccagtc tccaaagctc ctgatctaca aagtttccaa ccgattttct  240
ggggtcccag agaggttcag tggcagtgga tcagggacag atttcacact caagatcagc  300
agagtggagg ctgaggatct gggagtttat tactgctttc aaggttcaca tgttccattc  360
acgttcggct cggggacaaa gttggaaata aaacgggctg atgctgcacc aactgtatcc  420
atcttcccac catccagtga gcagttaaca tctggaggtg cctcagtcgt gtgcttcttg  480
aacaacttct accccaaaga catcaatgtc aagtggaaga ttgatggcag tgaacgacaa  540
aatggcgtcc tgaacagttg gactgatcag gacagcaaag acagcaccta cagcatgagc  600
agcaccctca cgttgaccaa ggacgagtat gaacgacata acagctatac ctgtgaggcc  660
actcacaaga catcaacttc acccattgtc aagagcttca acaggaatga gtgt        714

SEQ ID NO: 119           moltype = AA  length = 238
FEATURE                  Location/Qualifiers
REGION                   1..238
                         note = Description of Artificial Sequence:
                          Syntheticpolypeptide
source                   1..238
                         mol_type = protein
                         organism = synthetic construct
SEQUENCE: 119
MKLPVRLLVL MFWIPASRSD VLMTQTPLSL PVSLGDQASI SCRSSQSIVH SIGNTYLEWY  60
LQKPGQSPKL LIYKVSNRFS GVPERFSGSG SGTDFTLKIS RVEAEDLGVY YCFQGSHVPF  120
TFGSGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 120           moltype = DNA  length = 1374
FEATURE                  Location/Qualifiers
misc_feature             1..1374
                         note = Description of Artificial Sequence:
                          Syntheticpolynucleotide
source                   1..1374
                         mol_type = other DNA
                         organism = synthetic construct
SEQUENCE: 120
atgggatgga gctgtatcat tgtcctcttg gtatcaacag ctacatgtgt ccactcccag  60
gtccaactgc tgcagcctgg ggctgagctg gtgaggcctg ggacttcagt gaagttgtcc  120
tgcaagactt ctggctacac cttctccagc tactggatgc actgggtaaa gcagaggcct  180
ggacaaggcc ttgagtggat cggaatgatt gatccttctg atgtttatac taactacaat  240
ccaaagttca agggcaaggc cacattgact gttgacacat cctccagcac agcctacatg  300
cagctcagca gcctgacatc tgaggactct gcggtctatt actgtgcaag aaactactct  360
ggggactact ggggccaagg caccactctc acagtctcct cagccaaaac gacaccccca  420
tctgtctatc cactggcccc tggatctgct gcccaaacta actccatggt gaccctggga  480
tgcctggtca agggctattt ccctgagcca gtgacagtga cctggaactc tggatccctg  540
tccagcggtg tgcacacctt cccagctgtc ctgcagtctg acctctacac tctgagcagc  600
tcagtgactg tcccctccag cacctggccc agccagaccg tcacctgcaa cgttgcccac  660
ccggccagca gcaccaaggt ggacaagaaa attgtgccca gggattgtgg ttgtaagcct  720
tgcatatgta cagtcccaga agtatcatct gtcttcatct tccccccaaa gcccaaggat  780
gtgctcacca ttactctgac tcctaaggtc acgtgtgttg tggtagacat cagcaaggat  840
gatcccgagg tccagttcag ctggtttgta gatgatgtgg aggtgcacac agctcagacg  900
caaccccggg aggagcagtt caacagcact ttccgctcag tcagtgaact tcccatcatg  960
caccaggact ggctcaatgg caaggagttc aaatgcaggg tcaacagtgc agctttccct  1020
gcccccatcg agaaaaccat ctccaaaacc aaaggcagac cgaaggctcc acaggtgtac  1080
accattccac ctcccaagga gcagatggcc aaggataaag tcagtctgac ctgcatgata  1140
acagacttct tccctgaaga cattactgtg gagtggcagt ggaatgggca gccagcggag  1200
aactacaaga acactcagcc catcatggac acagatggct cttacttcgt ctacagcaag  1260
ctcaatgtgc agaagagcaa ctgggaggca ggaaatactt tcacctgctc tgtgttacat  1320
```

```
gagggcctgc acaaccacca tactgagaag agcctctccc actctcctgg taaa       1374

SEQ ID NO: 121          moltype = AA  length = 458
FEATURE                 Location/Qualifiers
REGION                  1..458
                        note = Description of Artificial Sequence:
                         Syntheticpolypeptide
source                  1..458
                        mol_type = protein
                        organism = synthetic construct
SEQUENCE: 121
MGWSCIIVLL VSTATCVHSQ VQLLQPGAEL VRPGTSVKLS CKTSGYTFSS YWMHWVKQRP  60
GQGLEWIGMI DPSDVYTNYN PKFKGKATLT VDTSSSTAYM QLSSLTSEDS AVYYCARNYS  120
GDYWGQGTTL TVSSAKTTPP SVYPLAPGSA AQTNSMVTLG CLVKGYFPEP VTVTWNSGSL  180
SSGVHTFPAV LQSDLYTLSS SVTVPSSTWP SQTVTCNVAH PASSTKVDKK IVPRDCGCKP  240
CICTVPEVSS VFIFPPKPKD VLTITLTPKV TCVVVDISKD DPEVQFSWFV DDVEVHTAQT  300
QPREEQFNST FRSVSELPIM HQDWLNGKEF KCRVNSAAFP APIEKTISKT KGRPKAPQVY  360
TIPPPKEQMA KDKVSLTCMI TDFFPEDITV EWQWNGQPAE NYKNTQPIMD TDGSYFVYSK  420
LNVQKSNWEA GNTFTCSVLH EGLHNHHTEK SLSHSPGK                          458

SEQ ID NO: 122          moltype = DNA  length = 714
FEATURE                 Location/Qualifiers
misc_feature            1..714
                        note = Description of Artificial Sequence:
                         Syntheticpolynucleotide
source                  1..714
                        mol_type = other DNA
                        organism = synthetic construct
SEQUENCE: 122
atgaagttgc ctgttaggct gttggtgctg atgttctgga ttcctgcttc cagcagtgat  60
gttttgatga cccaaattcc actctccctg cctgtcagtc ttggagatca agcctccatc  120
tcttgtagat ctagtcagag cattgtccat agtaatggaa acacctattt agaatggtac  180
ctgcagaaac caggccagtc tccaaagctc ctgatctaca aagtttccaa ccgattttct  240
ggggtcccag acaggttcag tggcagtgga tcagggacag atttcacact caagatcagc  300
agagtggagg ctgaggatct gggagtttat tactgctttc aaggttcata tgttccgtgg  360
acgttcggtg gaggcaccaa gctggaaatc aaacgggctg atgctgcacc aactgtatcc  420
atcttcccac catccagtga gcagttaaca tctggaggtg cctcagtcgt gtgcttcttg  480
aacaacttct accccagaga catcaatgtc aagtggaaga ttgatggcag tgaacgacaa  540
aatggtgtcc tgaacagttg gactgatcag gacagcaaag acagcaccta cagcatgagc  600
agcaccctca cattgaccaa ggacgagtat gaacgacata acagctatac ctgtgaggcc  660
actcacaaga catcaacttc acccattgtc aagagcttca acaggaatga gtgt        714

SEQ ID NO: 123          moltype = AA  length = 238
FEATURE                 Location/Qualifiers
REGION                  1..238
                        note = Description of Artificial Sequence:
                         Syntheticpolypeptide
source                  1..238
                        mol_type = protein
                        organism = synthetic construct
SEQUENCE: 123
MKLPVRLLVL MFWIPASSSD VLMTQIPLSL PVSLGDQASI SCRSSQSIVH SNGNTYLEWY  60
LQKPGQSPKL LIYKVSNRFS GVPDRFSGSG SGTDFTLKIS RVEAEDLGVY YCFQGSYVPW  120
TFGGGTKLEI KRADAAPTVS IFPPSSEQLT SGGASVVCFL NNFYPRDINV KWKIDGSERQ  180
NGVLNSWTDQ DSKDSTYSMS STLTLTKDEY ERHNSYTCEA THKTSTSPIV KSFNRNEC    238

SEQ ID NO: 124          moltype = DNA  length = 1395
FEATURE                 Location/Qualifiers
misc_feature            1..1395
                        note = Description of Artificial Sequence:
                         Syntheticpolynucleotide
source                  1..1395
                        mol_type = other DNA
                        organism = synthetic construct
SEQUENCE: 124
atgggttggc tgtggaactt gctattcctg atggcagctg cccaaagtgc ccaagcacag  60
atccagttgg tacagtctgg acctgaactg aagaagcctg gagaggcagt caagatctcc  120
tgcaagtctt ctgggtatac cttcacaacc tatggaatga gctgggtgaa acaggctcca  180
ggaagggctt taaagtggat gggctggata aacacctact ctggagtgcc aacatatgct  240
gatgacttca agggacggtt tgccttctct ttggaatcct ctgccagcac tgcctatttg  300
cagatcaaca acctcaaaaa tgaggacacg gctacatatt tctgtgcaag agggagggat  360
ggttaccaag tggcctggtt tgcttactgg ggccaaggga cgctggtcac tgtctctgca  420
gccaaaacga cacccccatc tgtctatcca ctggcccctg gatctgctgc ccaaactaac  480
tccatggtga ccctgggatg cctggtcaag ggctatttcc ctgagccagt gacagtgacc  540
tggaactctg gatccctgtc cagcggtgtg cacaccttcc cagctgtcct gcagtctgac  600
ctctacactc tgagcagctc agtgactgtc ccctccagca cctggcccag ccagaccgtc  660
acctgcaacg ttgcccaccc ggccagcagc accaaggtgg acaagaaaat tgtgcccagg  720
gattgtggtt gtaagccttg catatgtaca gtcccagaag tatcatctgt cttcatcttc  780
cccccaaagc ccaaggatgt gctcaccatt actctgactc ctaaggtcac gtgtgttgtg  840
```

```
gtagacatca gcaaggatga tcccgaggtc cagttcagct ggtttgtaga tgatgtggag  900
gtgcacacag ctcagacgca accccgggag gagcagttca acagcacttt ccgctcagtc  960
agtgaacttc ccatcatgca ccaggactgg ctcaatggca aggagttcaa atgcagggtc  1020
aacagtgcag ctttccctgc ccccatcgag aaaaccatct ccaaaaccaa aggcagaccg  1080
aaggctccac aggtgtacac cattccacct cccaaggagc agatggccaa ggataaagtc  1140
agtctgacct gcatgataac agacttcttc cctgaagaca ttactgtgga gtggcagtgg  1200
aatgggcagc cagcggagaa ctacaagaac actcagccca tcatggacac agatggctct  1260
tacttcgtct acagcaagct caatgtgcag aagagcaact gggaggcagg aaatactttc  1320
acctgctctg tgttacatga gggcctgcac aaccaccata ctgagaagag cctctcccac  1380
tctcctggta aatga                                                   1395

SEQ ID NO: 125         moltype = AA  length = 464
FEATURE                Location/Qualifiers
REGION                 1..464
                       note = Description of Artificial Sequence:
                        Syntheticpolypeptide
source                 1..464
                       mol_type = protein
                       organism = synthetic construct
SEQUENCE: 125
MGWLWNLLFL MAAAQSAQAQ IQLVQSGPEL KKPGEAVKIS CKSSGYTFTT YGMSWVKQAP  60
GRALKWMGWI NTYSGVPTYA DDFKGRFAFS LESSASTAYL QINNLKNEDT ATYFCARGRD  120
GYQVAWFAYW GQGTLVTVSA AKTTPPSVYP LAPGSAAQTN SMVTLGCLVK GYFPEPVTVT  180
WNSGSLSSGV HTFPAVLQSD LYTLSSSVTV PSSTWPSQTV TCNVAHPASS TKVDKKIVPR  240
DCGCKPCICT VPEVSSVFIF PPKPKDVLTI TLTPKVTCVV VDISKDDPEV QFSWFVDDVE  300
VHTAQTQPRE EQFNSTFRSV SELPIMHQDW LNGKEFKCRV NSAAFPAPIE KTISKTKGRP  360
KAPQVYTIPP PKEQMAKDKV SLTCMITDFF PEDITVEWQW NGQPAENYKN TQPIMDTDGS  420
YFVYSKLNVQ KSNWEAGNTF TCSVLHEGLH NHHTEKSLSH SPGK                  464

SEQ ID NO: 126         moltype = DNA  length = 705
FEATURE                Location/Qualifiers
misc_feature           1..705
                       note = Description of Artificial Sequence:
                        Syntheticpolynucleotide
source                 1..705
                       mol_type = other DNA
                       organism = synthetic construct
SEQUENCE: 126
atgttctcac tagctcttct cctcagtctt cttctcctct gtgtctctga ttctagggca  60
gaaacaactg tgacccagtc tccagcatcc ctgtccatgg ctataggaga taaagtcacc  120
atcagatgca taaccagcac tgatattgat gatgatatga actggttcca gcagaagcca  180
ggggaacctc ctaagctcct tatttcagaa ggcaatactc ttcgtcctgg agtcccatcc  240
cgattctccg gcagtggcta tggtacagat tttattttta caattgaaaa catgctctct  300
gaagatgttg cagattacta ctgtttgcaa agtgataact tgccgtacac gttcggaggg  360
gggaccaagc tggaaataaa acgggctgat gctgcaccaa ctgtatccat cttcccacca  420
tccagtgagc agttaacatc tggaggtgcc tcagtcgtgt gcttcttgaa caacttctac  480
cccagagaca tcaatgtcaa gtggaagatt gatggcagtg aacgacaaaa tggtgtcctg  540
aacagttgga ctgatcagga cagcaaagac agcacctaca gcatgagcag caccctcaca  600
ttgaccaagg acgagtatga acgacataac agctatacct gtgaggccac tcacaagaca  660
tcaacttcac ccattgtcaa gagcttcaac aggaatgagt gttag                  705

SEQ ID NO: 127         moltype = AA  length = 234
FEATURE                Location/Qualifiers
REGION                 1..234
                       note = Description of Artificial Sequence:
                        Syntheticpolypeptide
source                 1..234
                       mol_type = protein
                       organism = synthetic construct
SEQUENCE: 127
MFSLALLLSL LLLCVSDSRA ETTVTQSPAS LSMAIGDKVT IRCITSTDID DDMNWFQQKP  60
GEPPKLLISE GNTLRPGVPS RFSGSGYGTD FIFTIENMLS EDVADYYCLQ SDNLPYTFGG  120
GTKLEIKRAD AAPTVSIFPP SSEQLTSGGA SVVCFLNNFY PRDINVKWKI DGSERQNGVL  180
NSWTDQDSKD STYSMSSTLT LTKDEYERHN SYTCEATHKT STSPIVKSFN RNEC        234

SEQ ID NO: 128         moltype = DNA  length = 1374
FEATURE                Location/Qualifiers
misc_feature           1..1374
                       note = Description of Artificial Sequence:
                        Syntheticpolynucleotide
source                 1..1374
                       mol_type = other DNA
                       organism = synthetic construct
SEQUENCE: 128
atgggatgga gctgtatcat tgtcctcttg gtatcaacag ctacaggtgt ccactcccag  60
gtccaactgc agcagcctgg ggctgagctg gtgaggcctg ggacttcagt gaagttgtcc  120
tgcaaggctt ctggctacac cttcaccaac tactggatgc actgggtaaa gcagaggcct  180
ggacaaggcc ttgagtggat cggaatgatt gatccttctg atagttatac taactacaat  240
ccaaagttca agggtaaggc cacattgact gtagacacat cctccagcac agcctacatg  300
```

```
cagctcagca gcctgacatc tgaggactct gcggtctatt actgtgcaag aaactactct  360
ggggactact ggggccaagg caccactctc acagtctcct cagccaaaac gacaccccca  420
tctgtctatc cactggcccc tggatctgct gcccaaacta actccatggt gaccctggga  480
tgcctggtca agggctattt ccctgagcca gtgacagtga cctggaactc tggatccctg  540
tccagcggtg tgcacacctt cccagctgtc ctgcagtctg acctctacac tctgagcagc  600
tcagtgactg tcccctccag cacctggccc agccagaccg tcacctgcaa cgttgcccac  660
ccggccagca gcaccaaggt ggacaagaaa attgtgccca gggattgtgg ttgtaagcct  720
tgcatatgta cagtcccaga agtatcatct gtcttcatct tccccccaaa gcccaaggat  780
gtgctcacca ttactctgac tcctaaggtc acgtgtgttg tggtagacat cagcaaggat  840
gatcccgagg tccagttcag ctggtttgta gatgatgtgg aggtgcacac agctcagacg  900
caaccccggg aggagcagtt caacagcact ttccgctcag tcagtgaact tcccatcatg  960
caccaggact ggctcaatgg caaggagttc aaatgcaggg tcaacagtgc agctttccct  1020
gcccccatcg agaaaaccat ctccaaaacc aaaggcagac cgaaggctcc acaggtgtac  1080
accattccac ctcccaagga gcagatggcc aaggataaag tcagtctgac ctgcatgata  1140
acagacttct tccctgaaga cattactgtg gagtggcagt ggaatgggca gccagcggag  1200
aactacaaga acactcagcc catcatggac acagatggct cttacttcgt ctacagcaag  1260
ctcaatgtgc agaagagcaa ctgggaggca ggaaatactt tcacctgctc tgtgttacat  1320
gagggcctgc acaaccacca tactgagaag agcctctccc actctcctgg taaa        1374

SEQ ID NO: 129         moltype = AA  length = 458
FEATURE                Location/Qualifiers
REGION                 1..458
                       note = Description of Artificial Sequence:
                        Syntheticpolypeptide
source                 1..458
                       mol_type = protein
                       organism = synthetic construct
SEQUENCE: 129
MGWSCIIVLL VSTATGVHSQ VQLQQPGAEL VRPGTSVKLS CKASGYTFTN YWMHWVKQRP  60
GQGLEWIGMI DPSDSYTNYN PKFKGKATLT VDTSSSTAYM QLSSLTSEDS AVYYCARNYS  120
GDYWGQGTTL TVSSAKTTPP SVYPLAPGSA AQTNSMVTLG CLVKGYFPEP VTVTWNSGSL  180
SSGVHTFPAV LQSDLYTLSS SVTVPSSTWP SQTVTCNVAH PASSTKVDKK IVPRDCGCKP  240
CICTVPEVSS VFIFPPKPKD VLTITLTPKV TCVVVDISKD DPEVQFSWFV DDVEVHTAQT  300
QPREEQFNST FRSVSELPIM HQDWLNGKEF KCRVNSAAFP APIEKTISKT KGRPKAPQVY  360
TIPPPKEQMA KDKVSLTCMI TDFFPEDITV EWQWNGQPAE NYKNTQPIMD TDGSYFVYSK  420
LNVQKSNWEA GNTFTCSVLH EGLHNHHTEK SLSHSPGK                          458

SEQ ID NO: 130         moltype = DNA  length = 714
FEATURE                Location/Qualifiers
misc_feature           1..714
                       note = Description of Artificial Sequence:
                        Syntheticpolynucleotide
source                 1..714
                       mol_type = other DNA
                       organism = synthetic construct
SEQUENCE: 130
atgaagttgc ctgttaggct gttggtgctg atgttctgga ttcctgcttc cagcagtgat  60
gttttgatga cccaaactcc actctccctg cctgtcagtc ttggagatca agcctccatc  120
tcttgcagat ctagtcagag cattgtacat agtaatggaa acacctattt agaatggtac  180
ctgcagaaac caggccagtc tccaaagctc ctgatctaca aagtttccaa ccgattttct  240
ggggtcccag acaggttcag tggcagtgga tcagggacag atttcacact caagatcagc  300
agagtggagg ctgaggatct gggagtttat tattgctttc aaggttcata tgttccgtgg  360
acgttcggtg gaggcaccaa gctggaaatc aaacgggctg atgctgcacc aactgtatcc  420
atcttcccac catccagtga gcagttaaca tctggaggtg cctcagtcgt gtgcttcttg  480
aacaacttct accccagaga catcaatgtc aagtggaaga ttgatggcag tgaacgacaa  540
aatggtgtcc tgaacagttg gactgatcag gacagcaaag acagcaccta cagcatgagc  600
agcaccctca cattgaccaa ggacgagtat gaacgacata acagctatac ctgtgaggcc  660
actcacaaga catcaacttc acccattgtc aagagcttca acaggaatga gtgt        714

SEQ ID NO: 131         moltype = AA  length = 238
FEATURE                Location/Qualifiers
REGION                 1..238
                       note = Description of Artificial Sequence:
                        Syntheticpolypeptide
source                 1..238
                       mol_type = protein
                       organism = synthetic construct
SEQUENCE: 131
MKLPVRLLVL MFWIPASSSD VLMTQTPLSL PVSLGDQASI SCRSSQSIVH SNGNTYLEWY  60
LQKPGQSPKL LIYKVSNRFS GVPDRFSGSG SGTDFTLKIS RVEAEDLGVY YCFQGSYVPW  120
TFGGGTKLEI KRADAAPTVS IFPPSSEQLT SGGASVVCFL NNFYPRDINV KWKIDGSERQ  180
NGVLNSWTDQ DSKDSTYSMS STLTLTKDEY ERHNSYTCEA THKTSTSPIV KSFNRNEC    238

SEQ ID NO: 132         moltype = DNA  length = 1386
FEATURE                Location/Qualifiers
misc_feature           1..1386
                       note = Description of Artificial Sequence:
                        Syntheticpolynucleotide
source                 1..1386
```

```
                         mol_type = other DNA
                         organism = synthetic construct
SEQUENCE: 132
atgaacttcg ggctcagctt gatgttcctt gtccttgtct taaaaggtgt ccagtgtgag  60
gtgcagctgg tggaatctgg gggaggctta gtgaagcctg gagggtccct gaaactctcc  120
tgtgcagcct ctggattcac tttcagtgac tatgccatgt cttgggttcg ccagactccg  180
gaaaagaggc tggagtgggt cgcaaccatt agtgatggtg gtacttacac ctactatcca  240
gacaatgtaa agggccgatt caccatctcc agagacaatg ccaagaacaa cctgtacctg  300
caaatgagcc atctgaagtc tgaggacaca gccatgtatt actgtgcaag agaatggggt  360
gattacgacg gatttgacta ctggggccaa ggcaccactc tcacagtctc ctcggccaaa  420
acgacacccc catctgtcta tccactggcc cctggatctg ctgcccaaac taactccatg  480
gtgaccctgg gatgcctggt caagggctat ttccctgagc cagtgacagt gacctggaac  540
tctggatccc tgtccagcgg tgtgcacacc ttcccagctg tcctgcagtc tgacctctac  600
actctgagca gctcagtgac tgtcccctcc agcacctggc ccagccagac cgtcacctgc  660
aacgttgccc acccggccag cagcaccaag gtggacaaga aaattgtgcc cagggattgt  720
ggttgtaagc cttgcatatg tacagtccca gaagtatcat ctgtcttcat cttcccccca  780
aagcccaagg atgtgctcac cattactctg actcctaagg tcacgtgtgt tgtggtagac  840
atcagcaagg atgatcccga ggtccagttc agctggtttg tagatgatgt ggaggtgcac  900
acagctcaga cgcaaccccg ggaggagcag ttcaacagca ctttccgctc agtcagtgaa  960
cttcccatca tgcaccagga ctggctcaat ggcaaggagt tcaaatgcag ggtcaacagt  1020
gcagctttcc ctgcccccat cgagaaaacc atctccaaaa ccaaaggcag accgaaggct  1080
ccacaggtgt acaccattcc acctcccaag gagcagatgg ccaaggataa agtcagtctg  1140
acctgcatga taacagactt cttccctgaa gacattactg tggagtggca gtggaatggg  1200
cagccagcgg agaactacaa gaacactcag cccatcatgg acacagatgg ctcttacttc  1260
gtctacagca agctcaatgt gcagaagagc aactgggagg caggaaatac tttcacctgc  1320
tctgtgttac atgagggcct gcacaaccac catactgaga agagcctctc ccactctcct  1380
ggtaaa                                                             1386

SEQ ID NO: 133           moltype = AA  length = 462
FEATURE                  Location/Qualifiers
REGION                   1..462
                         note = Description of Artificial Sequence:
                          Syntheticpolypeptide
source                   1..462
                         mol_type = protein
                         organism = synthetic construct
SEQUENCE: 133
MNFGLSLMFL VLVLKGVQCE VQLVESGGGL VKPGGSLKLS CAASGFTFSD YAMSWVRQTP  60
EKRLEWVATI SDGGTYTYYP DNVKGRFTIS RDNAKNNLYL QMSHLKSEDT AMYYCAREWG  120
DYDGFDYWGQ GTTLTVSSAK TTPPSVYPLA PGSAAQTNSM VTLGCLVKGY FPEPVTVTWN  180
SGSLSSGVHT FPAVLQSDLY TLSSSVTVPS STWPSQTVTC NVAHPASSTK VDKKIVPRDC  240
GCKPCICTVP EVSSVFIFPP KPKDVLTITL TPKVTCVVVD ISKDDPEVQF SWFVDDVEVH  300
TAQTQPREEQ FNSTFRSVSE LPIMHQDWLN GKEFKCRVNS AAFPAPIEKT ISKTKGRPKA  360
PQVYTIPPPK EQMAKDKVSL TCMITDFFPE DITVEWQWNG QPAENYKNTQ PIMDTDGSYF  420
VYSKLNVQKS NWEAGNTFTC SVLHEGLHNH HTEKSLSHSP GK                    462

SEQ ID NO: 134           moltype = DNA  length = 708
FEATURE                  Location/Qualifiers
misc_feature             1..708
                         note = Description of Artificial Sequence:
                          Syntheticpolynucleotide
source                   1..708
                         mol_type = other DNA
                         organism = synthetic construct
SEQUENCE: 134
atggacatga gggttcctgc tcacgttttt ggcttcttgt tgctctggtt tccaggtacc  60
agatgtgaca tccagatgac ccagtctcca tcctccttat ctgcctctct gggagaaaga  120
gtcagtctca cttgtcgggc aagtcaggaa attagtggtt acttaagctg gcttcagcag  180
aaaccagatg gaactattaa acgcctgatc tacgccgcat ccactttaga ttctggtgtc  240
ccaaaaaggt tcagtggcag taggtctggg tcagattatt ctctcaccat cggcagcctt  300
gagtctgaag atcttgcaga ctattactgt ctacaatatg atagttatcc gtacacgttc  360
ggagggggga ccaagctgga aataaaacgg gctgatgctg caccaactgt atccatcttc  420
ccaccatcca gtgagcagtt aacatctgga ggtgcctcag tcgtgtgctt cttgaacaac  480
ttctacccca gagacatcaa tgtcaagtgg aagattgatg gcagtgaacg acaaaatggt  540
gtcctgaaca gttggactga tcaggacagc aaagacagca cctacagcat gagcagcacc  600
ctcacattga ccaaggacga gtatgaacga cataacagct atacctgtga ggccactcac  660
aagacatcaa cttcacccat tgtcaagagc ttcaacagga atgagtgt              708

SEQ ID NO: 135           moltype = AA  length = 236
FEATURE                  Location/Qualifiers
REGION                   1..236
                         note = Description of Artificial Sequence:
                          Syntheticpolypeptide
source                   1..236
                         mol_type = protein
                         organism = synthetic construct
SEQUENCE: 135
MDMRVPAHVF GFLLLWFPGT RCDIQMTQSP SSLSASLGER VSLTCRASQE ISGYLSWLQQ  60
KPDGTIKRLI YAASTLDSGV PKRFSGSRSG SDYSLTIGSL ESEDLADYYC LQYDSYPYTF  120
```

```
GGGTKLEIKR ADAAPTVSIF PPSSEQLTSG GASVVCFLNN FYPRDINVKW KIDGSERQNG  180
VLNSWTDQDS KDSTYSMSST LTLTKDEYER HNSYTCEATH KTSTSPIVKS FNRNEC      236

SEQ ID NO: 136         moltype = DNA  length = 23
FEATURE                Location/Qualifiers
misc_feature           1..23
                       note = Description of Artificial Sequence: Syntheticprimer
source                 1..23
                       mol_type = other DNA
                       organism = synthetic construct
SEQUENCE: 136
cgactggagc acgaggacac tga                                          23

SEQ ID NO: 137         moltype = DNA  length = 45
FEATURE                Location/Qualifiers
misc_feature           1..45
                       note = Description of Artificial Sequence: Syntheticprimer
source                 1..45
                       mol_type = other DNA
                       organism = synthetic construct
SEQUENCE: 137
ctaatacgac tcactatagg gcaagcagtg gtatcaacgc agagt                  45

SEQ ID NO: 138         moltype = DNA  length = 22
FEATURE                Location/Qualifiers
misc_feature           1..22
                       note = Description of Artificial Sequence: Syntheticprimer
source                 1..22
                       mol_type = other DNA
                       organism = synthetic construct
SEQUENCE: 138
ctaatacgac tcactatagg gc                                           22

SEQ ID NO: 139         moltype = DNA  length = 21
FEATURE                Location/Qualifiers
misc_feature           1..21
                       note = Description of Artificial Sequence: Syntheticprimer
source                 1..21
                       mol_type = other DNA
                       organism = synthetic construct
SEQUENCE: 139
tatgcaaggc ttacaaccac a                                            21

SEQ ID NO: 140         moltype = DNA  length = 28
FEATURE                Location/Qualifiers
misc_feature           1..28
                       note = Description of Artificial Sequence: Syntheticprimer
source                 1..28
                       mol_type = other DNA
                       organism = synthetic construct
SEQUENCE: 140
gccagtggat agacagatgg gggtgtcg                                     28

SEQ ID NO: 141         moltype = DNA  length = 21
FEATURE                Location/Qualifiers
misc_feature           1..21
                       note = Description of Artificial Sequence: Syntheticprimer
source                 1..21
                       mol_type = other DNA
                       organism = synthetic construct
SEQUENCE: 141
aggacagggg ttgattgttg a                                            21

SEQ ID NO: 142         moltype = DNA  length = 30
FEATURE                Location/Qualifiers
misc_feature           1..30
                       note = Description of Artificial Sequence: Syntheticprimer
source                 1..30
                       mol_type = other DNA
                       organism = synthetic construct
SEQUENCE: 142
ggccagtgga tagactgatg ggggtgttgt                                   30

SEQ ID NO: 143         moltype = DNA  length = 28
FEATURE                Location/Qualifiers
misc_feature           1..28
                       note = Description of Artificial Sequence: Syntheticprimer
source                 1..28
                       mol_type = other DNA
```

```
                         organism = synthetic construct
SEQUENCE: 143
ggaggaacca gttgtatctc cacaccca                                          28

SEQ ID NO: 144           moltype = DNA  length = 27
FEATURE                  Location/Qualifiers
misc_feature             1..27
                         note = Description of Artificial Sequence: Syntheticprimer
source                   1..27
                         mol_type = other DNA
                         organism = synthetic construct
SEQUENCE: 144
ctcattcctg ttgaagctct tgacaat                                           27

SEQ ID NO: 145           moltype = DNA  length = 23
FEATURE                  Location/Qualifiers
misc_feature             1..23
                         note = Description of Artificial Sequence: Syntheticprimer
source                   1..23
                         mol_type = other DNA
                         organism = synthetic construct
SEQUENCE: 145
cgactgaggc acctccagat gtt                                               23

SEQ ID NO: 146           moltype = DNA  length = 17
FEATURE                  Location/Qualifiers
misc_feature             1..17
                         note = Description of Artificial Sequence: Syntheticprimer
source                   1..17
                         mol_type = other DNA
                         organism = synthetic construct
SEQUENCE: 146
gtaaaacgac ggccagt                                                      17

SEQ ID NO: 147           moltype = DNA  length = 18
FEATURE                  Location/Qualifiers
misc_feature             1..18
                         note = Description of Artificial Sequence: Syntheticprimer
source                   1..18
                         mol_type = other DNA
                         organism = synthetic construct
SEQUENCE: 147
caggaaacag ctatgacc                                                     18

SEQ ID NO: 148           moltype = AA  length = 17
FEATURE                  Location/Qualifiers
REGION                   1..17
                         note = Description of Artificial Sequence: Syntheticpeptide
source                   1..17
                         mol_type = protein
                         organism = synthetic construct
SEQUENCE: 148
TISDGGTYTY YPDSVKG                                                      17

SEQ ID NO: 149           moltype = DNA  length = 357
FEATURE                  Location/Qualifiers
misc_feature             1..357
                         note = Description of Artificial Sequence:
                          Syntheticpolynucleotide
source                   1..357
                         mol_type = other DNA
                         organism = synthetic construct
SEQUENCE: 149
gaggttcagc tggtggaatc tggcggtggg cttgtacaac caggaggctc cctcagactg  60
agttgtgccg cttcagggtt cacattctcc gactatgcga tgtcatgggt gcgccaagca  120
cccgggaaag gactggagtg ggttgccact atcagcgatg gcggaacgta tacctattac  180
cctgacaatg tgaagggtcg gttcaccatt tccagggata acgcaaagaa cagtctctac  240
ctgcagatga acagcctgag ggctgaggac accgccgtct actactgcgc ccgagaatgg  300
ggagattatg atgggtttga ctattggggc cagggcactt tggtgacagt cagttct     357

SEQ ID NO: 150           moltype = AA  length = 119
FEATURE                  Location/Qualifiers
REGION                   1..119
                         note = Description of Artificial Sequence:
                          Syntheticpolypeptide
source                   1..119
                         mol_type = protein
                         organism = synthetic construct
SEQUENCE: 150
```

```
EVQLVESGGG LVQPGGSLRL SCAASGFTFS DYAMSWVRQA PGKGLEWVAT ISDGGTYTYY  60
PDNVKGRFTI SRDNAKNSLY LQMNSLRAED TAVYYCAREW GDYDGFDYWG QGTLVTVSS   119

SEQ ID NO: 151         moltype = DNA  length = 357
FEATURE                Location/Qualifiers
misc_feature           1..357
                       note = Description of Artificial Sequence:
                        Syntheticpolynucleotide
source                 1..357
                       mol_type = other DNA
                       organism = synthetic construct
SEQUENCE: 151
caagttcagc tggtggaatc tggcggtggg cttgtaaagc caggaggctc cctcagactg  60
agttgtgccg cttcagggtt cacattctcc gactatgcga tgtcatggat caggcaagca  120
cccgggaaag gactggagtg ggttagcact atcagcgatg gcggaacgta tacctattac  180
cctgacaatg tgaagggtcg gttcaccatt tccagggata acgcaaagaa cagtctctac  240
cttcagatga acagcctgag ggctgaggac accgccgtct actactgcgc ccgagaatgg  300
ggagattatg atgggtttga ctattggggc cagggcactt tggtgacagt cagttct     357

SEQ ID NO: 152         moltype = AA  length = 119
FEATURE                Location/Qualifiers
REGION                 1..119
                       note = Description of Artificial Sequence:
                        Syntheticpolypeptide
source                 1..119
                       mol_type = protein
                       organism = synthetic construct
SEQUENCE: 152
QVQLVESGGG LVKPGGSLRL SCAASGFTFS DYAMSWIRQA PGKGLEWVST ISDGGTYTYY  60
PDNVKGRFTI SRDNAKNSLY LQMNSLRAED TAVYYCAREW GDYDGFDYWG QGTLVTVSS   119

SEQ ID NO: 153         moltype = DNA  length = 357
FEATURE                Location/Qualifiers
misc_feature           1..357
                       note = Description of Artificial Sequence:
                        Syntheticpolynucleotide
source                 1..357
                       mol_type = other DNA
                       organism = synthetic construct
SEQUENCE: 153
caagttcagc tggtggaatc tggcggtggg cttgtaaagc caggaggctc cctcagactg  60
agttgtgccg cttcagggtt cacattctcc gactatgcga tgtcatggat caggcaagca  120
cccgggaaag gactggagtg ggttagcact atcagcgatg gcggaacgta tacctattac  180
cctgactccg tgaagggtcg gttcaccatt tccagggata acgcaaagaa cagtctctac  240
cttcagatga acagcctgag ggctgaggac accgccgtct actactgcgc ccgagaatgg  300
ggagattatg atgggtttga ctattggggc cagggcactt tggtgacagt cagttct     357

SEQ ID NO: 154         moltype = AA  length = 119
FEATURE                Location/Qualifiers
REGION                 1..119
                       note = Description of Artificial Sequence:
                        Syntheticpolypeptide
source                 1..119
                       mol_type = protein
                       organism = synthetic construct
SEQUENCE: 154
QVQLVESGGG LVKPGGSLRL SCAASGFTFS DYAMSWIRQA PGKGLEWVST ISDGGTYTYY  60
PDSVKGRFTI SRDNAKNSLY LQMNSLRAED TAVYYCAREW GDYDGFDYWG QGTLVTVSS   119

SEQ ID NO: 155         moltype = DNA  length = 357
FEATURE                Location/Qualifiers
misc_feature           1..357
                       note = Description of Artificial Sequence:
                        Syntheticpolynucleotide
source                 1..357
                       mol_type = other DNA
                       organism = synthetic construct
SEQUENCE: 155
gaggttcagc tggtggaatc tggcggtggg cttgtaaagc caggaggctc cctcagactg  60
agttgtgccg cttcagggtt cacattctcc gactatgcga tgtcatgggt gcgccaagca  120
cccgggaaag gactggagtg ggttagcact atcagcgatg gcggaacgta tacctattac  180
cctgacaatg tgaagggtcg gttcaccatt tccagggata acgcaaagaa cagtctctat  240
ttgcagatga acagcctgag ggctgaggac accgccgtct actactgcgc ccgagaatgg  300
ggagattatg atgggtttga ctattggggc cagggcactt tggtgacagt cagttct     357

SEQ ID NO: 156         moltype = AA  length = 119
FEATURE                Location/Qualifiers
REGION                 1..119
                       note = Description of Artificial Sequence:
```

```
                         Syntheticpolypeptide
source                   1..119
                         mol_type = protein
                         organism = synthetic construct
SEQUENCE: 156
EVQLVESGGG LVKPGGSLRL SCAASGFTFS DYAMSWVRQA PGKGLEWVST ISDGGTYTYY  60
PDNVKGRFTI SRDNAKNSLY LQMNSLRAED TAVYYCAREW GDYDGFDYWG QGTLVTVSS   119

SEQ ID NO: 157           moltype = DNA  length = 357
FEATURE                  Location/Qualifiers
misc_feature             1..357
                         note = Description of Artificial Sequence:
                          Syntheticpolynucleotide
source                   1..357
                         mol_type = other DNA
                         organism = synthetic construct
SEQUENCE: 157
gaggttcagc ttctggaatc tggcggtggg cttgtacagc caggaggctc cctcagactg  60
agttgtgccg cttcagggtt cacattctcc gactatgcga tgtcatgggt gcgccaagca  120
cccgggaaag gactggagtg ggtttcaact atcagcgatg gcggaacgta tacctattac  180
cctgacaatg tgaagggtcg gttcaccatt tccagggata acagcaagaa cacactctat  240
ctccagatga acagcctgag ggctgaggac accgccgtct actactgcgc ccgagaatgg  300
ggagattatg atgggtttga ctattggggc cagggcactt tggtgacagt cagttct     357

SEQ ID NO: 158           moltype = AA  length = 119
FEATURE                  Location/Qualifiers
REGION                   1..119
                         note = Description of Artificial Sequence:
                          Syntheticpolypeptide
source                   1..119
                         mol_type = protein
                         organism = synthetic construct
SEQUENCE: 158
EVQLLESGGG LVQPGGSLRL SCAASGFTFS DYAMSWVRQA PGKGLEWVST ISDGGTYTYY  60
PDNVKGRFTI SRDNSKNTLY LQMNSLRAED TAVYYCAREW GDYDGFDYWG QGTLVTVSS   119

SEQ ID NO: 159           moltype = DNA  length = 357
FEATURE                  Location/Qualifiers
misc_feature             1..357
                         note = Description of Artificial Sequence:
                          Syntheticpolynucleotide
source                   1..357
                         mol_type = other DNA
                         organism = synthetic construct
SEQUENCE: 159
caggttcagc tggtggaatc tggcggtggg gtagtacaac caggacggtc cctcagactg  60
agttgtgccg cttcagggtt cacattctcc gactatgcga tgtcatgggt gcgccaagca  120
cccgggaaag gactggagtg ggttgccact atcagcgatg gcggaacgta tacctattac  180
cctgacaatg tgaagggtcg gttcaccatt tccagggata actcaaagaa caccctctat  240
ctccaaatga gtagcctgag ggctgaggac accgccgtct actactgcgc ccgagaatgg  300
ggagattatg atgggtttga ctattggggc cagggcactt tggtgacagt cagttct     357

SEQ ID NO: 160           moltype = AA  length = 119
FEATURE                  Location/Qualifiers
REGION                   1..119
                         note = Description of Artificial Sequence:
                          Syntheticpolypeptide
source                   1..119
                         mol_type = protein
                         organism = synthetic construct
SEQUENCE: 160
QVQLVESGGG VVQPGRSLRL SCAASGFTFS DYAMSWVRQA PGKGLEWVAT ISDGGTYTYY  60
PDNVKGRFTI SRDNSKNTLY LQMSSLRAED TAVYYCAREW GDYDGFDYWG QGTLVTVSS   119

SEQ ID NO: 161           moltype = DNA  length = 357
FEATURE                  Location/Qualifiers
misc_feature             1..357
                         note = Description of Artificial Sequence:
                          Syntheticpolynucleotide
source                   1..357
                         mol_type = other DNA
                         organism = synthetic construct
SEQUENCE: 161
gaggttcagc tggtggaatc tggcggtggg cttgtaaagc caggaggctc cctcagactg  60
agttgtgccg cttcagggtt cacattctcc gactatgcga tgtcatgggt gcgccaagca  120
cccgggaaag gactggagtg ggttgccact atcagcgatg gcggaacgta tacctattac  180
cctgacaatg tgaagggtcg gttcaccatt tccagggata acgcaaagaa cagtctctac  240
cttcagatga acagcctgag ggctgaggac accgccgtct actactgcgc ccgagaatgg  300
ggagattatg atgggtttga ctattggggc cagggcactt tggtgacagt cagttct     357
```

```
SEQ ID NO: 162         moltype = AA  length = 119
FEATURE                Location/Qualifiers
REGION                 1..119
                       note = Description of Artificial Sequence:
                        Syntheticpolypeptide
source                 1..119
                       mol_type = protein
                       organism = synthetic construct
SEQUENCE: 162
EVQLVESGGG LVKPGGSLRL SCAASGFTFS DYAMSWVRQA PGKGLEWVAT ISDGGTYTYY  60
PDNVKGRFTI SRDNAKNSLY LQMNSLRAED TAVYYCAREW GDYDGFDYWG QGTLVTVSS   119

SEQ ID NO: 163         moltype = DNA  length = 321
FEATURE                Location/Qualifiers
misc_feature           1..321
                       note = Description of Artificial Sequence:
                        Syntheticpolynucleotide
source                 1..321
                       mol_type = other DNA
                       organism = synthetic construct
SEQUENCE: 163
gatattcagt tgacccaatc acctagcttc ctctcagctt ccgtgggcga cagagttacc  60
ataacctgtc gggcaagcca ggagatttct gggtacctgt cctggtacca acagaagccc  120
ggaaaagccc ctaagctgtt gatctatgct gcgtcaacct tggatagcgg tgtcccgagt  180
cgattctccg gttctggctc cggaacagag ttcactctga caatttctag ccttcagcca  240
gaagatttcg ccacgtacta ttgcctccag tacgacagct atccctatac atttgggcag  300
ggcactaaac tggagatcaa a                                            321

SEQ ID NO: 164         moltype = AA  length = 107
FEATURE                Location/Qualifiers
REGION                 1..107
                       note = Description of Artificial Sequence:
                        Syntheticpolypeptide
source                 1..107
                       mol_type = protein
                       organism = synthetic construct
SEQUENCE: 164
DIQLTQSPSF LSASVGDRVT ITCRASQEIS GYLSWYQQKP GKAPKLLIYA ASTLDSGVPS  60
RFSGSGSGTE FTLTISSLQP EDFATYYCLQ YDSYPYTFGQ GTKLEIK                107

SEQ ID NO: 165         moltype = DNA  length = 321
FEATURE                Location/Qualifiers
misc_feature           1..321
                       note = Description of Artificial Sequence:
                        Syntheticpolynucleotide
source                 1..321
                       mol_type = other DNA
                       organism = synthetic construct
SEQUENCE: 165
gatattcaga tgacccaatc acctagcagt ctctcagctt ccgtgggcga cagagttacc  60
ataacctgtc gggcaagcca ggagatttct gggtacctgt cctggtttca acagaagccc  120
ggaaaggccc cgaagagctt gatctatgct gcgtcaacct tggatagcgg tgtcccgagt  180
cgattctccg gttctggctc cggaaccgac tttactctga caatttctag ccttcagcca  240
gaagatttcg ccacgtacta ttgcctccag tacgacagct atccctatac atttgggcag  300
ggcactaaac tggagatcaa a                                            321

SEQ ID NO: 166         moltype = AA  length = 107
FEATURE                Location/Qualifiers
REGION                 1..107
                       note = Description of Artificial Sequence:
                        Syntheticpolypeptide
source                 1..107
                       mol_type = protein
                       organism = synthetic construct
SEQUENCE: 166
DIQMTQSPSS LSASVGDRVT ITCRASQEIS GYLSWFQQKP GKAPKSLIYA ASTLDSGVPS  60
RFSGSGSGTD FTLTISSLQP EDFATYYCLQ YDSYPYTFGQ GTKLEIK                107

SEQ ID NO: 167         moltype = DNA  length = 321
FEATURE                Location/Qualifiers
misc_feature           1..321
                       note = Description of Artificial Sequence:
                        Syntheticpolynucleotide
source                 1..321
                       mol_type = other DNA
                       organism = synthetic construct
SEQUENCE: 167
gatattcaga tgacccaatc acctagcagt ctctcagctt ccgtgggcga cagagttacc  60
```

```
ataacctgtc gggcaagcca ggagatttct gggtacctgt cctggtatca acagaagccc  120
ggaaaagccc caaagaggtt gatctatgct gcgtcaacct tggatagcgg tgtcccgagt  180
cgattctccg gttctggctc cggaaccgag ttcactctga caatttctag ccttcagcca  240
gaagatttcg ccacgtacta ttgcctccag tacgacagct atccctatac atttgggcag  300
ggcactaaac tggagatcaa a                                            321

SEQ ID NO: 168         moltype = AA  length = 107
FEATURE                Location/Qualifiers
REGION                 1..107
                       note = Description of Artificial Sequence:
                        Syntheticpolypeptide
source                 1..107
                       mol_type = protein
                       organism = synthetic construct
SEQUENCE: 168
DIQMTQSPSS LSASVGDRVT ITCRASQEIS GYLSWYQQKP GKAPKRLIYA ASTLDSGVPS  60
RFSGSGSGTE FTLTISSLQP EDFATYYCLQ YDSYPYTFGQ GTKLEIK                107

SEQ ID NO: 169         moltype = DNA  length = 321
FEATURE                Location/Qualifiers
misc_feature           1..321
                       note = Description of Artificial Sequence:
                        Syntheticpolynucleotide
source                 1..321
                       mol_type = other DNA
                       organism = synthetic construct
SEQUENCE: 169
gatattcaga tgacccaatc acctagcagt ctctcagctt ccgtgggcga cagagttacc  60
ataacctgtc gggcaagcca ggagatttct gggtacctgt cctggtacca acagaagccc  120
ggaaaggccc ccaagctgtt gatctatgct gcgtcaacct tggatagcgg tgtcccgagt  180
cgattctccg gttctggctc cggaacagac tttactttta caatttctag ccttcagcca  240
gaggacatcg ccacgtacta ttgcctccag tacgacagct atccctatac atttgggcag  300
ggcactaaac tggagatcaa a                                            321

SEQ ID NO: 170         moltype = AA  length = 107
FEATURE                Location/Qualifiers
REGION                 1..107
                       note = Description of Artificial Sequence:
                        Syntheticpolypeptide
source                 1..107
                       mol_type = protein
                       organism = synthetic construct
SEQUENCE: 170
DIQMTQSPSS LSASVGDRVT ITCRASQEIS GYLSWYQQKP GKAPKLLIYA ASTLDSGVPS  60
RFSGSGSGTD FTFTISSLQP EDIATYYCLQ YDSYPYTFGQ GTKLEIK                107

SEQ ID NO: 171         moltype = DNA  length = 321
FEATURE                Location/Qualifiers
misc_feature           1..321
                       note = Description of Artificial Sequence:
                        Syntheticpolynucleotide
source                 1..321
                       mol_type = other DNA
                       organism = synthetic construct
SEQUENCE: 171
gatattcaga tgacccaatc acctagcagt ctctcagctt ccgtgggcga cagagttacc  60
ataacctgtc gggcaagcca ggagatttct gggtacctgt cctggtatca acagaagccc  120
ggaaaagccc ctaagctgtt gatctatgct gcgtcaacct tggatagcgg tgtcccgagt  180
cgattctccg gttctggctc cggaactgac ttcactctga caatttctag ccttcagcca  240
gaagatttcg ccacgtacta ttgcctccag tacgacagct atccctatac atttgggcag  300
ggcactaaac tggagatcaa a                                            321

SEQ ID NO: 172         moltype = AA  length = 107
FEATURE                Location/Qualifiers
REGION                 1..107
                       note = Description of Artificial Sequence:
                        Syntheticpolypeptide
source                 1..107
                       mol_type = protein
                       organism = synthetic construct
SEQUENCE: 172
DIQMTQSPSS LSASVGDRVT ITCRASQEIS GYLSWYQQKP GKAPKLLIYA ASTLDSGVPS  60
RFSGSGSGTD FTLTISSLQP EDFATYYCLQ YDSYPYTFGQ GTKLEIK                107

SEQ ID NO: 173         moltype = DNA  length = 321
FEATURE                Location/Qualifiers
misc_feature           1..321
                       note = Description of Artificial Sequence:
                        Syntheticpolynucleotide
```

```
source                1..321
                      mol_type = other DNA
                      organism = synthetic construct
SEQUENCE: 173
gatattcaga tgacccaatc acctagcagt ctctcagctt ccgtgggcga cagagttacc  60
ataacctgtc gggcaagcca ggagatttct gggtacctgt cctggctgca acagaagccc  120
ggaggcgcca tcaagaggtt gatctatgct gcgtcaacct tggatagcgg tgtcccgagt  180
cgattctccg gttctggctc cggaagtgac tacactctga caatttctag ccttcagcca  240
gaagatttcg ccacgtacta ttgcctccag tacgacagct atccctatac atttgggcag  300
ggcactaaac tggagatcaa a                                            321

SEQ ID NO: 174        moltype = AA  length = 107
FEATURE               Location/Qualifiers
REGION                1..107
                      note = Description of Artificial Sequence:
                       Syntheticpolypeptide
source                1..107
                      mol_type = protein
                      organism = synthetic construct
SEQUENCE: 174
DIQMTQSPSS LSASVGDRVT ITCRASQEIS GYLSWLQQKP GGAIKRLIYA ASTLDSGVPS  60
RFSGSGSGSD YTLTISSLQP EDFATYYCLQ YDSYPYTFGQ GTKLEIK                107

SEQ ID NO: 175        moltype = DNA  length = 990
FEATURE               Location/Qualifiers
misc_feature          1..990
                      note = Description of Artificial Sequence:
                       Syntheticpolynucleotide
source                1..990
                      mol_type = other DNA
                      organism = synthetic construct
SEQUENCE: 175
gcctcaacaa aaggaccaag tgtgttccca ctcgccccta gcagcaagag tacatccggg  60
ggcactgcag cactcggctg cctcgtcaag gattattttc cagagccagt aaccgtgagc  120
tggaacagtg gagcactcac ttctggtgtc catacttttc ctgctgtcct gcaaagctct  180
ggcctgtact cactcagctc cgtcgtgacc gtgccatctt catctctggg cactcagacc  240
tacatctgta atgtaaacca caagcctagc aatactaagg tcgataagcg ggtggaaccc  300
aagagctgcg acaagactca cacttgtccc ccatgccctg cccctgaact tctgggcggt  360
cccagcgtct ttttgttccc accaaagcct aaagatactc tgatgataag tagaacaccc  420
gaggtgacat gtgttgttgt agacgtttcc cacgaggacc cagaggttaa gttcaactgg  480
tacgttgatg gagtcgaagt acataatgct aagaccaagc ctagagagga gcagtataat  540
agtacatacc gtgtagtcag tgttctcaca gtgctgcacc aagactggct caacggcaaa  600
gaatacaaat gcaaagtgtc caacaaagca ctcccagccc ctatcgagaa gactattagt  660
aaggcaaagg ggcagcctcg tgaaccacag gtgtacactc tgccacccag tagagaggaa  720
atgacaaaga accaagtctc attgacctgc ctggtgaaag gcttctaccc cagcgacatc  780
gccgttgagt gggagagtaa cggtcagcct gagaacaatt acaagacaac ccccccagtg  840
ctggatagtg acgggtcttt ctttctgtac agtaagctga ctgtggacaa gtcccgctgg  900
cagcagggta acgtcttcag ctgttccgtg atgcacgagg cattgcacaa ccactacacc  960
cagaagtcac tgagcctgag cccagggaag                                   990

SEQ ID NO: 176        moltype = AA  length = 330
FEATURE               Location/Qualifiers
REGION                1..330
                      note = Description of Artificial Sequence:
                       Syntheticpolypeptide
source                1..330
                      mol_type = protein
                      organism = synthetic construct
SEQUENCE: 176
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 177        moltype = DNA  length = 978
FEATURE               Location/Qualifiers
misc_feature          1..978
                      note = Description of Artificial Sequence:
                       Syntheticpolynucleotide
source                1..978
                      mol_type = other DNA
                      organism = synthetic construct
SEQUENCE: 177
gcctccacca agggcccatc ggtcttcccc ctggcgccct gctccaggag cacctccgag  60
agcacagcgg ccctgggctg cctggtcaag gactacttcc ccgaaccggt gacggtgtcg  120
tggaactcag gcgctctgac cagcggcgtg cacaccttcc cagctgtcct acagtcctca  180
ggactctact ccctcagcag cgtggtgacc gtgccctcca gcaacttcgg cacccagacc  240
```

```
tacacctgca acgtagatca caagcccagc aacaccaagg tggacaagac agttgagcgc  300
aaatgttgtg tcgagtgccc accgtgccca gcaccacctg tggcaggacc gtcagtcttc  360
ctcttccccc caaaacccaa ggacaccctc atgatctccc ggacccctga ggtcacgtgc  420
gtggtggtgg acgtgagcca cgaagacccc gaggtccagt tcaactggta cgtggacggc  480
gtggaggtgc ataatgccaa gacaaagcca cgggaggagc agttcaacag cacgttccgt  540
gtggtcagcg tcctcaccgt tgtgcaccag gactggctga acggcaagga gtacaagtgc  600
aaggtctcca acaaaggcct cccagccccc atcgagaaaa ccatctccaa aaccaaaggg  660
cagccccgag aaccacaggt gtacaccctg cccccatccc gggaggagat gaccaagaac  720
caggtcagcc tgacctgcct ggtcaaaggc ttctacccca gcgacatcgc cgtggagtgg  780
gagagcaatg ggcagccgga gaacaactac aagaccacac ctcccatgct ggactccgac  840
ggctccttct tcctctacag caagctcacc gtggacaaga gcaggtggca gcaggggaac  900
gtcttctcat gctccgtgat gcatgaggct ctgcacaacc actacacgca gaagagcctc  960
tccctgtctc cgggtaaa                                                 978

SEQ ID NO: 178          moltype = AA  length = 326
FEATURE                 Location/Qualifiers
REGION                  1..326
                        note = Description of Artificial Sequence:
                         Syntheticpolypeptide
source                  1..326
                        mol_type = protein
                        organism = synthetic construct
SEQUENCE: 178
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                      326

SEQ ID NO: 179          moltype = DNA  length = 321
FEATURE                 Location/Qualifiers
misc_feature            1..321
                        note = Description of Artificial Sequence:
                         Syntheticpolynucleotide
source                  1..321
                        mol_type = other DNA
                        organism = synthetic construct
SEQUENCE: 179
cgcacagttg ctgcccccag cgtgttcatt ttcccaccta gcgatgagca gctgaaaagc  60
ggtactgcct ctgtcgtatg cttgctcaac aacttttacc cacgtgaggc taaggtgcag  120
tggaaagtgg ataatgcact tcaatctgga aacagtcaag agtccgtgac agaacaggac  180
agcaaagact caacttattc actctcttcc accctgactc tgtccaaggc agactatgaa  240
aaacacaagg tatacgcctg cgaggttaca caccagggtt tgtctagtcc tgtcaccaag  300
tccttcaata ggggcgaatg t                                              321

SEQ ID NO: 180          moltype = AA  length = 107
FEATURE                 Location/Qualifiers
REGION                  1..107
                        note = Description of Artificial Sequence:
                         Syntheticpolypeptide
source                  1..107
                        mol_type = protein
                        organism = synthetic construct
SEQUENCE: 180
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 181          moltype = DNA  length = 1404
FEATURE                 Location/Qualifiers
misc_feature            1..1404
                        note = Description of Artificial Sequence:
                         Syntheticpolynucleotide
source                  1..1404
                        mol_type = other DNA
                        organism = synthetic construct
SEQUENCE: 181
atgaacttcg ggctcagctt gatgttcctt gtccttgtct taaaaggtgt ccagtgtgag  60
gtgcagctgg tggaatctgg gggaggctta gtgaagcctg gagggtccct gaaactctcc  120
tgtgcagcct ctggattcac tttcagtgac tatgccatgt cttgggttcg ccagactccg  180
gaaaagaggc tggagtgggt cgcaaccatt agtgatggtg gtacttacac ctactatcca  240
gacaatgtaa agggccgatt caccatctcc agagacaatg ccaagaacaa cctgtacctg  300
caaatgagcc atctgaagtc tgaggacaca gccatgtatt actgtgcaag agaatggggt  360
gattacgacg gatttgacta ctggggccaa ggcaccactc tcacagtctc ctcggcctca  420
acaaaaggac caagtgtgtt cccactcgcc cctagcagca agagtacatc cgggggcact  480
gcagcactcg gctgcctcgt caaggattat tttccagagc cagtaaccgt gagctggaac  540
agtggagcac tcacttctgg tgtccatact tttcctgctg tcctgcaaag ctctggcctg  600
tactcactca gctccgtcgt gaccgtgcca tcttcatctc tgggcactca gacctacatc  660
tgtaatgtaa accacaagcc tagcaatact aaggtcgata agcgggtgga acccaagagc  720
```

```
tgcgacaaga ctcacacttg tcccccatgc cctgcccctg aacttctggg cggtcccagc  780
gtctttttgt tcccaccaaa gcctaaagat actctgatga taagtagaac acccgaggtg  840
acatgtgttg ttgtagacgt ttcccacgag gacccagagg ttaagttcaa ctggtacgtt  900
gatggagtcg aagtacataa tgctaagacc aagcctagag aggagcagta taatagtaca  960
taccgtgtag tcagtgttct cacagtgctg caccaagact ggctcaacgg caaagaatac  1020
aaatgcaaag tgtccaacaa agcactccca gcccctatcg agaagactat tagtaaggca  1080
aaggggcagc ctcgtgaacc acaggtgtac actctgccac ccagtagaga ggaaatgaca  1140
aagaaccaag tctcattgac ctgcctggtg aaaggcttct accccagcga catcgccgtt  1200
gagtgggaga gtaacggtca gcctgagaac aattacaaga caaccccccc agtgctggat  1260
agtgacgggt ctttctttct gtacagtaag ctgactgtgg acaagtcccg ctggcagcag  1320
ggtaacgtct tcagctgttc cgtgatgcac gaggcattgc acaaccacta cacccagaag  1380
tcactgagcc tgagcccagg gaag                                        1404
```

```
SEQ ID NO: 182          moltype = AA  length = 468
FEATURE                 Location/Qualifiers
REGION                  1..468
                        note = Description of Artificial Sequence:
                         Syntheticpolypeptide
source                  1..468
                        mol_type = protein
                        organism = synthetic construct
SEQUENCE: 182
MNFGLSLMFL VLVLKGVQCE VQLVESGGGL VKPGGSLKLS CAASGFTFSD YAMSWVRQTP  60
EKRLEWVATI SDGGTYTYYP DNVKGRFTIS RDNAKNNLYL QMSHLKSEDT AMYYCAREWG  120
DYDGFDYWGQ GTTLTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKRVEPKS  240
CDKTHTCPPC PAPELLGGPS VFLFPPKPKD TLMISRTPEV TCVVVDVSHE DPEVKFNWYV  300
DGVEVHNAKT KPREEQYNST YRVVSVLTVL HQDWLNGKEY KCKVSNKALP APIEKTISKA  360
KGQPREPQVY TLPPSREEMT KNQVSLTCLV KGFYPSDIAV EWESNGQPEN NYKTTPPVLD  420
SDGSFFLYSK LTVDKSRWQQ GNVFSCSVMH EALHNHYTQK SLSLSPGK              468
```

```
SEQ ID NO: 183          moltype = DNA  length = 708
FEATURE                 Location/Qualifiers
misc_feature            1..708
                        note = Description of Artificial Sequence:
                         Syntheticpolynucleotide
source                  1..708
                        mol_type = other DNA
                        organism = synthetic construct
SEQUENCE: 183
atggacatga gggttcctgc tcacgttttt ggcttcttgt tgctctggtt tccaggtacc  60
agatgtgaca tccagatgac ccagtctcca tcctccttat ctgcctctct gggagaaaga  120
gtcagtctca cttgtcgggc aagtcaggaa attagtggtt acttaagctg gcttcagcag  180
aaaccagatg gaactattaa acgcctgatc tacgccgcat ccactttaga ttctggtgtc  240
ccaaaaaggt tcagtggcag taggtctggg tcagattatt ctctcaccat cggcagcctt  300
gagtctgaag atcttgcaga ctattactgt ctacaatatg atagttatcc gtacacgttc  360
ggaggggggga ccaagctgga aataaaacgc acagtcgccg ctccctccgt gttcatcttt  420
ccaccaagtg atgagcaact gaagtctggt actgcttcag tcgtgtgtct gctgaacaat  480
ttctaccctc gagaagccaa agtccaatgg aaggtagaca acgcactgca gtccggcaat  540
agccaagaat cagttaccga acaggattca aaggacagta catattccct gagcagcact  600
ctgaccctgt caaaggccga ttacgagaaa cacaaggtct atgcttgcga agtgacacat  660
cagggactgt ccagcccagt gacaaaatct tttaaccgtg ggagtgt               708
```

```
SEQ ID NO: 184          moltype = AA  length = 236
FEATURE                 Location/Qualifiers
REGION                  1..236
                        note = Description of Artificial Sequence:
                         Syntheticpolypeptide
source                  1..236
                        mol_type = protein
                        organism = synthetic construct
SEQUENCE: 184
MDMRVPAHVF GFLLLWFPGT RCDIQMTQSP SSLSASLGER VSLTCRASQE ISGYLSWLQQ  60
KPDGTIKRLI YAASTLDSGV PKRFSGSRSG SDYSLTIGSL ESEDLADYYC LQYDSYPYTF  120
GGGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236
```

```
SEQ ID NO: 185          moltype = DNA  length = 1413
FEATURE                 Location/Qualifiers
misc_feature            1..1413
                        note = Description of Artificial Sequence:
                         Syntheticpolynucleotide
source                  1..1413
                        mol_type = other DNA
                        organism = synthetic construct
SEQUENCE: 185
atggacatga gagttcctgc tcagctgctc gggttgctgt tgctttggct ccggggtgct  60
aggtgcgagg ttcagctggt ggaatctggc ggtgggcttg tacaaccagg aggctccctc  120
agactgagtt gtgccgcttc agggttcaca ttctccgact atgcgatgtc atgggtgcgc  180
```

```
caagcacccg ggaaaggact ggagtgggtt gccactatca gcgatggcgg aacgtatacc  240
tattaccctg acaatgtgaa gggtcggttc accatttcca gggataacgc aaagaacagt  300
ctctacctgc agatgaacag cctgagggct gaggacaccg ccgtctacta ctgcgcccga  360
gaatggggag attatgatgg gtttgactat tggggccagg gcactttggt gacagtcagt  420
tctgcctcaa caaaaggacc aagtgtgttc ccactcgccc ctagcagcaa gagtacatcc  480
gggggcactg cagcactcgg ctgcctcgtc aaggattatt ttccagagcc agtaaccgtg  540
agctggaaca gtggagcact cacttctggt gtccatactt ttcctgctgt cctgcaaagc  600
tctggcctgt actcactcag ctccgtcgtg accgtgccat cttcatctct gggcactcag  660
acctacatct gtaatgtaaa ccacaagcct agcaatacta aggtcgataa gcgggtggaa  720
cccaagagct gcgacaagac tcacacttgt cccccatgcc ctgcccctga acttctgggc  780
ggtcccagcg tctttttgtt cccaccaaag cctaaagata ctctgatgat aagtagaaca  840
cccgaggtga catgtgttgt tgtagacgtt tcccacgagg acccagaggt taagttcaac  900
tggtacgttg atggagtcga agtacataat gctaagacca agcctagaga ggagcagtat  960
aatagtacat accgtgtagt cagtgttctc acagtgctgc accaagactg gctcaacggc  1020
aaagaataca aatgcaaagt gtccaacaaa gcactcccag cccctatcga gaagactatt  1080
agtaaggcaa aggggcagcc tcgtgaacca caggtgtaca ctctgccacc cagtagagag  1140
gaaatgacaa agaaccaagt ctcattgacc tgcctggtga aaggcttcta ccccagcgac  1200
atcgccgttg agtgggagag taacggtcag cctgagaaca attacaagac aacccccccca  1260
gtgctggata gtgacgggtc tttctttctg tacagtaagc tgactgtgga caagtcccgc  1320
tggcagcagg gtaacgtctt cagctgttcc gtgatgcacg aggcattgca caaccactac  1380
acccagaagt cactgagcct gagcccaggg aag                               1413

SEQ ID NO: 186          moltype = AA  length = 471
FEATURE                 Location/Qualifiers
REGION                  1..471
                        note = Description of Artificial Sequence:
                         Syntheticpolypeptide
source                  1..471
                        mol_type = protein
                        organism = synthetic construct
SEQUENCE: 186
MDMRVPAQLL GLLLLWLRGA RCEVQLVESG GGLVQPGGSL RLSCAASGFT FSDYAMSWVR  60
QAPGKGLEWV ATISDGGTYT YYPDNVKGRF TISRDNAKNS LYLQMNSLRA EDTAVYYCAR  120
EWGDYDGFDY WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 187          moltype = DNA  length = 1413
FEATURE                 Location/Qualifiers
misc_feature            1..1413
                        note = Description of Artificial Sequence:
                         Syntheticpolynucleotide
source                  1..1413
                        mol_type = other DNA
                        organism = synthetic construct
SEQUENCE: 187
atggacatga gagttcctgc tcagctgctc gggttgctgt tgctttggct ccggggtgct  60
aggtgccaag ttcagctggt ggaatctggc ggtgggcttg taaagccagg aggctccctc  120
agactgagtt gtgccgcttc agggttcaca ttctccgact atgcgatgtc atggatcagg  180
caagcacccg ggaaaggact ggagtgggtt agcactatca gcgatggcgg aacgtatacc  240
tattaccctg acaatgtgaa gggtcggttc accatttcca gggataacgc aaagaacagt  300
ctctaccttc agatgaacag cctgagggct gaggacaccg ccgtctacta ctgcgcccga  360
gaatggggag attatgatgg gtttgactat tggggccagg gcactttggt gacagtcagt  420
tctgcctcaa caaaaggacc aagtgtgttc ccactcgccc ctagcagcaa gagtacatcc  480
gggggcactg cagcactcgg ctgcctcgtc aaggattatt ttccagagcc agtaaccgtg  540
agctggaaca gtggagcact cacttctggt gtccatactt ttcctgctgt cctgcaaagc  600
tctggcctgt actcactcag ctccgtcgtg accgtgccat cttcatctct gggcactcag  660
acctacatct gtaatgtaaa ccacaagcct agcaatacta aggtcgataa gcgggtggaa  720
cccaagagct gcgacaagac tcacacttgt cccccatgcc ctgcccctga acttctgggc  780
ggtcccagcg tctttttgtt cccaccaaag cctaaagata ctctgatgat aagtagaaca  840
cccgaggtga catgtgttgt tgtagacgtt tcccacgagg acccagaggt taagttcaac  900
tggtacgttg atggagtcga agtacataat gctaagacca agcctagaga ggagcagtat  960
aatagtacat accgtgtagt cagtgttctc acagtgctgc accaagactg gctcaacggc  1020
aaagaataca aatgcaaagt gtccaacaaa gcactcccag cccctatcga gaagactatt  1080
agtaaggcaa aggggcagcc tcgtgaacca caggtgtaca ctctgccacc cagtagagag  1140
gaaatgacaa agaaccaagt ctcattgacc tgcctggtga aaggcttcta ccccagcgac  1200
atcgccgttg agtgggagag taacggtcag cctgagaaca attacaagac aacccccccca  1260
gtgctggata gtgacgggtc tttctttctg tacagtaagc tgactgtgga caagtcccgc  1320
tggcagcagg gtaacgtctt cagctgttcc gtgatgcacg aggcattgca caaccactac  1380
acccagaagt cactgagcct gagcccaggg aag                               1413

SEQ ID NO: 188          moltype = AA  length = 471
FEATURE                 Location/Qualifiers
REGION                  1..471
                        note = Description of Artificial Sequence:
                         Syntheticpolypeptide
```

```
source                  1..471
                        mol_type = protein
                        organism = synthetic construct
SEQUENCE: 188
MDMRVPAQLL GLLLLWLRGA RCQVQLVESG GGLVKPGGSL RLSCAASGFT FSDYAMSWIR  60
QAPGKGLEWV STISDGGTYT YYPDNVKGRF TISRDNAKNS LYLQMNSLRA EDTAVYYCAR  120
EWGDYDGFDY WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 189          moltype = DNA  length = 1413
FEATURE                 Location/Qualifiers
misc_feature            1..1413
                        note = Description of Artificial Sequence:
                         Syntheticpolynucleotide
source                  1..1413
                        mol_type = other DNA
                        organism = synthetic construct
SEQUENCE: 189
atggacatga gagttcctgc tcagctgctc gggttgctgt tgctttggct ccggggtgct  60
aggtgccaag ttcagctggt ggaatctggc ggtgggcttg taaagccagg aggctccctc  120
agactgagtt gtgccgcttc agggttcaca ttctccgact atgcgatgtc atggatcagg  180
caagcacccg ggaaaggact ggagtgggtt agcactatca gcgatggcgg aacgtatacc  240
tattaccctg actccgtgaa gggtcggttc accatttcca gggataacgc aaagaacagt  300
ctctaccttc agatgaacag cctgagggct gaggacaccg ccgtctacta ctgcgcccga  360
gaatggggag attatgatgg gtttgactat tggggccagg gcactttggt gacagtcagt  420
tctgcctcaa caaaaggacc aagtgtgttc ccactcgccc ctagcagcaa gagtacatcc  480
gggggcactg cagcactcgg ctgcctcgtc aaggattatt ttccagagcc agtaaccgtg  540
agctggaaca gtggagcact cacttctggt gtccatactt ttcctgctgt cctgcaaagc  600
tctggcctgt actcactcag ctccgtcgtg accgtgccat cttcatctct gggcactcag  660
acctacatct gtaatgtaaa ccacaagcct agcaatacta aggtcgataa gcgggtggaa  720
cccaagagct gcgacaagac tcacacttgt cccccatgcc ctgcccctga acttctgggc  780
ggtcccagcg tctttttgtt cccaccaaag cctaaagata ctctgatgat aagtagaaca  840
cccgaggtga catgtgttgt tgtagacgtt tcccacgagg acccagaggt taagttcaac  900
tggtacgttg atggagtcga agtacataat gctaagacca agcctagaga ggagcagtat  960
aatagtacat accgtgtagt cagtgttctc acagtgctgc accaagactg gctcaacggc  1020
aaagaataca aatgcaaagt gtccaacaaa gcactcccag cccctatcga gaagactatt  1080
agtaaggcaa aggggcagcc tcgtgaacca caggtgtaca ctctgccacc cagtagagag  1140
gaaatgacaa agaaccaagt ctcattgacc tgcctggtga aaggcttcta ccccagcgac  1200
atcgccgttg agtgggagag taacggtcag cctgagaaca attacaagac aaccccccca  1260
gtgctggata gtgacgggtc tttctttctg tacagtaagc tgactgtgga caagtcccgc  1320
tggcagcagg gtaacgtctt cagctgttcc gtgatgcacg aggcattgca caaccactac  1380
acccagaagt cactgagcct gagcccaggg aag                               1413

SEQ ID NO: 190          moltype = AA  length = 471
FEATURE                 Location/Qualifiers
REGION                  1..471
                        note = Description of Artificial Sequence:
                         Syntheticpolypeptide
source                  1..471
                        mol_type = protein
                        organism = synthetic construct
SEQUENCE: 190
MDMRVPAQLL GLLLLWLRGA RCQVQLVESG GGLVKPGGSL RLSCAASGFT FSDYAMSWIR  60
QAPGKGLEWV STISDGGTYT YYPDSVKGRF TISRDNAKNS LYLQMNSLRA EDTAVYYCAR  120
EWGDYDGFDY WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 191          moltype = DNA  length = 1401
FEATURE                 Location/Qualifiers
misc_feature            1..1401
                        note = Description of Artificial Sequence:
                         Syntheticpolynucleotide
source                  1..1401
                        mol_type = other DNA
                        organism = synthetic construct
SEQUENCE: 191
atggacatga gagttcctgc tcagctgctc gggttgctgt tgctttggct ccggggtgct  60
aggtgccaag ttcagctggt ggaatctggc ggtgggcttg taaagccagg aggctccctc  120
agactgagtt gtgccgcttc agggttcaca ttctccgact atgcgatgtc atggatcagg  180
caagcacccg ggaaaggact ggagtgggtt agcactatca gcgatggcgg aacgtatacc  240
tattaccctg actccgtgaa gggtcggttc accatttcca gggataacgc aaagaacagt  300
```

```
ctctaccttc agatgaacag cctgagggct gaggacaccg ccgtctacta ctgcgcccga  360
gaatggggag attatgatgg gtttgactat tggggccagg gcactttggt gacagtcagt  420
tctgcctcca ccaagggccc atcggtcttc cccctggcgc cctgctccag gagcacctcc  480
gagagcacag cggccctggg ctgcctggtc aaggactact tccccgaacc ggtgacggtg  540
tcgtggaact caggcgctct gaccagcggc gtgcacacct tcccagctgt cctacagtcc  600
tcaggactct actccctcag cagcgtggtg accgtgccct ccagcaactt cggcacccag  660
acctacacct gcaacgtaga tcacaagccc agcaacacca aggtggacaa gacagttgag  720
cgcaaatgtt gtgtcgagtg cccaccgtgc ccagcaccac ctgtggcagg accgtcagtc  780
ttcctcttcc ccccaaaacc caaggacacc ctcatgatct cccggacccc tgaggtcacg  840
tgcgtggtgg tggacgtgag ccacgaagac cccgaggtcc agttcaactg gtacgtggac  900
ggcgtggagg tgcataatgc caagacaaag ccacgggagg agcagttcaa cagcacgttc  960
cgtgtggtca gcgtcctcac cgttgtgcac caggactggc tgaacggcaa ggagtacaag  1020
tgcaaggtct ccaacaaagg cctcccagcc cccatcgaga aaaccatctc caaaaccaaa  1080
gggcagcccc gagaaccaca ggtgtacacc ctgcccccat cccgggagga gatgaccaag  1140
aaccaggtca gcctgacctg cctggtcaaa ggcttctacc ccagcgacat cgccgtggag  1200
tgggagagca atgggcagcc ggagaacaac tacaagacca cacctcccat gctggactcc  1260
gacggctcct tcttcctcta cagcaagctc accgtggaca agagcaggtg gcagcagggg  1320
aacgtcttct catgctccgt gatgcatgag gctctgcaca accactacac gcagaagagc  1380
ctctccctgt ctccgggtaa a                                           1401

SEQ ID NO: 192         moltype = AA  length = 467
FEATURE                Location/Qualifiers
REGION                 1..467
                       note = Description of Artificial Sequence:
                        Syntheticpolypeptide
source                 1..467
                       mol_type = protein
                       organism = synthetic construct
SEQUENCE: 192
MDMRVPAQLL GLLLLWLRGA RCQVQLVESG GGLVKPGGSL RLSCAASGFT FSDYAMSWIR  60
QAPGKGLEWV STISDGGTYT YYPDSVKGRF TISRDNAKNS LYLQMNSLRA EDTAVYYCAR  120
EWGDYDGFDY WGQGTLVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTVE  240
RKCCVECPPC PAPPVAGPSV FLFPPKPKDT LMISRTPEVT CVVVDVSHED PEVQFNWYVD  300
GVEVHNAKTK PREEQFNSTF RVVSVLTVVH QDWLNGKEYK CKVSNKGLPA PIEKTISKTK  360
GQPREPQVYT LPPSREEMTK NQVSLTCLVK GFYPSDIAVE WESNGQPENN YKTTPPMLDS  420
DGSFFLYSKL TVDKSRWQQG NVFSCSVMHE ALHNHYTQKS LSLSPGK                467

SEQ ID NO: 193         moltype = DNA  length = 1413
FEATURE                Location/Qualifiers
misc_feature           1..1413
                       note = Description of Artificial Sequence:
                        Syntheticpolynucleotide
source                 1..1413
                       mol_type = other DNA
                       organism = synthetic construct
SEQUENCE: 193
atggacatga gagttcctgc tcagctgctc gggttgctgt tgctttggct ccggggtgct  60
aggtgcgagg ttcagctggt ggaatctggc ggtgggcttg taaagccagg aggctccctc  120
agactgagtt gtgccgcttc agggttcaca ttctccgact atgcgatgtc atgggtgcgc  180
caagcacccg ggaaaggact ggagtgggtt agcactatca gcgatggcgg aacgtatacc  240
tattaccctg acaatgtgaa gggtcggttc accatttcca gggataacgc aaagaacagt  300
ctctatttgc agatgaacag cctgagggct gaggacaccg ccgtctacta ctgcgcccga  360
gaatggggag attatgatgg gtttgactat tggggccagg gcactttggt gacagtcagt  420
tctgcctcaa caaaaggacc aagtgtgttc ccactcgccc ctagcagcaa gagtacatcc  480
gggggcactg cagcactcgg ctgcctcgtc aaggattatt ttccagagcc agtaaccgtg  540
agctggaaca gtggagcact cacttctggt gtccatactt ttcctgctgt cctgcaaagc  600
tctggcctgt actcactcag ctccgtcgtg accgtgccat cttcatctct gggcactcag  660
acctacatct gtaatgtaaa ccacaagcct agcaatacta aggtcgataa gcgggtggaa  720
cccaagagct gcgacaagac tcacacttgt cccccatgcc ctgcccctga acttctgggc  780
ggtcccagcg tctttttgtt cccaccaaag cctaaagata ctctgatgat aagtagaaca  840
cccgaggtga catgtgttgt tgtagacgtt tcccacgagg acccagaggt taagttcaac  900
tggtacgttg atggagtcga agtacataat gctaagacca agcctagaga ggagcagtat  960
aatagtacat accgtgtagt cagtgttctc acagtgctgc accaagactg gctcaacggc  1020
aaagaataca aatgcaaagt gtccaacaaa gcactcccag cccctatcga gaagactatt  1080
agtaaggcaa aggggcagcc tcgtgaacca caggtgtaca ctctgccacc cagtagagag  1140
gaaatgacaa agaaccaagt ctcattgacc tgcctggtga aaggcttcta ccccagcgac  1200
atcgccgttg agtgggagag taacggtcag cctgagaaca attacaagac aacccccccca  1260
gtgctggata gtgacgggtc tttctttctg tacagtaagc tgactgtgga caagtcccgc  1320
tggcagcagg gtaacgtctt cagctgttcc gtgatgcacg aggcattgca caaccactac  1380
acccagaagt cactgagcct gagcccaggg aag                              1413

SEQ ID NO: 194         moltype = AA  length = 471
FEATURE                Location/Qualifiers
REGION                 1..471
                       note = Description of Artificial Sequence:
                        Syntheticpolypeptide
source                 1..471
                       mol_type = protein
```

```
                         organism = synthetic construct
SEQUENCE: 194
MDMRVPAQLL GLLLLWLRGA RCEVQLVESG GGLVKPGGSL RLSCAASGFT FSDYAMSWVR  60
QAPGKGLEWV STISDGGTYT YYPDNVKGRF TISRDNAKNS LYLQMNSLRA EDTAVYYCAR  120
EWGDYDGFDY WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 195           moltype = DNA  length = 1413
FEATURE                  Location/Qualifiers
misc_feature             1..1413
                         note = Description of Artificial Sequence:
                          Syntheticpolynucleotide
source                   1..1413
                         mol_type = other DNA
                         organism = synthetic construct
SEQUENCE: 195
atggacatga gagttcctgc tcagctgctc gggttgctgt tgctttggct ccggggtgct  60
aggtgcgagg ttcagcttct ggaatctggc ggtgggcttg tacagccagg aggctccctc  120
agactgagtt gtgccgcttc agggttcaca ttctccgact atgcgatgtc atgggtgcgc  180
caagcacccg ggaaaggact ggagtgggtt tcaactatca gcgatggcgg aacgtatacc  240
tattaccctg acaatgtgaa gggtcggttc accatttcca gggataacag caagaacaca  300
ctctatctcc agatgaacag cctgagggct gaggacaccg ccgtctacta ctgcgcccga  360
gaatggggag attatgatgg gtttgactat tggggccagg gcactttggt gacagtcagt  420
tctgcctcaa caaaaggacc aagtgtgttc ccactcgccc ctagcagcaa gagtacatcc  480
gggggcactg cagcactcgg ctgcctcgtc aaggattatt ttccagagcc agtaaccgtg  540
agctggaaca gtggagcact cacttctggt gtccatactt ttcctgctgt cctgcaaagc  600
tctggcctgt actcactcag ctccgtcgtg accgtgccat cttcatctct gggcactcag  660
acctacatct gtaatgtaaa ccacaagcct agcaatacta aggtcgataa gcgggtggaa  720
cccaagagct gcgacaagac tcacacttgt cccccatgcc ctgcccctga acttctgggc  780
ggtcccagcg tctttttgtt cccaccaaag cctaaagata ctctgatgat aagtagaaca  840
cccgaggtga catgtgttgt tgtagacgtt tcccacgagg acccagaggt taagttcaac  900
tggtacgttg atggagtcga agtacataat gctaagacca agcctagaga ggagcagtat  960
aatagtacat accgtgtagt cagtgttctc acagtgctgc accaagactg gctcaacggc  1020
aaagaataca aatgcaaagt gtccaacaaa gcactcccag cccctatcga gaagactatt  1080
agtaaggcaa aggggcagcc tcgtgaacca caggtgtaca ctctgccacc cagtagagag  1140
gaaatgacaa agaaccaagt ctcattgacc tgcctggtga aaggcttcta ccccagcgac  1200
atcgccgttg agtgggagag taacggtcag cctgagaaca attacaagac aacccccccca  1260
gtgctggata gtgacgggtc tttctttctg tacagtaagc tgactgtgga caagtcccgc  1320
tggcagcagg gtaacgtctt cagctgttcc gtgatgcacg aggcattgca caaccactac  1380
acccagaagt cactgagcct gagcccaggg aag                               1413

SEQ ID NO: 196           moltype = AA  length = 471
FEATURE                  Location/Qualifiers
REGION                   1..471
                         note = Description of Artificial Sequence:
                          Syntheticpolypeptide
source                   1..471
                         mol_type = protein
                         organism = synthetic construct
SEQUENCE: 196
MDMRVPAQLL GLLLLWLRGA RCEVQLLESG GGLVQPGGSL RLSCAASGFT FSDYAMSWVR  60
QAPGKGLEWV STISDGGTYT YYPDNVKGRF TISRDNSKNT LYLQMNSLRA EDTAVYYCAR  120
EWGDYDGFDY WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 197           moltype = DNA  length = 1413
FEATURE                  Location/Qualifiers
misc_feature             1..1413
                         note = Description of Artificial Sequence:
                          Syntheticpolynucleotide
source                   1..1413
                         mol_type = other DNA
                         organism = synthetic construct
SEQUENCE: 197
atggacatga gagttcctgc tcagctgctc gggttgctgt tgctttggct ccggggtgct  60
aggtgccagg ttcagctggt ggaatctggc ggtggggtag tacaaccagg acggtccctc  120
agactgagtt gtgccgcttc agggttcaca ttctccgact atgcgatgtc atgggtgcgc  180
caagcacccg ggaaaggact ggagtgggtt gccactatca gcgatggcgg aacgtatacc  240
tattaccctg acaatgtgaa gggtcggttc accatttcca gggataactc aaagaacacc  300
ctctatctcc aaatgagtag cctgagggct gaggacaccg ccgtctacta ctgcgcccga  360
gaatggggag attatgatgg gtttgactat tggggccagg gcactttggt gacagtcagt  420
```

```
tctgcctcaa caaaaggacc aagtgtgttc ccactcgccc ctagcagcaa gagtacatcc  480
gggggcactg cagcactcgg ctgcctcgtc aaggattatt ttccagagcc agtaaccgtg  540
agctggaaca gtggagcact cacttctggt gtccatactt ttcctgctgt cctgcaaagc  600
tctggcctgt actcactcag ctccgtcgtg accgtgccat cttcatctct gggcactcag  660
acctacatct gtaatgtaaa ccacaagcct agcaatacta aggtcgataa gcgggtggaa  720
cccaagagct gcgacaagac tcacacttgt cccccatgcc ctgcccctga acttctgggc  780
ggtcccagcg tctttttgtt cccaccaaag cctaaagata ctctgatgat aagtagaaca  840
cccgaggtga catgtgttgt tgtagacgtt tcccacgagg acccagaggt taagttcaac  900
tggtacgttg atggagtcga agtacataat gctaagacca agcctagaga ggagcagtat  960
aatagtacat accgtgtagt cagtgttctc acagtgctgc accaagactg gctcaacggc  1020
aaagaataca aatgcaaagt gtccaacaaa gcactcccag cccctatcga gaagactatt  1080
agtaaggcaa aggggcagcc tcgtgaacca caggtgtaca ctctgccacc cagtagagag  1140
gaaatgacaa agaaccaagt ctcattgacc tgcctggtga aaggcttcta ccccagcgac  1200
atcgccgttg agtgggagag taacggtcag cctgagaaca attacaagac aacccccca  1260
gtgctggata gtgacgggtc tttctttctg tacagtaagc tgactgtgga caagtcccgc  1320
tggcagcagg gtaacgtctt cagctgttcc gtgatgcacg aggcattgca caaccactac  1380
acccagaagt cactgagcct gagcccaggg aag                              1413
```

```
SEQ ID NO: 198         moltype = AA  length = 471
FEATURE                Location/Qualifiers
REGION                 1..471
                       note = Description of Artificial Sequence:
                        Syntheticpolypeptide
source                 1..471
                       mol_type = protein
                       organism = synthetic construct
SEQUENCE: 198
MDMRVPAQLL GLLLLWLRGA RCQVQLVESG GGVVQPGRSL RLSCAASGFT FSDYAMSWVR  60
QAPGKGLEWV ATISDGGTYT YYPDNVKGRF TISRDNSKNT LYLQMSSLRA EDTAVYYCAR  120
EWGDYDGFDY WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471
```

```
SEQ ID NO: 199         moltype = DNA  length = 1413
FEATURE                Location/Qualifiers
misc_feature           1..1413
                       note = Description of Artificial Sequence:
                        Syntheticpolynucleotide
source                 1..1413
                       mol_type = other DNA
                       organism = synthetic construct
SEQUENCE: 199
atggacatga gagttcctgc tcagctgctc gggttgctgt tgctttggct ccggggtgct  60
aggtgcgagg ttcagctggt ggaatctggc ggtgggcttg taaagccagg aggctccctc  120
agactgagtt gtgccgcttc agggttcaca ttctccgact atgcgatgtc atgggtgcgc  180
caagcacccg ggaaaggact ggagtgggtt gccactatca gcgatggcgg aacgtatacc  240
tattaccctg acaatgtgaa gggtcggttc accatttcca gggataacgc aaagaacagt  300
ctctaccttc agatgaacag cctgagggct gaggacaccg ccgtctacta ctgcgcccga  360
gaatggggag attatgatgg gtttgactat tggggccagg gcactttggt gacagtcagt  420
tctgcctcaa caaaaggacc aagtgtgttc ccactcgccc ctagcagcaa gagtacatcc  480
gggggcactg cagcactcgg ctgcctcgtc aaggattatt ttccagagcc agtaaccgtg  540
agctggaaca gtggagcact cacttctggt gtccatactt ttcctgctgt cctgcaaagc  600
tctggcctgt actcactcag ctccgtcgtg accgtgccat cttcatctct gggcactcag  660
acctacatct gtaatgtaaa ccacaagcct agcaatacta aggtcgataa gcgggtggaa  720
cccaagagct gcgacaagac tcacacttgt cccccatgcc ctgcccctga acttctgggc  780
ggtcccagcg tctttttgtt cccaccaaag cctaaagata ctctgatgat aagtagaaca  840
cccgaggtga catgtgttgt tgtagacgtt tcccacgagg acccagaggt taagttcaac  900
tggtacgttg atggagtcga agtacataat gctaagacca agcctagaga ggagcagtat  960
aatagtacat accgtgtagt cagtgttctc acagtgctgc accaagactg gctcaacggc  1020
aaagaataca aatgcaaagt gtccaacaaa gcactcccag cccctatcga gaagactatt  1080
agtaaggcaa aggggcagcc tcgtgaacca caggtgtaca ctctgccacc cagtagagag  1140
gaaatgacaa agaaccaagt ctcattgacc tgcctggtga aaggcttcta ccccagcgac  1200
atcgccgttg agtgggagag taacggtcag cctgagaaca attacaagac aacccccca  1260
gtgctggata gtgacgggtc tttctttctg tacagtaagc tgactgtgga caagtcccgc  1320
tggcagcagg gtaacgtctt cagctgttcc gtgatgcacg aggcattgca caaccactac  1380
acccagaagt cactgagcct gagcccaggg aag                              1413
```

```
SEQ ID NO: 200         moltype = AA  length = 471
FEATURE                Location/Qualifiers
REGION                 1..471
                       note = Description of Artificial Sequence:
                        Syntheticpolypeptide
source                 1..471
                       mol_type = protein
                       organism = synthetic construct
SEQUENCE: 200
```

```
MDMRVPAQLL GLLLLWLRGA RCEVQLVESG GGLVKPGGSL RLSCAASGFT FSDYAMSWVR  60
QAPGKGLEWV ATISDGGTYT YYPDNVKGRF TISRDNAKNS LYLQMNSLRA EDTAVYYCAR  120
EWGDYDGFDY WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 201         moltype = DNA  length = 708
FEATURE                Location/Qualifiers
misc_feature           1..708
                       note = Description of Artificial Sequence:
                        Syntheticpolynucleotide
source                 1..708
                       mol_type = other DNA
                       organism = synthetic construct
SEQUENCE: 201
atggacatga gggtgcccgc tcaactgctg ggctgctgc tgctgtggct gagaggagct  60
cgttgcgata ttcagttgac ccaatcacct agcttcctct cagcttccgt gggcgacaga  120
gttaccataa cctgtcgggc aagccaggag atttctgggt acctgtcctg gtaccaacag  180
aagcccggaa aagcccctaa gctgttgatc tatgctgcgt caaccttgga tagcggtgtc  240
ccgagtcgat tctccggttc tggctccgga acagagttca ctctgacaat ttctagcctt  300
cagccagaag atttcgccac gtactattgc ctccagtacg acagctatcc ctatacattt  360
gggcagggca ctaaactgga gatcaaacgc acagttgctg cccccagcgt gttcattttc  420
ccacctagcg atgagcagct gaaaagcggt actgcctctg tcgtatgctt gctcaacaac  480
ttttacccac gtgaggctaa ggtgcagtgg aaagtggata atgcacttca atctggaaac  540
agtcaagagt ccgtgacaga acaggacagc aaagactcaa cttattcact ctcttccacc  600
ctgactctgt ccaaggcaga ctatgaaaaa cacaaggtat acgcctgcga ggttacacac  660
cagggtttgt ctagtcctgt caccaagtcc ttcaataggg gcgaatgt              708

SEQ ID NO: 202         moltype = AA  length = 236
FEATURE                Location/Qualifiers
REGION                 1..236
                       note = Description of Artificial Sequence:
                        Syntheticpolypeptide
source                 1..236
                       mol_type = protein
                       organism = synthetic construct
SEQUENCE: 202
MDMRVPAQLL GLLLLWLRGA RCDIQLTQSP SFLSASVGDR VTITCRASQE ISGYLSWYQQ  60
KPGKAPKLLI YAASTLDSGV PSRFSGSGSG TEFTLTISSL QPEDFATYYC LQYDSYPYTF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 203         moltype = DNA  length = 708
FEATURE                Location/Qualifiers
misc_feature           1..708
                       note = Description of Artificial Sequence:
                        Syntheticpolynucleotide
source                 1..708
                       mol_type = other DNA
                       organism = synthetic construct
SEQUENCE: 203
atggacatga gggtgcccgc tcaactgctg ggctgctgc tgctgtggct gagaggagct  60
cgttgcgata ttcagatgac ccaatcacct agcagtctct cagcttccgt gggcgacaga  120
gttaccataa cctgtcgggc aagccaggag atttctgggt acctgtcctg gtttcaacag  180
aagcccggaa aggccccgaa gagcttgatc tatgctgcgt caaccttgga tagcggtgtc  240
ccgagtcgat tctccggttc tggctccgga accgacttta ctctgacaat ttctagcctt  300
cagccagaag atttcgccac gtactattgc ctccagtacg acagctatcc ctatacattt  360
gggcagggca ctaaactgga gatcaaacgc acagttgctg cccccagcgt gttcattttc  420
ccacctagcg atgagcagct gaaaagcggt actgcctctg tcgtatgctt gctcaacaac  480
ttttacccac gtgaggctaa ggtgcagtgg aaagtggata atgcacttca atctggaaac  540
agtcaagagt ccgtgacaga acaggacagc aaagactcaa cttattcact ctcttccacc  600
ctgactctgt ccaaggcaga ctatgaaaaa cacaaggtat acgcctgcga ggttacacac  660
cagggtttgt ctagtcctgt caccaagtcc ttcaataggg gcgaatgt              708

SEQ ID NO: 204         moltype = AA  length = 236
FEATURE                Location/Qualifiers
REGION                 1..236
                       note = Description of Artificial Sequence:
                        Syntheticpolypeptide
source                 1..236
                       mol_type = protein
                       organism = synthetic construct
SEQUENCE: 204
MDMRVPAQLL GLLLLWLRGA RCDIQMTQSP SSLSASVGDR VTITCRASQE ISGYLSWFQQ  60
KPGKAPKSLI YAASTLDSGV PSRFSGSGSG TDFTLTISSL QPEDFATYYC LQYDSYPYTF  120
GQGTKLEIKR TVAAPSVFIF PPSDEQLKSG TASVVCLLNN FYPREAKVQW KVDNALQSGN  180
```

```
SQESVTEQDS KDSTYSLSST LTLSKADYEK HKVYACEVTH QGLSSPVTKS FNRGEC      236

SEQ ID NO: 205         moltype = DNA  length = 708
FEATURE                Location/Qualifiers
misc_feature           1..708
                       note = Description of Artificial Sequence:
                        Syntheticpolynucleotide
source                 1..708
                       mol_type = other DNA
                       organism = synthetic construct
SEQUENCE: 205
atggacatga gggtgcccgc tcaactgctg gggctgctgc tgctgtggct gagaggagct  60
cgttgcgata ttcagatgac ccaatcacct agcagtctct cagcttccgt gggcgacaga  120
gttaccataa cctgtcgggc aagccaggag atttctgggt acctgtcctg gtatcaacag  180
aagcccggaa aagccccaaa gaggttgatc tatgctgcgt caaccttgga tagcggtgtc  240
ccgagtcgat tctccggttc tggctccgga accgagttca ctctgacaat ttctagcctt  300
cagccagaag atttcgccac gtactattgc ctccagtacg acagctatcc ctatacattt  360
gggcagggca ctaaactgga gatcaaacgc acagttgctg cccccagcgt gttcattttc  420
ccacctagcg atgagcagct gaaaagcggt actgcctctg tcgtatgctt gctcaacaac  480
ttttacccac gtgaggctaa ggtgcagtgg aaagtggata atgcacttca atctggaaac  540
agtcaagagt ccgtgacaga acaggacagc aaagactcaa cttattcact ctcttccacc  600
ctgactctgt ccaaggcaga ctatgaaaaa cacaaggtat acgcctgcga ggttacacac  660
cagggtttgt ctagtcctgt caccaagtcc ttcaataggg gcgaatgt               708

SEQ ID NO: 206         moltype = AA  length = 236
FEATURE                Location/Qualifiers
REGION                 1..236
                       note = Description of Artificial Sequence:
                        Syntheticpolypeptide
source                 1..236
                       mol_type = protein
                       organism = synthetic construct
SEQUENCE: 206
MDMRVPAQLL GLLLLWLRGA RCDIQMTQSP SSLSASVGDR VTITCRASQE ISGYLSWYQQ  60
KPGKAPKRLI YAASTLDSGV PSRFSGSGSG TEFTLTISSL QPEDFATYYC LQYDSYPYTF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 207         moltype = DNA  length = 708
FEATURE                Location/Qualifiers
misc_feature           1..708
                       note = Description of Artificial Sequence:
                        Syntheticpolynucleotide
source                 1..708
                       mol_type = other DNA
                       organism = synthetic construct
SEQUENCE: 207
atggacatga gggtgcccgc tcaactgctg gggctgctgc tgctgtggct gagaggagct  60
cgttgcgata ttcagatgac ccaatcacct agcagtctct cagcttccgt gggcgacaga  120
gttaccataa cctgtcgggc aagccaggag atttctgggt acctgtcctg gtaccaacag  180
aagcccggaa aggcccccaa gctgttgatc tatgctgcgt caaccttgga tagcggtgtc  240
ccgagtcgat tctccggttc tggctccgga acagacttta cttttacaat ttctagcctt  300
cagccagagg acatcgccac gtactattgc ctccagtacg acagctatcc ctatacattt  360
gggcagggca ctaaactgga gatcaaacgc acagttgctg cccccagcgt gttcattttc  420
ccacctagcg atgagcagct gaaaagcggt actgcctctg tcgtatgctt gctcaacaac  480
ttttacccac gtgaggctaa ggtgcagtgg aaagtggata atgcacttca atctggaaac  540
agtcaagagt ccgtgacaga acaggacagc aaagactcaa cttattcact ctcttccacc  600
ctgactctgt ccaaggcaga ctatgaaaaa cacaaggtat acgcctgcga ggttacacac  660
cagggtttgt ctagtcctgt caccaagtcc ttcaataggg gcgaatgt               708

SEQ ID NO: 208         moltype = AA  length = 236
FEATURE                Location/Qualifiers
REGION                 1..236
                       note = Description of Artificial Sequence:
                        Syntheticpolypeptide
source                 1..236
                       mol_type = protein
                       organism = synthetic construct
SEQUENCE: 208
MDMRVPAQLL GLLLLWLRGA RCDIQMTQSP SSLSASVGDR VTITCRASQE ISGYLSWYQQ  60
KPGKAPKLLI YAASTLDSGV PSRFSGSGSG TDFTFTISSL QPEDIATYYC LQYDSYPYTF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 209         moltype = DNA  length = 708
FEATURE                Location/Qualifiers
misc_feature           1..708
                       note = Description of Artificial Sequence:
                        Syntheticpolynucleotide
```

```
source                  1..708
                        mol_type = other DNA
                        organism = synthetic construct
SEQUENCE: 209
atggacatga gggtgcccgc tcaactgctg gggctgctgc tgctgtggct gagaggagct  60
cgttgcgata ttcagatgac ccaatcacct agcagtctct cagcttccgt gggcgacaga  120
gttaccataa cctgtcgggc aagccaggag atttctgggt acctgtcctg gtatcaacag  180
aagcccggaa aagcccctaa gctgttgatc tatgctgcgt caaccttgga tagcggtgtc  240
ccgagtcgat tctccggttc tggctccgga actgacttca ctctgacaat ttctagcctt  300
cagccagaag atttcgccac gtactattgc ctccagtacg acagctatcc ctatacattt  360
gggcagggca ctaaactgga gatcaaacgc acagttgctg cccccagcgt gttcattttc  420
ccacctagcg atgagcagct gaaaagcggt actgcctctg tcgtatgctt gctcaacaac  480
ttttacccac gtgaggctaa ggtgcagtgg aaagtggata atgcacttca atctggaaac  540
agtcaagagt ccgtgacaga acaggacagc aaagactcaa cttattcact ctcttccacc  600
ctgactctgt ccaaggcaga ctatgaaaaa cacaaggtat acgcctgcga ggttacacac  660
cagggtttgt ctagtcctgt caccaagtcc ttcaataggg gcgaatgt               708

SEQ ID NO: 210          moltype = AA  length = 236
FEATURE                 Location/Qualifiers
REGION                  1..236
                        note = Description of Artificial Sequence:
                         Syntheticpolypeptide
source                  1..236
                        mol_type = protein
                        organism = synthetic construct
SEQUENCE: 210
MDMRVPAQLL GLLLLWLRGA RCDIQMTQSP SSLSASVGDR VTITCRASQE ISGYLSWYQQ  60
KPGKAPKLLI YAASTLDSGV PSRFSGSGSG TDFTLTISSL QPEDFATYYC LQYDSYPYTF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 211          moltype = DNA  length = 708
FEATURE                 Location/Qualifiers
misc_feature            1..708
                        note = Description of Artificial Sequence:
                         Syntheticpolynucleotide
source                  1..708
                        mol_type = other DNA
                        organism = synthetic construct
SEQUENCE: 211
atggacatga gggtgcccgc tcaactgctg gggctgctgc tgctgtggct gagaggagct  60
cgttgcgata ttcagatgac ccaatcacct agcagtctct cagcttccgt gggcgacaga  120
gttaccataa cctgtcgggc aagccaggag atttctgggt acctgtcctg gctgcaacag  180
aagcccggag gcgccatcaa gaggttgatc tatgctgcgt caaccttgga tagcggtgtc  240
ccgagtcgat tctccggttc tggctccgga agtgactaca ctctgacaat ttctagcctt  300
cagccagaag atttcgccac gtactattgc ctccagtacg acagctatcc ctatacattt  360
gggcagggca ctaaactgga gatcaaacgc acagttgctg cccccagcgt gttcattttc  420
ccacctagcg atgagcagct gaaaagcggt actgcctctg tcgtatgctt gctcaacaac  480
ttttacccac gtgaggctaa ggtgcagtgg aaagtggata atgcacttca atctggaaac  540
agtcaagagt ccgtgacaga acaggacagc aaagactcaa cttattcact ctcttccacc  600
ctgactctgt ccaaggcaga ctatgaaaaa cacaaggtat acgcctgcga ggttacacac  660
cagggtttgt ctagtcctgt caccaagtcc ttcaataggg gcgaatgt               708

SEQ ID NO: 212          moltype = AA  length = 236
FEATURE                 Location/Qualifiers
REGION                  1..236
                        note = Description of Artificial Sequence:
                         Syntheticpolypeptide
source                  1..236
                        mol_type = protein
                        organism = synthetic construct
SEQUENCE: 212
MDMRVPAQLL GLLLLWLRGA RCDIQMTQSP SSLSASVGDR VTITCRASQE ISGYLSWLQQ  60
KPGGAIKRLI YAASTLDSGV PSRFSGSGSG SDYTLTISSL QPEDFATYYC LQYDSYPYTF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236
```

ANTI-ERBB3 ANTIBODIES

CROSS-REFERENCE TO RELATED APPLICATIONS

This application is a divisional of U.S. patent application Ser. No. 16/667,056, filed Oct. 29, 2019, now U.S. Pat. No. 11,680,108, which is a continuation of U.S. patent application Ser. No. 15/448,164, filed Mar. 2, 2017, now U.S. Pat. No. 10,494,441, which is a divisional of U.S. patent application Ser. No. 14/987,374, filed Jan. 4, 2016, now U.S. Pat. No. 9,598,498, which is a divisional of U.S. patent application Ser. No. 13/919,582, filed Jun. 17, 2013, now U.S. Pat. No. 9,228,021, which is a divisional of U.S. patent application Ser. No. 13/082,852 filed Apr. 8, 2011, now U.S. Pat. No. 8,481,687, which claims priority to and the benefit of U.S. Provisional Patent Application No. 61/322,712, filed Apr. 9, 2010; the entire contents of each of which is incorporated herein by reference.

SEQUENCE LISTING

The instant application contains a Sequence Listing which has been submitted electronically in XML format and is hereby incorporated by reference in its entirety. Said XML file, created Apr. 26, 2023, is named AVO-009USD4_SL.xml and is 334,239 bytes in size.

FIELD OF THE INVENTION

The field of the invention is molecular biology, immunology and oncology. More particularly, the field is humanized antibodies that bind human ErbB3/HER3.

BACKGROUND

HER3/c-ErbB3 (referred to herein as ErbB3) is a member of the epidermal growth factor receptor (EGFR) family. ErbB3 binds neuregulin/heregulin (NRG/HRG). Receptors in the EGFR family are single transmembrane receptors with an intracellular tyrosine kinase domain. While the other EGFR family members, i.e., EGFR/HER1/ErbB1, HER2/ErbB2, and HER4/ErbB4, each have tyrosine kinase activity, ErbB3 has little or no tyrosine kinase activity, and thus is "kinase-dead."

The extracellular domain (ECD) of the EGFR family contains four domains. Domains 1 and 3 (also known as domains L1 and L2) are responsible for ligand binding. Cysteine-rich domains 2 and 4 (also known as domains C1 and C2) are involved in dimerization with receptor partners. Upon ligand binding, the ECD undergoes conformational changes. The interaction of domains 2 and 4, which maintains the tethered (inactive) conformation of the receptor, is relieved, and an extended (active) conformation is adopted. The extended conformation favors dimerization with other receptor partners. HER2/ErbB2 is the only exception to this general rule, i.e., Her2-ECD is constitutively in the extended conformation. No ligand for HER2 has been identified thus far.

Because ErbB3 lacks an intrinsic kinase activity, it must dimerize with another active tyrosine kinase receptor to be activated by tyrosine phosphorylation. Dimerization can occur between two different receptors (heterodimerization), e.g., ErbB3 and EGFR/HER1/ErbB1, HER2/ErbB2, or HER4/ErbB4. Recently, ErbB3 was also shown to dimerize with MET. Upon association with another tyrosine kinase receptor, ErbB3 is activated by phosphorylation of at least nine tyrosine residues in the ErbB3 intracellular domain, and then rapidly associates with adaptors or downstream signaling molecules. Six of the ErbB3 phosphorylated tyrosine residues associate directly with the p85 subunit of Phosphatidylinositol 3-Kinase (PIK3), which results in activation of the cellular survival pathway controlled by the PI3K/Akt axis. Constitutive activation of ErbB3 by unregulated dimerization and/or unregulated phosphorylation of ErbB3 can lead to certain cancers.

Overexpression of ErbB3 is associated with poor prognosis in various carcinomas (e.g., breast, ovarian, prostate, colorectal, pancreatic, gastric, and head and neck cancers). Overexpression of ErbB3 also correlates with local to distal metastasis in lung, gastric, and colorectal cancers, and bone invasion in prostate cancer (Sithanandam et al., 2008, Cancer Gene Therapy 15:413). Overexpression of ErbB3 has been linked to resistance to several cancer treatments, including treatment with EGFR tyrosine kinase inhibitors in non-small cell lung cancer (NSCLC) and head and neck cancers, treatment with Her2 inhibitor in breast cancers, and treatment with radiotherapy in pancreatic cancers. Moreover, overexpression of NRG, a ligand for ErbB3, was also linked to resistance to EGFR tyrosine kinase inhibitor treatment. Chen et al. describe the use of anti-ErbB3 monoclonal antibodies that inhibit NRG function and show growth inhibitory activity against breast and ovarian cancer cells (Chen et al., 1996, J. Biol. Chem. 271: 7620).

There is a need for improved anti-ErbB3 antibodies that can be used as therapeutic agents.

SUMMARY

The invention is based on the discovery of a family of antibodies that specifically bind human ErbB3. The antibodies contain ErbB3 binding sites based on CDRs that specifically bind human ErbB3. When used as therapeutic agents, the antibodies are engineered, e.g., humanized, to reduce or eliminate an immune response when administered to a human patient.

The antibodies disclosed herein prevent or inhibit the activation of human ErbB3. In some embodiments, the antibodies prevent ErbB3 from binding to a ligand, e.g., NRG/HRG, thereby neutralizing the biological activity of ErbB3. In other embodiments, the anti-ErbB3 antibodies inhibit ErbB3 dimerization, thereby neutralizing the biological activity of ErbB3. The antibodies disclosed herein can be used to inhibit the proliferation of tumor cells in vitro or in vivo. When administered to a human cancer patient (or an animal model such as a mouse model), the antibodies inhibit or reduce tumor growth in the human patient (or animal model).

These and other aspects and advantages of the invention are illustrated by the following figures, detailed description and claims. As used herein, "including" means without limitation, and examples cited are non-limiting.

DESCRIPTION OF THE DRAWINGS

The invention can be more completely understood with reference to the following drawings.

FIG. 2 is a schematic diagram showing the amino acid sequence of the complete immunoglobulin heavy chain variable region of the antibodies denoted as 04D01, 09D03, 11G01, 12A07, 18H02, 22A02, and 24C05. The amino acid sequences for each antibody are aligned against one another, and Complementary Determining Sequences (CDR) (Kabat definition), $CDR_1$, $CDR_2$, and $CDR_3$, are identified in boxes. The unboxed sequences represent framework (FR) sequences.

FIG. 3 is a schematic diagram showing the $CDR_1$, $CDR_2$, and $CDR_3$ sequences (Kabat definition) for each of the immunoglobulin heavy chain variable region sequences in FIG. 2.

FIG. 4 is a schematic diagram showing the amino acid sequence of the complete immunoglobulin light chain variable region of antibodies 04D01, 09D03, 11G01, 12A07, 18H02, 22A02, and 24C05. The amino acid sequences for each antibody are aligned against one another, and $CDR_1$, $CDR_2$, and $CDR_3$ sequences (Kabat definition) are identified in boxes. The unboxed sequences represent framework (FR) sequences.

FIG. 5 is a schematic diagram showing the $CDR_1$, $CDR_2$, and $CDR_3$ sequences (Kabat definition) for each of the immunoglobulin light chain variable region sequences in FIG. 4.

FIG. 15 is a schematic diagram showing the amino acid sequences of the complete heavy chain variable region of 24C05 and the complete humanized heavy chain variable regions denoted as Sh24C05 Hv3-7, Sh24C05 Hv3-11, Sh24C05 Hv3-11 N62S, Sh24C05 Hv3-21, Sh24C05 Hv3-23, Sh24C05 Hv3-30, and Hu24C05 HvA. The amino acid sequences for each heavy chain variable regions are aligned against one another, and Complementary Determining Sequences (CDR) (Kabat definition), $CDR_1$, $CDR_2$, and $CDR_3$, are identified in boxes. The unboxed sequences represent framework (FR) sequences.

FIG. 16 is a schematic diagram showing the amino acid sequences of the complete light chain variable region of 24C05 and the complete humanized light chain variable regions denoted as Sh24C05 Kv1-9, Sh24C05 Kv1-16, Sh24C05 Kv1-17, Sh24C05 Kv1-33, Sh24C05 Kv1-39, and Hu24C05 KvA. The amino acid sequences for each light chain variable regions are aligned against one another, and $CDR_1$, $CDR_2$, and $CDR_3$ sequences (Kabat definition) are identified in boxes. The unboxed sequences represent framework (FR) sequences.

DETAILED DESCRIPTION

Figure 1:
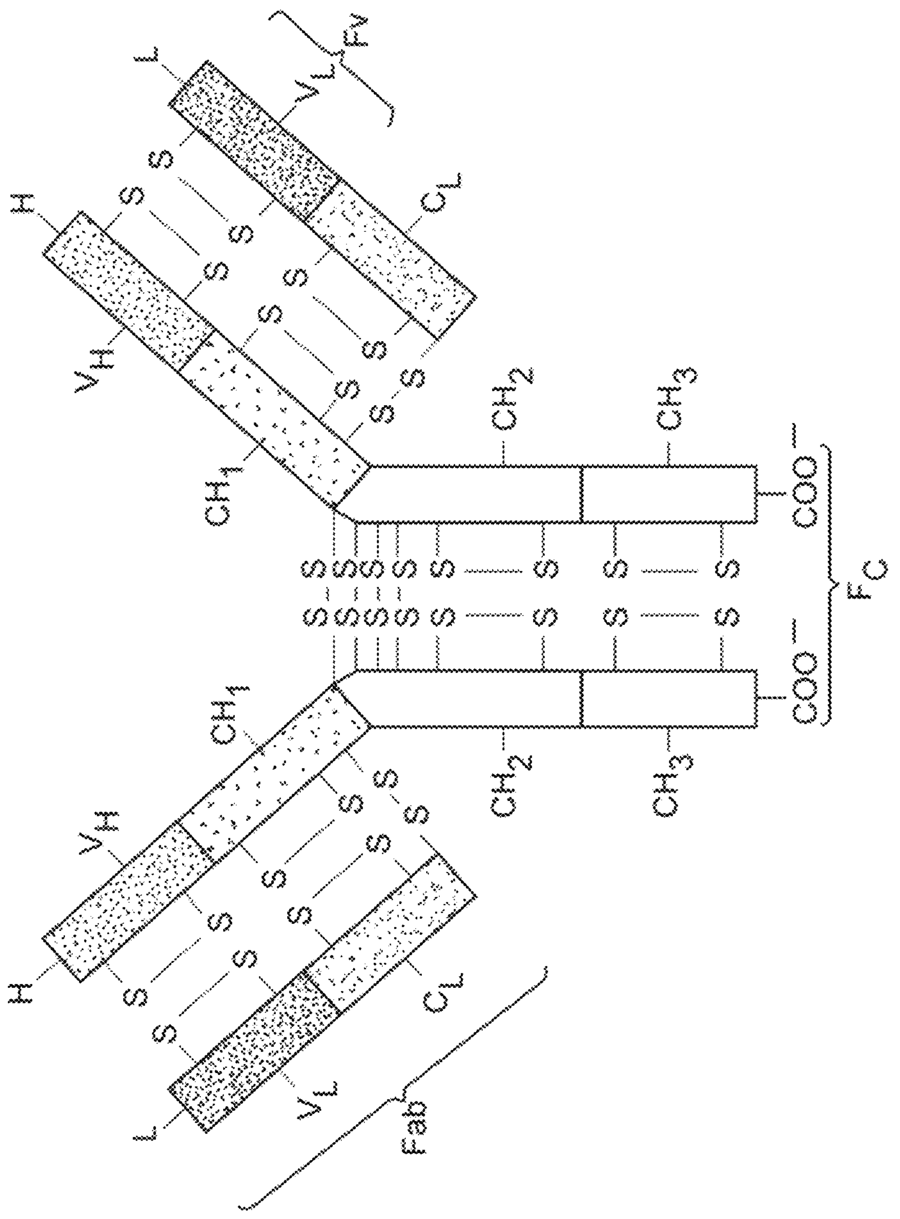
FIG. 1 (prior art) is a schematic representation of a typical antibody.

The ErbB3 antibodies disclosed herein are based on the antigen binding sites of certain monoclonal antibodies selected for their ability to neutralize the biological activity of human ErbB3 polypeptides. The antibodies contain immunoglobulin variable region CDR sequences that define a binding site for ErbB3. In some embodiments, the antibodies prevent ErbB3 from binding to a ligand, e.g., NRG/HRG, thereby neutralizing the biological activity of ErbB3. In other embodiments, the anti-ErbB3 antibodies inhibit ErbB3 dimerization, thereby neutralizing the biological activity of ErbB3. In still other embodiments, the anti-ErbB3 antibodies inhibit phosphorylation of ErbB3 and downstream signaling.

Because of the neutralizing activity of these antibodies, they are useful for inhibiting the growth and/or proliferation of certain cancer cells and tumors. The antibodies can be engineered to minimize or eliminate an immune response when administered to a human patient. In some embodiments, the antibodies are fused or conjugated to other moieties, such as detectable labels or effector molecules such as small molecule toxins.

I. Antibodies that Bind ErbB3

In some embodiments, the antibody comprises: (a) an immunoglobulin heavy chain variable region comprising the structure $CDR_{H1}$-$CDR_{H2}$—$CDR_{H3}$ and (b) immunoglobulin light chain variable region, wherein the heavy chain variable region and the light chain variable region together define a single binding site for binding human ErbB3. A $CDR_{H1}$ comprises an amino acid sequence selected from the group consisting of SEQ ID NO: 5 (04D01), SEQ ID NO:15 (09D03), SEQ ID NO: 25 (11G01), SEQ ID NO: 34 (12A07), SEQ ID NO: 41 (18H02), SEQ ID NO: 51 (22A02), SEQ ID NO: 57 (24C05), and SEQ ID NO: 75 (24C05); a $CDR_{H2}$ comprises an amino acid sequence selected from the group consisting of SEQ ID NO: 6 (04D01), SEQ ID NO:16 (09D03), SEQ ID NO: 26 (11G01), SEQ ID NO: 35 (12A07), SEQ ID NO: 42 (18H02), SEQ ID NO: 52 (22A02), SEQ ID NO: 58 (24C05), and SEQ ID NO: 148 (Sh24C05 Hv3-11 N62S); and a $CDR_{H3}$ comprises an amino acid sequence selected from the group consisting of SEQ ID NO: 7 (04D01), SEQ ID NO: 17 (09D03), SEQ ID NO: 27 (11G01), SEQ ID NO: 36 (12A07, 22A02), SEQ ID NO: 43 (18H02), and SEQ ID NO: 59 (24C05). Throughout the specification a particular SEQ ID NO. is followed in parentheses by the antibody that was the origin of that sequence. For example, "SEQ ID NO: 5 (04D01)" means that SEQ ID NO: 5 comes from antibody 04D01.

In some embodiments, the antibody comprises an immunoglobulin heavy chain variable region comprising a $CDR_{H1}$ comprising the amino acid sequence of SEQ ID NO: 5 (04D01), a $CDR_{H2}$ comprising the amino acid sequence of SEQ ID NO: 6 (04D01), and a $CDR_{H3}$ comprising the amino acid sequence of SEQ ID NO: 7 (04D01).

In some embodiments, the antibody comprises an immunoglobulin heavy chain variable region comprising a $CDR_{H1}$ comprising the amino acid sequence of SEQ ID NO: 15 (09D03), a $CDR_{H2}$ comprising the amino acid sequence of SEQ ID NO: 16 (09D03), and a $CDR_{H3}$ comprising the amino acid sequence of SEQ ID NO: 17 (09D03).

In some embodiments, the antibody comprises an immunoglobulin heavy chain variable region comprising a $CDR_{H1}$ comprising the amino acid sequence of SEQ ID NO: 25 (11G01), a $CDR_{H2}$ comprising the amino acid sequence of SEQ ID NO: 26 (11G01), and a $CDR_{H3}$ comprising the amino acid sequence of SEQ ID NO: 27 (11G01).

In some embodiments, the antibody comprises an immunoglobulin heavy chain variable region comprising a $CDR_{H1}$ comprising the amino acid sequence of SEQ ID NO: 34 (12A07), a $CDR_{H2}$ comprising the amino acid sequence of SEQ ID NO: 35 (12A07), and a $CDR_{H3}$ comprising the amino acid sequence of SEQ ID NO: 36 (12A07, 22A02).

In some embodiments, the antibody comprises an immunoglobulin heavy chain variable region comprising a $CDR_{H1}$ comprising the amino acid sequence of SEQ ID NO: 41 (18H02), a $CDR_{H2}$ comprising the amino acid sequence of SEQ ID NO: 42 (18H02), and a $CDR_{H3}$ comprising the amino acid sequence of SEQ ID NO: 43 (18H02).

In some embodiments, the antibody comprises an immunoglobulin heavy chain variable region comprising a $CDR_{H1}$ comprising the amino acid sequence of SEQ ID NO: 51 (22A02), a $CDR_{H2}$ comprising the amino acid sequence of SEQ ID NO: 52 (22A02), and a $CDR_{H3}$ comprising the amino acid sequence of SEQ ID NO: 36 (12A07, 22A02).

In some embodiments, the antibody comprises an immunoglobulin heavy chain variable region comprising a $CDR_{H1}$ comprising the amino acid sequence of SEQ ID NO: 57 (24C05) or SEQ ID NO: 75 (24C05), a $CDR_{H2}$ comprising the amino acid sequence of SEQ ID NO: 58 (24C05), and a $CDR_{H3}$ comprising the amino acid sequence of SEQ ID NO: 59 (24C05).

In certain embodiments, the antibody comprises an immunoglobulin heavy chain variable region comprising a $CDR_{H1}$ comprising the amino acid sequence of SEQ ID NO: 57 (24C05), a $CDR_{H2}$ comprising the amino acid sequence of SEQ ID NO: 58 (24C05), and a $CDR_{H3}$ comprising the amino acid sequence of SEQ ID NO: 59 (24C05).

In other embodiments, the antibody comprises an immunoglobulin heavy chain variable region comprising a $CDR_{H1}$ comprising the amino acid sequence of SEQ ID NO: 75 (24C05), a $CDR_{H2}$ comprising the amino acid sequence of SEQ ID NO: 58 (24C05), and a $CDR_{H3}$ comprising the amino acid sequence of SEQ ID NO: 59 (24C05).

In certain embodiments, the antibody comprises an immunoglobulin heavy chain variable region a $CDR_{H1}$ comprising the amino acid sequence of SEQ ID NO: 57 (24C05) or SEQ ID NO: 75 (24C05), a $CDR_{H2}$ comprising the amino acid sequence of SEQ ID NO: 148 (Sh24C05 Hv3-11 N62S), and a $CDR_{H3}$ comprising the amino acid sequence of SEQ ID NO: 59 (24C05).

Preferably, the $CDR_{H1}$, $CDR_{H2}$, and $CDR_{H3}$ sequences are interposed between human or humanized immunoglobulin FRs. The antibody can be an intact antibody or an antigen-binding antibody fragment.

In some embodiments, the antibody comprises (a) an immunoglobulin light chain variable region comprising the structure $CDR_{L1}$-$CDR_{L2}$-$CDR_3$, and (b) an immunoglobulin heavy chain variable region, wherein the IgG light chain variable region and the IgG heavy chain variable region together define a single binding site for binding human ErbB3. A $CDR_{L1}$ comprises an amino acid sequence selected from the group consisting of SEQ ID NO: 8 (04D01, 12A07, 22A02), SEQ ID NO: 18 (09D03), SEQ ID NO: 28 (11G01), SEQ ID NO: 44 (18H02), and SEQ ID NO: 60 (24C05); a $CDR_{L2}$ comprises an amino acid sequence selected from the group consisting of SEQ ID NO: 9 (04D01, 11G01, 12A07, 22A02), SEQ ID NO: 19 (09D03), SEQ ID NO: 45 (18H02), and SEQ ID NO: 61 (24C05); and a $CDR_{L3}$ comprises an amino acid sequence selected from the group consisting of SEQ ID NO: 10 (04D01, 12A07, 22A02), SEQ ID NO: 20 (09D03), SEQ ID NO: 29 (11G01), SEQ ID NO: 46 (18H02), and SEQ ID NO: 62 (24C05).

In some embodiments, the antibody comprises an immunoglobulin light chain variable region comprising: a $CDR_{L1}$ comprising the amino acid sequence of SEQ ID NO: 8 (04D01, 12A07, 22A02); a $CDR_{L2}$ comprising the amino acid sequence of SEQ ID NO: 9 (04D01, 11G01, 12A07, 22A02); and a $CDR_{L3}$ comprising the amino acid sequence of SEQ ID NO: 10 (04D01, 12A07, 22A02).

In some embodiments, the antibody comprises an immunoglobulin light chain variable region comprising: a $CDR_{L1}$ comprising the amino acid sequence of SEQ ID NO: 18 (09D03); a $CDR_{L2}$ comprising the amino acid sequence of SEQ ID NO: 19 (09D03); and a $CDR_{L3}$ comprising the amino acid sequence of SEQ ID NO: 20 (09D03).

In some embodiments, the antibody comprises an immunoglobulin light chain variable region comprising: a $CDR_{L1}$ comprising the amino acid sequence of SEQ ID NO: 28 (11G01); a $CDR_{L2}$ comprising the amino acid sequence of SEQ ID NO: 9 (04D01, 11G01, 12A07, 22A02); and a $CDR_{L3}$ comprising the amino acid sequence of SEQ ID NO: 29 (11G01).

In some embodiments, the antibody comprises an immunoglobulin light chain variable region comprising: a $CDR_{L1}$ comprising the amino acid sequence of SEQ ID NO: 44 (18H02); a $CDR_{L2}$ comprising the amino acid sequence of SEQ ID NO: 45 (18H02); and a $CDR_{L3}$ comprising the amino acid sequence of SEQ ID NO: 46 (18H02).

In one embodiment, the antibody comprises an immunoglobulin light chain variable region comprising: a $CDR_{L1}$ comprising the amino acid sequence of SEQ ID NO: 60 (24C05); a $CDR_{L2}$ comprising the amino acid sequence of SEQ ID NO: 61 (24C05); and a $CDR_{L3}$ comprising the amino acid sequence of SEQ ID NO: 62 (24C05).

Preferably, the $CDR_{L1}$, $CDR_{L2}$, and $CDR_{L3}$ sequences are interposed between human or humanized immunoglobulin FRs. The antibody can be an intact antibody or an antigen-binding antibody fragment.

In some embodiments, the antibody comprises: (a) an IgG heavy chain variable region comprising the structure $CDR_{H1}$-$CDR_{H2}$-$CDR_{H3}$ and (b) an IgG light chain variable region comprising the structure $CDR_{L1}$-$CDR_{L2}$-$CDR_{L3}$, wherein the heavy chain variable region and the light chain variable region together define a single binding site for binding human ErbB3. The $CDR_{H1}$ is an amino acid sequence selected from the group consisting of SEQ ID NO: 5 (04D01), SEQ ID NO:15 (09D03), SEQ ID NO: 25 (11G01), SEQ ID NO: 34 (12A07), SEQ ID NO: 41 (18H02), SEQ ID NO: 51 (22A02), SEQ ID NO: 57 (24C05), and SEQ ID NO: 75 (24C05); the $CDR_{H2}$ is an amino acid sequence selected from the group consisting of SEQ ID NO: 6 (04D01), SEQ ID NO:16 (09D03), SEQ ID NO: 26 (11G01), SEQ ID NO: 35 (12A07), SEQ ID NO: 42 (18H02), SEQ ID NO: 52 (22A02), SEQ ID NO: 58 (24C05), and SEQ ID NO: 148 (Sh24C05 Hv3-11 N62S); and the $CDR_{H3}$ is an amino acid sequence selected from the group consisting of SEQ ID NO: 7 (04D01), SEQ ID NO: 17 (09D03), SEQ ID NO: 27 (11G01), SEQ ID NO: 36 (12A07, 22A02), SEQ ID NO: 43 (18H02), and SEQ ID NO: 59 (24C05). The $CDR_{L1}$ is an amino acid sequence selected from the group consisting of SEQ ID NO: 8 (04D01, 12A07, 22A02), SEQ ID NO: 18 (09D03), SEQ ID NO: 28 (11G01), SEQ ID NO: 44 (18H02), and SEQ ID NO: 60 (24C05); the $CDR_{L2}$ is an amino acid sequence selected from the group consisting of SEQ ID NO: 9 (04D01, 11G01, 12A07, 22A02), SEQ ID NO: 19 (09D03), SEQ ID NO: 45 (18H02), and SEQ ID NO: 61 (24C05); and the $CDR_{L3}$ is an amino acid sequence selected from the group consisting of SEQ ID NO: 10 (04D01, 12A07, 22A02), SEQ ID NO: 20 (09D03), SEQ ID NO: 29 (11G01), SEQ ID NO: 46 (18H02), and SEQ ID NO: 62 (24C05).

In another embodiment, the antibody comprises an immunoglobulin heavy chain variable region selected from the group consisting of SEQ ID NO: 2 (04D01), SEQ ID NO: 12 (09D03), SEQ ID NO: 22 (11G01), SEQ ID NO: 31 (12A07), SEQ ID NO: 38 (18H02), SEQ ID NO: 48 (22A02), SEQ ID NO: 54 (24C05), and SEQ ID NO: 154 (Sh24C05 Hv3-11 N62S), and an immunoglobulin light chain variable region selected from the group consisting of SEQ ID NO: 4 (04D01), SEQ ID NO: 14 (09D03), SEQ ID NO: 24 (11G01), SEQ ID NO: 33 (12A07), SEQ ID NO: 40 (18H02), SEQ ID NO: 50 (22A02), SEQ ID NO: 56 (24C05), SEQ ID NO: 166 (Sh24C05 Kv1-16), and SEQ ID NO: 168 (Sh24C05 Kv1-17).

In another embodiment, the antibody comprises an immunoglobulin heavy chain variable region comprising the amino acid sequence of SEQ ID NO: 2 (04D01), and an immunoglobulin light chain variable region comprising the amino acid sequence of SEQ ID NO: 4 (04D01).

In another embodiment, the antibody comprises an immunoglobulin heavy chain variable region comprising the amino acid sequence of SEQ ID NO: 12 (09D03), and an immunoglobulin light chain variable region comprising the amino acid sequence of SEQ ID NO: 14 (09D03).

In another embodiment, the antibody comprises an immunoglobulin heavy chain variable region comprising the amino acid sequence of SEQ ID NO: 22 (11G01), and an immunoglobulin light chain variable region comprising the amino acid sequence of SEQ ID NO: 24 (11G01).

In another embodiment, the antibody comprises an immunoglobulin heavy chain variable region comprising the amino acid sequence of SEQ ID NO: 31 (12A07), and an immunoglobulin light chain variable region comprising the amino acid sequence of SEQ ID NO: 33 (12A07).

In another embodiment, the antibody comprises an immunoglobulin heavy chain variable region comprising the amino acid sequence of SEQ ID NO: 38 (18H02), and an immunoglobulin light chain variable region comprising the amino acid sequence of SEQ ID NO: 40 (18H02).

In another embodiment, the antibody comprises an immunoglobulin heavy chain variable region comprising the amino acid sequence of SEQ ID NO: 48 (22A02), and an immunoglobulin light chain variable region comprising the amino acid sequence of SEQ ID NO: 50 (22A02).

In another embodiment, the antibody comprises an immunoglobulin heavy chain variable region comprising the amino acid sequence of SEQ ID NO: 54 (24C05), and an immunoglobulin light chain variable region comprising the amino acid sequence of SEQ ID NO: 56 (24C05).

In another embodiment, the antibody comprises an immunoglobulin heavy chain variable region comprising the amino acid sequence of SEQ ID NO: 154 (Sh24C05 Hv3-11 N62S), and an immunoglobulin light chain variable region comprising the amino acid sequence of SEQ ID NO: 166 (Sh24C05 Kv1-16).

In another embodiment, the antibody comprises an immunoglobulin heavy chain variable region comprising the amino acid sequence of SEQ ID NO: 154 (Sh24C05 Hv3-11 N62S), and an immunoglobulin light chain variable region comprising the amino acid sequence of SEQ ID NO: 168 (Sh24C05 Kv1-17).

In other embodiments, the antibody comprises (i) an immunoglobulin heavy chain selected from the group consisting of SEQ ID NO: 109 (04D01), SEQ ID NO: 113 (09D03), SEQ ID NO: 117 (11G01), SEQ ID NO: 121 (12A07), SEQ ID NO: 125 (18H02), SEQ ID NO: 129 (22A07), SEQ ID NO: 133 (24C05), SEQ ID NO: 190 (Sh24C05 Hv3-11 N62S IgG1), and SEQ ID NO: 192 (Sh24C05 Hv3-11 N62S IgG2), and (ii) an immunoglobulin light chain selected from the group consisting of SEQ ID NO: 111 (04D01), SEQ ID NO: 115 (09D03), SEQ ID NO: 119 (11G01), SEQ ID NO: 123 (12A07), SEQ ID NO: 127 (18H02), SEQ ID NO: 131 (22A07), SEQ ID NO: 135 (24C05), SEQ ID NO: 204 (Sh24C05 Kv1-16 kappa), and SEQ ID NO: 206 (Sh24C05 Kv1-17 kappa).

In another embodiment, the antibody comprises an immunoglobulin heavy chain comprising the amino acid sequence of SEQ ID NO: 109 (04D01), and an immunoglobulin light chain comprising the amino acid sequence of SEQ ID NO: 111 (04D01).

In another embodiment, the antibody comprises an immunoglobulin heavy chain comprising the amino acid sequence of SEQ ID NO: 113 (09D03), and an immunoglobulin light chain comprising the amino acid sequence of SEQ ID NO: 115 (09D03).

In another embodiment, the antibody comprises an immunoglobulin heavy chain comprising the amino acid sequence of SEQ ID NO: 117 (11G01), and an immunoglobulin light chain comprising the amino acid sequence of SEQ ID NO: 119 (11G01).

In another embodiment, the antibody comprises an immunoglobulin heavy chain comprising the amino acid sequence of SEQ ID NO: 121 (12A07), and an immunoglobulin light chain comprising the amino acid sequence of SEQ ID NO: 123 (12A07).

In another embodiment, the antibody comprises an immunoglobulin heavy chain comprising the amino acid sequence of SEQ ID NO: 125 (18H02), and an immunoglobulin light chain comprising the amino acid sequence of SEQ ID NO: 127 (18H02).

In another embodiment, the antibody comprises an immunoglobulin heavy chain comprising the amino acid sequence of SEQ ID NO: 129 (22A02), and an immunoglobulin light chain comprising the amino acid sequence of SEQ ID NO: 131 (22A02).

In another embodiment, the antibody comprises an immunoglobulin heavy chain comprising the amino acid sequence of SEQ ID NO: 133 (24C05), and an immunoglobulin light chain comprising the amino acid sequence of SEQ ID NO: 135 (24C05).

In another embodiment, the antibody comprises an immunoglobulin heavy chain comprising the amino acid sequence of SEQ ID NO: 190 (Sh24C05 Hv3-11 N62S IgG1), and an immunoglobulin light chain comprising the amino acid sequence of SEQ ID NO: 204 (Sh24C05 Kv1-16 kappa).

In another embodiment, the antibody comprises an immunoglobulin heavy chain comprising the amino acid sequence of SEQ ID NO: 192 (Sh24C05 Hv3-11 N62S IgG2), and an immunoglobulin light chain comprising the amino acid sequence of SEQ ID NO: 204 (Sh24C05 Kv1-16 kappa).

In another embodiment, the antibody comprises an immunoglobulin heavy chain comprising the amino acid sequence of SEQ ID NO: 190 (Sh24C05 Hv3-11 N62S IgG1), and an immunoglobulin light chain comprising the amino acid sequence of SEQ ID NO: 206 (Sh24C05 Kv1-17 kappa).

In another embodiment, the antibody comprises an immunoglobulin heavy chain comprising the amino acid sequence of SEQ ID NO: 192 (Sh24C05 Hv3-11 N62S IgG2), and an immunoglobulin light chain comprising the amino acid sequence of SEQ ID NO: 206 (Sh24C05 Kv1-17 kappa).

As used herein, unless otherwise indicated, the term "antibody" means an intact antibody (e.g., an intact monoclonal antibody) or antigen-binding fragment of a antibody (e.g., an antigen-binding fragment of a monoclonal antibody), including an intact antibody or antigen-binding fragment that has been modified, engineered, or chemically conjugated. Examples of antibodies that have been modified or engineered include chimeric antibodies, humanized antibodies, and multispecific antibodies (e.g., bispecific antibodies). Examples of antigen-binding fragments include Fab, Fab', $(Fab')_2$, Fv, single chain antibodies (e.g., scFv), minibodies, and diabodies. An example of a chemically conjugated antibody is an antibody conjugated to a toxin moiety.

FIG. 1 shows a schematic representation of an intact monoclonal antibody that contains four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($CH_1$, $CH_2$ and $CH_3$ in FIG. 1). The variable regions determine the specificity of the antibody.

Each variable region contains three hypervariable regions known as complementarity determining regions (CDRs) flanked by four relatively conserved regions known as framework regions (FRs). The three CDRs, referred to as $CDR_1$, $CDR_2$, and $CDR_3$, contribute to the antibody binding specificity.

In certain embodiments, an isolated antibody that binds human ErbB3 comprises an immunoglobulin heavy chain variable region comprising an amino acid sequence that is at least 70%, 75%, 80%, 85%, 90%, 95%, 98%, or 99% identical to the entire variable region or the framework region sequence of SEQ ID NO: 2 (04D01), SEQ ID NO: 12 (09D03), SEQ ID NO: 22 (11G01), SEQ ID NO: 31 (12A07), SEQ ID NO: 38 (18H02), SEQ ID NO: 48 (22A02), SEQ ID NO: 54 (24C05), and SEQ ID NO: 154 (Sh24C05 Hv3-11 N62S).

In certain embodiments, an isolated antibody that binds human ErbB3 comprises an immunoglobulin light chain variable region comprising an amino acid sequence that is at least 70%, 75%, 80%, 85%, 90%, 95%, 98%, or 99% identical to the entire variable region or the framework region sequence of SEQ ID NO: 4 (04D01), SEQ ID NO: 14 (09D03), SEQ ID NO: 24 (11G01), SEQ ID NO: 33 (12A07), SEQ ID NO: 40 (18H02), SEQ ID NO: 50 (22A02), SEQ ID NO: 56 (24C05), SEQ ID NO: 166 (Sh24C05 Kv1-16), and SEQ ID NO: 168 (Sh24C05 Kv1-17).

In each of the foregoing embodiments, it is contemplated herein that immunoglobulin heavy chain variable region sequences and/or light chain variable region sequences that together bind human ErbB3 may contain amino acid alterations (e.g., at least 1, 2, 3, 4, 5, or 10 amino acid substitutions, deletions, or additions) in the framework regions of the heavy and/or light chain variable regions.

In some embodiments, an isolated antibody binds hErbB3 with a $K_D$ of 350 pM, 300 pM, 250 pM, 200 pM, 150 pM, 100 pM, 75 pM, 50 pM, 20 pM, 10 pM or lower. Unless otherwise specified, $K_D$ values are determined by surface plasmon resonance methods. The surface plasmon resonance methods can be performed using the conditions described, for example, in Examples 3 and 12, where the measurements were performed at 25° C. and 37° C., respectively.

In some embodiments, the antibodies inhibit hErbB3 binding to NRG1-β1. For example, the antibodies can have an $IC_{50}$ (concentration at 50% of maximum inhibition) of about 5 nM, 2 nM or lower, when assayed using the protocols described in Examples 4 and 13.

II. Production of Antibodies

Methods for producing antibodies disclosed herein are known in the art. For example, DNA molecules encoding light chain variable regions and heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding the antibodies disclosed herein can be incorporated (ligated) into expression vectors, which can be introduced into host cells through conventional transfection or transformation techniques. Exemplary host cells are E. coli cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If a DNA construct encoding an antibody disclosed herein is to be expressed in eukayotic host cells, e.g., CHO cells, it is first inserted into an expression vector containing a suitable eukaryotic promoter, a secretion signal, IgG enhancers, and various introns. This expression vector optionally contains sequences encoding all or part of a constant region, enabling an entire, or a part of, a heavy and/or light chain to be expressed. In some embodiments, a single expression vector contains both heavy and light chain variable regions to be expressed.

The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A method of producing a polypeptide comprising an immunoglobulin heavy chain variable region or a polypeptide comprising an immunoglobulin light chain variable region may comprise growing a host cell transfected with an expression vector under conditions that permits expression of the polypeptide comprising the immunoglobulin heavy chain variable region or the polypeptide comprising the immunoglobulin light chain variable region. The polypeptide comprising a heavy chain variable region or the polypeptide comprising the light chain variable region then may be purified using techniques well known in the art, e.g., affinity tags such as glutathione-S-transferase (GST) and histidine tags.

A method of producing a monoclonal antibody that binds human ErbB3, or an antigen-binding fragment of the antibody, may comprise growing a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial chains), under conditions that permit expression of both chains. The intact antibody (or antigen-binding fragment) can be harvested and purified using techniques well known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

III. Modifications to the Antibodies

Methods for reducing or eliminating the antigenicity of antibodies and antibody fragments are known in the art. When the antibodies are to be administered to a human, the antibodies preferably are "humanized" to reduce or eliminate antigenicity in humans. Preferably, a humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, Proc. Nat. Acad. Sci. 81:6851-6855, Neuberger et al., 1984, Nature 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-ErbB3 antibody are grafted onto human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) Nature 332: 323-327; Verhoeyen et al. (1988) Science 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL 169:1119-1125.

Other methods to reduce immunogenicity include "reshaping," "hyperchimerization," and "veneering/resurfacing." See, e.g., Vaswami et al., 1998, Annals of Allergy, Asthma, & Immunol. 81:105; Roguska et al., 1996, Prot. Engineer 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, NY), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and 6,872,518 (Zauderer).

Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. Nos. 5,766,886; 5,770,196; 5,821,123; and 5,869,619.

Any suitable approach, including any of the above approaches, can be used to reduce or eliminate human immunogenicity of an antibody disclosed herein.

Methods of making multispecific antibodies are known in the art. Multi-specific antibodies include bispecific antibodies. Bispecific antibodies are antibodies that have binding specificities for at least two different epitopes. Exemplary bispecific antibodies bind to two different epitopes of the antigen of interest. Bispecific antibodies can be prepared as full length antibodies or antibody fragments (e.g., $F(ab')_2$ bispecific antibodies and diabodies) as described, for example, in Milstein et al., Nature 305:537-539 (1983), WO 93/08829, Traunecker et al., EMBO J., 10:3655-3659 (1991), WO 94/04690, Suresh et al., Methods in Enzymology, 121:210 (1986), WO96/27011, Brennan et al., Science, 229: 81 (1985), Shalaby et al., J. Exp. Med., 175: 217-225 (1992), Kostelny et al., J. Immunol., 148(5):1547-1553 (1992), Hollinger et al., PNAS, 90:6444-6448, Gruber et al., J. Immunol., 152:5368 (1994), Wu et al., Nat. Biotechnol., 25(11): 1290-1297, U.S. Patent Publication No. 2007/0071675, and Bostrom et al., Science 323:1640-1644 (2009).

In some embodiments, the antibody is conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

IV. Use of the Antibodies

The antibodies disclosed herein can be used to treat various forms of cancer, e.g., breast, ovarian, prostate, cervical, colorectal, lung (e.g., non-small cell lung cancer), pancreatic, gastric, skin, kidney, head and neck, and schwannoma cancers. The cancer cells are exposed to a therapeutically effective amount of the antibody so as to inhibit or reduce proliferation of the cancer cell. In some embodiments, the antibodies inhibit cancer cell proliferation by at least 40%, 50%, 60%, 70%, 80%, 90%, 95%, 98%, 99%, or 100%.

In some embodiments, the antibody inhibits or reduces proliferation of a tumor cell by inhibiting binding of human ErbB3 to an ErbB3 ligand, e.g., Neuregulin/Heregulin especially NRGβ1/NRG1-β1/NRGβ1/HRGβ1 and NRGα1/NRG1-α1/NRGα1/HRGα1. The antibody can be used in a method to inhibit tumor growth in a human patient. The method comprises administering to the patient a therapeutically effective amount of the antibody.

Cancers associated with ErbB3 overexpression and/or activation include breast cancer, ovarian cancer, prostate cancer, cervical cancer, lung cancer (e.g., non-small cell lung cancer), some forms of brain cancer (e.g., schwannoma), melanomas, skin, kidney, and gastrointestinal cancers (e.g., colorectal, pancreatic, gastric, head and neck).

As used herein, "treat, "treating" and "treatment" mean the treatment of a disease in a mammal, e.g., in a human. This includes: (a) inhibiting the disease, i.e., arresting its development; and (b) relieving the disease, i.e., causing regression of the disease state; and (c) curing the disease.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount and the disease being treated. Exemplary dosing frequencies are once per day, once per week and once every two weeks. A preferred route of administration is parenteral, e.g., intravenous infusion. Formulation of monoclonal antibody-based drugs is within ordinary skill in the art. In some embodiments, the monoclonal antibody is lyophilized and reconstituted in buffered saline at the time of administration.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods well known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

EXAMPLES

The following Examples are merely illustrative and are not intended to limit the scope or content of the invention in any way.

Example 1—Production of Anti-Herbb3 Monoclonal Antibodies

Immunizations, fusions, and primary screens were conducted at Maine Biotechnology Services Inc. following the Repetitive Immunization Multiple Sites (RIMMS) protocol. Three AJ mice and three Balb/c mice were immunized with recombinant human ErbB3/Fc (R&D Systems, Cat. No. 348-RB). Two sets of immunization were performed with either cleaved rhErbB3 (Immunization A) or with cleaved rhErbB3 cross-linked to its ligand, recombinant human NRG1-β1/HRG1-β1-EGF domain (R&D Systems, Cat. No. 396-HB) (Immunization B). Two AJ mice per immunization with sera displaying high anti-ErbB3 activity by Enzyme Linked Immunosorbent Assay (ELISA) were chosen for subsequent fusion. Spleens and lymph nodes from the appropriate mice were harvested. B-cells then were harvested and fused with a myeloma line. Fusion products were serially diluted onto forty 96-well plates to near clonality. A total of 5280 supernatants from the resulting fusions were screened for binding to recombinant rhErbB3/Fc, using ELISA. The same supernatants were also screened for their binding to human ErbB3 overexpressed in CHO cells (by Mesoscale electrochemiluminescence assay). Three hundred supernatants identified as containing antibodies against ErbB3 were further characterized by in vitro biochemical and cell-based assays as discussed below. A panel of hybridomas was selected, and the hybridomas were subcloned and expanded. Hybridoma cell lines were transferred to BioXCell (formerly Bio-Express) for antibody expression and purification by affinity chromatography on Protein G resin under standard conditions.

Anti-hErbB3 monoclonal antibody 04D01 was generated from Immunization A described above. Anti-hErbB3 monoclonal antibodies 09D03, 11G01, 12A07, 18H02, 22A02 and 24C05 were generated from Immunization B described above.

Example 2—Sequence Analysis of Anti-hErbB3 Monoclonal Antibodies

The light-chain isotype and heavy chain isotype of each monoclonal antibody in Example 1 was determined using the IsoStrip™ Mouse Monoclonal Antibody Isotyping Kit according the manufacturer's instructions (Roche Applied Science). All antibodies were determined to be Kappa light chain and IgG1 or IgG2b IgG heavy chain.

The heavy and light chain variable regions of the mouse monoclonal antibodies were sequenced using 5' RACE (Rapid Amplification of cDNA Ends). Total RNA was extracted from each monoclonal hybridoma cell line using the RNeasy® Miniprep kit according to the vendor's instructions (Qiagen). Full-length first strand cDNA containing 5' ends was generated using either the GeneRacer™ Kit (Invitrogen) or SMARTer™ RACE cDNA Amplification Kit (Clontech) according to the manufacturer's instructions using random primers for 5' RACE.

The variable regions of the Kappa and Heavy (IgG1 or IgG2b) IgG chains were amplified by PCR, using KOD Hot Start Polymerase (Novagen) or Advantage 2 Polymerase Mix (Clontech) according to the manufacturer's instructions. For amplification of 5' cDNA ends in conjunction with the GeneRacer™ Kit, the GeneRacer™ 5' Primer, 5' cgactggagcacgaggacactga 3' (SEQ ID NO: 136) (Invitrogen) was used as a 5' primer. For amplification of 5' cDNA ends in conjunction with the SMARTer™ RACE cDNA Amplification Kit, the Universal Primer Mix A primer (Clontech), a mix of 5'CTAATACGACTCACTATAGGGCAAGCAGTGGTATCAACGCAGAGT 3' (SEQ ID NO: 137) and 5' CTAATACGACTCACTATAGGGC 3' (SEQ ID NO: 138), was used as a 5' primer. Heavy chain variable regions were amplified using the above 5' primers and a 3' IgG1 Constant Region specific primer, either 5' TATGCAAGGCTTACAACCACA 3' (SEQ ID NO: 139) or 5' GCCAGTGGATAGACAGATGGGGGTGTCG 3' (SEQ ID NO: 140). IgG2b sequences were amplified with either 5' AGGACAGGGGTTGATTGTTGA 3' (SEQ ID NO: 141), 5' GGCCAGTGGATAGACTGATGGGGGTGTTGT 3' (SEQ ID NO: 142), or 5' GGAGGAACCAGTTGTATCTCCACACCCA 3' (SEQ ID NO: 143). Kappa chain variable regions were amplified with the above 5' primers and a 3' Kappa Constant Region specific primer, either 5' CTCATTCCTGTTGAAGCTCTTGACAAT 3' (SEQ ID NO: 144) or 5' CGACTGAGGCACCTCCAGATGTT 3' (SEQ ID NO: 145).

Individual PCR products were isolated by agarose gel electrophoresis and purified using the Qiaquick® Gel Purification kit according to the manufacturer's instructions (Qiagen). The PCR products were subsequently cloned into the pCR®4Blunt plasmid using the Zero Blunt® TOPO® PCR Cloning Kit according to the manufacturer's instructions (Invitrogen) and transformed into DH5-α bacteria (Invitrogen) through standard molecular biology techniques. Plasmid DNA isolated from transformed bacterial clones was sequenced using M13 Forward (5' GTAAAACGACGGCCAGT 3') (SEQ ID NO: 146) and M13 Reverse primers (5' CAGGAAACAGCTATGACC 3') (SEQ ID NO: 147) by Beckman Genomics, using standard dideoxy DNA sequencing methods to identify the sequence of the variable region sequences. The sequences were analyzed using Vector NTI software (Invitrogen) and the IMGT/V-Quest software to identify and confirm variable region sequences.

The nucleic acid sequences encoding and the protein sequences defining variable regions of the murine monoclonal antibodies are summarized below (amino terminal signal peptide sequences are not shown). CDR sequences (Kabat definition) are shown in bold/underlined in the amino acid sequences.

Nucleic Acid Sequence Encoding the Heavy Chain Variable Region of the 04D01 Antibody (SEQ ID NO: 1)

```
  1  caggtccaac tgcagcagcc tggggctgaa ctggtgaggc ctgggacttc agtgaagttg
 61  tcctgcaagg cttctggcta caccttcacc agccactggt tgcactgggt gaagcagagg
121  cctggacaag gccttgagtg gatcggagtg cttgatcctt ctgattttta tagtaactac
181  aatcaaaact tcaagggcaa ggccacattg actgtagaca catcctccag cacagcctac
241  atgcagctca gcagcctgac atctgaggac tctgcggtct attactgtgc acgaggccta
301  ctatccgggg actatgctat ggactactgg ggtcaaggaa cctcagtcac cgtctcctca
```

Protein Sequence Defining the Heavy Chain Variable Region of the 04D01 Antibody (SEQ ID NO: 2)

1 qvqlqqpgae lvrpgtsvkl sckasgytft shwlhwvkqr pgqglewigv ldpsdfysny

61 nqnfkgkatl tvdtssstay mqlssltsed savyycargl lsgdyamdyw gqgtsvtvss Nucleic Acid Sequence Encoding the Kappa Chain Variable Region of the 04D01 Antibody (SEQ ID NO: 3)

```
  1  gatgttttga tgacccaaat tocactctcc ctgcctgtca gtcttggaga tcaagcctcc
 61  atctcttgca gatctagtca gagcattgta catagtaatg gaaacaccta tttagaatgg
121  tacctgcaga aaccaggcca gtctccaaag tccctgatct acaaagtttc taaccgattt
181  tctggggtcc cagacaggtt cagtggcagt ggatcaggga cagatttcac actcaagatc
```

-continued 241 agcagagtgg aggctgagga tctgggagtt tattactgct ttcaaggttc atatgttccg 301 tggacgttcg gtggaggcac caagctggaa atcaaa Protein Sequence Defining the Kappa Chain Variable Region of the 04D01 Antibody (SEQ ID NO: 4)

1 dvlmtqipls lpvslgdqas iscrssqsiv hsngntylew ylqkpgqspk sliykvsnrf

61 sgvpdrfsgs gsgtdftlki srveaedlgv yycfqgsyvp wtfgggtkle ik

Nucleic Acid Sequence Encoding the Heavy Chain Variable Region of the 09D03 Antibody (SEQ ID NO: 11)

1 caggttactc taaaagagtc tggccctggg atattgcggc cctcccagac cctcagtctg 61 acttgttctt tctctgggtt ttcactgagc acttttggtt tgagtgtagg ctggattcgt 121 cagccttcag ggaagggtct ggagtggctg gcacacattt ggtgggatga tgataagtac 181 tataacccag cccttaagag tcggctcaca atctccaagg atacctccaa aaaccaggta 241 ttcctcaaga tcgccaatgt ggacactgca gatactgcca catactactg tgctcgaata 301 ggggcggacg cccttccttt tgactactgg ggccaaggca ccactctcac agtctcctca Protein Sequence Defining the Heavy Chain Variable Region of the 09D03 Antibody (SEQ ID NO: 12)

1 qvtlkesgpg ilrpsqtlsl tcsfsgfsls tfglsvgwir qpsgkglewl ahiwwdddky

61 ynpalksrlt iskdtsknqv flkianvdta dtatyycari gadalpfdyw gqgttltvss Nucleic Acid Sequence Encoding the Kappa Chain Variable Region of the 09D03 Antibody (SEQ ID NO: 13)

1 gatattgtgt tgactcagac tgcaccctct gtacctgtca ctcctggaga gtcagtatcc 61 atctcctgca ggtctagtaa gagtctcctg catagtaatg gcaacactta cttgtattgg 121 ttcctgcaga ggccaggcca gtctcctcag ctcctgatat atcggatgtc caaccttgcc 181 tcaggagtcc cagacaggtt cagtggcagt gggtcaggaa ctgctttcac actgagaatc 241 agtagagtgg aggctgagga tgtgggtgtt tattactgta tgcaacatct agaatatcct 301 ttcacgttcg gctcggggac aaagttggaa ataaaa Protein Sequence Defining the Kappa Chain Variable Region of the 09D03 Antibody (SEQ ID NO: 14)

1 divltqtaps vpvtpgesvs iscrssksll hsngntylyw flqrpgqspq lliyrmsnla

61 sgvpdrfsgs gsgtaftlri srveaedvgv yycmqhleyp ftfgsgtkle ik

Nucleic Acid Sequence Encoding the Heavy Chain Variable Region of the 11G01 Antibody (SEQ ID NO: 21)

1 caggttcagc tgcaacagtc tgacgctgag ttggtgaaac ctggagcttc agtgaagata 61 tcctgcaagg tttctggcta caccttcact gaccatatta ttcactggat gaagcagagg 121 cctgaacagg gcctggaatg gattggatat atttatccta gagatggtta tattaagtac 181 aatgagaagt tcaagggcaa ggccacattg actgcagaca aatcctccag cacagcctac 241 atgcaggtca acagcctgac atctgaggac tctgcagtct atttctgtgc aaggggttac 301 tattatgcta tggactactg gggtcaagga acctcagtca ccgtctcctc a Protein Sequence Defining the Heavy Chain Variable Region of the 11G01 Antibody (SEQ ID NO: 22)

1 qvqlqqsdae lvkpgasvki sckvsgytft dhiihwmkqr peqglewigy iyprdgyiky

61 nekfkgkatl tadkssstay mqvnsltsed savyfcargy yyamdywgqg tsvtvss

Nucleic Acid Sequence Encoding the Kappa Chain Variable Region of the 11G01 Antibody (SEQ ID NO: 23)

1 gatgttttga tgacccaaac tccactctcc ctgcctgtca gtcttggaga tcaagcctcc 61 atctcttgca gatctagtca gagcattgta catagtattg gaaacaccta tttagaatgg -continued 121 tacctgcaga aaccaggcca gtctccaaag ctcctgatct acaaagtttc caaccgattt 181 tctggggtcc cagagaggtt cagtggcagt ggatcaggga cagatttcac actcaagatc 241 agcagagtgg aggctgagga tctgggagtt tattactgct ttcaaggttc acatgttcca 301 ttcacgttcg gctcggggac aaagttggaa ataaaa Protein Sequence Defining the Kappa Chain Variable Region of the 11G01 Antibody (SEQ ID NO: 24)

1 dvlmtqtpls lpvslgdqas iscrssqsiv hsigntylew ylqkpgqspk lliykvsnrf

61 sgvperfsgs gsgtdftlki srveaedlgv yycfqgshvp ftfgsgtkle ik

Nucleic Acid Sequence Encoding the Heavy Chain Variable Region of the 12A07 Antibody (SEQ ID NO: 30)

1 caggtccaac tgctgcagcc tggggctgag ctggtgaggc ctgggacttc agtgaagttg 61 tcctgcaaga cttctggcta caccttctcc agctactgga tgcactgggt aaagcagagg 121 cctggacaag gccttgagtg gatcggaatg attgatcctt ctgatgttta tactaactac 181 aatccaaagt tcaagggcaa ggccacattg actgttgaca catcctccag cacagcctac 241 atgcagctca gcagcctgac atctgaggac tctgcggtct attactgtgc aagaaactac 301 tctggggact actggggcca aggcaccact ctcacagtct cctca Protein Sequence Defining the Heavy Chain Variable Region of the 12A07 Antibody (SEQ ID NO: 31)

1 qvqllqpgae lvrpgtsvkl scktsgytfs sywmhwvkqr pgqglewigm idpsdvytny

61 npkfkgkatl tvdtssstay mqlssltsed savyycarny sgdywgqgtt ltvss

Nucleic Acid Sequence Encoding the Kappa Chain Variable Region of the 12A07 Antibody (SEQ ID NO: 32)

1 gatgttttga tgacccaaat tccactctcc ctgcctgtca gtcttggaga tcaagcctcc 61 atctcttgta gatctagtca gagcattgtc catagtaatg gaaacaccta tttagaatgg 121 tacctgcaga aaccaggcca gtctccaaag ctcctgatct acaaagtttc caaccgattt 181 tctggggtcc cagacaggtt cagtggcagt ggatcaggga cagatttcac actcaagatc 241 agcagagtgg aggctgagga tctgggagtt tattactgct ttcaaggttc atatgttccg 301 tggacgttcg gtggaggcac caagctggaa atcaaa Protein Sequence Defining the Kappa Chain Variable Region of the 12A07 Antibody (SEQ ID NO: 33)

1 dvlmtqipls lpvslgdqas iscrssqsiv hsngntylew ylqkpgqspk lliykvsnrf

61 sgvpdrfsgs gsgtdftlki srveaedlgv yycfqgsyvp wtfgggtkle ik

Nucleic Acid Sequence Encoding the Heavy Chain Variable Region of the 18H02 Antibody (SEQ ID NO: 37)

1 cagatccagt tggtacagtc tggacctgaa ctgaagaagc ctggagaggc agtcaagatc 61 tcctgcaagt cttctgggta taccttcaca acctatggaa tgagctgggt gaaacaggct 121 ccaggaaggg ctttaaagtg gatgggctgg ataaacacct actctggagt gccaacatat 181 gctgatgact tcaagggacg gtttgccttc tctttggaat cctctgccag cactgcctat 241 ttgcagatca acaacctcaa aaatgaggac acggctacat atttctgtgc aagagggagg 301 gatggttacc aagtggcctg gtttgcttac tggggccaag ggacgctggt cactgtctct 361 gca Protein Sequence Defining the Heavy Chain Variable Region of the 18H02 Antibody (SEQ ID NO: 38)

1 qiqlvqsgpe lkkpgeavki sckssgytft tygmswvkqa pgralkwmgw intysgvpty

61 addfkgrfaf slessastay lqinnlkned tatyfcargr dgyqvawfay wgqgtlvtvs 121 a -continued Nucleic Acid Sequence Encoding the Kappa Chain Variable Region of the 18H02 Antibody (SEQ ID NO: 39)

```
  1   gaaacaactg tgacccagtc tccagcatcc ctgtccatgg ctataggaga taaagtcacc

 61   atcagatgca taaccagcac tgatattgat gatgatatga actggttcca gcagaagcca

121   ggggaacctc ctaagctcct tatttcagaa ggcaatactc ttcgtcctgg agtcccatcc

181   cgattctccg gcagtggcta tggtacagat tttattttta caattgaaaa catgctctct

241   gaagatgttg cagattacta ctgtttgcaa agtgataact tgccgtacac gttcggaggg

301   gggaccaagc tggaaataaa a
```

Protein Sequence Defining the Kappa Chain Variable Region of the 18H02 Antibody (SEQ ID NO: 40)

1 ettvtqspas lsmaigdkvt ircitstdid ddmnwfqqkp geppkllise gntlrpgvps 61 rfsgsgygtd fiftienmls edvadyyclq sdnlpytfgg gtkleik Nucleic Acid Sequence Encoding the Heavy Chain Variable Region of the 22A02 Antibody (SEQ ID NO: 47)

```
  1   caggtccaac tgcagcagcc tggggctgag ctggtgaggc ctgggacttc agtgaagttg

 61   tcctgcaagg cttctggcta caccttcacc aactactgga tgcactgggt aaagcagagg

121   cctggacaag gccttgagtg gatcggaatg attgatcctt ctgatagtta tactaactac

181   aatccaaagt tcaagggtaa ggccacattg actgtagaca catcctccag cacagcctac

241   atgcagctca gcagcctgac atctgaggac tctgcggtct attactgtgc aagaaactac

301   tctggggact actggggcca aggcaccact ctcacagtct cctca
```

Protein Sequence Defining the Heavy Chain Variable Region of the 22A02 Antibody (SEQ ID NO: 48)

1 qvqlqqpgae lvrpgtsvkl sckasgytft nywmhwvkqr pgqglewigm idpsdsytny

61 npkfkgkatl tvdtssstay mqlssltsed savyycarny sgdywgqgtt ltvss

Nucleic Acid Sequence Encoding the Kappa Chain Variable Region of the 22A02 Antibody (SEQ ID NO: 49)

```
  1   gatgttttga tgacccaaac tccactctcc ctgcctgtca gtcttggaga tcaagcctcc

 61   atctcttgca gatctagtca gagcattgta catagtaatg gaaacaccta tttagaatgg

121   tacctgcaga aaccaggcca gtctccaaag ctcctgatct acaaagtttc caaccgattt

181   tctggggtcc cagacaggtt cagtggcagt ggatcaggga cagatttcac actcaagatc

241   agcagagtgg aggctgagga tctgggagtt tattattgct ttcaaggttc atatgttccg

301   tggacgttcg gtggaggcac caagctggaa atcaaa
```

Protein Sequence Defining the Kappa Chain Variable Region of the 22A02 Antibody (SEQ ID NO: 50)

1 dvlmtqtpls lpvslgdqas iscrssqsiv hsngntylew ylqkpgqspk lliykvsnrf

61 sgvpdrfsgs gsgtdftlki srveaedlgv yycfqgsyvp wtfgggtkle ik

Nucleic Acid Sequence Encoding the Heavy Chain Variable Region of the 24C05 Antibody (SEQ ID NO: 53)

```
  1   gaggtgcagc tggtggaatc tgggggaggc ttagtgaagc ctggagggtc cctgaaactc

 61   tcctgtgcag cctctggatt cactttcagt gactatgcca tgtcttgggt tcgccagact

121   ccggaaaaga ggctggagtg ggtcgcaacc attagtgatg gtggtactta cacctactat

181   ccagacaatg taaagggccg attcaccatc tccagagaca atgccaagaa caacctgtac

241   ctgcaaatga gccatctgaa gtctgaggac acagccatgt attactgtgc aagagaatgg

301   ggtgattacg acggatttga ctactggggc caaggcacca ctctcacagt ctcctcg
```

-continued

Protein Sequence Defining the Heavy Chain Variable Region of the 24C05 Antibody
(SEQ ID NO: 54)

```
 1   evqlvesggg lvkpggslkl scaasgftfs dyamswvrqt pekrlewvat isdggtytyy

61   pdnvkgrfti srdnaknnly lqmshlksed tamyycarew gdydgfdywg qgttltvss
```

Nucleic Acid Sequence Encoding the Kappa Chain Variable Region of the 24C05 Antibody
(SEQ ID NO: 55)

```
  1   gacatccaga tgacccagtc tccatcctcc ttatctgcct ctctgggaga aagagtcagt

 61   ctcacttgtc gggcaagtca ggaaattagt ggttacttaa gctggcttca gcagaaacca

121   gatggaacta ttaaacgcct gatctacgcc gcatccactt tagattctgg tgtcccaaaa

181   aggttcagtg gcagtaggtc tgggtcagat tattctctca ccatcggcag ccttgagtct

241   gaagatcttg cagactatta ctgtctacaa tatgatagtt atccgtacac gttcggaggg

301   gggaccaagc tggaaataaa a
```

Protein Sequence Defining the Kappa Chain Variable Region of the 24C05 Antibody
(SEQ ID NO: 56)

```
 1   diqmtqspss lsaslgervs ltcrasgeis gylswlqqkp dgtikrliya astldsgvpk

61   rfsgsrsgsd ysltigsles edladyyclq ydsypytfgg gtkleik
```

The amino acid sequences defining the immunoglobulin heavy chain variable regions for the antibodies produced in Example 1 are aligned in FIG. 2. Amino terminal signal peptide sequences (for proper expression/secretion) are not shown. $CDR_1$, $CDR_2$, and $CDR_3$ (Kabat definition) are identified by boxes. FIG. 3 shows an alignment of the separate $CDR_1$, $CDR_2$, and $CDR_3$ sequences for each antibody.

The amino acid sequences defining the immunoglobulin light chain variable regions for the antibodies in Example 1 are aligned in FIG. 4. Amino terminal signal peptide sequences (for proper expression/secretion) are not shown. $CDR_1$, $CDR_2$ and $CDR_3$ are identified by boxes. FIG. 5 shows an alignment of the separate $CDR_1$, $CDR_2$, and $CDR_3$ sequences for each antibody.

Table 1 is a concordance chart showing the SEQ ID NO. of each sequence discussed in this Example.

TABLE 1

| SEQ. ID NO. | Nucleic Acid or Protein |
|---|---|
| 1 | 04D01 Heavy Chain Variable Region-nucleic acid |
| 2 | 04D01 Heavy Chain Variable Region-protein |
| 3 | 04D01 Light (kappa) Chain Variable Region-nucleic acid |
| 4 | 04D01 Light (kappa) Chain Variable Region-protein |
| 5 | 04D01 Heavy Chain $CDR_1$ |
| 6 | 04D01 Heavy Chain $CDR_2$ |
| 7 | 04D01 Heavy Chain $CDR_3$ |
| 8 | 04D01 Light (kappa) Chain $CDR_1$ |
| 9 | 04D01 Light (kappa) Chain $CDR_2$ |
| 10 | 04D01 Light (kappa) Chain $CDR_3$ |
| 11 | 09D03 Heavy Chain Variable Region-nucleic acid |
| 12 | 09D03 Heavy Chain Variable Region-protein |
| 13 | 09D03 Light (kappa) Chain Variable Region-nucleic acid |
| 14 | 09D03 Light (kappa) Chain Variable Region-protein |
| 15 | 09D03 Heavy Chain $CDR_1$ |
| 16 | 09D03 Heavy Chain $CDR_2$ |
| 17 | 09D03 Heavy Chain $CDR_3$ |
| 18 | 09D03 Light (kappa) Chain $CDR_1$ |
| 19 | 09D03 Light (kappa) Chain $CDR_2$ |

TABLE 1-continued

| SEQ. ID NO. | Nucleic Acid or Protein |
|---|---|
| 20 | 09D03 Light (kappa) Chain $CDR_3$ |
| 21 | 11G01 Heavy Chain Variable Region-nucleic acid |
| 22 | 11G01 Heavy Chain Variable Region-protein |
| 23 | 11G01 Light (kappa) Chain Variable Region-nucleic acid |
| 24 | 11G01 Light (kappa) Chain Variable Region-protein |
| 25 | 11G01 Heavy Chain $CDR_1$ |
| 26 | 11G01 Heavy Chain $CDR_2$ |
| 27 | 11G01 Heavy Chain $CDR_3$ |
| 28 | 11G01 Light (kappa) Chain $CDR_1$ |
| 9 | 11G01 Light (kappa) Chain $CDR_2$ |
| 29 | 11G01 Light (kappa) Chain $CDR_3$ |
| 30 | 12A07 Heavy Chain Variable Region-nucleic acid |
| 31 | 12A07 Heavy Chain Variable Region-protein |
| 32 | 12A07 Light (kappa) Chain Variable Region-nucleic acid |
| 33 | 12A07 Light (kappa) Chain Variable Region-protein |
| 34 | 12A07 Heavy Chain $CDR_1$ |
| 35 | 12A07 Heavy Chain $CDR_2$ |
| 36 | 12A07 Heavy Chain $CDR_3$ |
| 8 | 12A07 Light (kappa) Chain $CDR_1$ |
| 9 | 12A07 Light (kappa) Chain $CDR_2$ |
| 10 | 12A07 Light (kappa) Chain $CDR_3$ |
| 37 | 18H02 Heavy Chain Variable Region-nucleic acid |
| 38 | 18H02 Heavy Chain Variable Region-protein |
| 39 | 18H02 Light (kappa) Chain Variable Region-nucleic acid |
| 40 | 18H02 Light (kappa) Chain Variable Region-protein |
| 41 | 18H02 Heavy Chain $CDR_1$ |
| 42 | 18H02 Heavy Chain $CDR_2$ |
| 43 | 18H02 Heavy Chain $CDR_3$ |
| 44 | 18H02 Light (kappa) Chain $CDR_1$ |
| 45 | 18H02 Light (kappa) Chain $CDR_2$ |
| 46 | 18H02 Light (kappa) Chain $CDR_3$ |
| 47 | 22A02 Heavy Chain Variable Region-nucleic acid |
| 48 | 22A02 Heavy Chain Variable Region-protein |
| 49 | 22A02 Light (kappa) Chain Variable Region-nucleic acid |
| 50 | 22A02 Light (kappa) Chain Variable Region-protein |
| 51 | 22A02 Heavy Chain $CDR_1$ |
| 52 | 22A02 Heavy Chain $CDR_2$ |
| 36 | 22A02 Heavy Chain $CDR_3$ |
| 8 | 22A02 Light (kappa) Chain $CDR_1$ |
| 9 | 22A02 Light (kappa) Chain $CDR_2$ |
| 10 | 22A02 Light (kappa) Chain $CDR_3$ |
| 53 | 24C05 Heavy Chain Variable Region-nucleic acid |

TABLE 1-continued

| SEQ. ID NO. | Nucleic Acid or Protein |
|---|---|
| 54 | 24C05 Heavy Chain Variable Region-protein |
| 55 | 24C05 Light (kappa) Chain Variable Region-nucleic acid |
| 56 | 24C05 Light (kappa) Chain Variable Region-protein |
| 57 | 24C05 Heavy Chain $CDR_1$ |
| 58 | 24C05 Heavy Chain $CDR_2$ |
| 59 | 24C05 Heavy Chain $CDR_3$ |
| 60 | 24C05 Light (kappa) Chain $CDR_1$ |
| 61 | 24C05 Light (kappa) Chain $CDR_2$ |
| 62 | 24C05 Light (kappa) Chain $CDR_3$ |

Mouse monoclonal antibody heavy chain CDR sequences (Kabat, Chothia, and IMGT definitions) are shown in Table 2.

TABLE 2

| | Kabat | | |
|---|---|---|---|
| | CDR1 | **CDR2** | CDR3 |
| 04D01 | SHWLH (SEQ ID NO: 5) | **VLDPSDFYSNYNQNFKG** (SEQ ID NO: 6) | GLLSGDYAMDY (SEQ ID NO: 7) |
| 09D03 | TFGLSVG (SEQ ID NO: 15) | **HIWWDDDKYYNPALKS** (SEQ ID NO: 16) | IGADALPFDY (SEQ ID NO: 17) |
| 11G01 | DHIIH (SEQ ID NO: 25) | **YIYPRDGYIKYNEKFKG** (SEQ ID NO: 26) | GYYYAMDY (SEQ ID NO: 27) |
| 12A07 | SYWMH (SEQ ID NO: 34) | **MIDPSDVYTNYNPKFKG** (SEQ ID NO: 35) | NYSGDY (SEQ ID NO: 36) |
| 18H02 | TYGMS (SEQ ID NO: 41) | **WINTYSGVPTYADDFKG** (SEQ ID NO: 42) | GRDGYQVAWFAY (SEQ ID NO: 43) |
| 22A02 | NYWMH (SEQ ID NO: 51) | **MIDPSDSYTNYNPKFKG** (SEQ ID NO: 52) | NYSGDY (SEQ ID NO: 36) |
| 24C05 | DYAMS (SEQ ID NO: 57) | **TISDGGTYTYYPDNVKG** (SEQ ID NO: 58) | EWGDYDGFDY (SEQ ID NO: 59) |
| | Chothia | | |
| | **CDR1** | CDR2 | CDR3 |
| 04D01 | **GYTFTSH** (SEQ ID NO: 63) | DPSDFY (SEQ ID NO: 64) | GLLSGDYAMDY (SEQ ID NO: 7) |
| 09D03 | **GFSLSTFGL** (SEQ ID NO: 65) | WWDDD (SEQ ID NO: 66) | IGADALPFDY (SEQ ID NO: 17) |
| 11G01 | **GYTFTDH** (SEQ ID NO: 67) | YPRDGY (SEQ ID NO: 68) | GYYYAMDY (SEQ ID NO: 27) |
| 12A07 | **GYTFSSY** (SEQ ID NO: 69) | DPSDVY (SEQ ID NO: 70) | NYSGDY (SEQ ID NO: 36) |
| 18H02 | **GYTFTTY** (SEQ ID NO: 71) | NTYSGV (SEQ ID NO: 72) | GRDGYQVAWFAY (SEQ ID NO: 43) |
| 22A02 | **GYTFTNY** (SEQ ID NO: 73) | DPSDSY (SEQ ID NO: 74) | NYSGDY (SEQ ID NO: 36) |
| 24C05 | **GFTFSDY** (SEQ ID NO: 75) | SDGGTY (SEQ ID NO: 76) | EWGDYDGFDY (SEQ ID NO: 59) |
| | IMGT | | |
| | CDR1 | CDR2 | **CDR3** |
| 04D01 | GYTFTSHW (SEQ ID NO: 77) | LDPSDFYS (SEQ ID NO: 78) | **ARGLLSGDYAMDY** (SEQ ID NO: 79) |
| 09D03 | GFSLSTFGLS (SEQ ID NO: 80) | IWWDDDK (SEQ ID NO: 81) | **ARIGADALPFDY** (SEQ ID NO: 82) |
| 11G01 | GYTFTDHI (SEQ ID NO: 83) | IYPRDGYI (SEQ ID NO: 84) | **ARGYYYAMDY** (SEQ ID NO: 85) |
| 12A07 | GYTFSSYW (SEQ ID NO: 86) | IDPSDVYT (SEQ ID NO: 87) | **ARNYSGDY** (SEQ ID NO: 88) |

TABLE 2-continued

| | | | |
|---|---|---|---|
| 18H02 | GYTFTTYG (SEQ ID NO: 89) | INTYSGVP (SEQ ID NO: 90) | **ARGRDGYQVAWFAY** (SEQ ID NO: 91) |
| 22A02 | GYTFTNYW (SEQ ID NO: 92) | IDPSDSYT (SEQ ID NO: 93) | **ARNYSGDY** (SEQ ID NO: 88) |
| 24C05 | GFTFSDYA (SEQ ID NO: 94) | ISDGGTYT (SEQ ID NO: 95) | **AREWGDYDGFDY** (SEQ ID NO: 96) |

Mouse monoclonal antibody Kappa light chain CDR sequences (Kabat, Chothia, and IMGT definitions) are shown in Table 3.

TABLE 3

| Kabat/Chothia | | | |
|---|---|---|---|
| | **CDR1** | **CDR2** | **CDR3** |
| 04D01 | **RSSQSIVHSNGNTYLE** (SEQ ID NO: 8) | **KVSNRFS** (SEQ ID NO: 9) | **FQGSYVPWT** (SEQ ID NO: 10) |
| 09D03 | **RSSKSLLHSNGNTYLY** (SEQ ID NO: 18) | **RMSNLAS** (SEQ ID NO: 19) | **MQHLEYPFT** (SEQ ID NO: 20) |
| 11G01 | **RSSQSIVHSIGNTYLE** (SEQ ID NO: 28) | **KVSNRFS** (SEQ ID NO: 9) | **FQGSHVPFT** (SEQ ID NO: 29) |
| 12A07 | **RSSQSIVHSNGNTYLE** (SEQ ID NO: 8) | **KVSNRFS** (SEQ ID NO: 9) | **FQGSYVPWT** (SEQ ID NO: 10) |
| 18H02 | **ITSTDIDDDMN** (SEQ ID NO: 44) | **EGNTLRP** (SEQ ID NO: 45) | **LQSDNLPYT** (SEQ ID NO: 46) |
| 22A02 | **RSSQSIVHSNGNTYLE** (SEQ ID NO: 8) | **KVSNRFS** (SEQ ID NO: 9) | **FQGSYVPWT** (SEQ ID NO: 10) |
| 24C05 | **RASQEISGYLS** (SEQ ID NO: 60) | **AASTLDS** (SEQ ID NO: 61) | **LQYDSYPYT** (SEQ ID NO: 62) |
| IMGT | | | |
| | CDR1 | CDR2 | CDR3 |
| 04D01 | QSIVHSNGNTY (SEQ ID NO: 97) | KVS | FQGSYVPWT (SEQ ID NO: 10) |
| 09D03 | KSLLHSNGNTY (SEQ ID NO: 98) | RMS | MQHLEYPFT (SEQ ID NO: 20) |
| 11G01 | QSIVHSIGNTY (SEQ ID NO: 99) | KVS | FQGSHVPFT (SEQ ID NO: 29) |
| 12A07 | QSIVHSNGNTY (SEQ ID NO: 97) | KVS | FQGSYVPWT (SEQ ID NO: 10) |
| 18H02 | TDIDDD (SEQ ID NO: 100) | EGN | LQSDNLPYT (SEQ ID NO: 46) |
| 22A02 | QSIVHSNGNTY (SEQ ID NO: 97) | KVS | FQGSYVPWT (SEQ ID NO: 10) |
| 24C05 | QEISGY (SEQ ID NO: 101) | AAS | LQYDSYPYT (SEQ ID NO: 62) |

In Tables 2 and 3, the longest CDR sequences for the immunoglobulin heavy chain and light chain are shown in bold.

To create the complete heavy or kappa chain antibody sequences, each variable sequence above is combined with its respective constant region. For example, a complete heavy chain comprises a heavy variable sequence followed by the murine IgG1 or IgG2b heavy chain constant sequence and a complete kappa chain comprises a kappa variable sequence followed by the murine kappa light chain constant sequence.

```
Nucleic Acid Sequence Encoding the Murine IgG1 Heavy Chain Constant Region
                                                            (SEQ ID NO: 102)
  1   gccaaaacga cacccccatc tgtctatcca ctggcccctg gatctgctgc ccaaactaac

 61   tccatggtga ccctgggatg cctggtcaag ggctatttcc ctgagccagt gacagtgacc

121   tggaactctg gatccctgtc cagcggtgtg cacaccttcc cagctgtcct gcagtctgac

181   ctctacactc tgagcagctc agtgactgtc ccctccagca cctggcccag ccagaccgtc

241   acctgcaacg ttgcccaccc ggccagcagc accaaggtgg acaagaaaat tgtgcccagg

301   gattgtggtt gtaagccttg catatgtaca gtcccagaag tatcatctgt cttcatcttc

361   cccccaaagc ccaaggatgt gctcaccatt actctgactc ctaaggtcac gtgtgttgtg

421   gtagacatca gcaaggatga tcccgaggtc cagttcagct ggtttgtaga tgatgtggag

481   gtgcacacag ctcagacgca accccgggag gagcagttca acagcacttt ccgctcagtc

541   agtgaacttc ccatcatgca ccaggactgg ctcaatggca aggagttcaa atgcagggtc

601   aacagtgcag ctttccctgc ccccatcgag aaaaccatct ccaaaaccaa aggcagaccg

661   aaggctccac aggtgtacac cattccacct cccaaggagc agatggccaa ggataaagtc

721   agtctgacct gcatgataac agacttcttc cctgaagaca ttactgtgga gtggcagtgg

781   aatgggcagc cagcggagaa ctacaagaac actcagccca tcatggacac agatggctct

841   tacttcgtct acagcaagct caatgtgcag aagagcaact gggaggcagg aaatactttc

901   acctgctctg tgttacatga gggcctgcac aaccaccata ctgagaagag cctctcccac

961   tctcctggta aa

Protein Sequence Defining the Murine IgG1 Heavy Chain Constant Region
                                                            (SEQ ID NO: 103)
  1   akttppsvyp lapgsaaqtn smvtlgclvk gyfpepvtvt wnsgslssgv htfpavlqsd

 61   lytlsssvtv psstwpsqtv tcnvahpass tkvdkkivpr dcgckpcict vpevssvfif

121   ppkpkdvlti tltpkvtcvv vdiskddpev qfswfvddve vhtaqtqpre eqfnstfrsv

181   selpimhqdw lngkefkcrv nsaafpapie ktisktkgrp kapqvytipp pkeqmakdkv

241   sltcmitdff peditvewqw ngqpaenykn tqpimdtdgs yfvysklnvq ksnweagntf

301   tcsvlheglh nhhtekslsh spgk

Nucleic Acid Sequence Encoding the Murine IgG2b Heavy Chain Constant Region
                                                            (SEQ ID NO: 104)
  1   gccaaaacaa cacccccatc agtctatcca ctggcccctg ggtgtggaga tacaactggt

 61   tcctctgtga ctctgggatg cctggtcaag ggctacttcc ctgagtcagt gactgtgact

121   tggaactctg gatccctgtc cagcagtgtg cacaccttcc cagctctcct gcagtctgga

181   ctctacacta tgagcagctc agtgactgtc ccctccagca cctggccaag tcagaccgtc

241   acctgcagcg ttgctcaccc agccagcagc accacggtgg acaaaaaact tgagcccagc

301   gggcccattt caacaatcaa cccctgtcct ccatgcaagg agtgtcacaa atgcccagct

361   cctaacctcg agggtggacc atccgtcttc atcttccctc caaatatcaa ggatgtactc

421   atgatctccc tgacacccaa ggtcacgtgt gtggtggtgg atgtgagcga ggatgaccca

481   gacgtccaga tcagctggtt tgtgaacaac gtggaagtac acacagctca gacacaaacc

541   catagagagg attacaacag tactatccgg gtggtcagca ccctccccat ccagcaccag

601   gactggatga gtggcaagga gttcaaatgc aaggtcaaca acaaagacct cccatcaccc
```

-continued

```
661    atcgagagaa ccatctcaaa aattaaaggg ctagtcagag ctccacaagt atacatcttg

721    ccgccaccag cagagcagtt gtccaggaaa gatgtcagtc tcacttgcct ggtcgtgggc

781    ttcaaccctg gagacatcag tgtggagtgg accagcaatg ggcatacaga ggagaactac

841    aaggacaccg caccagtcct agactctgac ggttcttact tcatatatag caagctcaat

901    atgaaaacaa gcaagtggga gaaaacagat tccttctcat gcaacgtgag acacgagggt

961    ctgaaaaatt actacctgaa gaagaccatc tcccggtctc cgggtaaa
```

Protein Sequence Defining the Murine IgG2b Heavy Chain Constant Region (SEQ ID NO: 105)

```
  1    akttppsvyp lapgcgdttg ssvtlgclvk gyfpesvtvt wnsgslsssv htfpallqsg

 61    lytmsssvtv psstwpsqtv tcsvahpass ttvdkkleps gpistinpcp pckechkcpa

121    pnleggpsvf ifppnikdvl misltpkvtc vvvdvseddp dvqiswfvnn vevhtaqtqt

181    hredynstir vvstlpiqhq dwmsgkefkc kvnnkdlpsp iertiskikg lvrapqvyil

241    pppaeqlsrk dvsltclvvg fnpgdisvew tsnghteeny kdtapvldsd gsyfiyskln

301    mktskwektd sfscnvrheg lknyylkkti srspgk
```

Nucleic Acid Sequence Encoding the Murine Kappa Light Chain Constant Region (SEQ ID NO: 106)

```
  1    cgggctgatg ctgcaccaac tgtatccatc ttcccaccat ccagtgagca gttaacatct

 61    ggaggtgcct cagtcgtgtg cttcttgaac aacttctacc ccagagacat caatgtcaag

121    tggaagattg atggcagtga acgacaaaat ggtgtcctga acagttggac tgatcaggac

181    agcaaagaca gcacctacag catgagcage accctcacat tgaccaagga cgagtatgaa

241    cgacataaca gctatacctg tgaggccact cacaagacat caacttcacc cattgtcaag

301    agcttcaaca ggaatgagtg t
```

Protein Sequence Defining the Murine Kappa Light Chain Constant Region (SEQ ID NO: 107)

```
  1    radaaptvsi fppsseqlts ggasvvcfln nfyprdinvk wkidgserqn gvlnswtdqd

 61    skdstysmss tltltkdeye rhnsytceat hktstspivk sfnrnec
```

The following sequences represent the actual or contemplated full length heavy and light chain sequences (i.e., containing both the variable and constant regions sequences) for each antibody described in this Example. Signal sequences for proper secretion of the antibodies are also included at the 5' end of the DNA sequences or the amino terminal end of the protein sequences. The variable region sequences can be ligated to other constant region sequences, to produce active full length IgG heavy and light chains.

Nucleic Acid Sequence Encoding the Full Length Heavy Chain Sequence (Heavy Chain Variable Region and IgG1 Constant Region) of 04D01 (SEQ ID NO: 108)

```
  1    atgggatgga gctgtatcat tgtcctcttg gtatcaacag ctacaggtgt ccactcccag

 61    gtccaactgc agcagcctgg ggctgaactg gtgaggcctg ggacttcagt gaagttgtcc

121    tgcaaggctt ctggctacac cttcaccagc cactggttgc actgggtgaa gcagaggcct

181    ggacaaggcc ttgagtggat cggagtgctt gatccttctg atttttatag taactacaat

241    caaaacttca agggcaaggc cacattgact gtagacacat cctccagcac agcctacatg

301    cagctcagca gcctgacatc tgaggactct gcggtctatt actgtgcacg aggcctacta

361    tccggggact atgctatgga ctactggggt caaggaacct cagtcaccgt ctcctcagcc

421    aaaacgacac ccccatctgt ctatccactg gcccctggat ctgctgccca aactaactcc

481    atggtgaccc tgggatgcct ggtcaagggc tatttccctg agccagtgac agtgacctgg
```

-continued

```
541   aactctggat ccctgtccag cggtgtgcac accttcccag ctgtcctgca gtctgacctc

601   tacactctga gcagctcagt gactgtcccc tccagcacct ggcccagcca gaccgtcacc

661   tgcaacgttg cccacccggc cagcagcacc aaggtggaca agaaaattgt gcccagggat

721   tgtggttgta agccttgcat atgtacagtc ccagaagtat catctgtctt catcttcccc

781   ccaaagccca aggatgtgct caccattact ctgactccta aggtcacgtg tgttgtggta

841   gacatcagca aggatgatcc cgaggtccag ttcagctggt ttgtagatga tgtggaggtg

901   cacacagctc agacgcaacc ccgggaggag cagttcaaca gcactttccg ctcagtcagt

961   gaacttccca tcatgcacca ggactggctc aatggcaagg agttcaaatg cagggtcaac

1021  agtgcagctt tccctgcccc catcgagaaa accatctcca aaaccaaagg cagaccgaag

1081  gctccacagg tgtacaccat tccacctccc aaggagcaga tggccaagga taaagtcagt

1141  ctgacctgca tgataacaga cttcttccct gaagacatta ctgtggagtg gcagtggaat

1201  gggcagccag cggagaacta caagaacact cagcccatca tggacacaga tggctcttac

1261  ttcgtctaca gcaagctcaa tgtgcagaag agcaactggg aggcaggaaa tactttcacc

1321  tgctctgtgt tacatgaggg cctgcacaac caccatactg agaagagcct ctcccactct

1381  cctggtaaa
```

Protein Sequence Defining the Full Length Heavy Chain Sequence (Heavy Chain Variable Region and IgG1 Constant Region) of 04D01

(SEQ ID NO: 109)

```
  1   mgwsciivll vstatgvhsq vqlqqpgael vrpgtsvkls ckasgytfts hwlhwvkqrp

 61   gqglewigvl dpsdfysnyn qnfkgkatlt vdtssstaym qlssltseds avyycargll

121   sgdyamdywg qgtsvtvssa kttppsvypl apgsaaqtns mvtlgclvkg yfpepvtvtw

181   nsgslssgvh tfpavlqsdl ytlsssvtvp sstwpsqtvt cnvahpasst kvdkkivprd

241   cgckpcictv pevssvfifp pkpkdvltit ltpkvtcvvv diskddpevq fswfvddvev

301   htaqtqpree qfnstfrsvs elpimhqdwl ngkefkcrvn saafpapiek tisktkgrpk

361   apqvytippp keqmakdkvs ltcmitdffp editvewqwn gqpaenyknt qpimdtdgsy

421   fvysklnvqk snweagntft csvlheglhn hhtekslshs pgk
```

Nucleic Acid Sequence Encoding the Full Length Light Chain Sequence (Kappa Chain Variable Region and Constant Region) of 04D01

(SEQ ID NO: 110)

```
  1   atgaagttgc ctgttaggct gttggtgctg atgttctgga ttcctgcttc cagcagtgat

 61   gttttgatga cccaaattcc actctccctg cctgtcagtc ttggagatca agcctccatc

121   tcttgcagat ctagtcagag cattgtacat agtaatggaa acacctattt agaatggtac

181   ctgcagaaac caggccagtc tccaaagtcc ctgatctaca aagtttctaa ccgattttct

241   ggggtcccag acaggttcag tggcagtgga tcagggacag atttcacact caagatcagc

301   agagtggagg ctgaggatct gggagtttat tactgctttc aaggttcata tgttccgtgg

361   acgttcggtg gaggcaccaa gctggaaatc aaacgggctg atgctgcacc aactgtatcc

421   atcttcccac catccagtga gcagttaaca tctggaggtg cctcagtcgt gtgcttcttg

481   aacaacttct accccagaga catcaatgtc aagtggaaga ttgatggcag tgaacgacaa

541   aatggtgtcc tgaacagttg gactgatcag gacagcaaag acagcaccta cagcatgagc

601   agcaccctca cattgaccaa ggacgagtat gaacgacata acagctatac ctgtgaggcc

661   actcacaaga catcaacttc acccattgtc aagagcttca acaggaatga gtgt
```

-continued

Protein Sequence Defining the Full Length Light Chain Sequence (Kappa Chain Variable Region and Constant Region) of 04D01

(SEQ ID NO: 111)

```
  1 mklpvrllvl mfwipasssd vlmtqiplsl pvslgdqasi scrssqsivh sngntylewy
 61 lqkpgqspks liykvsnrfs gvpdrfsgsg sgtdftlkis rveaedlgvy ycfqgsyvpw
121 tfgggtklei kradaaptvs ifppsseqlt sggasvvcfl nnfyprdinv kwkidgserq
181 ngvlnswtdq dskdstysms stltltkdey erhnsytcea thktstspiv ksfnrnec
```

Nucleic Acid Sequence Encoding the Full Length Heavy Chain Sequence (Heavy Chain Variable Region and IgG2b Constant Region) of 09D03

(SEQ ID NO: 112)

```
   1 atgggcaggc ttacttcttc attcctgtta ctgattgtcc ctgcatatgt cctgtcccag
  61 gttactctaa aagagtctgg ccctgggata ttgcggccct cccagaccct cagtctgact
 121 tgttctttct ctgggttttc actgagcact tttggtttga gtgtaggctg gattcgtcag
 181 ccttcaggga agggtctgga gtggctggca cacatttggt gggatgatga taagtactat
 241 aacccagccc ttaagagtcg gctcacaatc tccaaggata cctccaaaaa ccaggtattc
 301 ctcaagatcg ccaatgtgga cactgcagat actgccacat actactgtgc tcgaataggg
 361 gcggacgccc ttccttttga ctactggggc caaggcacca ctctcacagt ctcctcagcc
 421 aaaacaacac ccccatcagt ctatccactg gcccctgggt gtggagatac aactggttcc
 481 tccgtgacct ctgggtgcct ggtcaagggg tacttccctg agccagtgac tgtgacttgg
 541 aactctggat ccctgtccag cagtgtgcac accttcccag ctctcctgca gtctggactc
 601 tacactatga gcagctcagt gactgtcccc tccagcacct ggccaagtca gaccgtcacc
 661 tgcagcgttg ctcacccagc cagcagcacc acggtggaca aaaaacttga gcccagcggg
 721 cccatttcaa caatcaaccc ctgtcctcca tgcaaggagt gtcacaaatg cccagctcct
 781 aacctcgagg gtggaccatc cgtcttcatc ttccctccaa atatcaagga tgtactcatg
 841 atctccctga cacccaaggt cacgtgtgtg gtggtggatg tgagcgagga tgacccagac
 901 gtccagatca gctggtttgt gaacaacgtg gaagtacaca cagctcagac acaaacccat
 961 agagaggatt acaacagtac tatccgggtg gtcagcaccc tccccatcca gcaccaggac
1021 tggatgagtg gcaaggagtt caaatgcaag gtgaacaaca aagacctccc atcacccatc
1081 gagagaacca tctcaaaaat taaagggcta gtcagagctc cacaagtata cactttgccg
1141 ccaccagcag agcagttgtc caggaaagat gtcagtctca cttgcctggt cgtgggcttc
1201 aaccctggag acatcagtgt ggagtggacc agcaatgggc atacagagga gaactacaag
1261 gacaccgcac cagttcttga ctctgacggt tcttacttca tatatagcaa gctcaatatg
1321 aaaacaagca agtgggagaa aacagattcc ttctcatgca acgtgagaca cgagggtctg
1381 aaaaattact acctgaagaa gaccatctcc cggtctccgg gtaaa
```

Protein Sequence Defining the Full Length Heavy Chain Sequence (Heavy Chain Variable Region and IgG2b Constant Region) of 09D03

(SEQ ID NO: 113)

```
  1 mgrltssfll livpayvlsq vtlkesgpgi lrpsqtlslt csfsgfslst fglsvgwirq
 61 psgkglewla hiwwdddkyy npalksrlti skdtsknqvf lkianvdtad tatyycarig
121 adalpfdywg qgttltvssa kttppsvypl apgcgdttgs svtsgclvkg yfpepvtvtw
181 nsgslsssvh tfpallqsgl ytmsssvtvp sstwpsqtvt csvahpasst tvdkklepsg
241 pistinpcpp ckechkcpap nleggpsvfi fppnikdvlm isltpkvtcv vvdvseddpd
301 vqiswfvnnv evhtaqtqth redynstirv vstlpiqhqd wmsgkefkck vnnkdlpspi
361 ertiskikgl vrapqvytlp ppaeqlsrkd vsltclvvgf npgdisvewt snghteenyk
421 dtapvldsdg syfiyskinm ktskwektds fscnvrhegl knyylkktis rspgk
```

-continued

Nucleic Acid Sequence Encoding the Full Length Light Chain Sequence (Kappa Chain Variable Region and Constant Region) of 09D03

(SEQ ID NO: 114)

```
  1 atgaggtgcc tagctgagtt cctggggctg cttgtgctct ggatccctgg agccattggg

 61 gatattgtgt tgactcagac tgcaccctct gtacctgtca ctcctggaga gtcagtatcc

121 atctcctgca ggtctagtaa gagtctcctg catagtaatg gcaacactta cttgtattgg

181 ttcctgcaga ggccaggcca gtctcctcag ctcctgatat atcggatgtc caaccttgcc

241 tcaggagtcc cagacaggtt cagtggcagt gggtcaggaa ctgctttcac actgagaatc

301 agtagagtgg aggctgagga tgtgggtgtt tattactgta tgcaacatct agaatatcct

361 ttcacgttcg gctcggggac aaagttggaa ataaaacggg ctgatgctgc accaactgta

421 tccatcttcc caccatccag tgagcagtta acatctggag gtgcctcagt cgtgtgcttc

481 ttgaacaact tctaccccag agacatcaat gtcaagtgga agattgatgg cagtgaacga

541 caaaatggtg tcctgaacag ttggactgat caggacagca aagacagcac ctacagcatg

601 agcagcaccc tcacattgac caaggacgag tatgaacgac ataacagcta tacctgtgag

661 gccactcaca agacatcaac ttcacccatt gtcaagagct tcaacaggaa tgagtgt
```

Protein Sequence Defining the Full Length Light Chain Sequence (Kappa Chain Variable Region and Constant Region) of 09D03

(SEQ ID NO: 115)

```
  1 mrclaeflgl lvlwipgaig divltqtaps vpvtpgesvs iscrssksll hsngntylyw

 61 flqrpgqspq lliyrmsnla sgvpdrfsgs gsgtaftlri srveaedvgv yycmqhleyp

121 ftfgsgtkle ikradaaptv sifppsseql tsggasvvcf lnnfyprdin vkwkidgser

181 qngvlnswtd qdskdstysm sstltltkde yerhnsytce athktstspi vksfnrnec
```

Nucleic Acid Sequence Encoding the Full Length Heavy Chain Sequence (Heavy Chain Variable Region and IgG1 Constant Region) of 11G01

(SEQ ID NO: 116)

```
   1 atggaatgga gctgggtctc tctcttcttc ctgtcagtaa ctacaggtgt ccactcccag

  61 gttcagctgc aacagtctga cgctgagttg gtgaaacctg gagcttcagt gaagatatcc

 121 tgcaaggttt ctggctacac cttcactgac catattattc actggatgaa gcagaggcct

 181 gaacagggcc tggaatggat tggatatatt tatcctagag atggttatat taagtacaat

 241 gagaagttca agggcaaggc cacattgact gcagacaaat cctccagcac agcctacatg

 301 caggtcaaca gcctgacatc tgaggactct gcagtctatt tctgtgcaag ggttactat

 361 tatgctatgg actactgggg tcaaggaacc tcagtcaccg tctcctcagc caaaacgaca

 421 cccccatctg tctatccact ggcccctgga tctgctgccc aaactaactc catggtgacc

 481 ctgggatgcc tggtcaaggg ctatttccct gagccagtga cagtgacctg gaactctgga

 541 tccctgtcca gcggtgtgca caccttccca gctgtcctgc agtctgacct ctacactctg

 601 agcagctcag tgactgtccc ctccagcacc tggcccagcc agaccgtcac ctgcaacgtt

 661 gcccacccgg ccagcagcac caaggtggac aagaaaattg tgcccaggga ttgtggttgt

 721 aagccttgca tatgtacagt cccagaagta tcatctgtct tcatcttccc cccaaagccc

 781 aaggatgtgc tcaccattac tctgactcct aaggtcacgt gtgttgtggt agacatcagc

 841 aaggatgatc ccgaggtcca gttcagctgg tttgtagatg atgtggaggt gcacacagct

 901 cagacgcaac cccgggagga gcagttcaac agcactttcc gctcagtcag tgaacttccc

 961 atcatgcacc aggactggct caatggcaag gagttcaaat gcagggtcaa cagtgcagct

1021 ttccctgccc ccatcgagaa aaccatctcc aaaaccaaag gcagaccgaa ggctccacag

1081 gtgtacacca ttccacctcc caaggagcag atggccaagg ataaagtcag tctgacctgc

1141 atgataacag acttcttccc tgaagacatt actgtggagt ggcagtggaa tggcagcca
```

-continued 1201 gcggagaact acaagaacac tcagcccatc atggacacag atggctctta cttcgtctac 1261 agcaagctca atgtgcagaa gagcaactgg gaggcaggaa atactttcac ctgctctgtg 1321 ttacatgagg gcctgcacaa ccaccatact gagaagagcc tctcccactc tcctggtaaa Protein Sequence Defining the Full Length Heavy Chain Sequence (Heavy Chain Variable Region and IgG1 Constant Region) of 11G01

(SEQ ID NO: 117)

1 mewswvslff lsvttgvhsq vqlqqsdael vkpgasvkis ckvsgytftd hiihwmkqrp 61 eqglewigyi yprdgyikyn ekfkgkatlt adkssstaym qvnsltseds avyfcargyy 121 yamdywgqgt svtvssaktt ppsvyplapg saaqtnsmvt lgclvkgyfp epvtvtwnsg 181 slssgvhtfp avlqsdlytl sssvtvpsst wpsqtvtcnv ahpasstkvd kkivprdcgc 241 kpcictvpev ssvfifppkp kdvltitltp kvtcvvvdis kddpevqfsw fvddvevhta 301 qtqpreeqfn stfrsvselp imhqdwlngk efkcrvnsaa fpapiektis ktkgrpkapq 361 vytipppkeq makdkvsltc mitdffpedi tvewqwngqp aenykntqpi mdtdgsyfvy 421 sklnvqksnw eagntftcsv lheglhnhht ekslshspgk Nucleic Acid Sequence Encoding the Full Length Light Chain Sequence (Kappa Chain Variable Region and Constant Region) of 11G01

(SEQ ID NO: 118)

1 atgaagttgc ctgttaggct gttggtgctg atgttctgga ttcctgcttc cagaagtgat 61 gttttgatga cccaaactcc actctccctg cctgtcagtc ttggagatca agcctccatc 121 tcttgcagat ctagtcagag cattgtacat agtattggaa acacctattt agaatggtac 181 ctgcagaaac caggccagtc tccaaagctc ctgatctaca aagtttccaa ccgattttct 241 ggggtcccag agaggttcag tggcagtgga tcagggacag atttcacact caagatcagc 301 agagtggagg ctgaggatct gggagtttat tactgctttc aaggttcaca tgttccattc 361 acgttcggct cggggacaaa gttggaaata aaacgggctg atgctgcacc aactgtatcc 421 atcttcccac catccagtga gcagttaaca tctggaggtg cctcagtcgt gtgcttcttg 481 aacaacttct accccaaaga catcaatgtc aagtggaaga ttgatggcag tgaacgacaa 541 aatggcgtcc tgaacagttg gactgatcag gacagcaaag acagcaccta cagcatgagc 601 agcaccctca cgttgaccaa ggacgagtat gaacgacata acagctatac ctgtgaggcc 661 actcacaaga catcaacttc acccattgtc aagagcttca acaggaatga gtgt Protein Sequence Defining the Full Length Light Chain Sequence (Kappa Chain Variable Region and Constant Region) of 11G01

(SEQ ID NO: 119)

1 mklpvrllvl mfwipasrsd vlmtqtplsl pvslgdqasi scrssqsivh signtylewy 61 lqkpgqspkl liykvsnrfs gvperfsgsg sgtdftlkis rveaedlgvy ycfqgshvpf 121 tfgsgtklei kradaaptvs ifppsseqlt sggasvvcfl nnfypkdinv kwkidgserq 181 ngvlnswtdq dskdstysms stltltkdey erhnsytcea thktstspiv ksfnrnec Nucleic Acid Sequence Encoding the Full Length Heavy Chain Sequence (Heavy Chain Variable Region and IgG1 Constant Region) of 12A07

(SEQ ID NO: 120)

1 atgggatgga gctgtatcat tgtcctcttg gtatcaacag ctacatgtgt ccactcccag 61 gtccaactgc tgcagcctgg ggctgagctg gtgaggcctg ggacttcagt gaagttgtcc 121 tgcaagactt ctggctacac cttctccage tactggatgc actgggtaaa gcagaggcct 181 ggacaaggcc ttgagtggat cggaatgatt gatccttctg atgtttatac taactacaat 241 ccaaagttca agggcaaggc cacattgact gttgacacat cctccagcac agcctacatg 301 cagctcagca gcctgacatc tgaggactct gcggtctatt actgtgcaag aaactactct 361 ggggactact ggggccaagg caccactctc acagtctcct cagccaaaac gacaccccca -continued

```
 421  tctgtctatc cactggcccc tggatctgct gcccaaacta actccatggt gaccctggga
 481  tgcctggtca agggctattt ccctgagcca gtgacagtga cctggaactc tggatccctg
 541  tccagcggtg tgcacacctt cccagctgtc ctgcagtctg acctctacac tctgagcagc
 601  tcagtgactg tcccctccag cacctggccc agccagaccg tcacctgcaa cgttgcccac
 661  ccggccagca gcaccaaggt ggacaagaaa attgtgccca gggattgtgg ttgtaagcct
 721  tgcatatgta cagtcccaga agtatcatct gtcttcatct tccccccaaa gcccaaggat
 781  gtgctcacca ttactctgac tcctaaggtc acgtgtgttg tggtagacat cagcaaggat
 841  gatcccgagg tccagttcag ctggtttgta gatgatgtgg aggtgcacac agctcagacg
 901  caaccccggg aggagcagtt caacagcact ttccgctcag tcagtgaact tcccatcatg
 961  caccaggact ggctcaatgg caaggagttc aaatgcaggg tcaacagtgc agctttccct
1021  gcccccatcg agaaaaccat ctccaaaacc aaaggcagac cgaaggctcc acaggtgtac
1081  accattccac ctcccaagga gcagatggcc aaggataaag tcagtctgac ctgcatgata
1141  acagacttct tccctgaaga cattactgtg gagtggcagt ggaatgggca gccagcggag
1201  aactacaaga acactcagcc catcatggac acagatggct cttacttcgt ctacagcaag
1261  ctcaatgtgc agaagagcaa ctgggaggca ggaaatactt tcacctgctc tgtgttacat
1321  gagggcctgc acaaccacca tactgagaag agcctctccc actctcctgg taaa
```

Protein Sequence Defining the Full Length Heavy Chain Sequence (Heavy Chain Variable Region and IgG1 Constant Region) of 12A07

(SEQ ID NO: 121)

```
   1  mgwsciivll vstatcvhsq vqllqpgael vrpgtsvkls cktsgytfss ywmhwvkqrp
  61  gqglewigmi dpsdvytnyn pkfkgkatlt vdtssstaym qlssltseds avyycarnys
 121  gdywgqgttl tvssakttpp svyplapgsa aqtnsmvtlg clvkgyfpep vtvtwnsgsl
 181  ssgvhtfpav lqsdlytlss svtvpsstwp sqtvtcnvah passtkvdkk ivprdcgckp
 241  cictvpevss vfifppkpkd vltitltpkv tcvvvdiskd dpevqfswfv ddvevhtaqt
 301  qpreeqfnst frsvselpim hqdwingkef kcrvnsaafp apiektiskt kgrpkapqvy
 361  tipppkeqma kdkvsltcmi tdffpeditv ewqwngqpae nykntqpimd tdgsyfvysk
 421  lnvqksnwea gntftcsvlh eglhnhhtek slshspgk
```

Nucleic Acid Sequence Encoding the Full Length Light Chain Sequence (Kappa Chain Variable Region and Constant Region) of 12A07

(SEQ ID NO: 122)

```
   1  atgaagttgc ctgttaggct gttggtgctg atgttctgga ttcctgcttc cagcagtgat
  61  gttttgatga cccaaattcc actctccctg cctgtcagtc ttggagatca agcctccatc
 121  tcttgtagat ctagtcagag cattgtccat agtaatggaa acacctattt agaatggtac
 181  ctgcagaaac caggccagtc tccaaagctc ctgatctaca aagtttccaa ccgattttct
 241  ggggtcccag acaggttcag tggcagtgga tcagggacag atttcacact caagatcagc
 301  agagtggagg ctgaggatct gggagtttat tactgctttc aaggttcata tgttccgtgg
 361  acgttcggtg gaggcaccaa gctggaaatc aaacgggctg atgctgcacc aactgtatcc
 421  atcttcccac catccagtga gcagttaaca tctggaggtg cctcagtcgt gtgcttcttg
 481  aacaacttct accccagaga catcaatgtc aagtggaaga ttgatggcag tgaacgacaa
 541  aatggtgtcc tgaacagttg gactgatcag gacagcaaag acagcaccta cagcatgagc
 601  agcaccctca cattgaccaa ggacgagtat gaacgacata acagctatac ctgtgaggcc
 661  actcacaaga catcaacttc acccattgtc aagagcttca acaggaatga gtgt
```

-continued

Protein Sequence Defining the Full Length Light Chain Sequence (Kappa Chain Variable Region and Constant Region) of 12A07

(SEQ ID NO: 123)

```
  1  mklpvrllvl mfwipasssd vlmtqiplsl pvslgdqasi scrsssqsivh sngntylewy
 61  lqkpgqspkl liykvsnrfs gvpdrfsgsg sgtdftlkis rveaedlgvy ycfqgsyvpw
121  tfgggtklei kradaaptvs ifppsseqlt sggasvvcfl nnfyprdinv kwkidgserq
181  ngvlnswtdq dskdstysms stltltkdey erhnsytcea thktstspiv ksfnrnec
```

Nucleic Acid Sequence Encoding the Full Length Heavy Chain Sequence (Heavy Chain Variable Region and IgG1 Constant Region) of 18H02

(SEQ ID NO: 124)

```
   1  atgggttggc tgtggaactt gctattcctg atggcagctg cccaaagtgc ccaagcacag
  61  atccagttgg tacagtctgg acctgaactg aagaagcctg gagaggcagt caagatctcc
 121  tgcaagtctt ctgggtatac cttcacaacc tatggaatga gctgggtgaa acaggctcca
 181  ggaagggctt taaagtggat gggctggata aacacctact ctggagtgcc aacatatgct
 241  gatgacttca agggacggtt tgccttctct ttggaatcct ctgccagcac tgcctatttg
 301  cagatcaaca acctcaaaaa tgaggacacg gctacatatt tctgtgcaag agggagggat
 361  ggttaccaag tggcctggtt tgcttactgg ggccaaggga cgctggtcac tgtctctgca
 421  gccaaaacga cacccccatc tgtctatcca ctggcccctg gatctgctgc ccaaactaac
 481  tccatggtga ccctgggatg cctggtcaag ggctatttcc ctgagccagt gacagtgacc
 541  tggaactctg gatccctgtc cagcggtgtg cacaccttcc cagctgtcct gcagtctgac
 601  ctctacactc tgagcagctc agtgactgtc ccctccagca cctggcccag ccagaccgtc
 661  acctgcaacg ttgcccaccc ggccagcagc accaaggtgg acaagaaaat tgtgcccagg
 721  gattgtggtt gtaagccttg catatgtaca gtcccagaag tatcatctgt cttcatcttc
 781  cccccaaagc ccaaggatgt gctcaccatt actctgactc ctaaggtcac gtgtgttgtg
 841  gtagacatca gcaaggatga tcccgaggtc cagttcagct ggtttgtaga tgatgtggag
 901  gtgcacacag ctcagacgca accccgggag gagcagttca acagcacttt ccgctcagtc
 961  agtgaacttc ccatcatgca ccaggactgg ctcaatggca aggagttcaa atgcagggtc
1021  aacagtgcag ctttccctgc ccccatcgag aaaaccatct ccaaaaccaa aggcagaccg
1081  aaggctccac aggtgtacac cattccacct cccaaggagc agatggccaa ggataaagtc
1141  agtctgacct gcatgataac agacttcttc cctgaagaca ttactgtgga gtggcagtgg
1201  aatgggcagc cagcggagaa ctacaagaac actcagccca tcatggacac agatggctct
1261  tacttcgtct acagcaagct caatgtgcag aagagcaact gggaggcagg aaatactttc
1321  acctgctctg tgttacatga gggcctgcac aaccaccata ctgagaagag cctctcccac
1381  tctcctggta aatga
```

Protein Sequence Defining the Full Length Heavy Chain Sequence (Heavy Chain Variable Region and IgG1 Constant Region) of 18H02

(SEQ ID NO: 125)

```
  1  mgwlwnllfl maaaqsaqaq iqlvqsgpel kkpgeavkis ckssgytftt ygmswvkqap
 61  gralkwmgwi ntysgvptya ddfkgrfafs lessastayl qinnlknedt atyfcargrd
121  gyqvawfayw gqgtlvtvsa akttppsvyp lapgsaaqtn smvtlgclvk gyfpepvtvt
181  wnsgslssgv htfpavlqsd lytlsssvtv psstwpsqtv tcnvahpass tkvdkkivpr
241  dcgckpcict vpevssvfif ppkpkdvlti tltpkvtcvv vdiskddpev qfswfvddve
301  vhtaqtqpre eqfnstfrsv selpimhqdw lngkefkcrv nsaafpapie ktisktkgrp
361  kapqvytipp pkeqmakdkv sltcmitdff peditvewqw ngqpaenykn tqpimdtdgs
421  yfvysklnvq ksnweagntf tcsvlheglh nhhtekslsh spgk
```

-continued

Nucleic Acid Sequence Encoding the Full Length Light Chain Sequence (Kappa Chain Variable Region and Constant Region) of 18H02

(SEQ ID NO: 126)

```
  1 atgttctcac tagctcttct cctcagtctt cttctcctct gtgtctctga ttctagggca
 61 gaaacaactg tgacccagtc tccagcatcc ctgtccatgg ctataggaga taaagtcacc
121 atcagatgca taaccagcac tgatattgat gatgatatga actggttcca gcagaagcca
181 ggggaacctc ctaagctcct tatttcagaa ggcaatactc ttcgtcctgg agtcccatcc
241 cgattctccg gcagtggcta tggtacagat tttattttta caattgaaaa catgctctct
301 gaagatgttg cagattacta ctgtttgcaa agtgataact tgccgtacac gttcggaggg
361 gggaccaagc tggaaataaa acgggctgat gctgcaccaa ctgtatccat cttcccacca
421 tccagtgagc agttaacatc tggaggtgcc tcagtcgtgt gcttcttgaa caacttctac
481 cccagagaca tcaatgtcaa gtggaagatt gatggcagtg aacgacaaaa tggtgtcctg
541 aacagttgga ctgatcagga cagcaaagac agcacctaca gcatgagcag caccctcaca
601 ttgaccaagg acgagtatga acgacataac agctatacct gtgaggccac tcacaagaca
661 tcaacttcac ccattgtcaa gagcttcaac aggaatgagt gttag
```

Protein Sequence Defining the Full Length Light Chain Sequence (Kappa Chain Variable Region and Constant Region) of 18H02

(SEQ ID NO: 127)

```
  1 mfslalllsl lllcvsdsra ettvtqspas lsmaigdkvt ircitstdid ddmnwfqqkp
 61 geppkllise gntlrpgvps rfsgsgygtd fiftienmls edvadyyclq sdnlpytfgg
121 gtkleikrad aaptvsifpp sseqltsgga svvcflnnfy prdinvkwki dgserqngvl
181 nswtdqdskd stysmsstlt ltkdeyerhn sytceathkt stspivksfn rnec
```

Nucleic Acid Sequence Encoding the Full Length Heavy Chain Sequence (Heavy Chain Variable Region and IgG1 Constant Region) of 22A02

(SEQ ID NO: 128)

```
   1 atgggatgga gctgtatcat tgtcctcttg gtatcaacag ctacaggtgt ccactcccag
  61 gtccaactgc agcagcctgg ggctgagctg gtgaggcctg ggacttcagt gaagttgtcc
 121 tgcaaggctt ctggctacac cttcaccaac tactggatgc actgggtaaa gcagaggcct
 181 ggacaaggcc ttgagtggat cggaatgatt gatccttctg atagttatac taactacaat
 241 ccaaagttca agggtaaggc cacattgact gtagacacat cctccagcac agcctacatg
 301 cagctcagca gcctgacatc tgaggactct gcggtctatt actgtgcaag aaactactct
 361 ggggactact ggggccaagg caccactctc acagtctcct cagccaaaac gacaccccca
 421 tctgtctatc cactggcccc tggatctgct gcccaaacta actccatggt gaccctggga
 481 tgcctggtca agggctattt ccctgagcca gtgacagtga cctggaactc tggatccctg
 541 tccagcggtg tgcacacctt cccagctgtc ctgcagtctg acctctacac tctgagcagc
 601 tcagtgactg tcccctccag cacctggccc agccagaccg tcacctgcaa cgttgcccac
 661 ccggccagca gcaccaaggt ggacaagaaa attgtgccca gggattgtgg ttgtaagcct
 721 tgcatatgta cagtcccaga agtatcatct gtcttcatct tccccccaaa gcccaaggat
 781 gtgctcacca ttactctgac tcctaaggtc acgtgtgttg tggtagacat cagcaaggat
 841 gatcccgagg tccagttcag ctggtttgta gatgatgtgg aggtgcacac agctcagacg
 901 caaccccggg aggagcagtt caacagcact ttccgctcag tcagtgaact tcccatcatg
 961 caccaggact ggctcaatgg caaggagttc aaatgcaggg tcaacagtgc agctttccct
1021 gcccccatcg agaaaaccat ctccaaaacc aaaggcagac cgaaggctcc acaggtgtac
1081 accattccac ctcccaagga gcagatggcc aaggataaag tcagtctgac ctgcatgata
1141 acagacttct tccctgaaga cattactgtg gagtggcagt ggaatgggca gccagcggag
```

-continued 1201 aactacaaga acactcagcc catcatggac acagatggct cttacttcgt ctacagcaag 1261 ctcaatgtgc agaagagcaa ctgggaggca ggaaatactt tcacctgctc tgtgttacat 1321 gagggcctgc acaaccacca tactgagaag agcctctccc actctcctgg taaa Protein Sequence Defining the Full Length Heavy Chain Sequence (Heavy Chain Variable Region and IgG1 Constant Region) of 22A02

(SEQ ID NO: 129)

1 mgwsciivll vstatgvhsq vqlqqpgael vrpgtsvkls ckasgytftn ywmhwvkqrp 61 gqglewigmi dpsdsytnyn pkfkgkatlt vdtssstaym qlssltseds avyycarnys 121 gdywgqgttl tvssakttpp svyplapgsa aqtnsmvtlg clvkgyfpep vtvtwnsgsl 181 ssgvhtfpav lqsdlytlss svtvpsstwp sqtvtcnvah passtkvdkk ivprdcgckp 241 cictvpevss vfifppkpkd vltitltpkv tcvvvdiskd dpevqfswfv ddvevhtaqt 301 qpreeqfnst frsvselpim hqdwlngkef kcrvnsaafp apiektiskt kgrpkapqvy 361 tipppkeqma kdkvsltcmi tdffpeditv ewqwngqpae nykntqpimd tdgsyfvysk 421 lnvqksnwea gntftcsvlh eglhnhhtek slshspgk Nucleic Acid Sequence Encoding the Full Length Light Chain Sequence (Kappa Chain Variable Region and Constant Region) of 22A02

(SEQ ID NO: 130)

1 atgaagttgc ctgttaggct gttggtgctg atgttctgga ttcctgcttc cagcagtgat 61 gttttgatga cccaaactcc actctccctg cctgtcagtc ttggagatca agcctccatc 121 tcttgcagat ctagtcagag cattgtacat agtaatggaa acacctattt agaatggtac 181 ctgcagaaac caggccagtc tccaaagctc ctgatctaca aagtttccaa ccgattttct 241 ggggtcccag acaggttcag tggcagtgga tcagggacag atttcacact caagatcagc 301 agagtggagg ctgaggatct gggagtttat tattgctttc aaggttcata tgttccgtgg 361 acgttcggtg gaggcaccaa gctggaaatc aaacgggctg atgctgcacc aactgtatcc 421 atcttcccac catccagtga gcagttaaca tctggaggtg cctcagtcgt gtgcttcttg 481 aacaacttct accccagaga catcaatgtc aagtggaaga ttgatggcag tgaacgacaa 541 aatggtgtcc tgaacagttg gactgatcag gacagcaaag acagcaccta cagcatgagc 601 agcaccctca cattgaccaa ggacgagtat gaacgacata acagctatac ctgtgaggcc 661 actcacaaga catcaacttc acccattgtc aagagcttca acaggaatga gtgt Protein Sequence Defining the Full Length Light Chain Sequence (Kappa Chain Variable Region and Constant Region) of 22A02

(SEQ ID NO: 131)

1 mklpvrllvl mfwipasssd vlmtqtplsl pvslgdqasi scrssqsivh sngntylewy 61 lqkpgqspkl liykvsnrfs gvpdrfsgsg sgtdftlkis rveaedlgvy ycfqgsyvpw 121 tfgggtklei kradaaptvs ifppsseqlt sggasvvcfl nnfyprdinv kwkidgserq 181 ngvlnswtdq dskdstysms stltltkdey erhnsytcea thktstspiv ksfnrnec Nucleic Acid Sequence Encoding the Full Length Heavy Chain Sequence (Heavy Chain Variable Region and IgG1 Constant Region) of 24C05

(SEQ ID NO: 132)

1 atgaacttcg ggctcagctt gatgttcctt gtccttgtct taaaaggtgt ccagtgtgag 61 gtgcagctgg tggaatctgg gggaggctta gtgaagcctg gagggtccct gaaactctcc 121 tgtgcagcct ctggattcac tttcagtgac tatgccatgt cttgggttcg ccagactccg 181 gaaaagaggc tggagtgggt cgcaaccatt agtgatggtg gtacttacac ctactatcca 241 gacaatgtaa agggccgatt caccatctcc agagacaatg ccaagaacaa cctgtacctg 301 caaatgagcc atctgaagtc tgaggacaca gccatgtatt actgtgcaag agaatggggt 361 gattacgacg gatttgacta ctggggccaa ggcaccactc tcacagtctc ctcggccaaa -continued

```
 421  acgacacccc catctgtcta tccactggcc cctggatctg ctgcccaaac taactccatg
 481  gtgaccctgg gatgcctggt caagggctat ttccctgagc cagtgacagt gacctggaac
 541  tctggatccc tgtccagcgg tgtgcacacc ttcccagctg tcctgcagtc tgacctctac
 601  actctgagca gctcagtgac tgtcccctcc agcacctggc ccagccagac cgtcacctgc
 661  aacgttgccc acccggccag cagcaccaag gtggacaaga aaattgtgcc cagggattgt
 721  ggttgtaagc cttgcatatg tacagtccca gaagtatcat ctgtcttcat cttcccccca
 781  aagcccaagg atgtgctcac cattactctg actcctaagg tcacgtgtgt tgtggtagac
 841  atcagcaagg atgatcccga ggtccagttc agctggtttg tagatgatgt ggaggtgcac
 901  acagctcaga cgcaaccccg ggaggagcag ttcaacagca ctttccgctc agtcagtgaa
 961  cttcccatca tgcaccagga ctggctcaat ggcaaggagt tcaaatgcag ggtcaacagt
1021  gcagctttcc ctgcccccat cgagaaaacc atctccaaaa ccaaaggcag accgaaggct
1081  ccacaggtgt acaccattcc acctcccaag gagcagatgg ccaaggataa agtcagtctg
1141  acctgcatga taacagactt cttccctgaa gacattactg tggagtggca gtggaatggg
1201  cagccagcgg agaactacaa gaacactcag cccatcatgg acacagatgg ctcttacttc
1261  gtctacagca agctcaatgt gcagaagagc aactgggagg caggaaatac tttcacctgc
1321  tctgtgttac atgagggcct gcacaaccac catactgaga agagcctctc ccactctcct
1381  ggtaaa
```

Protein Sequence Defining the Full Length Heavy Chain Sequence (Heavy Chain Variable Region and IgG1 Constant Region) of 24C05

(SEQ ID NO: 133)

```
   1  mnfglslmfl vlvlkgvqce valvesgggl vkpggslkls caasgftfsd yamswvrqtp
  61  ekrlewvati sdggtytyyp dnvkgrftis rdnaknnlyl qmshlksedt amyycarewg
 121  dydgfdywgq gttltvssak ttppsvypla pgsaaqtnsm vtlgclvkgy fpepvtvtwn
 181  sgslssgvht fpavlqsdly tlsssvtvps stwpsqtvtc nvahpasstk vdkkivprdc
 241  gckpcictvp evssvfifpp kpkdvltitl tpkvtcvvvd iskddpevqf swfvddvevh
 301  taqtqpreeq fnstfrsvse lpimhqdwln gkefkcrvns aafpapiekt isktkgrpka
 361  pqvytipppk eqmakdkvsl tcmitdffpe ditvewqwng qpaenykntq pimdtdgsyf
 421  vysklnvqks nweagntftc svlheglhnh htekslshsp gk
```

Nucleic Acid Sequence Encoding the Full Length Light Chain Sequence (Kappa Chain Variable Region and Constant Region) of 24C05

(SEQ ID NO: 134)

```
   1  atggacatga gggttcctgc tcacgttttt ggcttcttgt tgctctggtt tccaggtacc
  61  agatgtgaca tccagatgac ccagtctcca tcctccttat ctgcctctct gggagaaaga
 121  gtcagtctca cttgtcgggc aagtcaggaa attagtggtt acttaagctg gcttcagcag
 181  aaaccagatg gaactattaa acgcctgatc tacgccgcat ccactttaga ttctggtgtc
 241  ccaaaaaggt tcagtggcag taggtctggg tcagattatt ctctcaccat cggcagcctt
 301  gagtctgaag atcttgcaga ctattactgt ctacaatatg atagttatcc gtacacgttc
 361  ggagggggga ccaagctgga aataaaacgg gctgatgctg caccaactgt atccatcttc
 421  ccaccatcca gtgagcagtt aacatctgga ggtgcctcag tcgtgtgctt cttgaacaac
 481  ttctacccca gagacatcaa tgtcaagtgg aagattgatg gcagtgaacg acaaaatggt
 541  gtcctgaaca gttggactga tcaggacagc aaagacagca cctacagcat gagcagcacc
 601  ctcacattga ccaaggacga gtatgaacga cataacagct atacctgtga ggccactcac
 661  aagacatcaa cttcacccat tgtcaagagc ttcaacagga atgagtgt
```

-continued

Protein Sequence Defining the Full Length Light Chain Sequence (Kappa Chain Variable Region and Constant Region) of 24C05

(SEQ ID NO: 135)

```
  1  mdmrvpahvf gflllwfpgt rcdiqmtqsp sslsaslger vsltcrasqe isgylswlqq

 61  kpdgtikrli yaastldsgv pkrfsgsrsg sdysltigsl esedladyyc lqydsypytf

121  gggtkleikr adaaptvsif ppsseqltsg gasvvcflnn fyprdinvkw kidgserqng

181  vlnswtdqds kdstysmsst ltltkdeyer hnsytceath ktstspivks fnrnec
```

For convenience, Table 4 provides a concordance chart showing the correspondence between the full length sequences of the antibodies discussed in this Example with those presented in the Sequence Listing.

TABLE 4

| SEQ ID NO. | Nucleic Acid or Protein |
|---|---|
| 108 | 04D01 Heavy Variable + IgG1 Constant-nucleic acid |
| 109 | 04D01 Heavy Variable + IgG1 Constant-protein |
| 110 | 04D01 Kappa Variable + Constant-nucleic acid |
| 111 | 04D01 Kappa Variable + Constant-protein |
| 112 | 09D03 Heavy Variable + IgG2b Constant-nucleic acid |
| 113 | 09D03 Heavy Variable + IgG2b Constant-protein |
| 114 | 09D03 Kappa Variable + Constant-nucleic acid |
| 115 | 09D03 Kappa Variable + Constant-protein |
| 116 | 11G01 Heavy Variable + IgG1 Constant-nucleic acid |
| 117 | 11G01 Heavy Variable + IgG1 Constant-protein |
| 118 | 11G01 Kappa Variable + Constant-nucleic acid |
| 119 | 11G01 Kappa Variable + Constant-protein |
| 120 | 12A07 Heavy Variable + IgG1 Constant-nucleic acid |
| 121 | 12A07 Heavy Variable + IgG1 Constant-protein |
| 122 | 12A07 Kappa Variable + Constant-nucleic acid |
| 123 | 12A07 Kappa Variable + Constant-protein |
| 124 | 18H02 Heavy Variable + IgG1 Constant-nucleic acid |
| 125 | 18H02 Heavy Variable + IgG1 Constant-protein |
| 126 | 18H02 Kappa Variable + Constant-nucleic acid |
| 127 | 18H02 Kappa Variable + Constant-protein |
| 128 | 22A02 Heavy Variable + IgG1 Constant-nucleic acid |
| 129 | 22A02 Heavy Variable + IgG1 Constant-protein |
| 130 | 22A02 Kappa Variable + Constant-nucleic acid |
| 131 | 22A02 Kappa Variable + Constant-protein |
| 132 | 24C05 Heavy Variable + IgG1 Constant-nucleic acid |
| 133 | 24C05 Heavy Variable + IgG1 Constant-protein |
| 134 | 24C05 Kappa Variable + Constant-nucleic acid |
| 135 | 24C05 Kappa Variable + Constant-protein |

Example 3—Binding Affinities

The binding affinities and kinetics of the binding of monoclonal antibodies 04D01, 09D03, 1 IG01, 12A07, 18H02, 22A02 and 24C05 to recombinant human ErbB3/Fc fusion protein (rhErbB3-Fc) were measured by surface plasmon resonance using a Biacore® T100 (Biacore) instrument.

Rabbit anti-mouse IgGs (Biacore, Cat. No. BR-1008-38) were immobilized on carboxymethylated dextran CM4 sensor chips (Biacore, Cat. No. BR-1005-34) by amine coupling (BIAcore, Cat. No. BR-1000-50) using a standard coupling protocol according to vendor's instructions. The analyses were performed at 25° C., using PBS (Invitrogen, Cat. No. 14040-133) containing 0.05% surfactant P20 (Biacore, Cat. No. BR-1000-54) as running buffer.

The antibodies were captured in individual flow cells at a flow rate of 10 μl/minute. Injection time was varied for each antibody to yield an $R_{max}$ between 30 and 60 RU. Buffer or rhErbB3-Fc diluted in running buffer was injected sequentially over a reference surface (no antibody captured) and the active surface (antibody to be tested) for 300 seconds at 60 μl/minute. The dissociation phase was monitored for up to 3600 seconds. The surface was then regenerated with two 60-seconds injection of 10 mM Glycine-HCl, pH 1.7 (made from Glycine pH 1.5 (Biacore, Cat. No. BR-1003-54) and pH 2.0 (Biacore, Cat. No. BR-1003-55)) at a flow rate of 60 μl/minute. The rhErbB3-Fc concentration range tested was 0.125 nM to 20 nM.

Kinetic parameters were determined using the kinetic function of the BIAevaluation software (Biacore) with double reference subtraction. Kinetic parameters for each antibody, $k_a$ (association rate constant), $k_d$ (dissociation rate constant) and $K_D$ (equilibrium dissociation constant) were determined. Kinetic values of the monoclonal antibodies on rhErbB3-Fc at 25° C. are summarized in Table 5.

TABLE 5

| Antibody | $k_a$ (1/Ms) | Standard Deviation | $k_d$ (1/s) | Standard Deviation | $K_D$ (M) | Standard Deviation | n |
|---|---|---|---|---|---|---|---|
| 04D01 | 3.8E+05 | 3.0E+04 | 9.3E−05 | 1.9E−05 | 2.5E−10 | 5.6E−11 | 5 |
| 09D03 | 2.7E+05 | 3.2E+04 | 2.0E−05 | 1.2E−05 | 8.0E−11 | 5.5E−11 | 3 |
| 11G01 | 2.7E+05 | 9.2E+04 | 2.2E−05 | 9.6E−06 | 9.1E−11 | 5.5E−11 | 4 |
| 12A07 | 6.2E+05 | 8.1E+04 | 1.9E−04 | 1.0E−04 | 3.0E−10 | 1.4E−10 | 3 |
| 18H02 | 2.8E+05 | 3.1E+04 | 2.5E−05 | 8.8E−06 | 9.1E−11 | 3.7E−11 | 4 |
| 22A02 | 7.0E+05 | 8.1E+04 | 2.2E−04 | 1.4E−04 | 3.2E−10 | 2.4E−10 | 3 |
| 24C05 | 1.5E+06 | 2.0E+05 | 9.2E−06 | 3.0E−06 | 6.5E−12 | 2.8E−12 | 4 |

The data in Table 5 demonstrate that the antibodies bind rhErbB3 with a $K_D$ of about 350 pM or less, 250 pM or less, 200 pM or less, 150 pM or less, 100 pM or less, 50 pM or less, or 10 pM or less.

Example 4—Neutralization Activity

In this example, the antibodies produced in Example 1 were tested for ability to inhibit rhErbB3 binding to NRG1-β1 and NRG1-α1. The antibodies were tested by electrochemiluminescence (ECL) assay for inhibition of hErbB3 binding to NRG1-β1. MA2400 96-well standard binding plates (Meso Scale Discovery, Cat. No. L15XA-6) were coated with 50 μl of 0.5 pg/mL rhErbB3/Fc (R&D systems, Cat. No. 348-RB) in PBS (Invitrogen, Cat. No. 14040-133) for overnight at 4° C. with no agitation. The plates then were washed 3 times with PBS+0.1% Tween20 (Sigma P5927) and blocked with 200 μl of PBS containing 5% BSA (Sera Care Life Sciences, Cat. No. AP-4510-80) for 1.5 hour at room temperature. After washing the plates 3 times with PBS, 25 μl of the antibody dilutions were added to the plates for another hour at room temperature with agitation. Ligand NRG1-β1 (R&D Systems, Cat. No. 377-HB, 26 kDa) was added to the wells at the final concentration of 0.25 pg/ml. The plates were washed three times with PBS and incubated with 25 μl of 1 μg/mL biotinylated antibody against human NRG1-β1(R&D systems, Cat. No BAF377) preincubated for one hour with SULTO-TAG Streptavidin (Meso Scale Discovery, Cat. No R32AD-5) for one hour at room temperature with agitation. The plates then were washed 3 times with PBS, and 150 μl of 1× read buffer (Meso Scale Discovery, Cat. No. R92TC-1) was added to each well before the plates were analyzed on a Sector® Imager 2400 (Meso Scale Discovery) instrument.

Figure 6A:
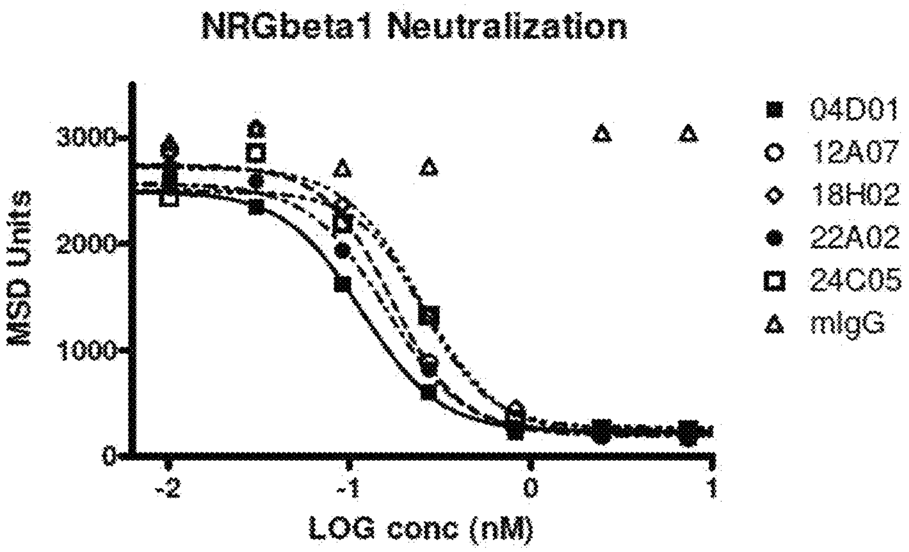
FIGS. 6A and 6B are graphs summarizing results from an experiment to measure the neutralization activity of negative control (murine IgG (Δ)) and anti-ErbB3 monoclonal antibodies 04D01 (■), 12A07 (○), 18H02 (◇), 22A02 (●) and 24C05 (□) to inhibit NRG1-β1 binding to hErbB3 (FIG. 6A) and to measure the enhanced binding of NRG1-β1 to rhErbB3 by the anti-ErbB3 mAb 09D03 (▲) and 11G01 (*) (FIG. 6B).
Figure 6B:
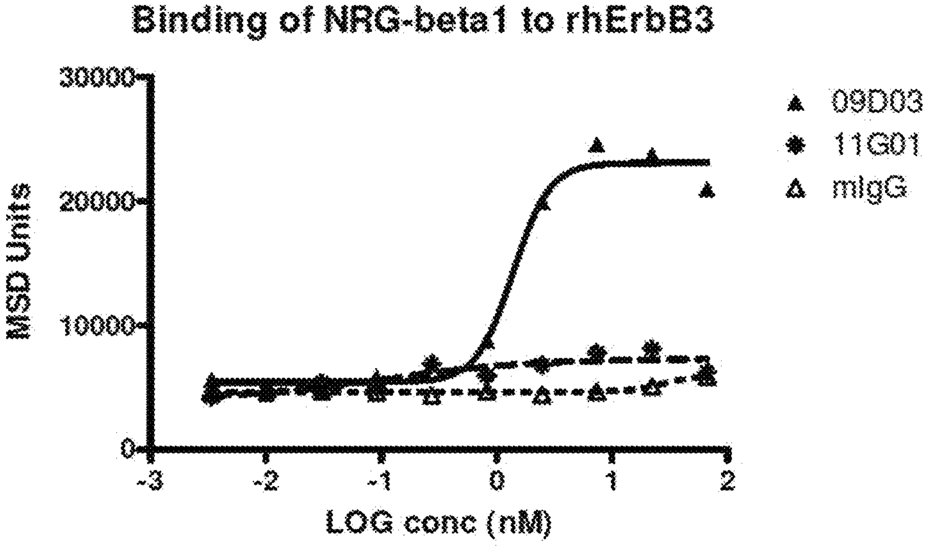

The interaction of NRG1-β1 with ErbB3 was inhibited by antibodies 04D01, 12A07, 18H02, 22A02 and 24C05 (FIG. 6A). The interaction of NRG1-β1 with rhErbB3 was enhanced by antibody 09D03, but not as well as by antibody 11G01 (FIG. 6B).

The murine anti-human ErbB3 antibody $IC_{50}$ values for neutralization of NRG1-β1 binding to rhErbB3 for the antibodies (i.e., 04D01, 12A07, 18H02, 22A02 and 24C05) were calculated and are summarized in Table 6.

TABLE 6

| | $IC_{50}$ (nM) | | |
|---|---|---|---|
| Antibody | Average | Standard Deviation | n |
| 04D01 | 0.2232 | 0.0711 | 4 |
| 12A07 | 0.2351 | 0.0530 | 4 |
| 18H02 | 0.3460 | 0.0873 | 4 |
| 22A02 | 0.2418 | 0.0755 | 4 |
| 24C05 | 0.3367 | 0.0764 | 4 |

The results show that antibodies 04D01, 12A07, 18H02, 22A02, and 24C05 efficiently neutralized NRG1-β1 binding to rhErbB3. Antibodies 09D03 and 11G01 enhanced hNRG1-β1 binding to hErbB3.

The antibodies were tested by ECL assay for inhibition of hErbB3 binding to the second ErbB3 ligand, NRG1-α1. To assay inhibition of binding of NRG1-α1 to rhErbB3, the same method used for NRG1-β1 was used, except for the following changes: concentrations of plated rhErbB3/Fc (R&D 4518-RB) and of ligand NRG1-α1 (Thermo Scientific, RP-317-P1AX) were 1 μg/ml and 1.5 μg/ml, respectively.

Figure 7:
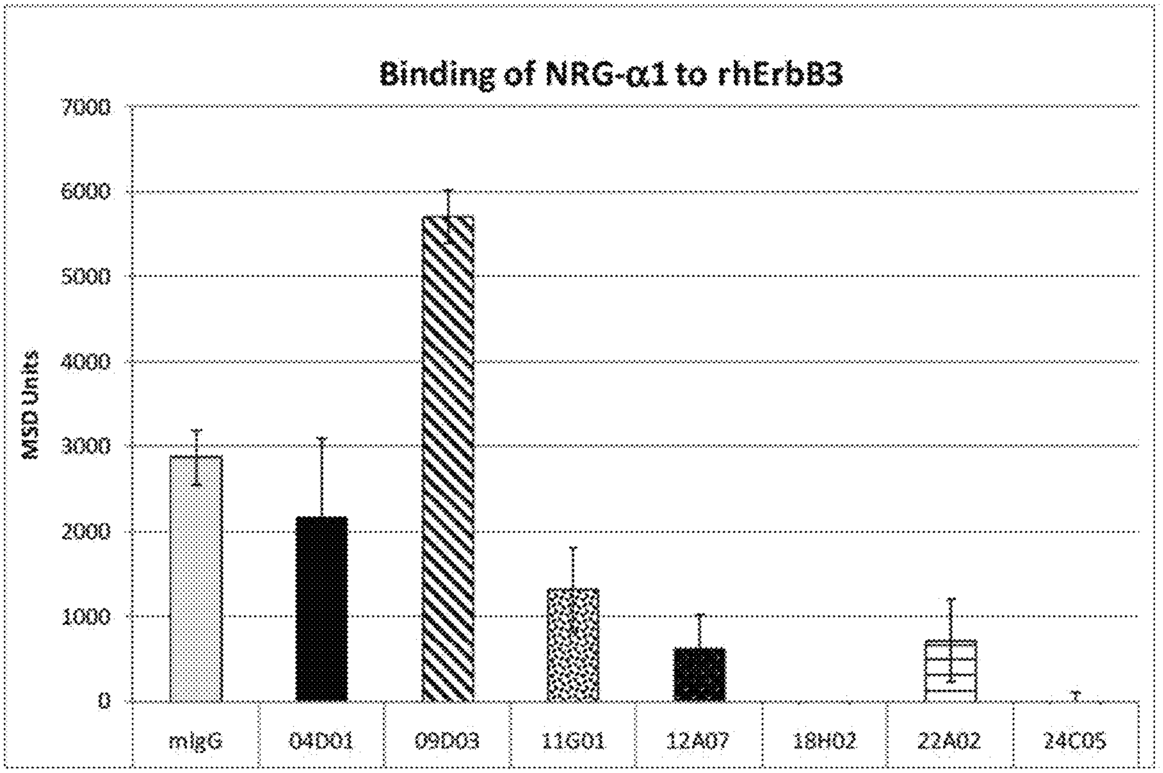
FIG. 7 is a graph summarizing results from an experiment to measure the neutralization activity of negative control (murine IgG) and anti-ErbB3 monoclonal antibodies 04D01, 09D03, 1 IG01, 12A07, 18H02, 22A02 and 24C05 to inhibit NRG1-al binding to rhErbB3.

The interaction of NRG1-α1 with rhErbB3 was inhibited by 11G01, 12A07, 18H02, 22A02, and 24C05 IgG1, and was enhanced by antibody 09D03 (FIG. 7).

Example 5—Binding to ErbB3 Domain II

Figure 8:
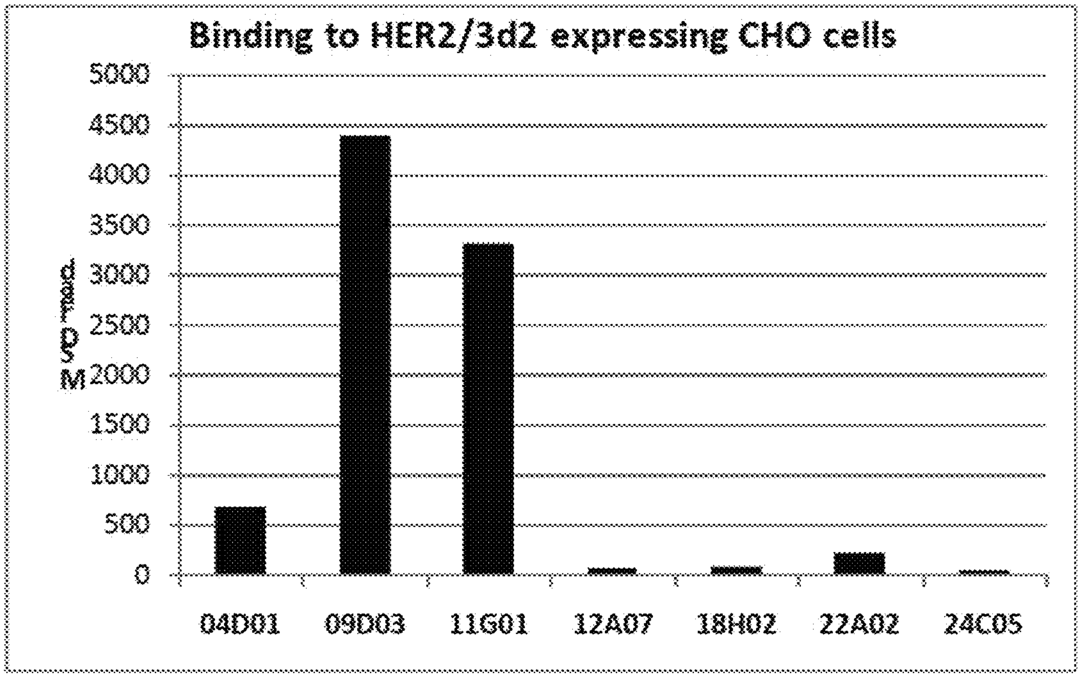
FIG. 8 is a graph summarizing results from an experiment to measure the cell surface recognition of the anti-ErbB3 antibodies of the chimeric protein Her2/3d2 expressed at the surface of CHO cells.

In this example, the antibodies produced in Example 1 were tested for binding to the dimerization domain (domain 2) of hErbB3-ECD. Domain 2 of hErbB3 (118 amino acids, position 210-327) was cloned in place of domain 2 of Her2 (119 amino acids, position AA220-338) into the full-length Her2 receptor. The hybrid construct Her2/3d2 was cloned into pLenti6.3 and packaged by transient transfection of 293T cells into a Lentivirus using the ViraPower™ Lentiviral Support Kit (Invitrogen, Cat. No. K497000). CHO cells were infected with the lentivirus expressing the Her2/3d2 hybrid protein. The binding of the anti-ErbB3 hybridoma supernatants to Her2/3d2 were tested on these engineered CHO cells by ECL with sulfo-tagged anti-mouse antibodies. Data on the binding of the hybridoma supernatants to the chimeric protein Her2/3d2 expressed on the cell surface of CHO cells are summarized in FIG. 8. These results show that antibodies 09D03 and 11G01 bound to the ErbB3 domain II, AA210-327.

Example 6—Anti-Proliferative Activity

This example describes a characterization of the antibodies produced in Example 1 for their ability to inhibit NRG1-β1 dependent proliferation of cells. Antibodies were tested in the BaF/3 cell system engineered to express both human Her2 and ErbB3 and in the human MCF7 breast cancer cells which naturally express both Her2 and ErbB3 and grow in response to NRG1-β1 stimulation.

BaF/3 cells were infected by two lentiviruses engineered to express human Her2 or human ErbB3. Infected cells were selected with blasticidin (15 μg/ml; Invitrogen, Cat. No. R21001) and individual colonies were isolated and tested for expression of both receptors. Her2/ErbB3 expressing clones were maintained in culture under blasticidin selection with [80% RPMI Medium 1640 (GIBCO, Cat. No. 11875-093), 10% fetal bovine serum (GIBCO, Cat. No. 10438-026) and 10% WEHI cell conditioned media {90% ISCOVE's Modified Dulbecco's Medium (GIBCO, Cat. No. 12440053), 10% fetal bovine serum (GIBCO, Cat. No. 10438-026)+2 mM L-glutamine (GIBCO, Cat. No. 25030-081)+0.0025 mM mercaptoethanol (Invitrogen, Cat. No. 21985-023)}]. To screen for antagonistic ErbB3 antibodies, cells were rinsed with PBS, and grown in the absence of blasticidin and WEHI conditioned media. Assays were conducted in a 96-well plate (5,000 cells/well) in the presence of NRG1-β1 (100 ng/ml) and various concentrations of antibodies (0.018-5000 ng/ml in 100 μl final volume). MTT (3-(4,5-Dimethylthiazol-2-yl)-2,5-diphenyltetrazolium bromide) assays were conducted 3-4 days post NRG1-β1 stimulation.

Figure 9:
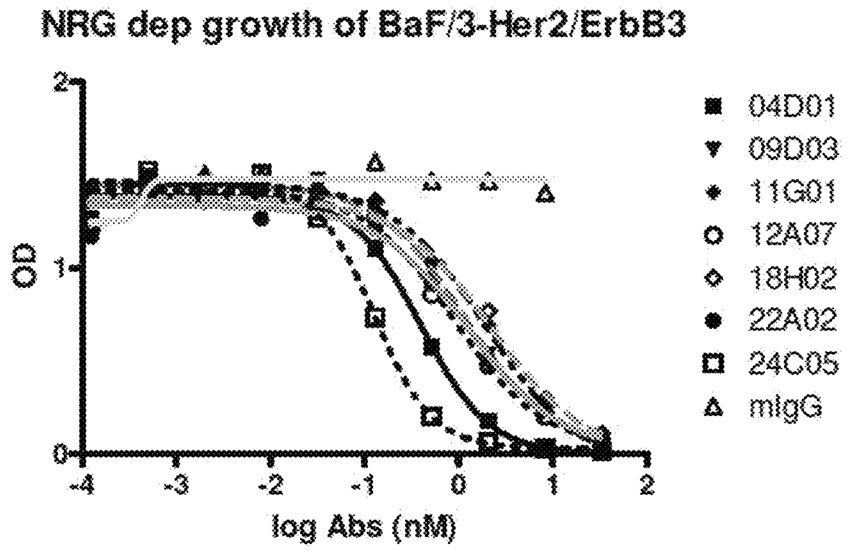
FIG. 9 is a graph summarizing results from an experiment to measure the anti-proliferation activity of negative control IgG (murine IgG (Δ)) and anti-ErbB3 monoclonal antibodies 04D01 (■), 09D03 (▼), 11G01 (♦), 12A07 (○), 18H02 (◇), 22A02 (●) and 24C05 (□) in BaF/3 cells expressing Her2 and ErbB3 in presence of NRG1-β1.

An example of the dose-dependent inhibition of NRG1-β1 dependent cell proliferation of Her2/ErbB3-BaF/3 by murine anti-human ErbB3 antibodies is shown in FIG. 9. Inhibition data of NRG1-β1 dependent Her2/ErbB3-BaF/3 cell line proliferation with monoclonal antibodies (i.e., 04D01, 09D03, 11G01, 12A07, 18H02, 22A02 and 24C05) are summarized in Table 7.

TABLE 7

| Her2/ErbB3-BaF/3, NRG1-β1 dep. Proliferation | | | |
|---|---|---|---|
| Antibody | $IC_{50}$ (nM)-Average | Standard deviation | n |
| 04D01 | 0.373 | 0.061 | 3 |
| 09D03 | 1.395 | 0.268 | 3 |
| 11G01 | 1.934 | 0.116 | 3 |
| 12A07 | 0.854 | 0.059 | 3 |
| 18H02 | 1.930 | 0.276 | 3 |
| 22A02 | 1.291 | 0.151 | 3 |
| 24C05 | 0.145 | 0.031 | 3 |

The results in Table 7 show that antibodies 04D01, 09D03, 11G01, 12A07, 18H02, 22A02 and 24C05 strongly inhibited NRG1-β1-induced proliferation of BaF/3 cells expressing Her2/ErbB3.

MCF7 cells (ATCC, Cat. No. HTB-22) were maintained as recommended by ATCC. Cells were plated at 5,000 cells/well in a 96-well plate. Cells were starved overnight in the absence of serum. The following day, NRG1-β1 (40 ng/ml) and various concentrations of antibodies (12.8 μg/ml-20 μg/ml in 100 μl final volume) were added to the cells. MTT (3-(4,5-Dimethylthiazol-2-yl)-2,5-diphenyltetrazolium bromide) assays were conducted three days post NRG1-β1 stimulation.

Figure 10:
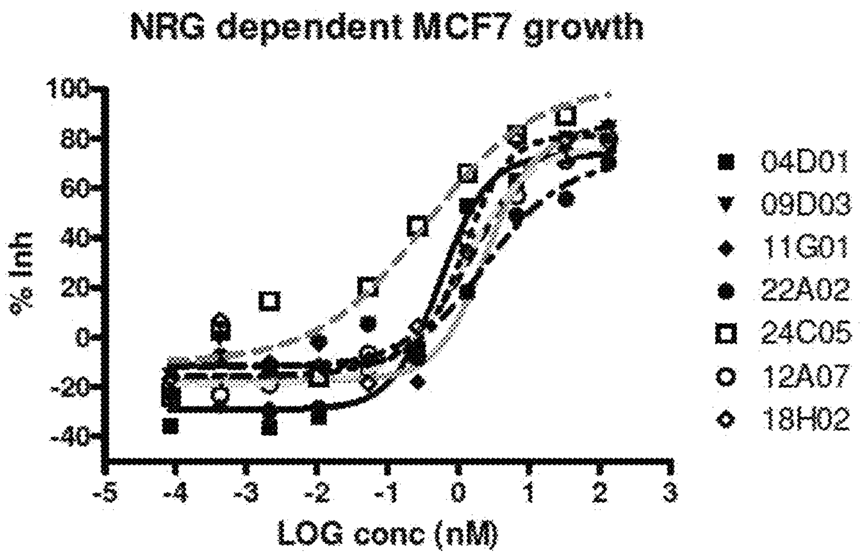
FIG. 10 is a graph summarizing results from an experiment to measure the anti-proliferation activity of anti-ErbB3 monoclonal antibodies 04D01 (■), 09D03 (▼), 11G01 (♦), 12A07 (○), 18H02 (◇), 22A02 (●) and 24C05 (□) in MCF7 cells in the presence of NRG1-β1.

An example of the dose-dependent inhibition of NRG1-β1 dependent proliferation of MCF7 cells by murine anti-human ErbB3 antibodies is shown in FIG. 10. Inhibition data of NRG1-β1 dependent MCF7 cell proliferation with antibodies 04D01, 09D03, 1 IG01, 12A07, 18H02, 22A02 and 24C05 are summarized in Table 8.

TABLE 8

| MCF7 cells, NRG1-β1 dependent Proliferation | | | |
|---|---|---|---|
| Antibody | $IC_{50}$ (nM)-Average | Standard deviation | n |
| 04D01 | 0.47 | 0.23 | 3 |
| 09D03 | 2.28 | 0.60 | 3 |
| 11G01 | 1.98 | 1.34 | 3 |
| 12A07 | 0.74 | 0.48 | 3 |
| 18H02 | 1.00 | 0.20 | 3 |
| 22A02 | 1.62 | 0.60 | 3 |
| 24C05 | 0.39 | 0.04 | 3 |

The results in Table 8 demonstrate that antibodies 04D01, 09D03, 1 IG01, 12A07, 18H02, 22A02, and 24C05 strongly inhibited NRG1-β1-induced proliferation of MCF7 cells.

The antibodies produced in Example 1 were also tested for their ability to inhibit proliferation of ErbB3 expressing human cancer cells. Breast cancer cells SKBR-3 overexpress Her2 and are sensitive to Her2-specific inhibitory antibodies.

SKBR-3 cells (ATCC, Cat. No. HTB-30) were maintained as recommended by ATCC. Cells were plated at 5,000 cells/well in a 96-well plate in the presence of 5 μg/ml of antibodies but without exogenous NRG1-β1. MTT (3-(4,5-Dimethylthiazol-2-yl)-2,5-diphenyltetrazolium bromide) assays were conducted after three days in culture.

Figure 11:
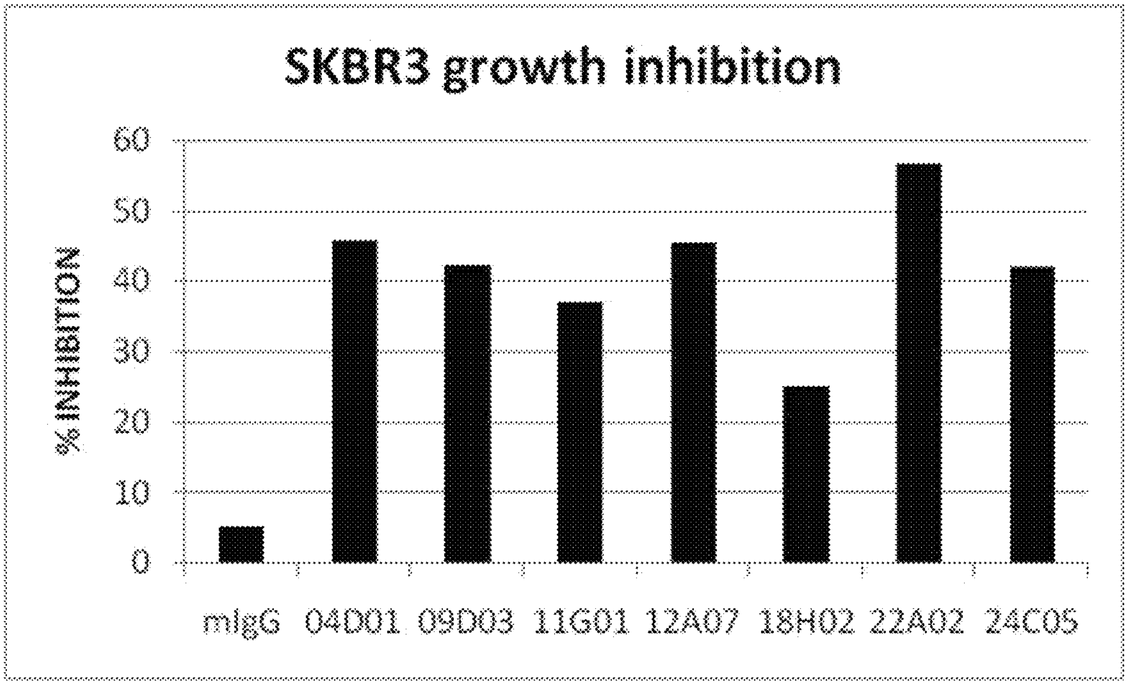
FIG. 11 is a graph summarizing results from an experiment to measure the anti-proliferation activity of negative control (murine IgG) and anti-ErbB3 monoclonal antibodies 04D01, 09D03, 1 IG01, 12A07, 18H02, 22A02 and 24C05 in SKBR-3 cells treated with 5 μg/ml of antibodies in the presence of serum.

An example of inhibition of cell proliferation of SKBR-3 cells by murine anti-human ErbB3 antibodies is shown in FIG. 11. The results in FIG. 11 show that antibodies 04D01, 09D03, 1 IG01, 12A07, 18H02, 22A02 and 24C05 inhibited proliferation of SKBR-3 cells.

Example 7—Inhibition of Downstream Signaling

This example describes a characterization of the antibodies produced in Example 1 for their ability to inhibit NRG1-β1 dependent phosphorylation of ErbB3 and the downstream kinase Akt, as the readout for PI3K activation. These antibodies were also tested for their ability to inhibit steady state phosphorylation of ErbB3 and Akt in exponentially growing cells.

Breast cancer cells SKBR-3 and MCF7 and prostate cancer cells DU145 were maintained as recommended by ATCC. Cells were starved overnight in 0% FBS, treated for one hour with 5 μg/ml of antibody followed by NRG1-β1 stimulation. Lysates were either analyzed by ELISA with the Phospho-ErbB3 kit from R&D Systems (Cat. No DYC1769) or with the Phospho-Akt ELISA kit from Cell Signaling (Cat. No 7143).

Figure 12:
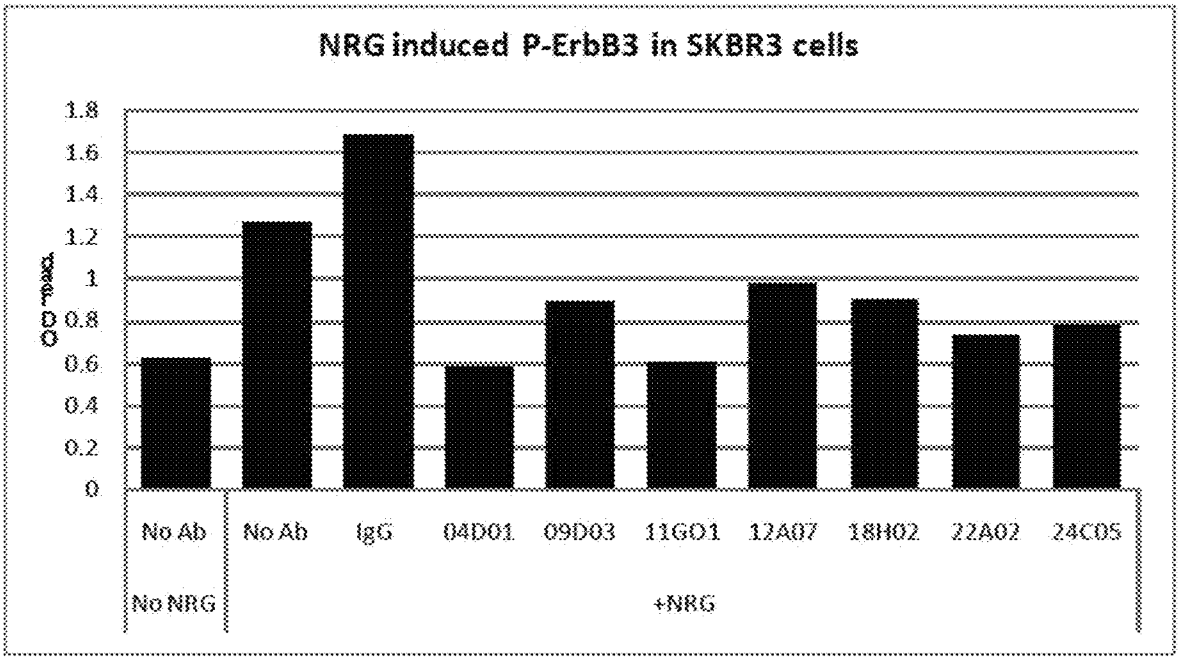
FIG. 12 is graph summarizing results from an experiment to measure the inhibitory activity of negative control IgG and anti-ErbB3 monoclonal antibodies 04D01, 09D03, 1 IG01, 12A07, 18H02, 22A02 and 24C05 on the phosphorylation of ErbB3 induced by NRG in SKBR-3 cells. No antibody/no ligand and no antibody controls are also shown.

An example of the inhibition of the NRG1-β1 induced phosphorylation of ErbB3 in SKBR-3 cells by murine anti-human ErbB3 antibodies is shown in FIG. 12. The results in FIG. 12 demonstrated that antibodies 04D01, 09D03, 11G01, 12A07, 18H02, 22A02 and 24C05 inhibited at least 50% of the phosphorylation of ErbB3 induced by NRG1-β1 in SKBR-3 cells.

Figure 13A:
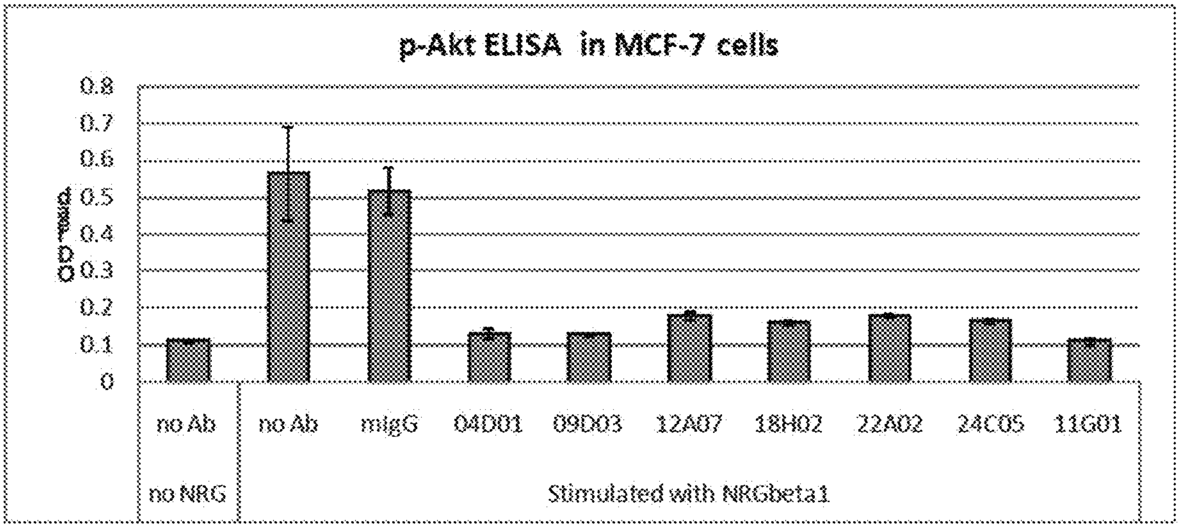
FIGS. 13A and 13B are graphs representing results from an experiment to measure the inhibitory activity of anti-ErbB3 monoclonal antibodies 04D01, 09D03, 11G01, 12A07, 18H02, 22A02 and 24C05 on the phosphorylation of Akt in response to NRG1-β1 in MCF7 cells (FIG. 13A) and in DU145 cells (FIG. 13B) as determined by ELISA. No antibody/no ligand and no antibody controls are also shown.
Figure 13B:
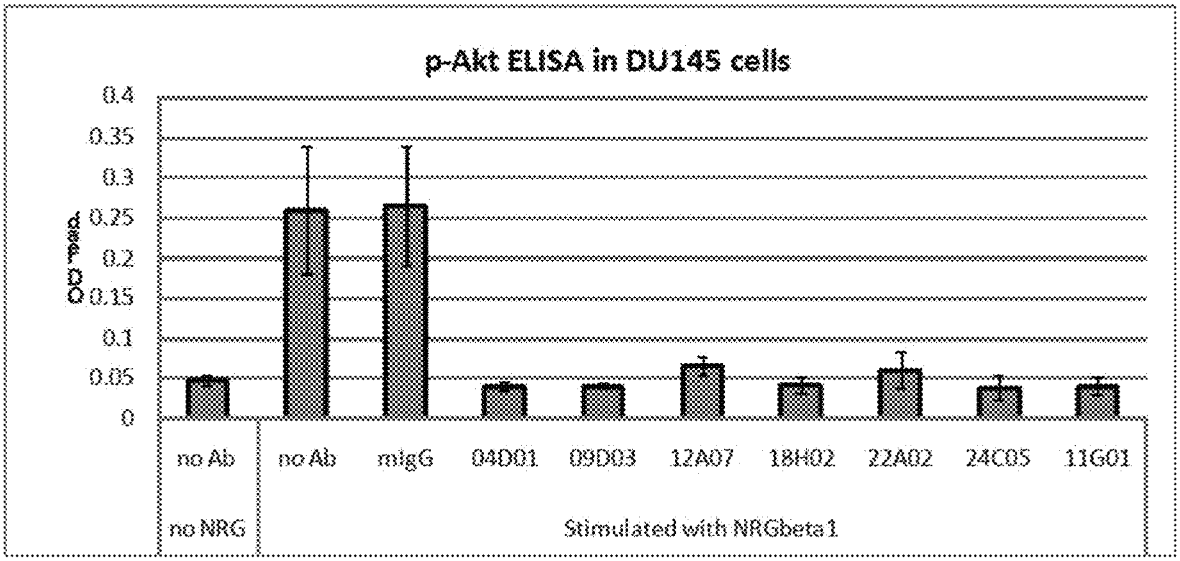

An example of the inhibition of the NRG1-β1 induced phosphorylation of Akt in MCF7 and DU145 cells by murine anti-human ErbB3 antibodies is shown in FIG. 13A and FIG. 13B, respectively. The results in FIGS. 13A and 13B demonstrated that antibodies 04D01, 09D03, 11G01, 12A07, 18H02, 22A02 and 24C05 inhibited at least 80% of the phosphorylation of Akt in response to the NRG1-β1 in both MCF7 and DU145 cells.

The capacity of the anti-ErbB3 antibodies to inhibit the steady state phosphorylation status of ErbB3 and Akt in a breast cancer cell line SKBR-3 and a pancreatic cancer cell line BxPC3 were tested by treating these exponentially growing cells for one hour in presence of antibodies at 5 μg/ml.

Western blot analysis of these experiments demonstrated that antibodies 04D01, 09D03, 11G01, 12A07, 18H02, 22A02 and 24C05 inhibited the steady state level of phosphorylation of Akt and ErbB3 in both SKBR-3 and BxPC3 cells.

Example 8—Inhibition of NRG1-β1-Induced EGFR Phosphorylation

In this example, the antibodies produced in Example 1 were tested for their ability to inhibit NRG1-β1 dependent phosphorylation of EGFR in the ovarian cancer cell line NCI/ADR-RES. NCI/ADR-RES cells (DTP/DCTD NCI tumor repository) were starved overnight in 0% FBS, pretreated with antibody (5 μg/ml) for one hour followed by NRG1-β1 (20 ng/ml) stimulation for 15 minutes. The phosphorylation of EGFR on tyrosine 1068 was analyzed by Western blot. The results of this experiment demonstrated that antibodies 04D01, 09D03, 11G01, 12A07, 18H02, 22A02 and 24C05 inhibited the phosphorylation of EGFR in response to the NRG1-β1 in NCI/ADR-RES cells.

Example 9—Inhibition of EGF-Induced ErbB3 Phosphorylation

In this example, the antibodies produced in Example 1 were tested for their ability to inhibit EGF dependent phosphorylation of ErbB3 in the EGFR overexpressing, epidermoid cancer cell line A431. A431 cells (ATCC, Cat. No CRL-1555) were starved overnight in 0% FBS, pretreated with antibody (5 μg/ml) for one hour followed by EGF (R&D Systems, Cat. No. 236-EG) (50 ng/ml) stimulation for 15 minutes. The phosphorylation of ErbB3 was analyzed by Western blot. The results of this experiment demonstrated that antibodies 04D01, 09D03, 12A07, 18H02, 22A02 and 24C05 inhibited to various extents the phosphorylation of ErbB3 in response to the EGF in A431 cells.

Example 10—Inhibition of NRG1-β1-Induced Her2/ErbB3 Heterodimer Formation

This example describes a characterization of the antibodies produced in Example 1 for their ability to inhibit the formation of the Her2/ErbB3 dimer in response to NRG1-β1 in SKBR-3 cells. Breast cancer cells SKBR-3 were starved overnight in 0% FBS, treated for one hour with 5 μg/ml of antibody followed by NRG1-β1 stimulation (30 ng/ml, 30 min). Lysates were immunoprecipitated with anti-Her2 antibody (R&D Systems, Cat. No. BAF1129) and analyzed by Western blot with polyclonal anti-ErbB3 antibody (Santa Cruz, Cat. No. SC285).

The results of this experiment demonstrated that antibodies 04D01, 09D03, 11G01, 12A07, 18H02, 22A02 and 24C05 inhibited NRG1-β1-induced Her2/ErbB3 dimer formation in SKBR-3 cells.

Example 11—Inhibition of BxPC3 Tumor Xenograft Growth

The ability of murine monoclonal antibodies produced in Example 1 to inhibit tumor growth was tested in a pancreatic BxPC3 xenograft model. Human pancreatic BxPC3 cells were grown in culture in 37° C. in an atmosphere containing 5% CO2, using RMPI medium containing 10% fetal bovine serum. BxPC3 cells were inoculated subcutaneously into the flank of 8-week old female CB.17 SCID mice (Taconic Labs) with $10\times10^{6}$ cells per mouse in 50% matrigel (BD Biosciences, Cat No. 356237). Tumor measurements were taken twice weekly using vernier calipers. Tumor volume was calculated using the formula: width×width×length/2. When tumors reached approximately 200 $mm^3$, the mice were randomized into 9 groups of 10 mice each. One group received PBS and another received human IgG control (huIgG). Each of the other eight groups received one of the antibody, 04D01, 09D03, 18H02, 1 IG01, 24C05, 22A02, or 12A07. All antibodies were dosed at 20 mg/kg body weight, twice per week, by intra-peritoneal injection for 6 weeks. Tumor volumes and mouse body weights were recorded twice per week. Tumor growth inhibition was analyzed using ANOVA and is expressed as percent inhibition compared to the PBS control.

Figure 14:
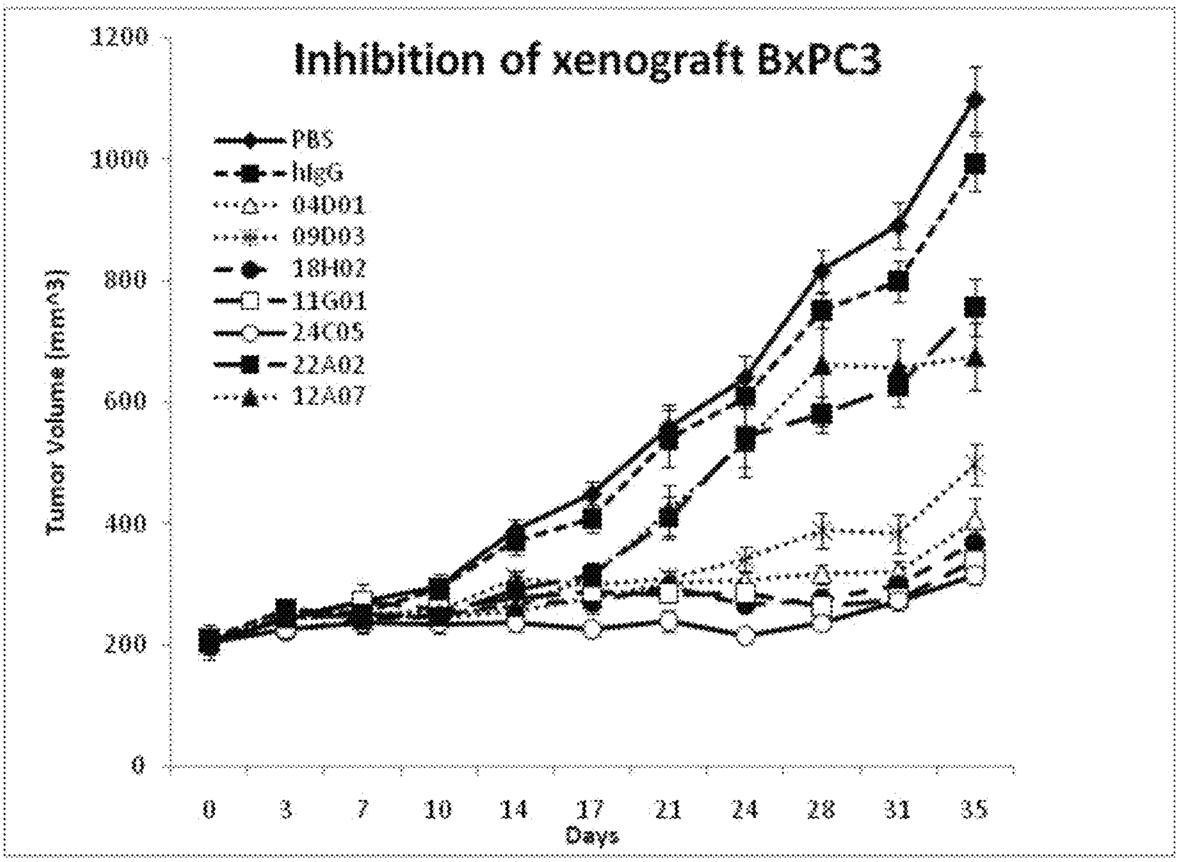
FIG. 14 is a graph summarizing results from an experiment to measure the tumor inhibitory activity of the anti-ErbB3 antibodies 04D01 (Δ), 09D03 (*), 11G01 (□), 12A07 (▲), 18H02 (●), 22A02 (■), 24C05 (○) and a human IgG control (--■--) dosed at 20 mg/kg in a BxPC3 pancreatic tumor xenograft model in CB17 SCID mice (vehicle control, PBS (♦)).

The results in FIG. 14 show that antibody 24C05 inhibited tumor growth by 76% in this model ($p<0.001$). Antibodies 04D01, 18H02 and 11G01 also inhibited tumor growth in this model at 64%, 71%, and 72%, respectively ($p<0.001$). Antibodies 12A07 and 22A02 demonstrated the least activity, i.e., near 40% tumor growth inhibition, while antibody 09D03 gave 60% tumor growth inhibition in this model.

Example 12—Humanization of Anti-ErbB3 Antibodies

A. Construction of Humanized and Chimeric Anti-ErbB3 Antibodies

This Example describes the humanization of the murine antibody designated 24C05, and the characterization of the resulting humanized antibodies. The humanized anti-ErbB3 antibodies were designed using the SUPERHUMANIZATION™ method (Arana Therapeutics Ltd. and Hwang, W. Y. et al. (2005) METHODS 36:35-42) or the CDR grafting method with back mutations (some human framework residues were changed to murine residues) (See e.g., U.S. Pat. Nos. 5,530,101; 5,693,761; 5,693,762; 5,585,089; 6,180,370; 7,022,500). With the exception of heavy chain CDR1, the Kabat CDR definitions were used for CDR grafting onto human frameworks. A combination of Kabat and Chothia definitions were used for grafting heavy CDR1. The designed amino acid sequences were converted to codon-optimized DNA sequences and synthesized by DNA2.0, Inc. to include (in the following order): 5' HindIII restriction site, Kozak consensus sequence, amino terminal signal sequence, humanized variable region, human IgG1 or Kappa constant region, stop codon, and a 3' EcoRI restriction site. Additionally, one humanized heavy chain, Sh24C05 Hv3-11 Heavy IgG1, was mutated using overlap extension PCR to enhance humanization, resulting in the Sh24C05 Hv3-11 N62S heavy chain IgG1. A human IgG2 version of the Sh24C05 Hv3-11 N62S heavy chain was also constructed.

The anti-ErbB3 antibody chains humanized according to the SUPERHUMANIZATION™ method, as described herein, are designated with the prefix "Sh" before the antibody chain name. The anti-ErbB3 antibody chains humanized by the CDR grafting method with back mutations, as described herein, are designated with the prefix "Hu" before the antibody chain name.

Chimeric (murine variable region and human constant region) 24C05 heavy (human IgG1) and light (human Kappa) chains were also constructed. The murine variable regions were fused to the human constant region using overlap extension PCR, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric heavy chains were subcloned into pEE6.4 (Lonza Biologics) via HindIII and EcoRI sites using In-Fusion™ PCR cloning (Clontech). The humanized and chimeric Kappa light chains were subcloned into pEE14.4 (Lonza Biologics) via HindIII and EcoRI sites using In-Fusion™ PCR cloning.

Humanized antibody chains or chimeric antibody chains were transiently transfected into 293T cells to produce antibody. Antibody was either purified or used in cell culture media supernatant for subsequent in vitro analysis. Binding of the chimeric and humanized antibodies to human ErbB3 was measured as described below. The results are summarized in Table 15.

Additionally, some humanized antibody heavy and light chain combinations were stably expressed in CHOKISV cells using the GS System™ (Lonza Biologics) in order to produce large quantities of purified humanized antibody. A single expression vector was constructed by combining pEE6.4 and pEE14.4 based vectors. First, pEE6.4 containing full length humanized heavy chain cDNA was digested with NotI and SalI to isolate the hCMV-MIE promoter+full length humanized heavy chain cDNA+SV40 polyA fragment. This fragment was inserted into the pEE14.4 vector already containing full length humanized light chain cDNA via NotI/SalI sites, thus creating an expression vector that simultaneously expresses heavy and light chains. The combined heavy and light chain vector was linearized and transfected into CHOKlSV cells. Stable clones were selected in the presence of methionine sulfoximine.

Each of the possible combinations of the humanized immunoglobulin heavy chain and immunoglobulin light chain variable regions are set forth below in Table 9.

TABLE 9

| Light Chain Variable Region | Heavy Chain Variable Region |
|---|---|
| Hu24C05 KvA (SEQ ID NO: 174) | Hu24C05 HvA (SEQ ID NO: 162) |
| Hu24C05 KvA (SEQ ID NO: 174) | Sh24C05 Hv3-21 (SEQ ID NO: 156) |
| Hu24C05 KvA (SEQ ID NO: 174) | Sh24C05 Hv3-23 (SEQ ID NO: 158) |
| Hu24C05 KvA (SEQ ID NO: 174) | Sh24C05 Hv3-30 (SEQ ID NO: 160) |
| Hu24C05 KvA (SEQ ID NO: 174) | Sh24C05 Hv3-7 (SEQ ID NO: 150) |
| Hu24C05 KvA (SEQ ID NO: 174) | Sh24C05 Hv3-11 (SEQ ID NO: 152) |
| Hu24C05 KvA (SEQ ID NO: 174) | Sh24C05 Hv3-11 N62S (SEQ ID NO: 154) |
| Sh24C05 Kv1-16 (SEQ ID NO: 166) | Hu24C05 HvA (SEQ ID NO: 162) |
| Sh24C05 Kv1-16 (SEQ ID NO: 166) | Sh24C05 Hv3-21 (SEQ ID NO: 156) |
| Sh24C05 Kv1-16 (SEQ ID NO: 166) | Sh24C05 Hv3-23 (SEQ ID NO: 158) |
| Sh24C05 Kv1-16 (SEQ ID NO: 166) | Sh24C05 Hv3-30 (SEQ ID NO: 160) |
| Sh24C05 Kv1-16 (SEQ ID NO: 166) | Sh24C05 Hv3-7 (SEQ ID NO: 150) |

TABLE 9-continued

| Light Chain Variable Region | Heavy Chain Variable Region |
|---|---|
| Sh24C05 Kv1-16 (SEQ ID NO: 166) | Sh24C05 Hv3-11 (SEQ ID NO: 152) |
| Sh24C05 Kv1-16 (SEQ ID NO: 166) | Sh24C05 Hv3-11 N62S (SEQ ID NO: 154) |
| Sh24C05 Kv1-17 (SEQ ID NO: 168) | Hu24C05 HvA (SEQ ID NO: 162) |
| Sh24C05 Kv1-17 (SEQ ID NO: 168) | Sh24C05 Hv3-21 (SEQ ID NO: 156) |
| Sh24C05 Kv1-17 (SEQ ID NO: 168) | Sh24C05 Hv3-23 (SEQ ID NO: 158) |
| Sh24C05 Kv1-17 (SEQ ID NO: 168) | Sh24C05 Hv3-30 (SEQ ID NO: 160) |
| Sh24C05 Kv1-17 (SEQ ID NO: 168) | Sh24C05 Hv3-7 (SEQ ID NO: 150) |
| Sh24C05 Kv1-17 (SEQ ID NO: 168) | Sh24C05 Hv3-11 (SEQ ID NO: 152) |
| Sh24C05 Kv1-17 (SEQ ID NO: 168) | Sh24C05 Hv3-11 N62S (SEQ ID NO: 154) |
| Sh24C05 Kv1-33 (SEQ ID NO: 170) | Hu24C05 HvA(SEQ ID NO: 162) |
| Sh24C05 Kv1-33 (SEQ ID NO: 170) | Sh24C05 Hv3-21 (SEQ ID NO: 156) |
| Sh24C05 Kv1-33 (SEQ ID NO: 170) | Sh24C05 Hv3-23 (SEQ ID NO: 158) |
| Sh24C05 Kv1-33 (SEQ ID NO: 170) | Sh24C05 Hv3-30 (SEQ ID NO: 160) |
| Sh24C05 Kv1-33 (SEQ ID NO: 170) | Sh24C05 Hv3-7 (SEQ ID NO: 150) |
| Sh24C05 Kv1-33 (SEQ ID NO: 170) | Sh24C05 Hv3-11 (SEQ ID NO: 152) |
| Sh24C05 Kv1-33 (SEQ ID NO: 170) | Sh24C05 Hv3-11 N62S (SEQ ID NO: 154) |
| Sh24C05 Kv1-9 (SEQ ID NO: 164) | Hu24C05 HvA(SEQ ID NO: 162) |
| Sh24C05 Kv1-9 (SEQ ID NO: 164) | Sh24C05 Hv3-21 (SEQ ID NO: 156) |
| Sh24C05 Kv1-9 (SEQ ID NO: 164) | Sh24C05 Hv3-23 (SEQ ID NO: 158) |
| Sh24C05 Kv1-9 (SEQ ID NO: 164) | Sh24C05 Hv3-30 (SEQ ID NO: 160) |
| Sh24C05 Kv1-9 (SEQ ID NO: 164) | Sh24C05 Hv3-7 (SEQ ID NO: 150) |
| Sh24C05 Kv1-9 (SEQ ID NO: 164) | Sh24C05 Hv3-11 (SEQ ID NO: 152) |
| Sh24C05 Kv1-9 (SEQ ID NO: 164) | Sh24C05 Hv3-11 N62S (SEQ ID NO: 154) |
| Sh24C05 Kv1-39 (SEQ ID NO: 172) | Hu24C05 HvA (SEQ ID NO: 162) |
| Sh24C05 Kv1-39 (SEQ ID NO: 172) | Sh24C05 Hv3-21 (SEQ ID NO: 156) |
| Sh24C05 Kv1-39 (SEQ ID NO: 172) | Sh24C05 Hv3-23 (SEQ ID NO: 158) |
| Sh24C05 Kv1-39 (SEQ ID NO: 172) | Sh24C05 Hv3-30 (SEQ ID NO: 160) |
| Sh24C05 Kv1-39 (SEQ ID NO: 172) | Sh24C05 Hv3-7 (SEQ ID NO: 150) |
| Sh24C05 Kv1-39 (SEQ ID NO: 172) | Sh24C05 Hv3-11 (SEQ ID NO: 152) |
| Sh24C05 Kv1-39 (SEQ ID NO: 172) | Sh24C05 Hv3-11 N62S (SEQ ID NO: 154) |

The nucleic acid sequences encoding and the protein sequences defining variable regions of the humanized 24C05 antibodies are summarized below (amino terminal signal peptide sequences are not shown). CDR sequences (Kabat definition) are shown in bold and are underlined in the amino acid sequences.

Nucleic Acid Sequence Encoding the Sh24C05 Hv3-7 Heavy Chain Variable Region (SEQ ID NO: 149)

```
  1   gaggttcagc tggtggaatc tggcggtggg cttgtacaac caggaggctc cctcagactg
 61   agttgtgccg cttcagggtt cacattctcc gactatgcga tgtcatgggt gcgccaagca
121   cccgggaaag gactggagtg ggttgccact atcagcgatg gcggaacgta tacctattac
181   cctgacaatg tgaagggtcg gttcaccatt tccagggata acgcaaagaa cagtctctac
241   ctgcagatga acagcctgag ggctgaggac accgccgtct actactgcgc ccgagaatgg
301   ggagattatg atgggtttga ctattggggc cagggcactt tggtgacagt cagttct
```

Protein Sequence Defining the Sh24C05 Hv3-7 Heavy Chain Variable Region (SEQ ID NO: 150)

1 evqlvesggg lvqpggslrl scaasgftfs <u>dyams</u>wvrqa pgkglewva<u>t isdggtytyy</u>

61 <u>pdnvkg</u>rfti srdnaknsly lqmnslraed tavyycar<u>ew gdydgfdy</u>wg qgtlvtvss Nucleic Acid Sequence Encoding the Sh24C05 Hv3-11 Heavy Chain Variable Region (SEQ ID NO: 151)

```
  1   caagttcagc tggtggaatc tggcggtggg cttgtaaagc caggaggctc cctcagactg
 61   agttgtgccg cttcagggtt cacattctcc gactatgcga tgtcatggat caggcaagca
121   cccgggaaag gactggagtg ggttagcact atcagcgatg gcggaacgta tacctattac
181   cctgacaatg tgaagggtcg gttcaccatt tccagggata acgcaaagaa cagtctctac
241   cttcagatga acagcctgag ggctgaggac accgccgtct actactgcgc ccgagaatgg
301   ggagattatg atgggtttga ctattggggc cagggcactt tggtgacagt cagttct
```

Protein Sequence Defining the Sh24C05 Hv3-11 Heavy Chain Variable Region (SEQ ID NO: 152)

1 qvqlvesggg lvkpggslrl scaasgftfs <u>dyams</u>wirqa pgkglewvs<u>t isdggtytyy</u>

61 <u>pdnvkg</u>rfti srdnaknsly lqmnslraed tavyycar<u>ew gdydgfdy</u>wg qgtlvtvss -continued Nucleic Acid Sequence Encoding the Sh24C05 Hv3-11 N62S Heavy Chain Variable Region (SEQ ID NO: 153)

1 caagttcagc tggtggaatc tggcggtggg cttgtaaagc caggaggctc cctcagactg 61 agttgtgccg cttcagggtt cacattctcc gactatgcga tgtcatggat caggcaagca 121 cccgggaaag gactggagtg ggttagcact atcagcgatg goggaacgta tacctattac 181 cctgactccg tgaagggtcg gttcaccatt tccagggata acgcaaagaa cagtctctac 241 cttcagatga acagcctgag ggctgaggac accgccgtct actactgcgc ccgagaatgg 301 ggagattatg atgggtttga ctattggggc cagggcactt tggtgacagt cagttct Protein Sequence Defining the Sh24C05 Hv3-11 N62S Heavy Chain Variable Region (SEQ ID NO: 154)

1 qvqlvesggg lvkpggslrl scaasgftfs dyamswirqa pgkglewvst isdggtytyy

61 pdsvkgrfti srdnaknsly lqmnslraed tavyycarew gdydgfdywg qgtlvtvss

Nucleic Acid Sequence Encoding the Sh24C05 Hv3-21 Heavy Chain Variable Region (SEQ ID NO: 155)

1 gaggttcagc tggtggaatc tggcggtggg cttgtaaagc caggaggctc cctcagactg 61 agttgtgccg cttcagggtt cacattctcc gactatgcga tgtcatgggt gcgccaagca 121 cccgggaaag gactggagtg ggttagcact atcagcgatg gcggaacgta tacctattac 181 cctgacaatg tgaagggtcg gttcaccatt tccagggata acgcaaagaa cagtctctat 241 ttgcagatga acagcctgag ggctgaggac accgccgtct actactgcgc ccgagaatgg 301 ggagattatg atgggtttga ctattggggc cagggcactt tggtgacagt cagttct Protein Sequence Defining the Sh24C05 Hv3-21 Heavy Chain Variable Region (SEQ ID NO: 156)

1 evqlvesggg lvkpggslrl scaasgftfs dyamswvrqa pgkglewvst isdggtytyy

61 pdnvkgrfti srdnaknsly lqmnslraed tavyycarew gdydgfdywg qgtlvtvss

Nucleic Acid Sequence Encoding the Sh24C05 Hv3-23 Heavy Chain Variable Region (SEQ ID NO: 157)

1 gaggttcagc ttctggaatc tggcggtggg cttgtacagc caggaggctc cctcagactg 61 agttgtgccg cttcagggtt cacattctcc gactatgcga tgtcatgggt gcgccaagca 121 cccgggaaag gactggagtg ggtttcaact atcagcgatg gcggaacgta tacctattac 181 cctgacaatg tgaagggtcg gttcaccatt tccagggata acagcaagaa cacactctat 241 ctccagatga acagcctgag ggctgaggac accgccgtct actactgcgc ccgagaatgg 301 ggagattatg atgggtttga ctattggggc cagggcactt tggtgacagt cagttct Protein Sequence Defining the Sh24C05 Hv3-23 Heavy Chain Variable Region (SEQ ID NO: 158)

1 evqllesggg lvqpggslrl scaasgftfs dyamswvrqa pgkglewvst isdggtytyy

61 pdnvkgrfti srdnskntly lqmnslraed tavyycarew gdydgfdywg qgtlvtvss

Nucleic Acid Sequence Encoding the Sh24C05 Hv3-30 Heavy Chain Variable Region (SEQ ID NO: 159)

1 caggttcagc tggtggaatc tggcggtggg gtagtacaac caggacggtc cctcagactg 61 agttgtgccg cttcagggtt cacattctcc gactatgcga tgtcatgggt gcgccaagca 121 cccgggaaag gactggagtg ggttgccact atcagcgatg gcggaacgta tacctattac 181 cctgacaatg tgaagggtcg gttcaccatt tccagggata actcaaagaa caccctctat 241 ctccaaatga gtagcctgag ggctgaggac accgccgtct actactgcgc ccgagaatgg 301 ggagattatg atgggtttga ctattggggc cagggcactt tggtgacagt cagttct -continued Protein Sequence Defining the Sh24C05 Hv3-30 Heavy Chain Variable Region
(SEQ ID NO: 160)

1 qvqlvesggg vvqpgrslrl scaasgftfs dyamswvrqa pgkglewvat isdggtytyy

61 pdnvkgrfti srdnskntly lqmsslraed tavyycarew gdydgfdywg qgtlvtvss

Nucleic Acid Sequence Encoding the Hu24C05 HvA Heavy Chain Variable Region
(SEQ ID NO: 161)

1 gaggttcagc tggtggaatc tggcggtggg cttgtaaagc caggaggctc cctcagactg 61 agttgtgccg cttcagggtt cacattctcc gactatgcga tgtcatgggt gcgccaagca 121 cccgggaaag gactggagtg ggttgccact atcagcgatg gcggaacgta tacctattac 181 cctgacaatg tgaagggtcg gttcaccatt tccagggata acgcaaagaa cagtctctac 241 cttcagatga acagcctgag ggctgaggac accgccgtct actactgcgc ccgagaatgg 301 ggagattatg atgggtttga ctattggggc cagggcactt tggtgacagt cagttct Protein Sequence Defining the Hu24C05 HvA Heavy Chain Variable Region
(SEQ ID NO: 162)

1 evqlvesggg lvkpggslrl scaasgftfs dyamswvrqa pgkglewvat isdggtytyy

61 pdnvkgrfti srdnaknsly lqmnslraed tavyycarew gdydgfdywg qgtlvtvss

Nucleic Acid Sequence Encoding the Sh24C05 Kv1-9 Kappa Chain Variable Region
(SEQ ID NO: 163)

1 gatattcagt tgacccaatc acctagcttc ctctcagctt ccgtgggcga cagagttacc 61 ataacctgtc gggcaagcca ggagatttct gggtacctgt cctggtacca acagaagccc 121 ggaaaagccc ctaagctgtt gatctatgct gcgtcaacct tggatagcgg tgtcccgagt 181 cgattctccg gttctggctc cggaacagag ttcactctga caatttctag ccttcagcca 241 gaagatttcg ccacgtacta ttgcctccag tacgacagct atccctatac atttgggcag 301 ggcactaaac tggagatcaa a Protein Sequence Defining the Sh24C05 Kv1-9 Kappa Chain Variable Region
(SEQ ID NO: 164)

1 diqltqspsf lsasvgdrvt itcrasqeis gylswyqqkp gkapklliya astldsgvps 61 rfsgsgsgte ftltisslqp edfatyyclq ydsypytfgq gtkleik Nucleic Acid Sequence Encoding the Sh24C05 Kv1-16 Kappa Chain Variable Region
(SEQ ID NO: 165)

1 gatattcaga tgacccaatc acctagcagt ctctcagctt ccgtgggcga cagagttacc 61 ataacctgtc gggcaagcca ggagatttct gggtacctgt cctggtttca acagaagccc 121 ggaaaggccc cgaagagctt gatctatgct gcgtcaacct tggatagcgg tgtcccgagt 181 cgattctccg gttctggctc cggaaccgac tttactctga caatttctag ccttcagcca 241 gaagatttcg ccacgtacta ttgcctccag tacgacagct atccctatac atttgggcag 301 ggcactaaac tggagatcaa a Protein Sequence Defining the Sh24C05 Kv1-16 Kappa Chain Variable Region
(SEQ ID NO: 166)

1 diqmtqspss lsasvgdrvt itcrasqeis gylswfqqkp gkapksliya astldsgvps 61 rfsgsgsgtd ftltisslqp edfatyyclq ydsypytfgq gtkleik Nucleic Acid Sequence Encoding the Sh24C05 Kv1-17 Kappa Chain Variable Region
(SEQ ID NO: 167)

1 gatattcaga tgacccaatc acctagcagt ctctcagctt ccgtgggcga cagagttacc 61 ataacctgtc gggcaagcca ggagatttct gggtacctgt cctggtatca acagaagccc 121 ggaaaagccc caaagaggtt gatctatgct gcgtcaacct tggatagcgg tgtcccgagt 181 cgattctccg gttctggctc cggaaccgag ttcactctga caatttctag ccttcagcca 241 gaagatttcg ccacgtacta ttgcctccag tacgacagct atccctatac atttgggcag 301 ggcactaaac tggagatcaa a -continued Protein Sequence Defining the Sh24C05 Kv1-17 Kappa Chain Variable Region (SEQ ID NO: 168)

```
1    diqmtqspss lsasvgdrvt itcrasqeis gylswyqqkp gkapkrliya astldsgvps
61   rfsgsgsgte ftltisslqp edfatyyclq ydsypytfgq gtkleik
```

Nucleic Acid Sequence Encoding the Sh24C05 Kv1-33 Kappa Chain Variable Region (SEQ ID NO: 169)

```
1    gatattcaga tgacccaatc acctagcagt ctctcagctt ccgtgggcga cagagttacc
61   ataacctgtc gggcaagcca ggagatttct gggtacctgt cctggtacca acagaagccc
121  ggaaaggccc ccaagctgtt gatctatgct gcgtcaacct tggatagcgg tgtcccgagt
181  cgattctccg gttctggctc cggaacagac tttactttta caatttctag ccttcagcca
241  gaggacatcg ccacgtacta ttgcctccag tacgacagct atccctatac atttgggcag
301  ggcactaaac tggagatcaa a
```

Protein Sequence Defining the Sh24C05 Kv1-33 Kappa Chain Variable Region (SEQ ID NO: 170)

```
1    diqmtqspss lsasvgdrvt itcrasqeis gylswyqqkp gkapklliya astldsgvps
61   rfsgsgsgtd ftftisslqp ediatyyclq ydsypytfgq gtkleik
```

Nucleic Acid Sequence Encoding the Sh24C05 Kv1-39 Kappa Chain Variable Region (SEQ ID NO: 171)

```
1    gatattcaga tgacccaatc acctagcagt ctctcagctt ccgtgggcga cagagttacc
61   ataacctgtc gggcaagcca ggagatttct gggtacctgt cctggtatca acagaagccc
121  ggaaaagccc ctaagctgtt gatctatgct gcgtcaacct tggatagcgg tgtcccgagt
181  cgattctccg gttctggctc cggaactgac ttcactctga caatttctag ccttcagcca
241  gaagatttcg ccacgtacta ttgcctccag tacgacagct atccctatac atttgggcag
301  ggcactaaac tggagatcaa a
```

Protein Sequence Defining the Sh24C05 Kv1-39 Kappa Chain Variable Region (SEQ ID NO: 172)

```
1    diqmtqspss lsasvgdrvt itcrasqeis gylswyqqkp gkapklliya astldsgvps
61   rfsgsgsgtd ftltisslqp edfatyyclq ydsypytfgq gtkleik
```

Nucleic Acid Sequence Encoding the Hu24C05 KvA Kappa Chain Variable Region (SEQ ID NO: 173)

```
1    gatattcaga tgacccaatc acctagcagt ctctcagctt ccgtgggcga cagagttacc
61   ataacctgtc gggcaagcca ggagatttct gggtacctgt cctggctgca acagaagccc
121  ggaggcgcca tcaagaggtt gatctatgct gcgtcaacct tggatagcgg tgtcccgagt
181  cgattctccg gttctggctc cggaagtgac tacactctga caatttctag ccttcagcca
241  gaagatttcg ccacgtacta ttgcctccag tacgacagct atccctatac atttgggcag
301  ggcactaaac tggagatcaa a
```

Protein Sequence Defining the Hu24C05 KvA Kappa Chain Variable Region (SEQ ID NO: 174)

```
1    diqmtqspss lsasvgdrvt itcrasqeis gylswlqqkp ggaikrliya astldsgvps
61   rfsgsgsgsd ytltisslqp edfatyyclq ydsypytfgq gtkleik
```

The amino acid sequences defining the immunoglobulin heavy chain variable regions for the antibodies produced in Example 12 are aligned in FIG. 15. Amino terminal signal peptide sequences (for proper expression/secretion) are not shown. $CDR_1$, $CDR_2$, and $CDR_3$ (Kabat definition) are identified by boxes.

The amino acid sequences defining the immunoglobulin light chain variable regions for the antibodies in Example 12 are aligned in FIG. 16. Amino terminal signal peptide sequences (for proper expression/secretion) are not shown. $CDR_1$, $CDR_2$ and $CDR_3$ are identified by boxes.

Table 10 is a concordance chart showing the SEQ ID NO. of each sequence discussed in this Example.

TABLE 10

| SEQ. ID NO. | Nucleic Acid or Protein |
|---|---|
| 149 | Sh24C05 Hv3-7 Heavy Chain Variable Region-nucleic acid |
| 150 | Sh24C05 Hv3-7 Heavy Chain Variable Region-protein |
| 57 | Sh24C05 Hv3-7 Heavy Chain $CDR_1$ |
| 58 | Sh24C05 Hv3-7 Heavy Chain $CDR_2$ |
| 59 | Sh24C05 Hv3-7 Heavy Chain $CDR_3$ |
| 151 | Sh24C05 Hv3-11 Heavy Chain Variable Region-nucleic acid |
| 152 | Sh24C05 Hv3-11 Heavy Chain Variable Region-protein |
| 57 | Sh24C05 Hv3-11 Heavy Chain $CDR_1$ |

TABLE 10-continued

| SEQ. ID NO. | Nucleic Acid or Protein |
|---|---|
| 58 | Sh24C05 Hv3-11 Heavy Chain $CDR_2$ |
| 59 | Sh24C05 Hv3-11 Heavy Chain $CDR_3$ |
| 153 | Sh24C05 Hv3-11 N62S Heavy Chain Variable Region-nucleic acid |
| 154 | Sh24C05 Hv3-11 N62S Heavy Chain Variable Region-protein |
| 57 | Sh24C05 Hv3-11 N62S Heavy Chain $CDR_1$ |
| 148 | Sh24C05 Hv3-11 N62S Heavy Chain $CDR_2$ |
| 59 | Sh24C05 Hv3-11 N62S Heavy Chain $CDR_3$ |
| 155 | Sh24C05 Hv3-21 Heavy Chain Variable Region-nucleic acid |
| 156 | Sh24C05 Hv3-21 Heavy Chain Variable Region-protein |
| 57 | Sh24C05 Hv3-21 Heavy Chain $CDR_1$ |
| 58 | Sh24C05 Hv3-21 Heavy Chain $CDR_2$ |
| 59 | Sh24C05 Hv3-21 Heavy Chain $CDR_3$ |
| 157 | Sh24C05 Hv3-23 Heavy Chain Variable Region-nucleic acid |
| 158 | Sh24C05 Hv3-23 Heavy Chain Variable Region-protein |
| 57 | Sh24C05 Hv3-23 Heavy Chain $CDR_1$ |
| 58 | Sh24C05 Hv3-23 Heavy Chain $CDR_2$ |
| 59 | Sh24C05 Hv3-23 Heavy Chain $CDR_3$ |
| 159 | Sh24C05 Hv3-30 Heavy Chain Variable Region-nucleic acid |
| 160 | Sh24C05 Hv3-30 Heavy Chain Variable Region-protein |
| 57 | Sh24C05 Hv3-30 Heavy Chain $CDR_1$ |
| 58 | Sh24C05 Hv3-30 Heavy Chain $CDR_2$ |
| 59 | Sh24C05 Hv3-30 Heavy Chain $CDR_3$ |
| 161 | Hu24C05 HvA Heavy Chain Variable Region-nucleic acid |
| 162 | Hu24C05 HvA Heavy Chain Variable Region-protein |
| 57 | Hu24C05 HvA Heavy Chain $CDR_1$ |
| 58 | Hu24C05 HvA Heavy Chain $CDR_2$ |
| 59 | Hu24C05 HvA Heavy Chain $CDR_3$ |
| 163 | Sh24C05 Kv1-9 Light (kappa) Chain Variable Region-nucleic acid |
| 164 | Sh24C05 Kv1-9 Light (kappa) Chain Variable Region-protein |
| 60 | Sh24C05 Kv1-9 Light (kappa) Chain $CDR_1$ |
| 61 | Sh24C05 Kv1-9 Light (kappa) Chain $CDR_2$ |
| 62 | Sh24C05 Kv1-9 Light (kappa) Chain $CDR_3$ |
| 165 | Sh24C05 Kv1-16 Light (kappa) Chain Variable Region-nucleic acid |

TABLE 10-continued

| SEQ. ID NO. | Nucleic Acid or Protein |
|---|---|
| 166 | Sh24C05 Kv1-16 Light (kappa) Chain Variable Region-protein |
| 60 | Sh24C05 Kv1-16 Light (kappa) Chain $CDR_1$ |
| 61 | Sh24C05 Kv1-16 Light (kappa) Chain $CDR_2$ |
| 62 | Sh24C05 Kv1-16 Light (kappa) Chain $CDR_3$ |
| 167 | Sh24C05 Kv1-17 Light (kappa) Chain Variable Region-nucleic acid |
| 168 | Sh24C05 Kv1-17 Light (kappa) Chain Variable Region-protein |
| 60 | Sh24C05 Kv1-17 Light (kappa) Chain $CDR_1$ |
| 61 | Sh24C05 Kv1-17 Light (kappa) Chain $CDR_2$ |
| 62 | Sh24C05 Kv1-17 Light (kappa) Chain $CDR_3$ |
| 169 | Sh24C05 Kv1-33 Light (kappa) Chain Variable Region-nucleic acid |
| 170 | Sh24C05 Kv1-33 Light (kappa) Chain Variable Region-protein |
| 60 | Sh24C05 Kv1-33 Light (kappa) Chain $CDR_1$ |
| 61 | Sh24C05 Kv1-33 Light (kappa) Chain $CDR_2$ |
| 62 | Sh24C05 Kv1-33 Light (kappa) Chain $CDR_3$ |
| 171 | Sh24C05 Kv1-39 Light (kappa) Chain Variable Region-nucleic acid |
| 172 | Sh24C05 Kv1-39 Light (kappa) Chain Variable Region-protein |
| 60 | Sh24C05 Kv1-39 Light (kappa) Chain $CDR_1$ |
| 61 | Sh24C05 Kv1-39 Light (kappa) Chain $CDR_2$ |
| 62 | Sh24C05 Kv1-39 Light (kappa) Chain $CDR_3$ |
| 173 | Hu24C05 KvA Light (kappa) Chain Variable Region-nucleic acid |
| 174 | Hu24C05 KvA Light (kappa) Chain Variable Region-protein |
| 60 | Hu24C05 KvA Light (kappa) Chain $CDR_1$ |
| 61 | Hu24C05 KvA Light (kappa) Chain $CDR_2$ |
| 62 | Hu24C05 KvA Light (kappa) Chain $CDR_3$ |

Humanized monoclonal antibody heavy chain CDR sequences (Kabat, Chothia, and IMGT definitions) are shown in Table 11.

TABLE 11

| | Kabat | | |
|---|---|---|---|
| | CDR1 | **CDR2** | CDR3 |
| 24C05 | DYAMS (SEQ ID NO: 57) | **TISDGGTYTYYPDNVKG** (SEQ ID NO: 58) | EWGDYDGFDY (SEQ ID NO: 59) |
| Sh24C05 Hv3-7 | DYAMS (SEQ ID NO: 57) | **TISDGGTYTYYPDNVKG** (SEQ ID NO: 58) | EWGDYDGFDY (SEQ ID NO: 59) |
| Sh24C05 Hv3-11 | DYAMS (SEQ ID NO: 57) | **TISDGGTYTYYPDNVKG** (SEQ ID NO: 58) | EWGDYDGFDY (SEQ ID NO: 59) |
| Sh24C05 Hv3-11 N62S | DYAMS (SEQ ID NO: 57) | **TISDGGTYTYYPDSVKG** (SEQ ID NO: 148) | EWGDYDGFDY (SEQ ID NO: 59) |
| Sh24C05 Hv3-21 | DYAMS (SEQ ID NO: 57) | **TISDGGTYTYYPDNVKG** (SEQ ID NO: 58) | EWGDYDGFDY (SEQ ID NO: 59) |
| Sh24C05 Hv3-23 | DYAMS (SEQ ID NO: 57) | **TISDGGTYTYYPDNVKG** (SEQ ID NO: 58) | EWGDYDGFDY (SEQ ID NO: 59) |
| Sh24C05 Hv3-30 | DYAMS (SEQ ID NO: 57) | **TISDGGTYTYYPDNVKG** (SEQ ID NO: 58) | EWGDYDGFDY (SEQ ID NO: 59) |
| Hu24C05 HvA | DYAMS (SEQ ID NO: 57) | **TISDGGTYTYYPDNVKG** (SEQ ID NO: 58) | EWGDYDGFDY (SEQ ID NO: 59) |

TABLE 11-continued

| Chothia | | | |
|---|---|---|---|
| | **CDR1** | CDR2 | CDR3 |
| 24C05 | **GFTFSDY** (SEQ ID NO: 75) | SDGGTY (SEQ ID NO: 76) | EWGDYDGFDY (SEQ ID NO: 59) |
| Sh24C05 Hv3-7 | **GFTFSDY** (SEQ ID NO: 75) | SDGGTY (SEQ ID NO: 76) | EWGDYDGFDY (SEQ ID NO: 59) |
| Sh24C05 Hv3-11 | **GFTFSDY** (SEQ ID NO: 75) | SDGGTY (SEQ ID NO: 76) | EWGDYDGFDY (SEQ ID NO: 59) |
| Sh24C05 Hv3-11 N62S | **GFTFSDY** (SEQ ID NO: 75) | SDGGTY (SEQ ID NO: 76) | EWGDYDGFDY (SEQ ID NO: 59) |
| Sh24C05 Hv3-21 | **GFTFSDY** (SEQ ID NO: 75) | SDGGTY (SEQ ID NO: 76) | EWGDYDGFDY (SEQ ID NO: 59) |
| Sh24C05 Hv3-23 | **GFTFSDY** (SEQ ID NO: 75) | SDGGTY (SEQ ID NO: 76) | EWGDYDGFDY (SEQ ID NO: 59) |
| Sh24C05 Hv3-30 | **GFTFSDY** (SEQ ID NO: 75) | SDGGTY (SEQ ID NO: 76) | EWGDYDGFDY (SEQ ID NO: 59) |
| Hu24C05 HvA | **GFTFSDY** (SEQ ID NO: 75) | SDGGTY (SEQ ID NO: 76) | EWGDYDGFDY (SEQ ID NO: 59) |

| IMGT | | | |
|---|---|---|---|
| | CDR1 | CDR2 | **CDR3** |
| 24C05 | GFTFSDYA (SEQ ID NO: 94) | ISDGGTYT (SEQ ID NO: 95) | **AREWGDYDGFDY** (SEQ ID NO: 96) |
| Sh24C05 Hv3-7 | GFTFSDYA (SEQ ID NO: 94) | ISDGGTYT (SEQ ID NO: 95) | **AREWGDYDGFDY** (SEQ ID NO: 96) |
| Sh24C05 Hv3-11 | GFTFSDYA (SEQ ID NO: 94) | ISDGGTYT (SEQ ID NO: 95) | **AREWGDYDGFDY** (SEQ ID NO: 96) |
| Sh24C05 Hv3-11 N62S | GFTFSDYA (SEQ ID NO: 94) | ISDGGTYT (SEQ ID NO: 95) | **AREWGDYDGFDY** (SEQ ID NO: 96) |
| Sh24C05 Hv3-21 | GFTFSDYA (SEQ ID NO: 94) | ISDGGTYT (SEQ ID NO: 95) | **AREWGDYDGFDY** (SEQ ID NO: 96) |
| Sh24C05 Hv3-23 | GFTFSDYA (SEQ ID NO: 94) | ISDGGTYT (SEQ ID NO: 95) | **AREWGDYDGFDY** (SEQ ID NO: 96) |
| Sh24C05 Hv3-30 | GFTFSDYA (SEQ ID NO: 94) | ISDGGTYT (SEQ ID NO: 95) | **AREWGDYDGFDY** (SEQ ID NO: 96) |
| Hu24C05 HvA | GFTFSDYA (SEQ ID NO: 94) | ISDGGTYT (SEQ ID NO: 95) | **AREWGDYDGFDY** (SEQ ID NO: 96) |

Humanized monoclonal antibody Kappa light chain CDR sequences (Kabat, Chothia, and IMGT definitions) are shown in Table 12.

TABLE 12

| Kabat/Chothia | | | |
|---|---|---|---|
| | **CDR1** | **CDR2** | **CDR3** |
| 24C05 | **RASQEISGYLS** (SEQ ID NO: 60) | **AASTLDS** (SEQ ID NO: 61) | **LQYDSYPYT** (SEQ ID NO: 62) |
| Sh24C05 Kv1-9 | **RASQEISGYLS** (SEQ ID NO: 60) | **AASTLDS** (SEQ ID NO: 61) | **LQYDSYPYT** (SEQ ID NO: 62) |
| Sh24C05 Kv1-16 | **RASQEISGYLS** (SEQ ID NO: 60) | **AASTLDS** (SEQ ID NO: 61) | **LQYDSYPYT** (SEQ ID NO: 62) |

TABLE 12-continued

| | | | |
|---|---|---|---|
| Sh24C05 Kv1-17 | **RASQEISGYLS** (SEQ ID NO: 60) | **AASTLDS** (SEQ ID NO: 61) | **LQYDSYPYT** (SEQ ID NO: 62) |
| Sh24C05 Kv1-33 | **RASQEISGYLS** (SEQ ID NO: 60) | **AASTLDS** (SEQ ID NO: 61) | **LQYDSYPYT** (SEQ ID NO: 62) |
| Sh24C05 Kv1-39 | **RASQEISGYLS** (SEQ ID NO: 60) | **AASTLDS** (SEQ ID NO: 61) | **LQYDSYPYT** (SEQ ID NO: 62) |
| Hu24C05 KvA | **RASQEISGYLS** (SEQ ID NO: 60) | **AASTLDS** (SEQ ID NO: 61) | **LQYDSYPYT** (SEQ ID NO: 62) |
| | | IMGT | |
| | CDR1 | CDR2 | CDR3 |
| 24C05 | QEISGY (SEQ ID NO: 101) | AAS | LQYDSYPYT (SEQ ID NO: 62) |
| Sh24C05 Kv1-9 | QEISGY (SEQ ID NO: 101) | AAS | LQYDSYPYT (SEQ ID NO: 62) |
| Sh24C05 Kv1-16 | QEISGY (SEQ ID NO: 101) | AAS | LQYDSYPYT (SEQ ID NO: 62) |
| Sh24C05 Kv1-17 | QEISGY (SEQ ID NO: 101) | AAS | LQYDSYPYT (SEQ ID NO: 62) |
| Sh24C05 Kv1-33 | QEISGY (SEQ ID NO: 101) | AAS | LQYDSYPYT (SEQ ID NO: 62) |
| Sh24C05 Kv1-39 | QEISGY (SEQ ID NO: 101) | AAS | LQYDSYPYT (SEQ ID NO: 62) |
| Hu24C05 KvA | QEISGY (SEQ ID NO: 101) | AAS | LQYDSYPYT (SEQ ID NO: 62) |

In Tables 11 and 12, the longest CDR sequences for the immunoglobulin heavy chain and light chain are shown in bold.

To create the complete chimeric and humanized heavy or kappa chain antibody sequences, each variable sequence above is combined with its respective human constant region. For example, a complete heavy chain comprises a heavy variable sequence followed by a human IgG1 heavy chain constant sequence or a human IgG2 heavy chain constant sequence. A complete kappa chain comprises a kappa variable sequence followed by the human kappa light chain constant sequence.

Nucleic Acid Sequence Encoding the Human IgG1 Heavy Chain Constant Region
(SEQ ID NO: 175)

```
  1     gcctcaacaa aaggaccaag tgtgttccca ctcgccccta gcagcaagag tacatccggg

 61     ggcactgcag cactcggctg cctcgtcaag gattattttc cagagccagt aaccgtgagc

121     tggaacagtg gagcactcac ttctggtgtc catacttttc ctgctgtcct gcaaagctct

181     ggcctgtact cactcagctc cgtcgtgacc gtgccatctt catctctggg cactcagacc

241     tacatctgta atgtaaacca caagcctagc aatactaagg tcgataagcg ggtggaaccc

301     aagagctgcg acaagactca cacttgtccc ccatgccctg cccctgaact tctgggcggt

361     cccagcgtct ttttgttccc accaaagcct aaagatactc tgatgataag tagaacaccc

421     gaggtgacat gtgttgttgt agacgtttcc cacgaggacc cagaggttaa gttcaactgg

481     tacgttgatg gagtcgaagt acataatgct aagaccaagc ctagagagga gcagtataat

541     agtacatacc gtgtagtcag tgttctcaca gtgctgcacc aagactggct caacggcaaa

601     gaatacaaat gcaaagtgtc caacaaagca ctcccagccc ctatcgagaa gactattagt

661     aaggcaaagg ggcagcctcg tgaaccacag gtgtacactc tgccacccag tagagaggaa

721     atgacaaaga accaagtctc attgacctgc ctggtgaaag gcttctaccc cagcgacatc

781     gccgttgagt gggagagtaa cggtcagcct gagaacaatt acaagacaac ccccccagtg

841     ctggatagtg acgggtcttt ctttctgtac agtaagctga ctgtggacaa gtcccgctgg
```

-continued 901 cagcagggta acgtcttcag ctgttccgtg atgcacgagg cattgcacaa ccactacacc 961 cagaagtcac tgagcctgag cccagggaag Protein Sequence Defining the Human IgG1 Heavy Chain Constant Region
(SEQ ID NO: 176)

1 astkgpsvfp lapsskstsg gtaalgclvk dyfpepvtvs wnsgaltsgv htfpavlqss 61 glyslssvvt vpssslgtqt yicnvnhkps ntkvdkrvep kscdkthtcp pcpapellgg 121 psvflfppkp kdtlmisrtp evtcvvvdvs hedpevkfnw yvdgvevhna ktkpreeqyn 181 styrvvsvlt vlhqdwlngk eykckvsnka lpapiektis kakgqprepq vytlppsree 241 mtknqvsltc lvkgfypsdi avewesngqp ennykttppv ldsdgsffly skltvdksrw 301 qqgnvfscsv mhealhnhyt qkslslspgk Nucleic Acid Sequence Encoding the Human IgG2 Heavy Chain Constant Region
(SEQ ID NO: 177)

1 gcctccacca agggcccatc ggtcttcccc ctggcgccct gctccaggag cacctccgag 61 agcacagcgg ccctgggctg cctggtcaag gactacttcc ccgaaccggt gacggtgtcg 121 tggaactcag gcgctctgac cagcggcgtg cacaccttcc cagctgtcct acagtcctca 181 ggactctact ccctcagcag cgtggtgacc gtgccctcca gcaacttcgg cacccagacc 241 tacacctgca acgtagatca caagcccagc aacaccaagg tggacaagac agttgagcgc 301 aaatgttgtg tcgagtgccc accgtgccca gcaccacctg tggcaggacc gtcagtcttc 361 ctcttccccc caaaacccaa ggacaccctc atgatctccc ggacccctga ggtcacgtgc 421 gtggtggtgg acgtgagcca cgaagacccc gaggtccagt tcaactggta cgtggacggc 481 gtggaggtgc ataatgccaa gacaaagcca cgggaggagc agttcaacag cacgttccgt 541 gtggtcagcg tcctcaccgt tgtgcaccag gactggctga acggcaagga gtacaagtgc 601 aaggtctcca acaaaggcct cccagccccc atcgagaaaa ccatctccaa aaccaaaggg 661 cagccccgag aaccacaggt gtacaccctg cccccatccc gggaggagat gaccaagaac 721 caggtcagcc tgacctgcct ggtcaaaggc ttctacccca gcgacatcgc cgtggagtgg 781 gagagcaatg ggcagccgga gaacaactac aagaccacac ctcccatgct ggactccgac 841 ggctccttct tcctctacag caagctcacc gtggacaaga gcaggtggca gcaggggaac 901 gtcttctcat gctccgtgat gcatgaggct ctgcacaacc actacacgca gaagagcctc 961 tccctgtctc cgggtaaa Protein Sequence Defining the Human IgG2 Heavy Chain Constant Region
(SEQ ID NO: 178)

1 astkgpsvfp lapcsrstse staalgclvk dyfpepvtvs wnsgaltsgv htfpavlqss 61 glyslssvvt vpssnfgtqt ytcnvdhkps ntkvdktver kccvecppcp appvagpsvf 121 lfppkpkdtl misrtpevtc vvvdvshedp evqfnwyvdg vevhnaktkp reeqfnstfr 181 vvsvltvvhq dwlngkeykc kvsnkglpap iektisktkg qprepqvytl ppsreemtkn 241 qvsltclvkg fypsdiavew esngqpenny kttppmldsd gsfflysklt vdksrwqqgn 301 vfscsvmhea lhnhytqksl slspgk Nucleic Acid Sequence Encoding the Human Kappa Light Chain Constant Region
(SEQ ID NO: 179)

1 cgcacagttg ctgcccccag cgtgttcatt ttcccaccta gcgatgagca gctgaaaagc 61 ggtactgcct ctgtcgtatg cttgctcaac aacttttacc cacgtgaggc taaggtgcag 121 tggaaagtgg ataatgcact tcaatctgga aacagtcaag agtccgtgac agaacaggac 181 agcaaagact caacttattc actctcttcc accctgactc tgtccaaggc agactatgaa -continued 241 aaacacaagg tatacgcctg cgaggttaca caccagggtt tgtctagtcc tgtcaccaag 301 tccttcaata ggggcgaatg t Protein Sequence Defining the Human Kappa Light Chain Constant Region
(SEQ ID NO: 180)

1 rtvaapsvfi fppsdeqlks gtasvvclln nfypreakvq wkvdnalqsg nsqesvteqd 61 skdstyslss tltlskadye khkvyacevt hqglsspvtk sfnrgec The following sequences represent the actual or contemplated full length heavy and light chain sequences (i.e., containing both the variable and constant regions sequences) for each antibody described in this Example. Signal sequences for proper secretion of the antibodies are also included at the 5' end of the DNA sequences or the amino terminal end of the protein sequences. It is also contemplated herein that the variable region sequences can be ligated to other constant region sequences to produce active full length IgG heavy and light chains.

Nucleic Acid Sequence Encoding the Full Length Chimeric 24C05 Heavy Chain (Mouse Heavy Chain Variable Region and Human IgG1 Constant Region)
(SEQ ID NO: 181)

1 atgaacttcg ggctcagctt gatgttcctt gtccttgtct taaaaggtgt ccagtgtgag 61 gtgcagctgg tggaatctgg gggaggctta gtgaagcctg gagggtccct gaaactctcc 121 tgtgcagcct ctggattcac tttcagtgac tatgccatgt cttgggttcg ccagactccg 181 gaaaagaggc tggagtgggt cgcaaccatt agtgatggtg gtacttacac ctactatcca 241 gacaatgtaa agggccgatt caccatctcc agagacaatg ccaagaacaa cctgtacctg 301 caaatgagcc atctgaagtc tgaggacaca gccatgtatt actgtgcaag agaatggggt 361 gattacgacg gatttgacta ctggggccaa ggcaccactc tcacagtctc ctcggcctca 421 acaaaaggac caagtgtgtt cccactcgcc cctagcagca agagtacatc cgggggcact 481 gcagcactcg gctgcctcgt caaggattat tttccagagc cagtaaccgt gagctggaac 541 agtggagcac tcacttctgg tgtccatact tttcctgctg tcctgcaaag ctctggcctg 601 tactcactca gctccgtcgt gaccgtgcca tcttcatctc tgggcactca gacctacatc 661 tgtaatgtaa accacaagcc tagcaatact aaggtcgata agcgggtgga acccaagagc 721 tgcgacaaga ctcacacttg tcccccatgc cctgcccctg aacttctggg cggtcccagc 781 gtctttttgt tcccaccaaa gcctaaagat actctgatga taagtagaac acccgaggtg 841 acatgtgttg ttgtagacgt ttcccacgag gacccagagg ttaagttcaa ctggtacgtt 901 gatggagtcg aagtacataa tgctaagacc aagcctagag aggagcagta taatagtaca 961 taccgtgtag tcagtgttct cacagtgctg caccaagact ggctcaacgg caaagaatac 1021 aaatgcaaag tgtccaacaa agcactccca gcccctatcg agaagactat tagtaaggca 1081 aaggggcagc ctcgtgaacc acaggtgtac actctgccac ccagtagaga ggaaatgaca 1141 aagaaccaag tctcattgac ctgcctggtg aaaggcttct accccagcga catcgccgtt 1201 gagtgggaga gtaacggtca gcctgagaac aattacaaga caaccccccc agtgctggat 1261 agtgacgggt ctttctttct gtacagtaag ctgactgtgg acaagtcccg ctggcagcag 1321 ggtaacgtct tcagctgttc cgtgatgcac gaggcattgc acaaccacta cacccagaag 1381 tcactgagcc tgagcccagg gaag Protein Sequence Defining the Full Length Chimeric 24C05 Heavy Chain (Mouse Heavy Chain Variable Region and Human IgG1 Constant Region)
(SEQ ID NO: 182)

1 mnfglslmfl vlvlkgvqce vqlvesgggl vkpggslkls caasgftfsd yamswvrqtp 61 ekrlewvati sdggtytyyp dnvkgrftis rdnaknnlyl qmshlksedt amyycarewg 121 dydgfdywgq gttltvssas tkgpsvfpla psskstsggt aalgclvkdy fpepvtvswn 181 sgaltsgvht fpavlqssgl yslssvvtvp ssslgtqtyi cnvnhkpsnt kvdkrvepks -continued 241 cdkthtcppc papellggps vflfppkpkd tlmisrtpev tcvvvdvshe dpevkfnwyv 301 dgvevhnakt kpreegynst yrvvsvltvl hqdwlngkey kckvsnkalp apiektiska 361 kgqprepqvy tlppsreemt knqvsltclv kgfypsdiav ewesngqpen nykttppvld 421 sdgsfflysk ltvdksrwqq gnvfscsvmh ealhnhytqk slslspgk Nucleic Acid Sequence Encoding the Full Length Chimeric 24C05 Light Chain (Mouse Kappa Chain Variable Region and Human Kappa Constant Region)
(SEQ ID NO: 183)

1 atggacatga gggttcctgc tcacgttttt ggcttcttgt tgctctggtt tccaggtacc 61 agatgtgaca tccagatgac ccagtctcca tcctccttat ctgcctctct gggagaaaga 121 gtcagtctca cttgtcgggc aagtcaggaa attagtggtt acttaagctg gcttcagcag 181 aaaccagatg gaactattaa acgcctgatc tacgccgcat ccactttaga ttctggtgtc 241 ccaaaaaggt tcagtggcag taggtctggg tcagattatt ctctcaccat cggcagcctt 301 gagtctgaag atcttgcaga ctattactgt ctacaatatg atagttatcc gtacacgttc 361 ggagggggga ccaagctgga aataaaacgc acagtcgccg ctccctccgt gttcatcttt 421 ccaccaagtg atgagcaact gaagtctggt actgcttcag tcgtgtgtct gctgaacaat 481 ttctaccctc gagaagccaa agtccaatgg aaggtagaca acgcactgca gtccggcaat 541 agccaagaat cagttaccga acaggattca aaggacagta catattccct gagcagcact 601 ctgaccctgt caaaggccga ttacgagaaa cacaaggtct atgcttgcga agtgacacat 661 cagggactgt ccagcccagt gacaaaatct tttaaccgtg gggagtgt Protein Sequence Defining the Full Length Chimeric 24C05 Light Chain (Mouse Kappa Chain Variable Region and Human Kappa Constant Region)
(SEQ ID NO: 184)

1 mdmrvpahvf gflllwfpgt rcdiqmtqsp sslsaslger vsltcrasqe isgylswlqq 61 kpdgtikrli yaastldsgv pkrfsgsrsg sdysltigsl esedladyyc lqydsypytf 121 gggtkleikr tvaapsvfif ppsdeqlksg tasvvcllnn fypreakvqw kvdnalqsgn 181 sqesvteqds kdstyslsst ltlskadyek hkvyacevth qglsspvtks fnrgec Nucleic Acid Sequence Encoding the Full Length Humanized sh24C05 Hv3-7 Heavy Chain (Humanized Heavy Chain Variable Region and Human IgG1 Constant Region)
(SEQ ID NO: 185)

1 atggacatga gagttcctgc tcagctgctc gggttgctgt tgctttggct ccggggtgct 61 aggtgcgagg ttcagctggt ggaatctggc ggtgggcttg tacaaccagg aggctccctc 121 agactgagtt gtgccgcttc agggttcaca ttctccgact atgcgatgtc atgggtgcgc 181 caagcacccg ggaaaggact ggagtgggtt gccactatca gcgatggcgg aacgtatacc 241 tattaccctg acaatgtgaa gggtcggttc accatttcca gggataacgc aaagaacagt 301 ctctacctgc agatgaacag cctgagggct gaggacaccg ccgtctacta ctgcgcccga 361 gaatggggag attatgatgg gtttgactat tggggccagg gcactttggt gacagtcagt 421 tctgcctcaa caaaaggacc aagtgtgttc ccactcgccc ctagcagcaa gagtacatcc 481 gggggcactg cagcactcgg ctgcctcgtc aaggattatt ttccagagcc agtaaccgtg 541 agctggaaca gtggagcact cacttctggt gtccatactt ttcctgctgt cctgcaaagc 601 tctggcctgt actcactcag ctccgtcgtg accgtgccat cttcatctct gggcactcag 661 acctacatct gtaatgtaaa ccacaagcct agcaatacta aggtcgataa gcgggtggaa 721 cccaagagct gcgacaagac tcacacttgt cccccatgcc ctgcccctga acttctgggc 781 ggtcccagcg tctttttgtt cccaccaaag cctaaagata ctctgatgat aagtagaaca 841 cccgaggtga catgtgttgt tgtagacgtt tcccacgagg acccagaggt taagttcaac -continued

```
 901  tggtacgttg atggagtcga agtacataat gctaagacca agcctagaga ggagcagtat

 961  aatagtacat accgtgtagt cagtgttctc acagtgctgc accaagactg gctcaacggc

1021  aaagaataca aatgcaaagt gtccaacaaa gcactcccag cccctatcga gaagactatt

1081  agtaaggcaa aggggcagcc tcgtgaacca caggtgtaca ctctgccacc cagtagagag

1141  gaaatgacaa agaaccaagt ctcattgacc tgcctggtga aaggcttcta ccccagcgac

1201  atcgccgttg agtgggagag taacggtcag cctgagaaca attacaagac aacccccccca

1261  gtgctggata gtgacgggtc tttctttctg tacagtaagc tgactgtgga caagtcccgc

1321  tggcagcagg gtaacgtctt cagctgttcc gtgatgcacg aggcattgca caaccactac

1381  acccagaagt cactgagcct gagcccaggg aag
```

Protein Sequence Defining the Full Length Humanized Sh24C05 Hv3-7 Heavy Chain (Humanized Heavy Chain Variable Region and Human IgG1 Constant Region)

(SEQ ID NO: 186)

```
   1  mdmrvpaqll gllllwlrga rcevqlvesg gglvqpggsl rlscaasgft fsdyamswvr

  61  qapgkglewv atisdggtyt yypdnvkgrf tisrdnakns lylqmnslra edtavyycar

 121  ewgdydgfdy wgqgtlvtvs sastkgpsvf plapsskst s ggtaalgclv kdyfpepvtv

 181  swnsgaltsg vhtfpavlqs sglyslssvv tvpssslgtq tyicnvnhkp sntkvdkrve

 241  pkscdkthtc ppcpapellg gpsvflfppk pkdtlmisrt pevtcvvvdv shedpevkfn

 301  wyvdgvevhn aktkpreegy nstyrvvsvl tvlhqdwlng keykckvsnk alpapiekti

 361  skakgqprep qvytlppsre emtknqvslt clvkgfypsd iavewesngq pennykttpp

 421  vldsdgsffl yskltvdksr wqqgnvfscs vmhealhnhy tqkslslspg k
```

Nucleic Acid Sequence Encoding the Full Length Humanized Sh24C05 Hv3-11 Heavy Chain (Humanized Heavy Chain Variable Region and Human IgG1 Constant Region)

(SEQ ID NO: 187)

```
   1  atggacatga gagttcctgc tcagctgctc gggttgctgt tgctttggct ccggggtgct

  61  aggtgccaag ttcagctggt ggaatctggc ggtgggcttg taaagccagg aggctccctc

 121  agactgagtt gtgccgcttc agggttcaca ttctccgact atgcgatgtc atggatcagg

 181  caagcacccg ggaaaggact ggagtgggtt agcactatca gcgatggcgg aacgtatacc

 241  tattaccctg acaatgtgaa gggtcggttc accatttcca gggataacgc aaagaacagt

 301  ctctaccttc agatgaacag cctgagggct gaggacaccg ccgtctacta ctgcgcccga

 361  gaatggggag attatgatgg gtttgactat tggggccagg gcactttggt gacagtcagt

 421  tctgcctcaa caaaaggacc aagtgtgttc ccactcgccc ctagcagcaa gagtacatcc

 481  gggggcactg cagcactcgg ctgcctcgtc aaggattatt ttccagagcc agtaaccgtg

 541  agctggaaca gtggagcact cacttctggt gtccatactt ttcctgctgt cctgcaaagc

 601  tctggcctgt actcactcag ctccgtcgtg accgtgccat cttcatctct gggcactcag

 661  acctacatct gtaatgtaaa ccacaagcct agcaatacta aggtcgataa gcgggtggaa

 721  cccaagagct gcgacaagac tcacacttgt cccccatgcc ctgcccctga acttctgggc

 781  ggtcccagcg tctttttgtt cccaccaaag cctaaagata ctctgatgat aagtagaaca

 841  cccgaggtga catgtgttgt tgtagacgtt tcccacgagg acccagaggt taagttcaac

 901  tggtacgttg atggagtcga agtacataat gctaagacca agcctagaga ggagcagtat

 961  aatagtacat accgtgtagt cagtgttctc acagtgctgc accaagactg gctcaacggc

1021  aaagaataca aatgcaaagt gtccaacaaa gcactcccag cccctatcga gaagactatt

1081  agtaaggcaa aggggcagcc tcgtgaacca caggtgtaca ctctgccacc cagtagagag

1141  gaaatgacaa agaaccaagt ctcattgacc tgcctggtga aaggcttcta ccccagcgac
```

-continued

```
1201   atcgccgttg agtgggagag taacggtcag cctgagaaca attacaagac aacccccca

1261   gtgctggata gtgacgggtc tttctttctg tacagtaagc tgactgtgga caagtcccgc

1321   tggcagcagg gtaacgtctt cagctgttcc gtgatgcacg aggcattgca caaccactac

1381   acccagaagt cactgagcct gagcccaggg aag
```

Protein Sequence Defining the Full Length Humanized Sh24C05 Hv3-11 Heavy Chain (Humanized Heavy Chain Variable Region and Human IgG1 Constant Region)

(SEQ ID NO: 188)

```
  1   mdmrvpaqll gllllwlrga rcqvqlvesg gglvkpggsl rlscaasgft fsdyamswir

 61   qapgkglewv stisdggtyt yypdnvkgrf tisrdnakns lylqmnslra edtavyycar

121   ewgdydgfdy wgqgtlvtvs sastkgpsvf plapssksts ggtaalgclv kdyfpepvtv

181   swnsgaltsg vhtfpavlqs sglyslssvv tvpssslgtq tyicnvnhkp sntkvdkrve

241   pkscdkthtc ppcpapellg gpsvflfppk pkdtlmisrt pevtcvvvdv shedpevkfn

301   wyvdgvevhn aktkpreegy nstyrvvsvl tvlhqdwlng keykckvsnk alpapiekti

361   skakgqprep qvytlppsre emtknqvslt clvkgfypsd iavewesngq pennykttpp

421   vldsdgsffl yskltvdksr wqqgnvfscs vmhealhnhy tqkslslspg k
```

Nucleic Acid Sequence Encoding the Full Length Humanized Sh24C05 Hv3-11 N62S IgG1 Heavy Chain (Humanized Heavy Chain Variable Region and Human IgG1 Constant Region)

(SEQ ID NO: 189)

```
   1   atggacatga gagttcctgc tcagctgctc gggttgctgt tgctttggct ccggggtgct

  61   aggtgccaag ttcagctggt ggaatctggc ggtgggcttg taaagccagg aggctccctc

 121   agactgagtt gtgccgcttc agggttcaca ttctccgact atgcgatgtc atggatcagg

 181   caagcacccg ggaaaggact ggagtgggtt agcactatca gcgatggcgg aacgtatacc

 241   tattaccctg actccgtgaa gggtcggttc accatttcca gggataacgc aaagaacagt

 301   ctctaccttc agatgaacag cctgagggct gaggacaccg ccgtctacta ctgcgcccga

 361   gaatggggag attatgatgg gtttgactat tggggccagg gcactttggt gacagtcagt

 421   tctgcctcaa caaaaggacc aagtgtgttc ccactcgccc ctagcagcaa gagtacatcc

 481   gggggcactg cagcactcgg ctgcctcgtc aaggattatt ttccagagcc agtaaccgtg

 541   agctggaaca gtggagcact cacttctggt gtccatactt ttcctgctgt cctgcaaagc

 601   tctggcctgt actcactcag ctccgtcgtg accgtgccat cttcatctct gggcactcag

 661   acctacatct gtaatgtaaa ccacaagcct agcaatacta aggtcgataa gcgggtggaa

 721   cccaagagct gcgacaagac tcacacttgt cccccatgcc ctgcccctga acttctgggc

 781   ggtcccagcg tctttttgtt cccaccaaag cctaaagata ctctgatgat aagtagaaca

 841   cccgaggtga catgtgttgt tgtagacgtt tcccacgagg acccagaggt taagttcaac

 901   tggtacgttg atggagtcga agtacataat gctaagacca agcctagaga ggagcagtat

 961   aatagtacat accgtgtagt cagtgttctc acagtgctgc accaagactg gctcaacggc

1021   aaagaataca aatgcaaagt gtccaacaaa gcactcccag cccctatcga gaagactatt

1081   agtaaggcaa aggggcagcc tcgtgaacca caggtgtaca ctctgccacc cagtagagag

1141   gaaatgacaa agaaccaagt ctcattgacc tgcctggtga aaggcttcta ccccagcgac

1201   atcgccgttg agtgggagag taacggtcag cctgagaaca attacaagac aacccccca

1261   gtgctggata gtgacgggtc tttctttctg tacagtaagc tgactgtgga caagtcccgc

1321   tggcagcagg gtaacgtctt cagctgttcc gtgatgcacg aggcattgca caaccactac

1381   acccagaagt cactgagcct gagcccaggg aag
```

-continued

Protein Sequence Defining the Full Length Humanized Sh24C05 Hv3-11 N62S IgG1 Heavy Chain (Humanized Heavy Chain Variable Region and Human IgG1 Constant Region)

(SEQ ID NO: 190)

```
  1  mdmrvpaqll gllllwlrga rcqvqlvesg gglvkpggsl rlscaasgft fsdyamswir

 61  qapgkglewv stisdggtyt yypdsvkgrf tisrdnakns lylqmnslra edtavyycar

121  ewgdydgfdy wgqgtlvtvs sastkgpsvf plapsskstS ggtaalgclv kdyfpepvtv

181  swnsgaltsg vhtfpavlqs sglyslssvv tvpssslgtq tyicnvnhkp sntkvdkrve

241  pkscdkthtc ppcpapellg gpsvflfppk pkdtlmisrt pevtcvvvdv shedpevkfn

301  wyvdgvevhn aktkpreegy nstyrvvsvl tvlhqdwlng keykckvsnk alpapiekti

361  skakgqprep qvytlppsre emtknqvslt clvkgfypsd iavewesngq pennykttpp

421  vldsdgsffl yskltvdksr wqqgnvfscs vmhealhnhy tqkslslspg k
```

Nucleic Acid Sequence Encoding the Full Length Humanized Sh24C05 Hv3-11 N62S IgG2 Heavy Chain (Humanized Heavy Chain Variable Region and Human IgG2 Constant Region)

(SEQ ID NO: 191)

```
   1  atggacatga gagttcctgc tcagctgctc gggttgctgt tgctttggct tccggggtgct

  61  aggtgccaag ttcagctggt ggaatctggc ggtgggcttg taaagccagg aggctccctc

 121  agactgagtt gtgccgcttc agggttcaca ttctccgact atgcgatgtc atggatcagg

 181  caagcacccg ggaaaggact ggagtgggtt agcactatca gcgatggcgg aacgtatacc

 241  tattaccctg actccgtgaa gggtcggttc accatttcca gggataacgc aaagaacagt

 301  ctctaccttc agatgaacag cctgagggct gaggacaccg ccgtctacta ctgcgcccga

 361  gaatggggag attatgatgg gtttgactat tggggccagg gcactttggt gacagtcagt

 421  tctgcctcca ccaagggccc atcggtcttc cccctggcgc cctgctccag gagcacctcc

 481  gagagcacag cggccctggg ctgcctggtc aaggactact tccccgaacc ggtgacggtg

 541  tcgtggaact caggcgctct gaccagcggc gtgcacacct tcccagctgt cctacagtcc

 601  tcaggactct actccctcag cagcgtggtg accgtgccct ccagcaactt cggcacccag

 661  acctacacct gcaacgtaga tcacaagccc agcaacacca aggtggacaa gacagttgag

 721  cgcaaatgtt gtgtcgagtg cccaccgtgc ccagcaccac ctgtggcagg accgtcagtc

 781  ttcctcttcc ccccaaaacc caaggacacc ctcatgatct cccggacccc tgaggtcacg

 841  tgcgtggtgg tggacgtgag ccacgaagac cccgaggtcc agttcaactg gtacgtggac

 901  ggcgtggagg tgcataatgc caagacaaag ccacgggagg agcagttcaa cagcacgttc

 961  cgtgtggtca gcgtcctcac cgttgtgcac caggactggc tgaacggcaa ggagtacaag

1021  tgcaaggtct ccaacaaagg cctcccagcc cccatcgaga aaaccatctc caaaaccaaa

1081  gggcagcccc gagaaccaca ggtgtacacc ctgcccccat cccgggagga gatgaccaag

1141  aaccaggtca gcctgacctg cctggtcaaa ggcttctacc ccagcgacat cgccgtggag

1201  tgggagagca atgggcagcc ggagaacaac tacaagacca cacctcccat gctggactcc

1261  gacggctcct tcttcctcta cagcaagctc accgtggaca agagcaggtg gcagcagggg

1321  aacgtcttct catgctccgt gatgcatgag gctctgcaca accactacac gcagaagagc

1381  ctctccctgt ctccgggtaa a
```

Protein Sequence Defining the Full Length Humanized Sh24C05 Hv3-11 N62S IgG2 Heavy Chain (Humanized Heavy Chain Variable Region and Human IgG2 Constant Region)

(SEQ ID NO: 192)

```
  1  mdmrvpaqll gllllwlrga rcqvqlvesg gglvkpggsl rlscaasgft fsdyamswir

 61  qapgkglewv stisdggtyt yypdsvkgrf tisrdnakns lylqmnslra edtavyycar

121  ewgdydgfdy wgqgtlvtvs sastkgpsvf plapcsrsts estaalgclv kdyfpepvtv
```

-continued

```
 181   swnsgaltsg vhtfpavlqs sglyslssvv tvpssnfgtq tytcnvdhkp sntkvdktve

 241   rkccvecppc pappvagpsv flfppkpkdt lmisrtpevt cvvvdvshed pevqfnwyvd

 301   gvevhnaktk preeqfnstf rvvsvltvvh qdwlngkeyk ckvsnkglpa piektisktk

 361   gqprepqvyt lppsreemtk nqvsltclvk gfypsdiave wesngqpenn ykttppmlds

 421   dgsfflyskl tvdksrwqqg nvfscsvmhe alhnhytqks lslspgk
```

Nucleic Acid Sequence Encoding the Full Length Humanized Sh24C05 Hv3-21 Heavy Chain (Humanized Heavy Chain Variable Region and Human IgG1 Constant Region)

(SEQ ID NO: 193)

```
   1   atggacatga gagttcctgc tcagctgctc gggttgctgt tgctttggct ccggggtgct

  61   aggtgcgagg ttcagctggt ggaatctggc ggtgggcttg taaagccagg aggctccctc

 121   agactgagtt gtgccgcttc agggttcaca ttctccgact atgcgatgtc atgggtgcgc

 181   caagcacccg ggaaaggact ggagtgggtt agcactatca gcgatggcgg aacgtatacc

 241   tattaccctg acaatgtgaa gggtcggttc accatttcca gggataacgc aaagaacagt

 301   ctctatttgc agatgaacag cctgagggct gaggacaccg ccgtctacta ctgcgcccga

 361   gaatggggag attatgatgg gtttgactat tggggccagg gcactttggt gacagtcagt

 421   tctgcctcaa caaaaggacc aagtgtgttc ccactcgccc ctagcagcaa gagtacatcc

 481   gggggcactg cagcactcgg ctgcctcgtc aaggattatt ttccagagcc agtaaccgtg

 541   agctggaaca gtggagcact cacttctggt gtccatactt ttcctgctgt cctgcaaagc

 601   tctggcctgt actcactcag ctccgtcgtg accgtgccat cttcatctct gggcactcag

 661   acctacatct gtaatgtaaa ccacaagcct agcaatacta aggtcgataa gcgggtggaa

 721   cccaagagct gcgacaagac tcacacttgt cccccatgcc ctgcccctga acttctgggc

 781   ggtcccagcg tctttttgtt cccaccaaag cctaaagata ctctgatgat aagtagaaca

 841   cccgaggtga catgtgttgt tgtagacgtt tcccacgagg acccagaggt taagttcaac

 901   tggtacgttg atggagtcga agtacataat gctaagacca agcctagaga ggagcagtat

 961   aatagtacat accgtgtagt cagtgttctc acagtgctgc accaagactg gctcaacggc

1021   aaagaataca aatgcaaagt gtccaacaaa gcactcccag cccctatcga gaagactatt

1081   agtaaggcaa aggggcagcc tcgtgaacca caggtgtaca ctctgccacc cagtagagag

1141   gaaatgacaa agaaccaagt ctcattgacc tgcctggtga aaggcttcta ccccagcgac

1201   atcgccgttg agtgggagag taacggtcag cctgagaaca attacaagac aacccccccca

1261   gtgctggata gtgacgggtc tttctttctg tacagtaagc tgactgtgga caagtcccgc

1321   tggcagcagg gtaacgtctt cagctgttcc gtgatgcacg aggcattgca caaccactac

1381   acccagaagt cactgagcct gagcccaggg aag
```

Protein Sequence Defining the Full Length Humanized 24C05 Hv3-21 Heavy Chain (Humanized Heavy Chain Variable Region and Human IgG1 Constant Region)

(SEQ ID NO: 194)

```
   1   mdmrvpaqll gllllwlrga rcevqlvesg gglvkpggsl rlscaasgft fsdyamswvr

  61   qapgkglewv stisdggtyt yypdnvkgrf tisrdnakns lylqmnslra edtavyycar

 121   ewgdydgfdy wgqgtlvtvs sastkgpsvf plapssksts ggtaalgclv kdyfpepvtv

 181   swnsgaltsg vhtfpavlqs sglyslssvv tvpssslgtq tyicnvnhkp sntkvdkrve

 241   pkscdkthtc ppcpapellg gpsvflfppk pkdtlmisrt pevtcvvvdv shedpevkfn
```

301 wyvdgvevhn aktkpreegy nstyrvvsvl tvlhqdwlng keykckvsnk alpapiekti 361 skakgqprep qvytlppsre emtknqvslt clvkgfypsd iavewesngq pennykttpp 421 vldsdgsffl yskltvdksr wqqgnvfscs vmhealhnhy tqkslslspg k Nucleic Acid Sequence Encoding the Full Length Humanized Sh24C05 Hv3-23 Heavy Chain (Humanized Heavy Chain Variable Region and Human IgG1 Constant Region)

(SEQ ID NO: 195)

1 atggacatga gagttcctgc tcagctgctc gggttgctgt tgctttggct ccggggtgct 61 aggtgcgagg ttcagcttct ggaatctggc ggtgggcttg tacagccagg aggctccctc 121 agactgagtt gtgccgcttc agggttcaca ttctccgact atgcgatgtc atgggtgcgc 181 caagcacccg ggaaaggact ggagtgggtt tcaactatca gcgatggcgg aacgtatacc 241 tattaccctg acaatgtgaa gggtcggttc accatttcca gggataacag caagaacaca 301 ctctatctcc agatgaacag cctgagggct gaggacaccg ccgtctacta ctgcgcccga 361 gaatggggag attatgatgg gtttgactat tggggccagg gcactttggt gacagtcagt 421 tctgcctcaa caaaaggacc aagtgtgttc ccactcgccc ctagcagcaa gagtacatcc 481 gggggcactg cagcactcgg ctgcctcgtc aaggattatt ttccagagcc agtaaccgtg 541 agctggaaca gtggagcact cacttctggt gtccatactt ttcctgctgt cctgcaaagc 601 tctggcctgt actcactcag ctccgtcgtg accgtgccat cttcatctct gggcactcag 661 acctacatct gtaatgtaaa ccacaagcct agcaatacta aggtcgataa gcgggtggaa 721 cccaagagct gcgacaagac tcacacttgt cccccatgcc ctgcccctga acttctgggc 781 ggtcccagcg tctttttgtt cccaccaaag cctaaagata ctctgatgat aagtagaaca 841 cccgaggtga catgtgttgt tgtagacgtt tcccacgagg acccagaggt taagttcaac 901 tggtacgttg atggagtcga agtacataat gctaagacca agcctagaga ggagcagtat 961 aatagtacat accgtgtagt cagtgttctc acagtgctgc accaagactg gctcaacggc 1021 aaagaataca aatgcaaagt gtccaacaaa gcactcccag cccctatcga gaagactatt 1081 agtaaggcaa aggggcagcc tcgtgaacca caggtgtaca ctctgccacc cagtagagag 1141 gaaatgacaa agaaccaagt ctcattgacc tgcctggtga aaggcttcta ccccagcgac 1201 atcgccgttg agtgggagag taacggtcag cctgagaaca attacaagac aacccccccca 1261 gtgctggata gtgacgggtc tttctttctg tacagtaagc tgactgtgga caagtcccgc 1321 tggcagcagg gtaacgtctt cagctgttcc gtgatgcacg aggcattgca caaccactac 1381 acccagaagt cactgagcct gagcccaggg aag Protein Sequence Defining the Full Length Humanized Sh24C05 Hv3-23 Heavy Chain (Humanized Heavy Chain Variable Region and Human IgG1 Constant Region)

(SEQ ID NO: 196)

1 mdmrvpaqll gllllwlrga rcevqllesg gglvqpggsl rlscaasgft fsdyamswvr 61 qapgkglewv stisdggtyt yypdnvkgrf tisrdnsknt lylqmnslra edtavyycar 121 ewgdydgfdy wgqgtlvtvs sastkgpsvf plapssksts ggtaalgclv kdyfpepvtv 181 swnsgaltsg vhtfpavlqs sglyslssvv tvpssslgtq tyicnvnhkp sntkvdkrve 241 pkscdkthtc ppcpapellg gpsvflfppk pkdtlmisrt pevtcvvvdv shedpevkfn 301 wyvdgvevhn aktkpreeqy nstyrvvsvl tvlhqdwlng keykckvsnk alpapiekti 361 skakgqprep qvytlppsre emtknqvslt clvkgfypsd iavewesngq pennykttpp 421 vldsdgsffl yskltvdksr wqqgnvfscs vmhealhnhy tqkslslspg k -continued Nucleic Acid Sequence Encoding the Full Length Humanized Sh24C05 Hv3-30 Heavy Chain (Humanized Heavy Chain Variable Region and Human IgG1 Constant Region)

(SEQ ID NO: 197)

```
   1 atggacatga gagttcctgc tcagctgctc gggttgctgt tgctttggct ccggggtgct
  61 aggtgccagg ttcagctggt ggaatctggc ggtggggtag tacaaccagg acggtccctc
 121 agactgagtt gtgccgcttc agggttcaca ttctccgact atgcgatgtc atgggtgcgc
 181 caagcacccg ggaaaggact ggagtgggtt gccactatca gcgatggcgg aacgtatacc
 241 tattaccctg acaatgtgaa gggtcggttc accatttcca gggataactc aaagaacacc
 301 ctctatctcc aaatgagtag cctgagggct gaggacaccg ccgtctacta ctgcgcccga
 361 gaatggggag attatgatgg gtttgactat tggggccagg gcactttggt gacagtcagt
 421 tctgcctcaa caaaaggacc aagtgtgttc ccactcgccc ctagcagcaa gagtacatcc
 481 gggggcactg cagcactcgg ctgcctcgtc aaggattatt ttccagagcc agtaaccgtg
 541 agctggaaca gtggagcact cacttctggt gtccatactt ttcctgctgt cctgcaaagc
 601 tctggcctgt actcactcag ctccgtcgtg accgtgccat cttcatctct gggcactcag
 661 acctacatct gtaatgtaaa ccacaagcct agcaatacta aggtcgataa gcgggtggaa
 721 cccaagagct gcgacaagac tcacacttgt cccccatgcc ctgcccctga acttctgggc
 781 ggtcccagcg tctttttgtt cccaccaaag cctaaagata ctctgatgat aagtagaaca
 841 cccgaggtga catgtgttgt tgtagacgtt tcccacgagg acccagaggt taagttcaac
 901 tggtacgttg atggagtcga agtacataat gctaagacca agcctagaga ggagcagtat
 961 aatagtacat accgtgtagt cagtgttctc acagtgctgc accaagactg gctcaacggc
1021 aaagaataca aatgcaaagt gtccaacaaa gcactcccag cccctatcga gaagactatt
1081 agtaaggcaa aggggcagcc tcgtgaacca caggtgtaca ctctgccacc cagtagagag
1141 gaaatgacaa agaaccaagt ctcattgacc tgcctggtga aaggcttcta ccccagcgac
1201 atcgccgttg agtgggagag taacggtcag cctgagaaca attacaagac aacccccccca
1261 gtgctggata gtgacgggtc tttctttctg tacagtaagc tgactgtgga caagtcccgc
1321 tggcagcagg gtaacgtctt cagctgttcc gtgatgcacg aggcattgca caaccactac
1381 acccagaagt cactgagcct gagcccaggg aag
```

Protein Sequence Defining the Full Length Humanized of Sh24C05 Hv3-30 Heavy Chain (Humanized Heavy Chain Variable Region and Human IgG1 Constant Region)

(SEQ ID NO: 198)

```
   1 mdmrvpaqll gllllwlrga rcqvqlvesg ggvvqpgrsl rlscaasgft fsdyamswvr
  61 qapgkglewv atisdggtyt yypdnvkgrf tisrdnsknt lylqmsslra edtavyycar
 121 ewgdydgfdy wgqgtlvtvs sastkgpsvf plapsskstS ggtaalgclv kdyfpepvtv
 181 swnsgaltsg vhtfpavlqs sglyslssvv tvpssslgtq tyicnvnhkp sntkvdkrve
 241 pkscdkthtc ppcpapellg gpsvflfppk pkdtlmisrt pevtcvvvdv shedpevkfn
 301 wyvdgvevhn aktkpreegy nstyrvvsvl tvlhqdwlng keykckvsnk alpapiekti
 361 skakgqprep qvytlppsre emtknqvslt clvkgfypsd iavewesngq pennykttpp
 421 vldsdgsffl yskltvdksr wqqgnvfscs vmhealhnhy tqkslslspg k
```

Nucleic Acid Sequence Encoding the Full Length Humanized Hu24C05 HvA Heavy Chain (Humanized Heavy Chain Variable Region and Human IgG1 Constant Region)

(SEQ ID NO: 199)

```
   1 atggacatga gagttcctgc tcagctgctc gggttgctgt tgctttggct ccggggtgct
  61 aggtgcgagg ttcagctggt ggaatctggc ggtgggcttg taaagccagg aggctccctc
```

-continued

```
121   agactgagtt gtgccgcttc agggttcaca ttctccgact atgcgatgtc atgggtgcgc
181   caagcacccg ggaaaggact ggagtgggtt gccactatca gcgatggcgg aacgtatacc
241   tattaccctg acaatgtgaa gggtcggttc accatttcca gggataacgc aaagaacagt
301   ctctaccttc agatgaacag cctgagggct gaggacaccg ccgtctacta ctgcgcccga
361   gaatggggag attatgatgg gtttgactat tggggccagg gcactttggt gacagtcagt
421   tctgcctcaa caaaaggacc aagtgtgttc ccactcgccc ctagcagcaa gagtacatcc
481   gggggcactg cagcactcgg ctgcctcgtc aaggattatt ttccagagcc agtaaccgtg
541   agctggaaca gtggagcact cacttctggt gtccatactt ttcctgctgt cctgcaaagc
601   tctggcctgt actcactcag ctccgtcgtg accgtgccat cttcatctct gggcactcag
661   acctacatct gtaatgtaaa ccacaagcct agcaatacta aggtcgataa gcgggtggaa
721   cccaagagct gcgacaagac tcacacttgt cccccatgcc ctgcccctga acttctgggc
781   ggtcccagcg tctttttgtt cccaccaaag cctaaagata ctctgatgat aagtagaaca
841   cccgaggtga catgtgttgt tgtagacgtt tcccacgagg acccagaggt taagttcaac
901   tggtacgttg atggagtcga agtacataat gctaagacca agcctagaga ggagcagtat
961   aatagtacat accgtgtagt cagtgttctc acagtgctgc accaagactg gctcaacggc
1021  aaagaataca aatgcaaagt gtccaacaaa gcactcccag cccctatcga gaagactatt
1081  agtaaggcaa aggggcagcc tcgtgaacca caggtgtaca ctctgccacc cagtagagag
1141  gaaatgacaa agaaccaagt ctcattgacc tgcctggtga aaggcttcta ccccagcgac
1201  atcgccgttg agtgggagag taacggtcag cctgagaaca attacaagac aaccccccca
1261  gtgctggata gtgacgggtc tttctttctg tacagtaagc tgactgtgga caagtcccgc
1321  tggcagcagg gtaacgtctt cagctgttcc gtgatgcacg aggcattgca caaccactac
1381  acccagaagt cactgagcct gagcccaggg aag
```

Protein Sequence Defining the Full Length Humanized Hu24C05 HvA Heavy Chain (Humanized Heavy Chain Variable Region and Human IgG1 Constant Region)

(SEQ ID NO: 200)

```
1     mdmrvpaqll gllllwlrga rcevqlvesg gglvkpggsl rlscaasgft fsdyamswvr
61    qapgkglewv atisdggtyt yypdnvkgrf tisrdnakns lylqmnslra edtavyycar
121   ewgdydgfdy wgqgtlvtvs sastkgpsvf plapssksts ggtaalgclv kdyfpepvtv
181   swnsgaltsg vhtfpavlqs sglyslssvv tvpssslgtq tyicnvnhkp sntkvdkrve
241   pkscdkthtc ppcpapellg gpsvflfppk pkdtlmisrt pevtcvvvdv shedpevkfn
301   wyvdgvevhn aktkpreegy nstyrvvsvl tvlhqdwlng keykckvsnk alpapiekti
361   skakgqprep qvytlppsre emtknqvslt clvkgfypsd iavewesngq pennykttpp
421   vldsdgsffl yskltvdksr wqqgnvfscs vmhealhnhy tqkslslspg k
```

Nucleic Acid Sequence Encoding the Full Length Humanized Sh24C05 Kv1-9 Light Chain (Humanized Kappa Chain Variable Region and Human Constant Region)

(SEQ ID NO: 201)

```
1     atggacatga gggtgcccgc tcaactgctg gggctgctgc tgctgtggct gagaggagct
61    cgttgcgata ttcagttgac ccaatcacct agcttcctct cagcttccgt gggcgacaga
121   gttaccataa cctgtcgggc aagccaggag atttctgggt acctgtcctg gtaccaacag
181   aagcccggaa aagcccctaa gctgttgatc tatgctgcgt caaccttgga tagcggtgtc
241   ccgagtcgat tctccggttc tggctccgga acagagttca ctctgacaat ttctagcctt
301   cagccagaag atttcgccac gtactattgc ctccagtacg acagctatcc ctatacattt
361   gggcagggca ctaaactgga gatcaaacgc acagttgctg cccccagcgt gttcattttc
```

-continued

```
421   ccacctagcg atgagcagct gaaaagcggt actgcctctg tcgtatgctt gctcaacaac

481   ttttacccac gtgaggctaa ggtgcagtgg aaagtggata atgcacttca atctggaaac

541   agtcaagagt ccgtgacaga acaggacagc aaagactcaa cttattcact ctcttccacc

601   ctgactctgt ccaaggcaga ctatgaaaaa cacaaggtat acgcctgcga ggttacacac

661   cagggtttgt ctagtcctgt caccaagtcc ttcaataggg gcgaatgt
```

Protein Sequence Defining the Full Length Humanized Sh24C05 Kv1-9 Light Chain (Humanized Kappa Chain Variable Region and Human Constant Region)

(SEQ ID NO: 202)

```
  1   mdmrvpaqll gllllwlrga rcdiqltqsp sflsasvgdr vtitcrasqe isgylswyqq

 61   kpgkapklli yaastldsgv psrfsgsgsg teftltissl qpedfatyyc lqydsypytf

121   gqgtkleikr tvaapsvfif ppsdeqlksg tasvvcllnn fypreakvqw kvdnalqsgn

181   sqesvteqds kdstyslsst ltlskadyek hkvyacevth qglsspvtks fnrgec
```

Nucleic Acid Sequence Encoding the Full Length Humanized Sh24C05 Kv1-16 Light Chain (Humanized Kappa Chain Variable Region and Human Constant Region)

(SEQ ID NO: 203)

```
  1   atggacatga gggtgcccgc tcaactgctg gggctgctgc tgctgtggct gagaggagct

 61   cgttgcgata ttcagatgac ccaatcacct agcagtctct cagcttccgt gggcgacaga

121   gttaccataa cctgtcgggc aagccaggag atttctgggt acctgtcctg gtttcaacag

181   aagcccggaa aggccccgaa gagcttgatc tatgctgcgt caaccttgga tagcggtgtc

241   ccgagtcgat tctccggttc tggctccgga accgacttta ctctgacaat ttctagcctt

301   cagccagaag atttcgccac gtactattgc ctccagtacg acagctatcc ctatacattt

361   gggcagggca ctaaactgga gatcaaacgc acagttgctg cccccagcgt gttcattttc

421   ccacctagcg atgagcagct gaaaagcggt actgcctctg tcgtatgctt gctcaacaac

481   ttttacccac gtgaggctaa ggtgcagtgg aaagtggata atgcacttca atctggaaac

541   agtcaagagt ccgtgacaga acaggacagc aaagactcaa cttattcact ctcttccacc

601   ctgactctgt ccaaggcaga ctatgaaaaa cacaaggtat acgcctgcga ggttacacac

661   cagggtttgt ctagtcctgt caccaagtcc ttcaataggg gcgaatgt
```

Protein Sequence Defining the Full Length Humanized Sh24C05 Kv1-16 Light Chain (Humanized Kappa Chain Variable Region and Human Constant Region)

(SEQ ID NO: 204)

```
  1   mdmrvpaqll gllllwlrga rcdiqmtqsp sslsasvgdr vtitcrasqe isgylswfqq

 61   kpgkapksli yaastldsgv psrfsgsgsg tdftltissl qpedfatyyc lqydsypytf

121   gqgtkleikr tvaapsvfif ppsdeqlksg tasvvcllnn fypreakvqw kvdnalqsgn

181   sqesvteqds kdstyslsst ltlskadyek hkvyacevth qglsspvtks fnrgec
```

Nucleic Acid Sequence Encoding the Full Length Humanized Sh24C05 Kv1-17 Light Chain (Humanized Kappa Chain Variable Region and Human Constant Region)

(SEQ ID NO: 205)

```
  1   atggacatga gggtgcccgc tcaactgctg gggctgctgc tgctgtggct gagaggagct

 61   cgttgcgata ttcagatgac ccaatcacct agcagtctct cagcttccgt gggcgacaga

121   gttaccataa cctgtcgggc aagccaggag atttctgggt acctgtcctg gtatcaacag

181   aagcccggaa aagccccaaa gaggttgatc tatgctgcgt caaccttgga tagcggtgtc

241   ccgagtcgat tctccggttc tggctccgga accgagttca ctctgacaat ttctagcctt

301   cagccagaag atttcgccac gtactattgc ctccagtacg acagctatcc ctatacattt

361   gggcagggca ctaaactgga gatcaaacgc acagttgctg cccccagcgt gttcattttc

421   ccacctagcg atgagcagct gaaaagcggt actgcctctg tcgtatgctt gctcaacaac
```

-continued

```
481   ttttacccac gtgaggctaa ggtgcagtgg aaagtggata atgcacttca atctggaaac
541   agtcaagagt ccgtgacaga acaggacagc aaagactcaa cttattcact ctcttccacc
601   ctgactctgt ccaaggcaga ctatgaaaaa cacaaggtat acgcctgcga ggttacacac
661   cagggtttgt ctagtcctgt caccaagtcc ttcaataggg gcgaatgt
```

Protein Sequence Defining the Full Length Humanized Sh24C05 Kv1-17 Light Chain (Humanized Kappa Chain Variable Region and Human Constant Region)
(SEQ ID NO: 206)

```
  1   mdmrvpaqll gllllwlrga rcdiqmtqsp sslsasvgdr vtitcrasqe isgylswyqq
 61   kpgkapkrli yaastldsgv psrfsgsgsg teftltissl qpedfatyyc lqydsypytf
121   gqgtkleikr tvaapsvfif ppsdeqlksg tasvvcllnn fypreakvqw kvdnalqsgn
181   sqesvteqds kdstyslsst ltlskadyek hkvyacevth qglsspvtks fnrgec
```

Nucleic Acid Sequence Encoding the Full Length Humanized sh24C05 Kv1-33 Light Chain (Humanized Kappa Chain Variable Region and Human Constant Region)
(SEQ ID NO: 207)

```
  1   atggacatga gggtgcccgc tcaactgctg gggctgctgc tgctgtggct gagaggagct
 61   cgttgcgata ttcagatgac ccaatcacct agcagtctct cagcttccgt gggcgacaga
121   gttaccataa cctgtcgggc aagccaggag atttctgggt acctgtcctg gtaccaacag
181   aagcccggaa aggcccccaa gctgttgatc tatgctgcgt caaccttgga tagcggtgtc
241   ccgagtcgat tctccggttc tggctccgga acagacttta cttttacaat ttctagcctt
301   cagccagagg acatcgccac gtactattgc ctccagtacg acagctatcc ctatacattt
361   gggcagggca ctaaactgga gatcaaacgc acagttgctg cccccagcgt gttcattttc
421   ccacctagcg atgagcagct gaaaagcggt actgcctctg tcgtatgctt gctcaacaac
481   ttttacccac gtgaggctaa ggtgcagtgg aaagtggata atgcacttca atctggaaac
541   agtcaagagt ccgtgacaga acaggacagc aaagactcaa cttattcact ctcttccacc
601   ctgactctgt ccaaggcaga ctatgaaaaa cacaaggtat acgcctgcga ggttacacac
661   cagggtttgt ctagtcctgt caccaagtcc ttcaataggg gcgaatgt
```

Protein Sequence Defining the Full Length Humanized Sh24C05 Kv1-33 Light Chain (Humanized Kappa Chain Variable Region and Human Constant Region)
(SEQ ID NO: 208)

```
  1   mdmrvpaqll gllllwlrga rcdiqmtqsp sslsasvgdr vtitcrasqe isgylswyqq
 61   kpgkapklli yaastldsgv psrfsgsgsg tdftftissl qpediatyyc lqydsypytf
121   gqgtkleikr tvaapsvfif ppsdeqlksg tasvvcllnn fypreakvqw kvdnalqsgn
181   sqesvteqds kdstyslsst ltlskadyek hkvyacevth qglsspvtks fnrgec
```

Nucleic Acid Sequence Encoding the Full Length Humanzied Sh24C05 Kv1-39 Light Chain (Humanized Kappa Chain Variable Region and Human Constant Region)
(SEQ ID NO: 209)

```
  1   atggacatga gggtgcccgc tcaactgctg gggctgctgc tgctgtggct gagaggagct
 61   cgttgcgata ttcagatgac ccaatcacct agcagtctct cagcttccgt gggcgacaga
121   gttaccataa cctgtcgggc aagccaggag atttctgggt acctgtcctg gtatcaacag
181   aagcccggaa aagcccctaa gctgttgatc tatgctgcgt caaccttgga tagcggtgtc
241   ccgagtcgat tctccggttc tggctccgga actgacttca ctctgacaat ttctagcctt
301   cagccagaag atttcgccac gtactattgc ctccagtacg acagctatcc ctatacattt
361   gggcagggca ctaaactgga gatcaaacgc acagttgctg cccccagcgt gttcattttc
421   ccacctagcg atgagcagct gaaaagcggt actgcctctg tcgtatgctt gctcaacaac
481   ttttacccac gtgaggctaa ggtgcagtgg aaagtggata atgcacttca atctggaaac
541   agtcaagagt ccgtgacaga acaggacagc aaagactcaa cttattcact ctcttccacc
```

-continued

```
601   ctgactctgt ccaaggcaga ctatgaaaaa cacaaggtat acgcctgcga ggttacacac

661   cagggtttgt ctagtcctgt caccaagtcc ttcaataggg gcgaatgt
```

Protein Sequence Defining the Full Length Humanized Sh24C05 Kv1-39 Light Chain (Humanized Kappa Chain Variable Region and Human Constant Region)
(SEQ ID NO: 210)

```
  1   mdmrvpaqll gllllwlrga rcdiqmtqsp sslsasvgdr vtitcrasqe isgylswyqq

 61   kpgkapklli yaastldsgv psrfsgsgsg tdftltissl qpedfatyyc lqydsypytf

121   gqgtkleikr tvaapsvfif ppsdeqlksg tasvvcllnn fypreakvqw kvdnalqsgn

181   sqesvteqds kdstyslsst ltlskadyek hkvyacevth qglsspvtks fnrgec
```

Nucleic Acid Sequence Encoding the Full Length Humanized Hu24C05 KvA Light Chain (Humanized Kappa Chain Variable Region and Human Constant Region)
(SEQ ID NO: 211)

```
  1   atggacatga gggtgcccgc tcaactgctg gggctgctgc tgctgtggct gagaggagct

 61   cgttgcgata ttcagatgac ccaatcacct agcagtctct cagcttccgt gggcgacaga

121   gttaccataa cctgtcgggc aagccaggag atttctgggt acctgtcctg gctgcaacag

181   aagcccggag gcgccatcaa gaggttgatc tatgctgcgt caaccttgga tagcggtgtc

241   ccgagtcgat tctccggttc tggctccgga agtgactaca ctctgacaat ttctagcctt

301   cagccagaag atttcgccac gtactattgc ctccagtacg acagctatcc ctatacattt

361   gggcagggca ctaaactgga gatcaaacgc acagttgctg cccccagcgt gttcattttc

421   ccacctagcg atgagcagct gaaaagcggt actgcctctg tcgtatgctt gctcaacaac

481   ttttacccac gtgaggctaa ggtgcagtgg aaagtggata atgcacttca atctggaaac

541   agtcaagagt ccgtgacaga acaggacagc aaagactcaa cttattcact ctcttccacc

601   ctgactctgt ccaaggcaga ctatgaaaaa cacaaggtat acgcctgcga ggttacacac

661   cagggtttgt ctagtcctgt caccaagtcc ttcaataggg gcgaatgt
```

Protein Sequence Defining the Full Length Humanized Hu24C05 KvA Light Chain (Humanized Kappa Chain Variable Region and Human Constant Region)
(SEQ ID NO: 212)

```
  1   mdmrvpaqll gllllwlrga rcdiqmtqsp sslsasvgdr vtitcrasqe isgylswlqq

 61   kpggaikrli yaastldsgv psrfsgsgsg sdytltissl qpedfatyyc lqydsypytf

121   gqgtkleikr tvaapsvfif ppsdeqlksg tasvvcllnn fypreakvqw kvdnalqsgn

181   sqesvteqds kdstyslsst ltlskadyek hkvyacevth qglsspvtks fnrgec
```

For convenience, Table 13 provides a concordance chart showing the SEQ ID NO. of each sequence discussed in this Example.

TABLE 13

| SEQ ID NO. | Nucleic Acid or Protein |
|---|---|
| 175 | Human IgG1 constant-nucleic acid |
| 176 | Human IgG1 constant-protein |
| 177 | Human IgG2 constant-nucleic acid |
| 178 | Human IgG2 constant-protein |
| 179 | Human Kappa constant-nucleic acid |
| 180 | Human Kappa constant-protein |
| 181 | Chimeric 24C05 Mouse Heavy Chain Variable + Human IgG1 constant-nucleic acid |
| 182 | Chimeric 24C05 Mouse Heavy Chain Variable + Human IgG1 constant-protein |
| 183 | Chimeric 24C05 Mouse Light Chain Variable + Human Kappa constant-nucleic acid |
| 184 | Chimeric 24C05 Mouse Light Chain Variable + Human Kappa constant-protein |
| 185 | Humanized Sh24C05 Hv3-7 Heavy Human Variable + Human IgG1 constant-nucleic acid |

TABLE 13-continued

| SEQ ID NO. | Nucleic Acid or Protein |
|---|---|
| 186 | Humanized Sh24C05 Hv3-7 Heavy Human Variable + Human IgG1 constant-protein |
| 187 | Humanized Sh24C05 Hv3-11 Heavy Human Variable + Human IgG1 constant-nucleic acid |
| 188 | Humanized Sh24C05 Hv3-11 Heavy Human Variable + Human IgG1 constant-protein |
| 189 | Humanized Sh24C05 Hv3-11 N62S IgG1 Heavy Human Variable + Human IgG1 constant-nucleic acid |
| 190 | Humanized Sh24C05 Hv3-11 N62S IgG1 Heavy Human Variable + Human IgG1 constant-protein |
| 191 | Humanized Sh24C05 Hv3-11 N62S IgG2 Heavy Human Variable + Human IgG2 constant-nucleic acid |
| 192 | Humanized Sh24C05 Hv3-11 N62S IgG2 Heavy Human Variable + Human IgG2 constant-protein |
| 193 | Humanized Sh24C05 Hv3-21Heavy Human Variable + Human IgG1 constant-nucleic acid |
| 194 | Humanized Sh24C05 Hv3-21 Heavy Human Variable + Human IgG1 constant-protein |
| 195 | Humanized Sh24C05 Hv3-23 Heavy Human Variable + Human IgG1 constant-nucleic acid |

TABLE 13-continued

| SEQ ID NO. | Nucleic Acid or Protein |
|---|---|
| 196 | Humanized Sh24C05 Hv3-23 Heavy Human Variable + Human IgG1 constant-protein |
| 197 | Humanized Sh24C05 Hv3-30 Heavy Human Variable + Human IgG1 constant-nucleic acid |
| 198 | Humanized Sh24C05 Hv3-30 Heavy Human Variable + Human IgG1 constant-protein |
| 199 | Humanized Hu24C05 HvA Heavy Human Variable + Human IgG1 constant-nucleic acid |
| 200 | Humanized Hu24C05 HvA Heavy Human Variable + Human IgG1 constant-protein |
| 201 | Humanized Sh24C05 Kv1-9 Human Variable + Human Kappa constant-nucleic acid |
| 202 | Humanized Sh24C05 Kv1-9 Human Variable + Human Kappa constant-protein |
| 203 | Humanized Sh24C05 Kv1-16 Human Variable + Human Kappa constant-nucleic acid |
| 204 | Humanized Sh24C05 Kv1-16 Human Variable + Human Kappa constant-protein |
| 205 | Humanized Sh24C05 Kv1-17 Human Variable + Human Kappa constant-nucleic acid |
| 206 | Humanized Sh24C05 Kv1-17 Human Variable + Human Kappa constant-protein |
| 207 | Humanized Sh24C05 Kv1-33 Human Variable + Human Kappa constant-nucleic acid |
| 208 | Humanized Sh24C05 Kv1-33 Human Variable + Human Kappa constant-protein |
| 209 | Humanized Sh24C05 Kv1-39 Human Variable + Human Kappa constant-nucleic acid |
| 210 | Humanized Sh24C05 Kv1-39 Human Variable + Human Kappa constant-protein |
| 211 | Humanized Hu24C05 KvA Human Variable + Human Kappa constant-nucleic acid |
| 212 | Humanized Hu24C05 KvA Human Variable + Human Kappa constant-protein |

Table 14 below shows antibodies containing chimeric immunoglobulin heavy and light chains and each of the possible combinations of the full-length humanized immunoglobulin heavy and light chains.

TABLE 14

| Antibody Name | Light Chain | Heavy Chain |
|---|---|---|
| Sh24C05-1 | 24C05 Chimeric Kappa (SEQ ID NO: 184) | GP203 24C05 Chimeric Heavy IgG1 (SEQ ID NO: 182) |
| Sh24C05-14 | Hu24C05 KvA Kappa (SEQ ID NO: 212) | Hu24C05 HvA IgG1 (SEQ ID NO: 200) |
| Sh24C05-15 | Hu24C05 KvA Kappa (SEQ ID NO: 212) | Sh24C05 Hv3-21 Heavy IgG1 (SEQ ID NO: 194) |
| Sh24C05-16 | Hu24C05 KvA Kappa (SEQ ID NO: 212) | Sh24C05 Hv3-23 Heavy IgG1 (SEQ ID NO: 196) |
| Sh24C05-17 | Hu24C05 KvA Kappa (SEQ ID NO: 212) | Sh24C05 Hv3-30 Heavy IgG1 (SEQ ID NO: 198) |
| Sh24C05-18 | Hu24C05 KvA Kappa (SEQ ID NO: 212) | Sh24C05 Hv3-7 Heavy IgG1 (SEQ ID NO: 186) |
| Sh24C05-19 | Hu24C05 KvA Kappa (SEQ ID NO: 212) | Sh24C05 Hv3-11 Heavy IgG1 (SEQ ID NO: 188) |
| Sh24C05-19 N62S IgG1 | Hu24C05 KvA Kappa (SEQ ID NO: 212) | Sh24C05 Hv3-11 N62S Heavy IgG1 (SEQ ID NO: 190) |
| Sh24C05-19 N62S IgG2 | Hu24C05 KvA Kappa (SEQ ID NO: 212) | Sh24C05 Hv3-11 N62S Heavy IgG2 (SEQ ID NO: 192) |
| Sh24C05-20 | Sh24C05 Kv1-16 Kappa (SEQ ID NO: 204) | Hu24C05 HvA IgG1 (SEQ ID NO: 200) |
| Sh24C05-21 | Sh24C05 Kv1-16 Kappa (SEQ ID NO: 204) | Sh24C05 Hv3-21 Heavy IgG1 (SEQ ID NO: 194) |
| Sh24C05-22 | Sh24C05 Kv1-16 Kappa (SEQ ID NO: 204) | Sh24C05 Hv3-23 Heavy IgG1 (SEQ ID NO: 196) |
| Sh24C05-23 | Sh24C05 Kv1-16 Kappa (SEQ ID NO: 204) | Sh24C05 Hv3-30 Heavy IgG1 (SEQ ID NO: 198) |

TABLE 14-continued

| Antibody Name | Light Chain | Heavy Chain |
|---|---|---|
| Sh24C05-24 | Sh24C05 Kv1-16 Kappa (SEQ ID NO: 204) | Sh24C05 Hv3-7 Heavy IgG1 (SEQ ID NO: 186) |
| Sh24C05-25 | Sh24C05 Kv1-16 Kappa (SEQ ID NO: 204) | Sh24C05 Hv3-11 Heavy IgG1 (SEQ ID NO: 188) |
| Sh24C05-25 N62S IgG1 | Sh24C05 Kv1-16 Kappa (SEQ ID NO: 204) | Sh24C05 Hv3-11 N62S Heavy IgG1 (SEQ ID NO: 190) |
| Sh24C05-25 N62S IgG2 | Sh24C05 Kv1-16 Kappa (SEQ ID NO: 204) | Sh24C05 Hv3-11 N62S Heavy IgG2 (SEQ ID NO: 192) |
| Sh24C05-26 | Sh24C05 Kv1-17 Kappa (SEQ ID NO: 206) | Hu24C05 HvA IgG1 (SEQ ID NO: 200) |
| Sh24C05-27 | Sh24C05 Kv1-17 Kappa (SEQ ID NO: 206) | Sh24C05 Hv3-21 Heavy IgG1 (SEQ ID NO: 194) |
| Sh24C05-28 | Sh24C05 Kv1-17 Kappa (SEQ ID NO: 206) | Sh24C05 Hv3-23 Heavy IgG1 (SEQ ID NO: 196) |
| Sh24C05-29 | Sh24C05 Kv1-17 Kappa (SEQ ID NO: 206) | Sh24C05 Hv3-30 Heavy IgG1 (SEQ ID NO: 198) |
| Sh24C05-30 | Sh24C05 Kv1-17 Kappa (SEQ ID NO: 206) | Sh24C05 Hv3-7 Heavy IgG1 (SEQ ID NO: 186) |
| Sh24C05-31 | Sh24C05 Kv1-17 Kappa (SEQ ID NO: 206) | Sh24C05 Hv3-11 Heavy IgG1 (SEQ ID NO: 188) |
| Sh24C05-31 N62S IgG1 | Sh24C05 Kv1-17 Kappa (SEQ ID NO: 206) | Sh24C05 Hv3-11 N62S Heavy IgG1 (SEQ ID NO: 190) |
| Sh24C05-31 N62S IgG2 | Sh24C05 Kv1-17 Kappa (SEQ ID NO: 206) | Sh24C05 Hv3-11 N62S Heavy IgG2 (SEQ ID NO: 192) |
| Sh24C05-32 | Sh24C05 Kv1-33 Kappa (SEQ ID NO: 208) | Hu24C05 HvA IgG1 (SEQ ID NO: 200) |
| Sh24C05-33 | Sh24C05 Kv1-33 Kappa (SEQ ID NO: 208) | Sh24C05 Hv3-21 Heavy IgG1 (SEQ ID NO: 194) |
| Sh24C05-34 | Sh24C05 Kv1-33 Kappa (SEQ ID NO: 208) | Sh24C05 Hv3-23 Heavy IgG1 (SEQ ID NO: 196) |
| Sh24C05-35 | Sh24C05 Kv1-33 Kappa (SEQ ID NO: 208) | Sh24C05 Hv3-30 Heavy IgG1 (SEQ ID NO: 198) |
| Sh24C05-36 | Sh24C05 Kv1-33 Kappa (SEQ ID NO: 208) | Sh24C05 Hv3-7 Heavy IgG1 (SEQ ID NO: 186) |
| Sh24C05-37 | Sh24C05 Kv1-33 Kappa (SEQ ID NO: 208) | Sh24C05 Hv3-11 Heavy IgG1 (SEQ ID NO: 188) |
| Sh24C05-37 N62S IgG1 | Sh24C05 Kv1-33 Kappa (SEQ ID NO: 208) | Sh24C05 Hv3-11 N62S Heavy IgG1 (SEQ ID NO: 190) |
| Sh24C05-37 N62S IgG2 | Sh24C05 Kv1-33 Kappa (SEQ ID NO: 208) | Sh24C05 Hv3-11 N62S Heavy IgG2 (SEQ ID NO: 192) |
| Sh24C05-38 | Sh24C05 Kv1-9 Kappa (SEQ ID NO: 202) | Hu24C05 HvA IgG1 (SEQ ID NO: 200) |
| Sh24C05-39 | Sh24C05 Kv1-9 Kappa (SEQ ID NO: 202) | Sh24C05 Hv3-21 Heavy IgG1 (SEQ ID NO: 194) |
| Sh24C05-40 | Sh24C05 Kv1-9 Kappa (SEQ ID NO: 202) | Sh24C05 Hv3-23 Heavy IgG1 (SEQ ID NO: 196) |
| Sh24C05-41 | Sh24C05 Kv1-9 Kappa (SEQ ID NO: 202) | Sh24C05 Hv3-30 Heavy IgG1 (SEQ ID NO: 198) |
| Sh24C05-42 | Sh24C05 Kv1-9 Kappa (SEQ ID NO: 202) | Sh24C05 Hv3-7 Heavy IgG1 (SEQ ID NO: 186) |
| Sh24C05-43 | Sh24C05 Kv1-9 Kappa (SEQ ID NO: 202) | Sh24C05 Hv3-11 Heavy IgG1 (SEQ ID NO: 188) |
| Sh24C05-43 N62S IgG1 | Sh24C05 Kv1-9 Kappa (SEQ ID NO: 202) | Sh24C05 Hv3-11 N62S Heavy IgG1 (SEQ ID NO: 190) |
| Sh24C05-43 N62S IgG2 | Sh24C05 Kv1-9 Kappa (SEQ ID NO: 202) | Sh24C05 Hv3-11 N62S Heavy IgG2 (SEQ ID NO: 192) |
| Sh24C05-44 | Sh24C05 Kv1-39 Kappa (SEQ ID NO: 210) | Hu24C05 HvA IgG1 (SEQ ID NO: 200) |
| Sh24C05-45 | Sh24C05 Kv1-39 Kappa (SEQ ID NO: 210) | Sh24C05 Hv3-21 Heavy IgG1 (SEQ ID NO: 194) |
| Sh24C05-46 | Sh24C05 Kv1-39 Kappa (SEQ ID NO: 210) | Sh24C05 Hv3-23 Heavy IgG1 (SEQ ID NO: 196) |
| Sh24C05-47 | Sh24C05 Kv1-39 Kappa (SEQ ID NO: 210) | Sh24C05 Hv3-30 Heavy IgG1 (SEQ ID NO: 198) |
| Sh24C05-48 | Sh24C05 Kv1-39 Kappa (SEQ ID NO: 210) | Sh24C05 Hv3-7 Heavy IgG1 (SEQ ID NO: 186) |
| Sh24C05-49 | Sh24C05 Kv1-39 Kappa (SEQ ID NO: 210) | Sh24C05 Hv3-11 Heavy IgG1 (SEQ ID NO: 188) |

TABLE 14-continued

| Antibody Name | Light Chain | Heavy Chain |
|---|---|---|
| Sh24C05-49 N62S IgG1 | Sh24C05 Kv1-39 Kappa (SEQ ID NO: 210) | Sh24C05 Hv3-11 N62S Heavy IgG1 (SEQ ID NO: 190) |
| Sh24C05-49 N62S IgG2 | Sh24C05 Kv1-39 Kappa (SEQ ID NO: 210) | Sh24C05 Hv3-11 N62S Heavy IgG2 (SEQ ID NO: 192) |

The antibody construct containing the full length chimeric heavy and light chains is designated below:

Chimeric 24C05=Full Length Chimeric 24C05 Heavy Chain (Mouse Variable Region and Human IgG1 Constant Region) (SEQ ID NO: 182) plus Full Length Chimeric 24C05 Light Chain (Mouse Variable Region and Human Kappa Constant Region) (SEQ ID NO: 184)

Four of the possible antibody constructs containing the full length immunoglobulin heavy and light chains containing humanized variable regions are designated below:

Sh24C05-25 N62S IgG1=Humanized Sh24C05 Hv3-11 N62S Heavy Chain Variable Region and Human IgG1 Constant Region (SEQ ID NO: 190) plus Sh24C05 Kv1-16 Light Chain Variable Region and Human Kappa Constant Region (SEQ ID NO: 204)

Sh24C05-25 N62S IgG2=Humanized Sh24C05 Hv3-11 N62S Heavy Chain Variable Region and Human IgG2 Constant Region (SEQ ID NO: 192) plus Sh24C05 Kv1-16 Light Chain Variable Region and Human Kappa Constant Region (SEQ ID NO: 204)

Sh24C05-31 N62S IgG1=Humanized Sh24C05 Hv3-11 N62S Heavy Chain Variable Region and Human IgG1 Constant Region (SEQ ID NO: 190) plus Sh24C05 Kv1-17 Light Chain Variable Region and Human Kappa Constant Region (SEQ ID NO: 206)

Sh24C05-31 N62S IgG2=Humanized Sh24C05 Hv3-11 N62S Heavy Chain Variable Region and Human IgG2 Constant Region (SEQ ID NO: 192) plus Sh24C05 Kv1-17 Light Chain Variable Region and Human Kappa Constant Region (SEQ ID NO: 206)

B. Binding Affinities of Humanized and Chimeric Anti-ErbB3 Monoclonal Antibodies The binding affinities and kinetics of interaction of monoclonal antibodies produced in Example 12 against recombinant human ErbB3 monomeric protein (cleaved rhErbB3) were measured by surface plasmon resonance using a Biacore® T100 (Biacore) instrument. Monomeric ErbB3 was obtained by protease cleavage of rhErbB3-Fc (R&D Systems, Cat. No. 348-RB).

Goat anti-human IgG Fc (Jackson ImmunoResearch, Catalog No. 109-005-098) was immobilized on carboxymethylated dextran CM4 sensor chips (Biacore, Catalog No. BR-1005-34) by amine coupling (Biacore, Catalog No. BR-1000-50) using a standard coupling protocol according to the vendor's instructions. The analyses were performed at 37° C. using PBS (Invitrogen, Catalog No. 14040-133) containing 0.05% surfactant P20 (Biacore, Catalog No. BR-1000-54) as running buffer.

The antibodies were captured in individual flow cells at a flow rate of 60 μl/minute. Injection time was varied for each antibody to yield an $R_{max}$ between 30 and 60 RU. Buffer or cleaved rhErbB3 diluted in running buffer was injected sequentially over a reference surface (no antibody captured) and the active surface (antibody to be tested) for 300 seconds at 60 μl/minute. The dissociation phase was monitored for up to 1200 seconds. The surface was then regenerated with two 60 second injections of Glycine pH 2.25 (made from Glycine pH 2.0 (Biacore, Catalog No. BR-1003-55) and pH 2.5 (Biacore, Catalog No. BR-1003-56)) at 60 μl/minute. For the initial screening, only one or two concentrations of cleaved rhErbB3 were tested, typically 5.0 and 1.25 nM (results are summarized in Table 15).

Kinetic parameters were determined using the kinetic function of the BIAevaluation software (Biacore) with double reference subtraction. Kinetic parameters for each antibody, $k_a$ (association rate constant), $k_d$ (dissociation rate constant) and $K_D$ (equilibrium dissociation constant) were determined. The initial monoclonal antibodies were screened using cell culture media supernatant containing secreted antibody, and kinetic values of the monoclonal antibodies on cleaved rhErbB3 at 37° C. are summarized in Table 15.

TABLE 15

| Antibody | $k_a$ (1/Ms) | $k_d$ (1/s) | $K_D$ (M) | n |
|---|---|---|---|---|
| Sh24C05-1 | 2.52E+06 | 4.48E−04 | 1.78E−10 | 3 |
| Sh24C05-14 | 2.88E+06 | 4.98E−04 | 1.73E−10 | 2 |
| Sh24C05-15 | 2.67E+06 | 4.99E−04 | 1.87E−10 | 2 |
| Sh24C05-16 | 2.75E+06 | 4.04E−04 | 1.47E−10 | 2 |
| Sh24C05-17 | 2.79E+06 | 4.17E−04 | 1.50E−10 | 2 |
| Sh24C05-18 | 2.88E+06 | 4.63E−04 | 1.61E−10 | 2 |
| Sh24C05-19 | 3.00E+06 | 2.55E−04 | 8.55E−11 | 2 |
| Sh24C05-20 | 2.67E+06 | 5.91E−04 | 2.21E−10 | 2 |
| Sh24C05-21 | 3.11E+06 | 6.62E−04 | 2.20E−10 | 2 |
| Sh24C05-22 | 2.79E+06 | 6.01E−04 | 2.16E−10 | 2 |
| Sh24C05-23 | 2.79E+06 | 7.21E−04 | 2.63E−10 | 2 |
| Sh24C05-24 | 2.90E+06 | 6.28E−04 | 2.18E−10 | 2 |
| Sh24C05-25 | 2.63E+06 | 4.59E−04 | 1.75E−10 | 2 |
| Sh24C05-26 | 3.36E+06 | 7.39E−04 | 2.20E−10 | 2 |
| Sh24C05-27 | 3.34E+06 | 7.98E−04 | 2.40E−10 | 2 |
| Sh24C05-28 | 3.26E+06 | 6.14E−04 | 1.89E−10 | 2 |
| Sh24C05-29 | 3.25E+06 | 5.88E−04 | 1.82E−10 | 2 |
| Sh24C05-30 | 4.48E+06 | 7.87E−04 | 1.90E−10 | 2 |
| Sh24C05-31 | 3.47E+06 | 2.92E−04 | 8.65E−11 | 2 |
| Sh24C05-32 | 9.98E+06 | 6.02E−03 | 6.03E−10 | 1 |
| Sh24C05-33 | 4.02E+06 | 4.33E−03 | 1.08E−09 | 1 |
| Sh24C05-34 | 1.09E+07 | 6.00E−03 | 5.52E−10 | 1 |
| Sh24C05-35 | 8.44E+06 | 5.53E−03 | 6.55E−10 | 1 |
| Sh24C05-36 | 5.18E+06 | 4.34E−03 | 8.37E−10 | 1 |
| Sh24C05-37 | 5.94E+06 | 2.00E−03 | 3.74E−10 | 2 |
| Sh24C05-38 | 2.71E+07 | 1.54E−02 | 5.67E−10 | 1 |
| Sh24C05-39 | 1.18E+07 | 9.67E−03 | 8.19E−10 | 1 |
| Sh24C05-40 | 2.11E+07 | 1.06E−02 | 5.03E−10 | 1 |
| Sh24C05-41 | 1.81E+07 | 1.21E−02 | 6.69E−10 | 1 |
| Sh24C05-42 | 7.35E+06 | 6.82E−03 | 9.27E−10 | 1 |
| Sh24C05-43 | 6.16E+06 | 3.58E−03 | 5.82E−10 | 1 |
| Sh24C05-44 | 7.96E+06 | 5.12E−03 | 6.44E−10 | 1 |
| Sh24C05-45 | 8.57E+06 | 6.06E−03 | 7.07E−10 | 1 |
| Sh24C05-46 | 7.99E+06 | 4.40E−03 | 5.51E−10 | 1 |
| Sh24C05-47 | 7.98E+06 | 4.41E−03 | 5.53E−10 | 1 |
| Sh24C05-48 | 8.72E+06 | 4.90E−03 | 5.62E−10 | 1 |
| Sh24C05-49 | 4.08E+06 | 1.70E−03 | 4.16E−10 | 2 |

The results in Table 15 demonstrate that the chimeric and each of the humanized 24C05 antibodies have fast association rates ($k_a$), very slow disassociation rates ($k_d$) and very high affinities ($K_D$). In particular, the antibodies have affinities ranging from about 87 pM to about 1 nM.

The binding affinities and kinetics of certain purified monoclonal antibodies were also determined. To further characterize certain antibodies, the surface plasmon resonance experiments described above were conducted using concentrations of cleaved rhErbB3 between 0.3125 nM and 5.0 nM (a 2-fold serial dilution).

The kinetic values of certain purified monoclonal antibodies (i.e., Sh24C05-1, Sh24C05-25, Sh24C05-25 N62S IgG1, Sh24C05-25 N62S IgG2, Sh24C05-31, Sh24C05-31

N62S IgG1, and Sh24C05-31 N62S IgG2) on cleaved rhErbB3 at 37° C. are summarized in Table 16.

TABLE 16

| Antibody | $k_a$ (1/Ms) | $k_d$ (1/s) | $K_D$ (M) | n |
|---|---|---|---|---|
| Sh24C05-1 | 3.5E+06 | 4.4E−04 | 1.4E−10 | 3 |
| Sh24C05-25 | 4.0E+06 | 5.0E−04 | 1.3E−10 | 4 |
| Sh24C05-25 N62S IgG1 | 2.9E+06 | 4.5E−04 | 1.6E−10 | 4 |
| Sh24C05-25 N62S IgG2 | 2.7E+06 | 3.4E−04 | 1.2E−10 | 4 |
| Sh24C05-31 | 4.7E+06 | 2.8E−04 | 6.3E−11 | 3 |
| Sh24C05-31 N62S IgG1 | 3.5E+06 | 2.7E−04 | 7.6E−11 | 6 |
| Sh24C05-31 N62S IgG2 | 3.2E+06 | 2.4E−04 | 7.4E−11 | 3 |

The results in Table 16 demonstrate the purified antibodies have a have affinities ranging from about 63 pM to about 160 pM when tested at 37° C.

C. Comparison of Other Anti-ErbB3 Antibodies

Three human antibodies that inhibit the function of human ErbB3 were constructed and expressed using published information. One antibody, referred to as Ab #6, was constructed as a human IgG2/Lambda antibody based the disclosure of Schoeberl et al., US 2009/0291085 (Merrimack Pharmaceuticals, Inc.). Two additional antibodies, referred to as U1-53 and U1-59, were constructed as human IgG1/Kappa antibodies based on the disclosure of Rothe et al., US 2008/0124345 (U3 Pharma AG and Amgen, Inc.).

Figure 17:
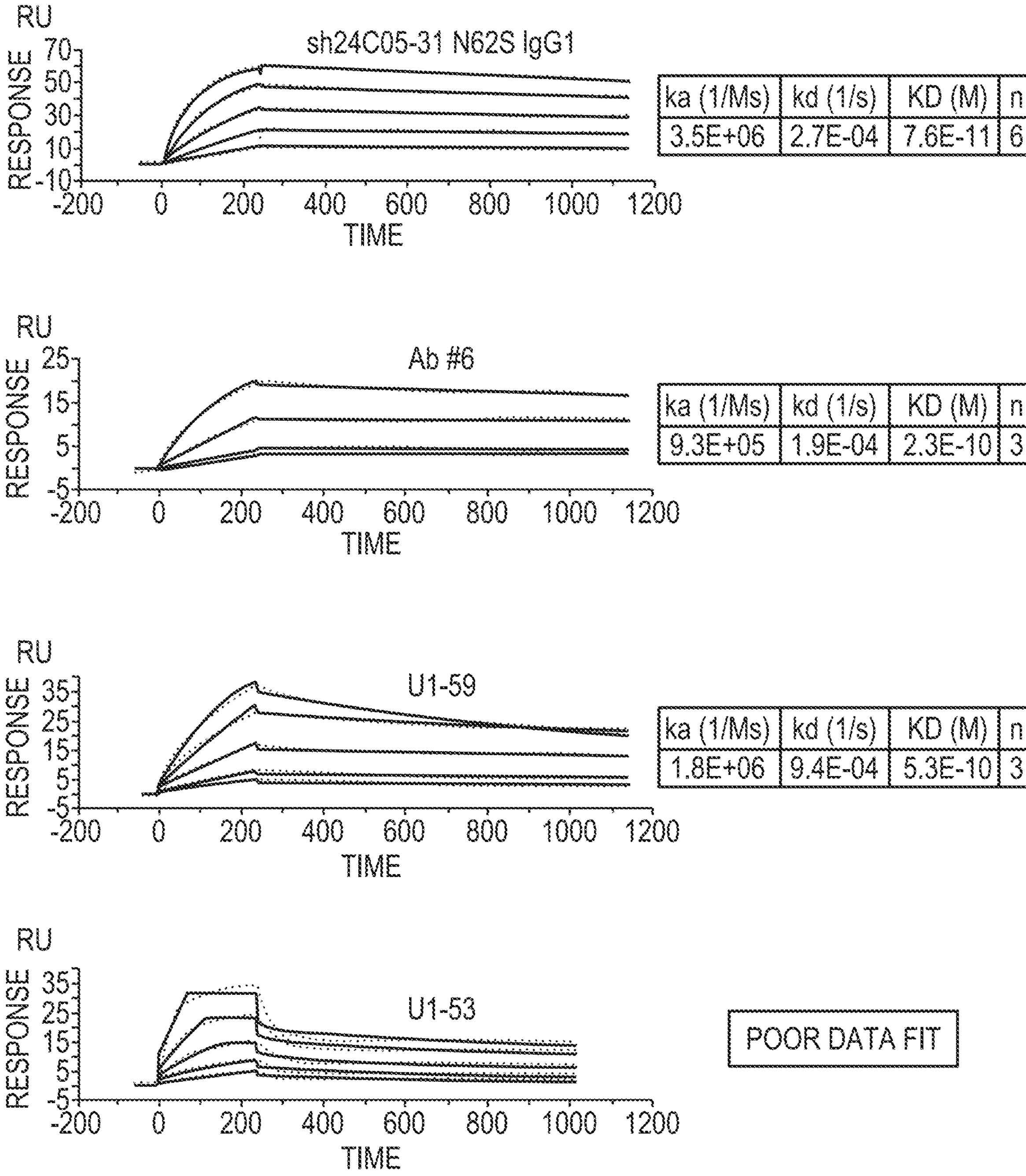
FIG. 17 are Biacore sensorgrams representing results from an experiment to measure the kinetic values of anti-ErbB3 monoclonal antibodies, Sh24C05-31 N62S-IgG1, Ab #6, U1-53, and U1-59.

Kinetic parameters for the Ab #6, U1-53, and U1-59 antibodies were determined by Biacore at 37° C. using cleaved rhErbB3 (monomer) as described above (See Section B. Binding Affinities of Humanized and Chimeric Anti-ErbB3 Monoclonal Antibodies). Both Biacore sensorgrams (FIG. 17) and kinetic values (Table 17) are displayed for each antibody.

TABLE 17

| Antibody | $k_a$ (1/Ms) | $k_d$ (1/s) | $K_D$ (M) | n |
|---|---|---|---|---|
| Sh24C05-31 N62S IgG1 | 3.5+06 | 2.7E−04 | 7.6E−11 | 6 |
| Ab#6 | 9.3E+05 | 1.9E−04 | 2.3E−10 | 3 |
| U1-59 | 1.8E+06 | 9.4E−04 | 5.3E−10 | 3 |
| U1-53 | — | — | — | — |

The results in Table 17 demonstrate that the overall equilibrium dissociation constant ($K_D$) for the Sh24C05-31 N62S IgG1 (76 pM) was smaller (i.e., higher affinity) than the $K_D$ for the Ab #6 and U1-59 antibodies (230 pM ($p<0.01$) and 530 pM ($p<0.0005$), respectively). The equilibrium dissociation constant ($K_D$) for U1-53 could not determined because of poor curve fits (see FIG. 17, which shows a fast $K_{off}$ rate of U1-53). The $K_D$ of Ab #6, U1-53, and U1-59 antibodies can also be compared with other humanized 24C05 variants by comparing Tables 16 and 17.

Therefore, the affinity for Sh24C05-31 N62S IgG1 is significantly higher than the affinity of Ab #6 and U1-59 as disclosed herein.

Example 13—Neutralization Activity of the Humanized Anti-ErbB3 Antibodies

In this example, the humanized antibodies produced in Example 12 were tested for their ability to inhibit rhErbB3 binding to NRG1-β1 by ECL assay. Multi-array 96-well standard binding plates (Meso Scale Discovery, Cat. No. L15XA-3) were coated with 50 µl of 0.5 µg/mL rhErbB3/Fc (R&D systems, Cat. No. 348-RB) in PBS (Invitrogen, Cat. No. 14040-133) for one hour at room temperature with no agitation. The plates then were washed three times with PBS+0.1% Tween20 (Sigma P5927) and blocked with 200 µl of 100% Horse Serum, heat inactivated (GIBCO, Cat. No. 26050-088) for 1.5 hours at room temperature. After washing the plates three times with PBS+0.1% Tween, 25 µl of the antibody dilutions were added to the plates for another hour at room temperature with agitation. Ligand NRG1-β1 (R&D Systems, Cat. No. 377-HB, 26 kDa) was added to the wells at a final concentration of 0.25 µg/ml. The plates were washed three times with PBS+0.1% Tween and incubated with 25 µl of 1 µg/mL biotinylated antibody against human NRG1-β1 (R&D systems, Cat. No BAF377) preincubated for one hour with SULTO-TAG Streptavidin (Meso Scale Discovery, Cat. No R32AD-5) for one hour at room temperature with agitation. The plates then were washed three times with PBS+0.1% Tween, and 150 µl of 1× read buffer (Meso Scale Discovery, Cat. No. R92TC-1) was added to each well before the plates were analyzed on a Sector® Imager 2400 (Meso Scale Discovery) instrument.

Figure 18A:
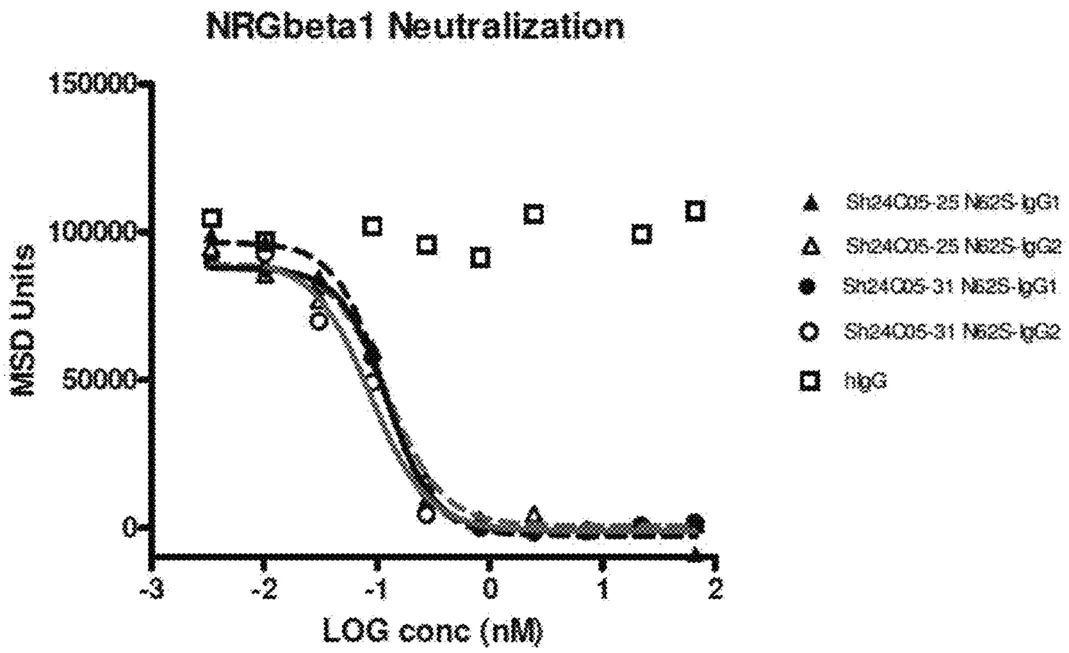
FIG. 18A is a graph summarizing results from an experiment to measure the neutralization activity of negative control (human IgG (□)) and anti-ErbB3 monoclonal antibodies Sh24C05-25 N62S-IgG1 (▲), Sh24C05-25 N62S-IgG2 (Δ), Sh24C05-31 N62S-IgG1 (●) and Sh24C05-31 N62S-IgG2 (○).
Figure 18B:
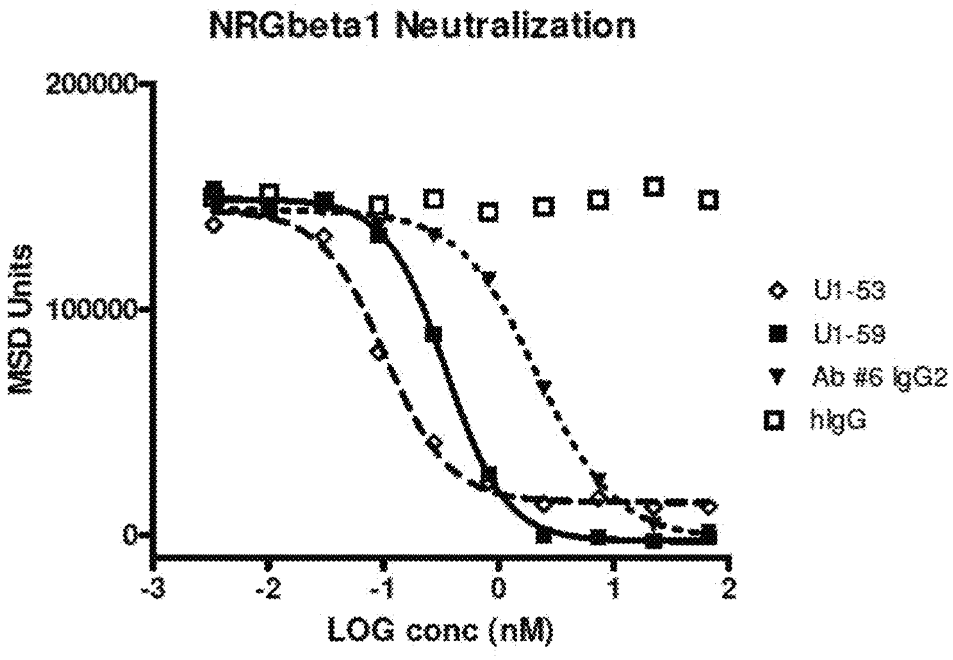
FIG. 18B is a graph summarizing results from an experiment to measure the neutralization activity of human IgG (□) and anti-ErbB3 monoclonal antibodies Ab #6 IgG2 (▼), U1-53 (◇) and U1-59 (■).

The interaction of NRG1-β1 with rhErbB3 was inhibited by antibodies Sh24C05-25 N62S-IgG1, Sh24C05-25 N62S-IgG2, Sh24C05-31 N62S-IgG1, and Sh24C05-31 N62S-IgG2 (FIG. 18A). The Ab #6 IgG2 antibody as described in Schoeberl et al. (supra) and the U1-53 and U1-59 antibodies as described in Rothe et al. (supra) were also tested for their ability to inhibit ErbB3 binding to NRG1-β1. As shown in FIG. 18B, each of the Ab #6 IgG2, U1-53, and U1-59 antibodies inhibited ErbB3 binding to NRG1-β1.

The $IC_{50}$ values for neutralization of NRG1-β1 binding to hErbB3 for the humanized 24C05 antibodies (i.e., Sh24C05-25 N62S-IgG1, Sh24C05-25 N62S-IgG2, Sh24C05-31 N62S-IgG1, and Sh24C05-31 N62S-IgG2) were calculated and are summarized in Table 18. The $IC_{50}$ values for the NRG1-β1 neutralization activity of the anti-ErbB3 human antibodies Ab #6 IgG2, U1-53 and U1-59 are also shown in Table 18.

TABLE 18

| | $IC_{50}$ (nM) | | |
|---|---|---|---|
| Antibody | Average | Standard Deviation | n |
| Sh24C05-25 N62S-IgG1 | 0.1219 | 0.0173 | 4 |
| Sh24C05-25 N62S-IgG2 | 0.1117 | 0.0154 | 4 |
| Sh24C05-31 N62S-IgG1 | 0.1242 | 0.0391 | 5 |
| Sh24C05-31 N62S-IgG2 | 0.0860 | 0.0588 | 4 |
| U1-53 | 0.1128 | 0.0615 | 3 |
| U1-59 | 0.3181 | 0.0274 | 3 |
| Ab#6 IgG2 | 1.5161 | 0.5883 | 5 |

The results in Table 18 demonstrate that antibodies Sh24C05-25 N62S-IgG1, Sh24C05-25 N62S-IgG2, Sh24C05-31 N62S-IgG1, and Sh24C05-31 N62S-IgG2 efficiently neutralized NRG1-β1 binding to rhErbB3. While the anti-ErbB3 human antibodies Ab #6 IgG2, U1-53 and U1-59 also showed neutralization activity, the humanized Sh24C05 antibodies (i.e., Sh24C05-25 N62S-IgG1, Sh24C05-25 N62S-IgG2, Sh24C05-31 N62S-IgG1, and Sh24C05-31 N62S-IgG2) had superior neutralization capacity than U1-59 or Ab #6 IgG2.

Example 14—Anti-Proliferative Activity

In this example, the humanized antibodies produced in Example 12 were tested for their ability to inhibit NRG1-β1 dependent proliferation of cells in the BaF/3 cell system engineered to express both human Her2 and ErbB3.

BaF/3 cells expressing Her2 and ErbB3 receptors as described in Example 6 were treated with anti-ErbB3 antibodies in the absence of WEHI conditioned media but in the presence of NRG1-β1 (100 ng/ml). Assays were conducted in a 96-well plate (5,000 cells/well) in the presence of NRG1-β1 (100 ng/ml) and various concentrations of antibodies (0.018-5000 ng/ml in 100 μl of final volume). MTT (3-(4,5-Dimethylthiazol-2-yl)-2,5-diphenyltetrazolium bromide) assays were conducted 3-4 days post NRG1-β1 stimulation.

Figure 19A:
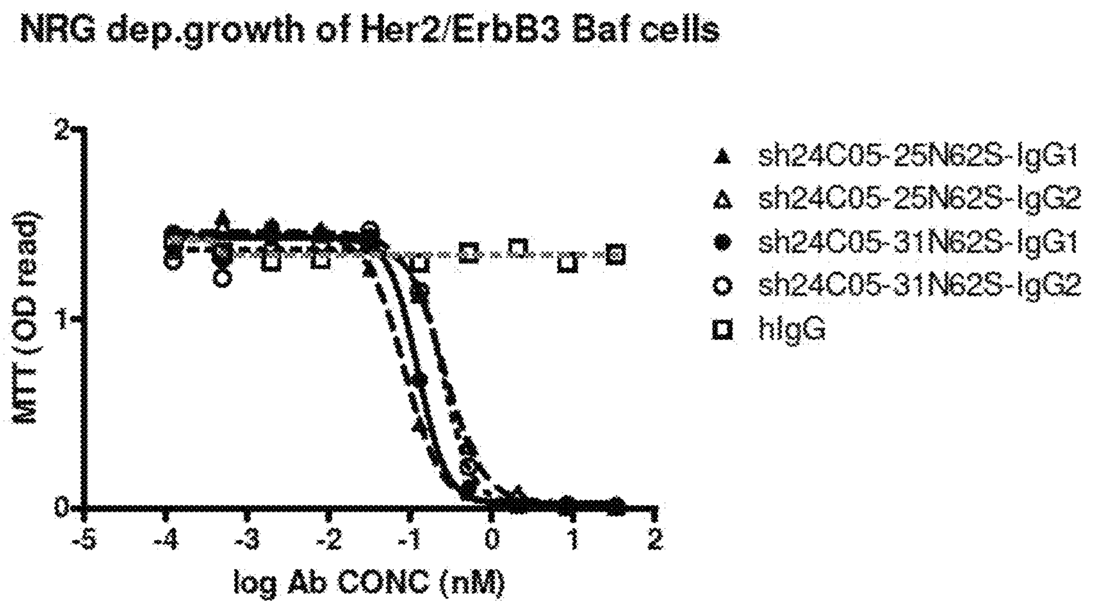
FIG. 19A is a graph summarizing results from an experiment to measure the inhibitory activity of negative control (human IgG (□)) and anti-ErbB3 monoclonal antibodies Sh24C05-25 N62S-IgG1 (▲), Sh24C05-25 N62S-IgG2 (Δ), Sh24C05-31 N62S-IgG1 (●) and Sh24C05-31 N62S-IgG2 (○) in BaF/3 cells expressing Her2 and ErbB3 in the presence of NRG1-β1.

The results demonstrate that Sh24C05-25 N62S-IgG1, Sh24C05-25 N62S-IgG2, Sh24C05-31 N62S-IgG1, and Sh24C05-31 N62S-IgG2 inhibited NRG induced Her2/ErbB3-BaF/3 cell proliferation in a dose dependent manner (FIG. 19A).

The $IC_{50}$ values for the inhibition of NRG1-β1 dependent Her2/ErbB3-BaF/3 cell line proliferation with the humanized 24C05 antibodies (i.e., Sh24C05-25 N62S-IgG1, Sh24C05-25 N62S-IgG2, Sh24C05-31 N62S-IgG1, Sh24C05-31 N62S-IgG2) were calculated and are summarized in Table 19.

TABLE 19

Her2/ErbB3-BaF/3, NRG1-β1 Dependent Proliferation

| Antibody | $IC_{50}$ (nM)-Average | Standard deviation | n |
|---|---|---|---|
| Sh24C05-25 N62S-IgG1 | 0.0981 | 0.0187 | 2 |
| Sh24C05-25 N62S-IgG2 | 0.2482 | 0.0124 | 2 |
| Sh24C05-31 N62S-IgG1 | 0.1245 | 0.0181 | 5 |
| Sh24C05-31 N62S-IgG2 | 0.2392 | 0.0217 | 2 |
| U1-53 | 0.8128 | 0.0268 | 3 |
| U1-59 | 0.8364 | 0.0434 | 5 |
| Ab#6 IgG2 | 6.3015 | 0.8577 | 2 |

The results in Table 19 demonstrate that antibodies Sh24C05-25 N62S-IgG1, Sh24C05-25 N62S-IgG2, Sh24C05-31 N62S-IgG1, and Sh24C05-31 N62S-IgG2 strongly inhibited NRG1-β1-induced proliferation of BaF/3 cells expressing Her2/ErbB3.

Figure 19B:
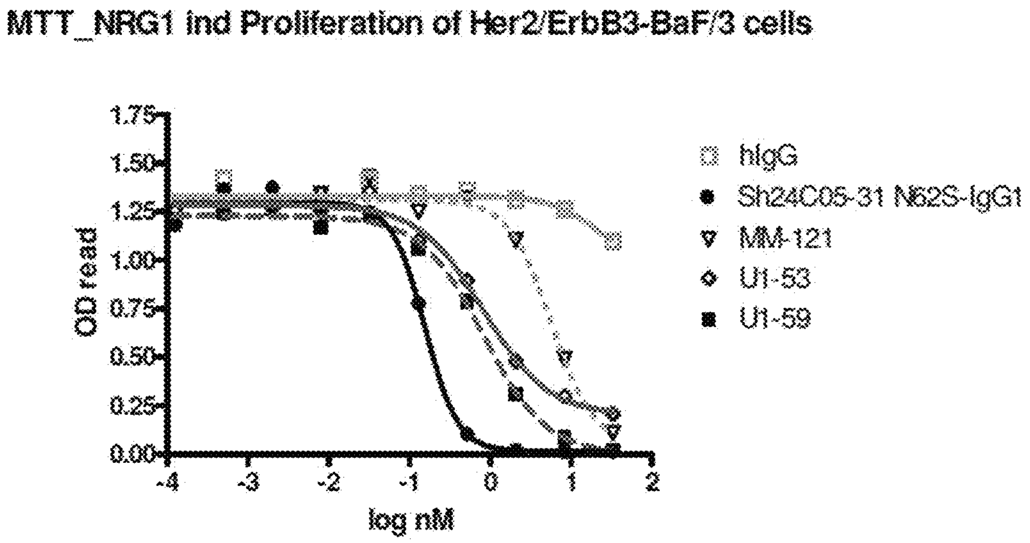
FIG. 19B is a graph summarizing results from an experiment to measure the inhibitory activity of human IgG (□) and anti-ErbB3 monoclonal antibodies Sh24C05-31 N62S-IgG1 (●), Ab #6 IgG2 (∇), U1-53 (◇) and U1-59 (■) in BaF/3 cells expressing Her2 and ErbB3 in the presence of NRG1-β1.

The inhibitory activity of anti-ErbB3 Ab #6 IgG2, U1-53 and U1-59 antibodies were also tested in the NRG1-β1 dependent Her2/ErbB3-BaF/3 cells proliferation assay. As shown in FIG. 19B, the results demonstrate that the Ab #6 IgG2, U1-53 and U1-59 antibodies inhibited NRG induced Her2/ErbB3-BaF/3 cell proliferation in a dose dependent manner. Inhibition data of NRG1-β1 dependent Her2/ErbB3-BaF/3 cell proliferation with antibodies Ab #6 IgG2, U1-53 and U1-59 are summarized in Table 19. The results in Table 19 demonstrate that antibodies Ab #6 IgG2, U1-53, and U1-59 inhibited NRG1-β1-induced proliferation of Her2/ErbB3-BaF/3 cells. A comparison of the inhibitory activity of the tested anti-ErbB3 antibodies in the NRG1-β1 dependent Her2/ErbB3-BaF/3 cells proliferation assay indicates that the inhibitory activity of the humanized Sh24C05 antibodies is superior to the inhibitory activity of the Ab #6 IgG2, U1-53 and U1-59 antibodies (e.g., the $IC_{50}$ was 0.1245 nM for Sh24C05-31 N62S-IgG1 compared to 0.8128 nM for U1-53).

Example 15—Inhibition of Downstream Signaling in SKBR-3 Cells

This example describes a characterization of the humanized antibodies produced in Example 12 for their ability to degrade total ErbB3 and inhibit phosphorylation of ErbB3 in exponentially growing SKBR-3 cells.

The breast cancer SKBR-3 cells were maintained as recommended by ATCC. Cells maintained in full serum condition were treated for 1, 2, 4 or 6 hours with 40 μg/ml of anti-ErbB3 antibody (i.e., Sh24C05-25 N62S-IgG1, Sh24C05-25 N62S-IgG2, Sh24C05-31 N62S-IgG1, and Sh24C05-31 N62S-IgG2). Lysates were either analyzed by ELISA with the Total-ErbB3 and the Phospho-ErbB3 kit from R&D Systems (Cat. No DYC234 and Cat. No DYC1769, respectively).

Figure 20:
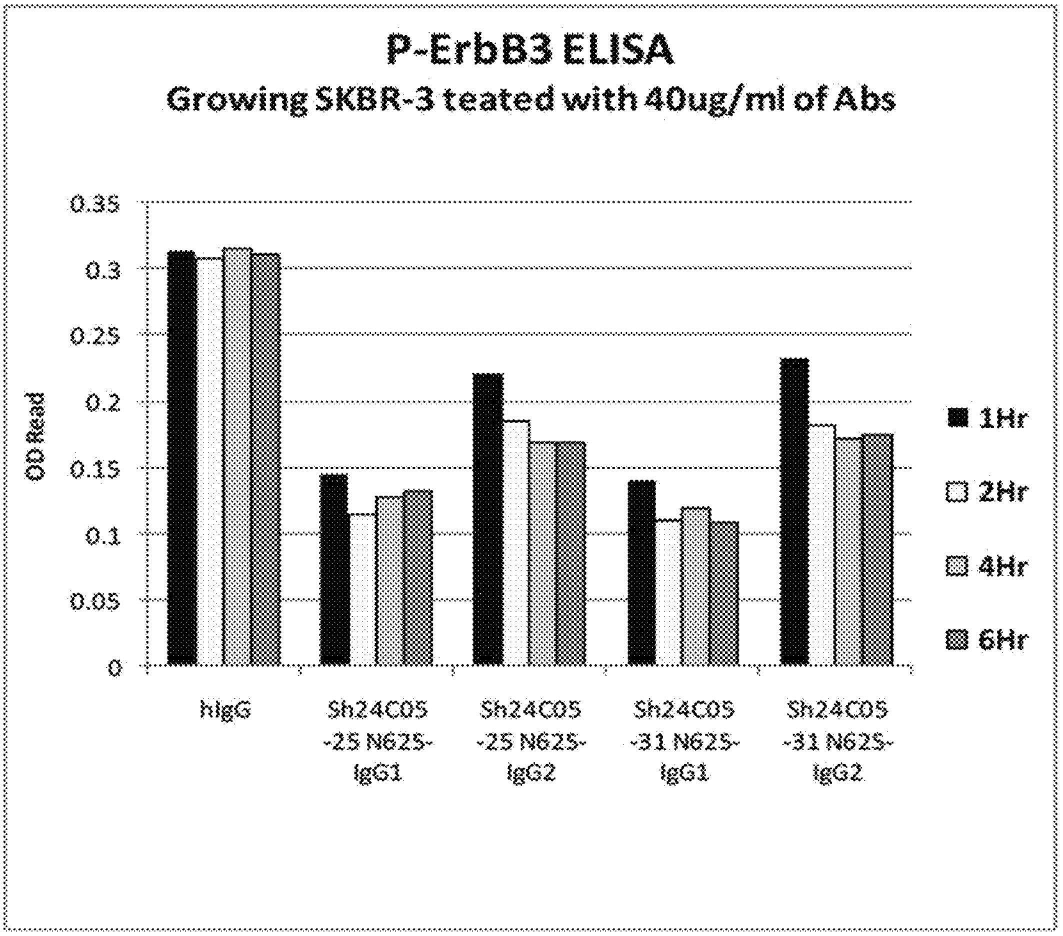
FIG. 20 is a graph summarizing results from an experiment to measure the inhibitory activity of negative control (human IgG) and anti-ErbB3 monoclonal antibodies Sh24C05-25 N62S-IgG1, Sh24C05-25 N62S-IgG2, Sh24C05-31 N62S-IgG1, and Sh24C05-31 N62S-IgG2 on the steady state phosphorylation of ErbB3 in growing SKBR-3 cells.

The results demonstrate that anti-ErbB3 antibodies Sh24C05-25 N62S-IgG1, Sh24C05-25 N62S-IgG2, Sh24C05-31 N62S-IgG1, and Sh24C05-31 N62S-IgG2 inhibit at least 50% of the phosphorylation of ErbB3 in exponentially growing SKBR-3 cells (FIG. 20).

Figure 21:
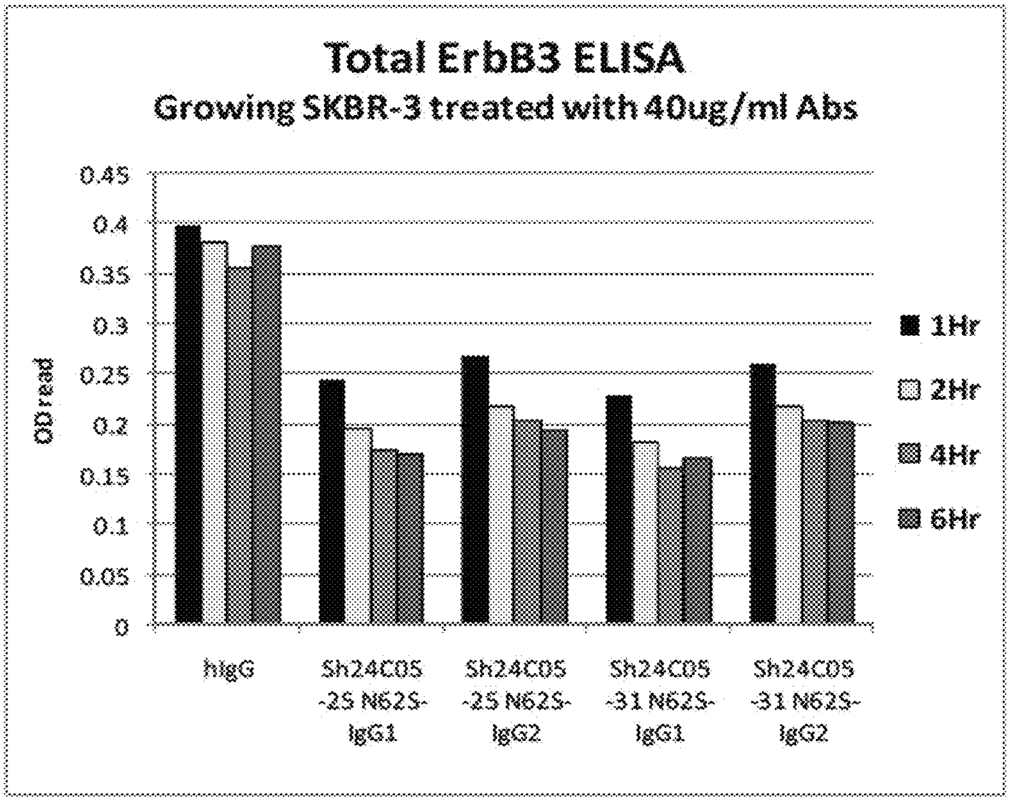
FIG. 21 is a graph summarizing results from an experiment to measure the degradation of ErbB3 receptor by negative control (human IgG) and anti-ErbB3 monoclonal antibodies Sh24C05-25 N62S-IgG1, Sh24C05-25 N62S-IgG2, Sh24C05-31 N62S-IgG1, and Sh24C05-31 N62S-IgG2 in growing SKBR-3 cells.

The results also demonstrate that anti-ErbB3 antibodies Sh24C05-25 N62S-IgG1, Sh24C05-25 N62S-IgG2, Sh24C05-31 N62S-IgG1, and Sh24C05-31 N62S-IgG2 degraded at least 50% of the total ErbB3 receptor present in exponentially growing SKBR-3 cells (FIG. 21).

Example 16—Inhibition of BxPC3 Tumor Xenograft Growth

The ability of the humanized monoclonal antibodies produced in Example 12 to inhibit tumor growth were tested in a BxPC3 pancreatic xenograft model. Human pancreatic BxPC3 cells were grown in culture in 37° C. in an atmosphere containing 5% CO2, using RMPI medium containing 10% fetal bovine serum. BxPC3 cells were inoculated subcutaneously into the flank of 8-week old female CB.17 SCID mice (Taconic Labs) with $10\times10^6$ cells per mouse in 50% matrigel (BD Biosciences, Cat No. 356237). Tumor measurements were taken twice weekly using vernier calipers. Tumor volume was calculated using the formula: width×width×length/2. When tumors reached approximately 200 $mm^3$, the mice were randomized into 8 groups of 10 mice each. One group received PBS, another received huIgG control, and another received muIgG control. Each of the remaining five groups received one of the antibodies (i.e., murine 24C05, Sh24C05-25 N62S-IgG1, Sh24C05-25 N62S-IgG2, Sh24C05-31 N62S-IgG1 or Sh24C05-31 N62S-IgG2). All of the antibodies were dosed at 2 mg/kg body weight, twice per week, by intra-peritoneal injection for 7 weeks. Tumor volumes and mouse body weights were recorded twice per week. Tumor growth inhibition was analyzed using ANOVA and is expressed as percent inhibition compared to the PBS control.

Figure 22:
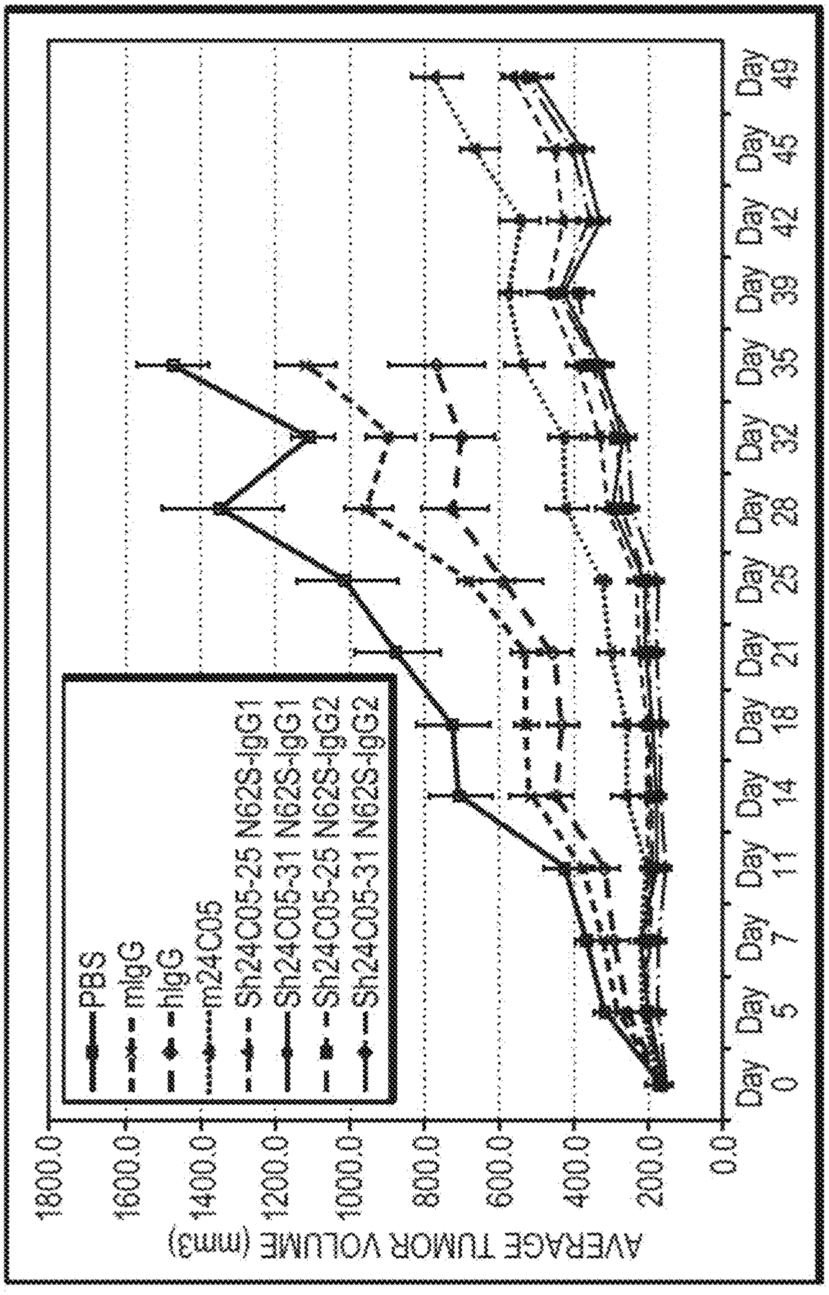
FIG. 22 is a graph summarizing the results from an experiment to measure tumor inhibitory activity of a human IgG, murine IgG, or anti-ErbB3 monoclonal antibodies dosed at 2 mg/kg in a BxPC3 pancreatic tumor xenograft model in CB17 SCID mice (murine 24C05 (Δ), Sh24C05-31 N62S IgG1 (●), Sh24C05-31 N62S IgG2 (♦), Sh24C05-25 N62S IgG1 (▲), Sh24C05-25 N62S IgG2 (■), vehicle control (□), murine IgG (x), and human IgG (♥)).
Figure 23A:
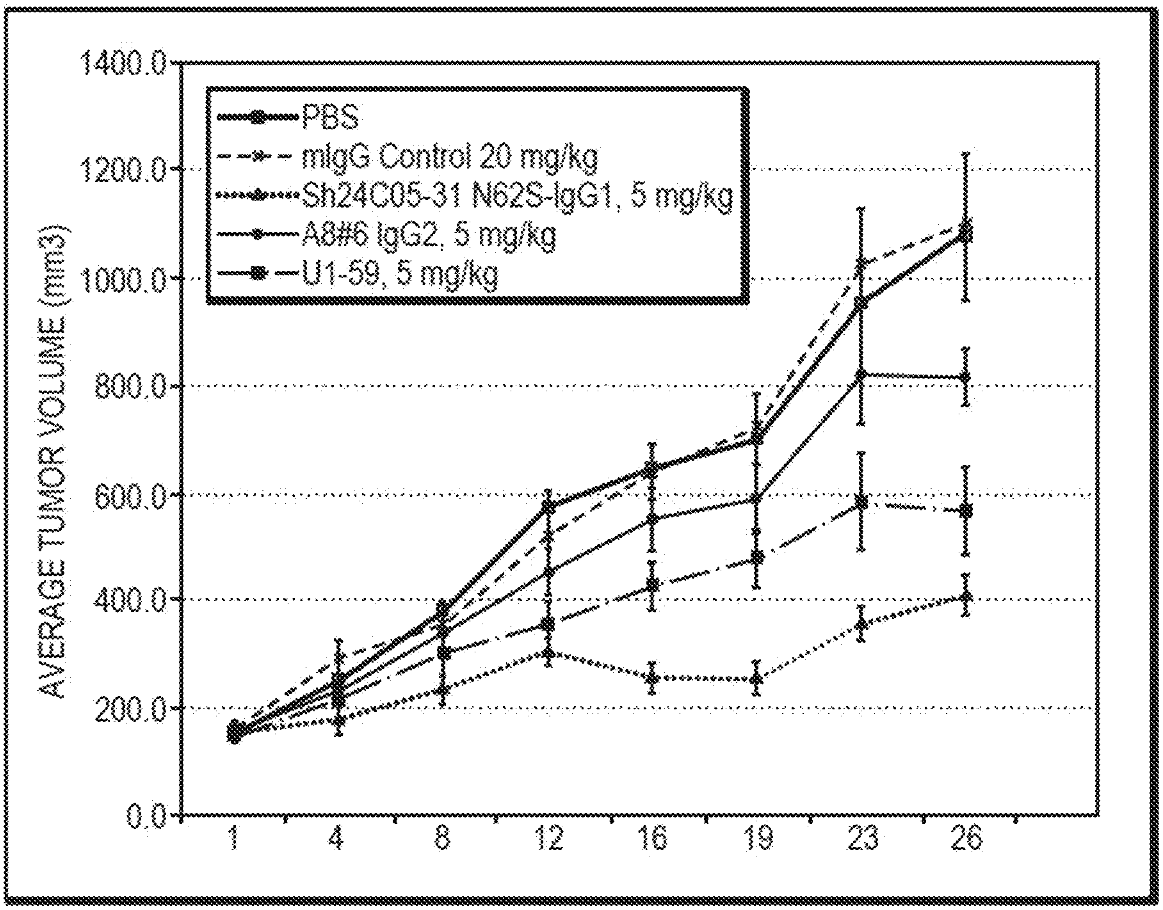
FIG. 23A is a graph summarizing the results from an experiment to measure tumor inhibitory activity of a murine IgG or anti-ErbB3 monoclonal antibodies dosed at 5 mg/kg in a Calu-3 non-small cell lung cancer xenograft model in NCR nude mice (vehicle control (□), murine IgG (x), Sh24C05-31 N62S IgG1 (▲), Ab #6 IgG2 (●), and U1-59 (■)).
Figure 23B:
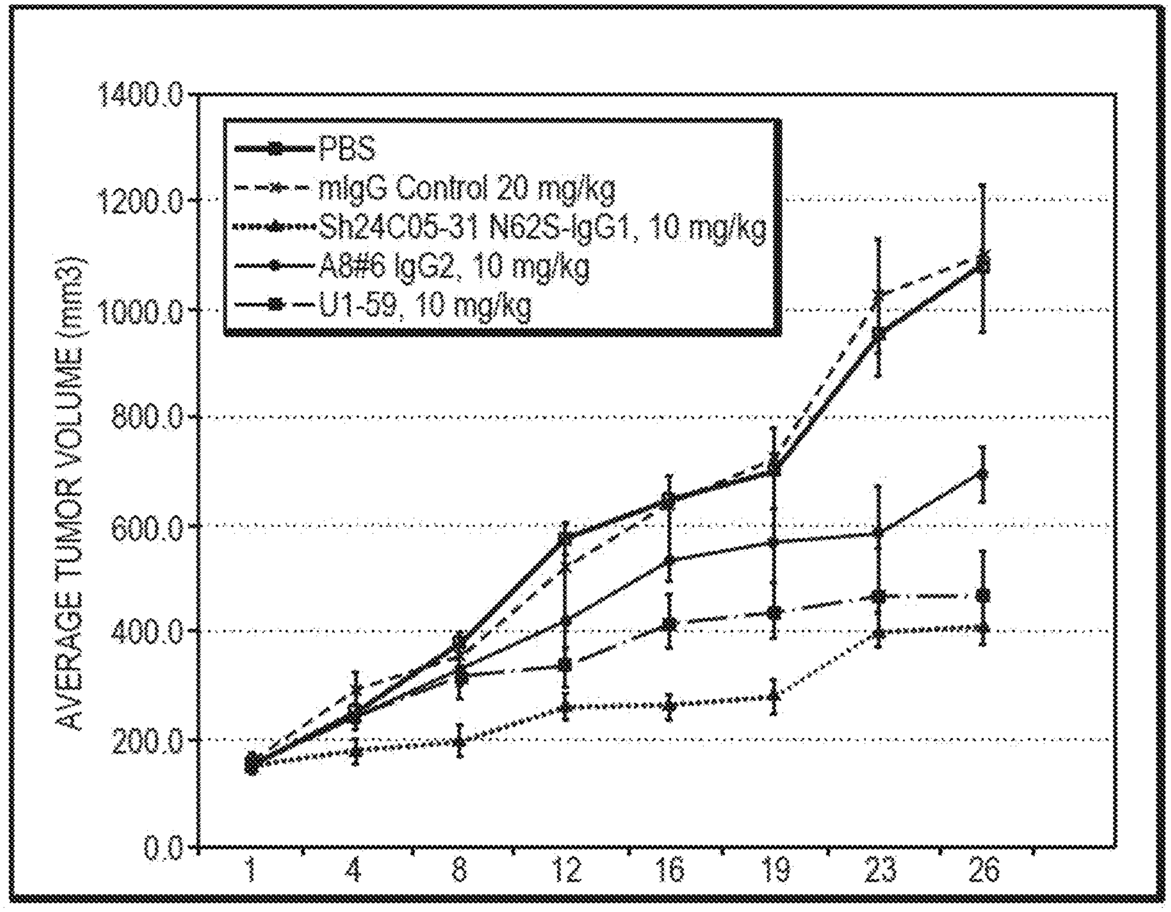
FIG. 23B is a graph summarizing the results from an experiment to measure tumor inhibitory activity of a murine IgG or anti-ErbB3 monoclonal antibodies dosed at 10 mg/kg in a Calu-3 non-small cell lung cancer xenograft model in NCR nude mice (vehicle control (□), murine IgG (x), Sh24C05-31 N62S IgG1 (▲), Ab #6 IgG2 (●), and U1-59 (■)).
Figure 23C:
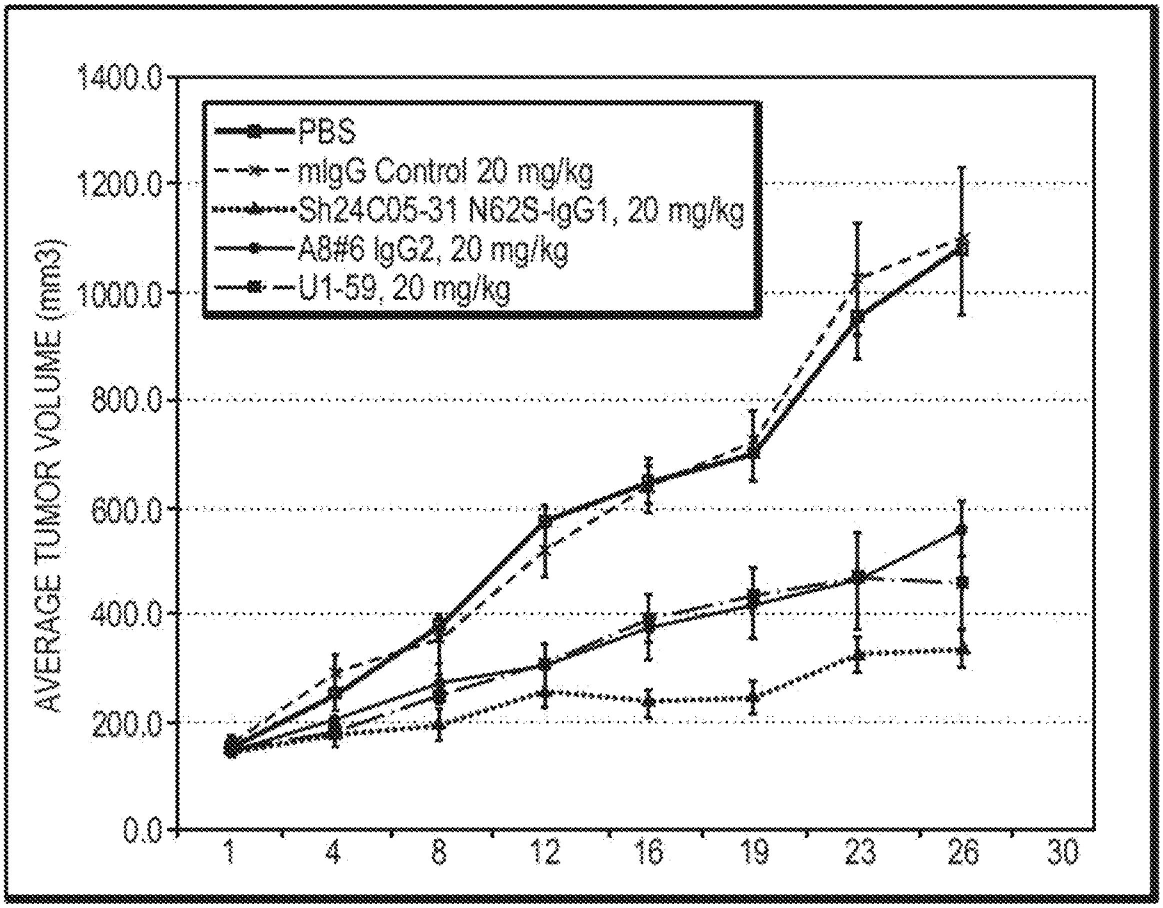
FIG. 23C is a graph summarizing the results from an experiment to measure tumor inhibitory activity of a murine IgG or anti-ErbB3 monoclonal antibodies dosed at 20 mg/kg in a Calu-3 non-small cell lung cancer xenograft model in NCR nude mice (vehicle control (□), murine IgG (x), Sh24C05-31 N62S IgG1 (▲), Ab #6 IgG2 (●), and U1-59 (■)).
Figure 24:
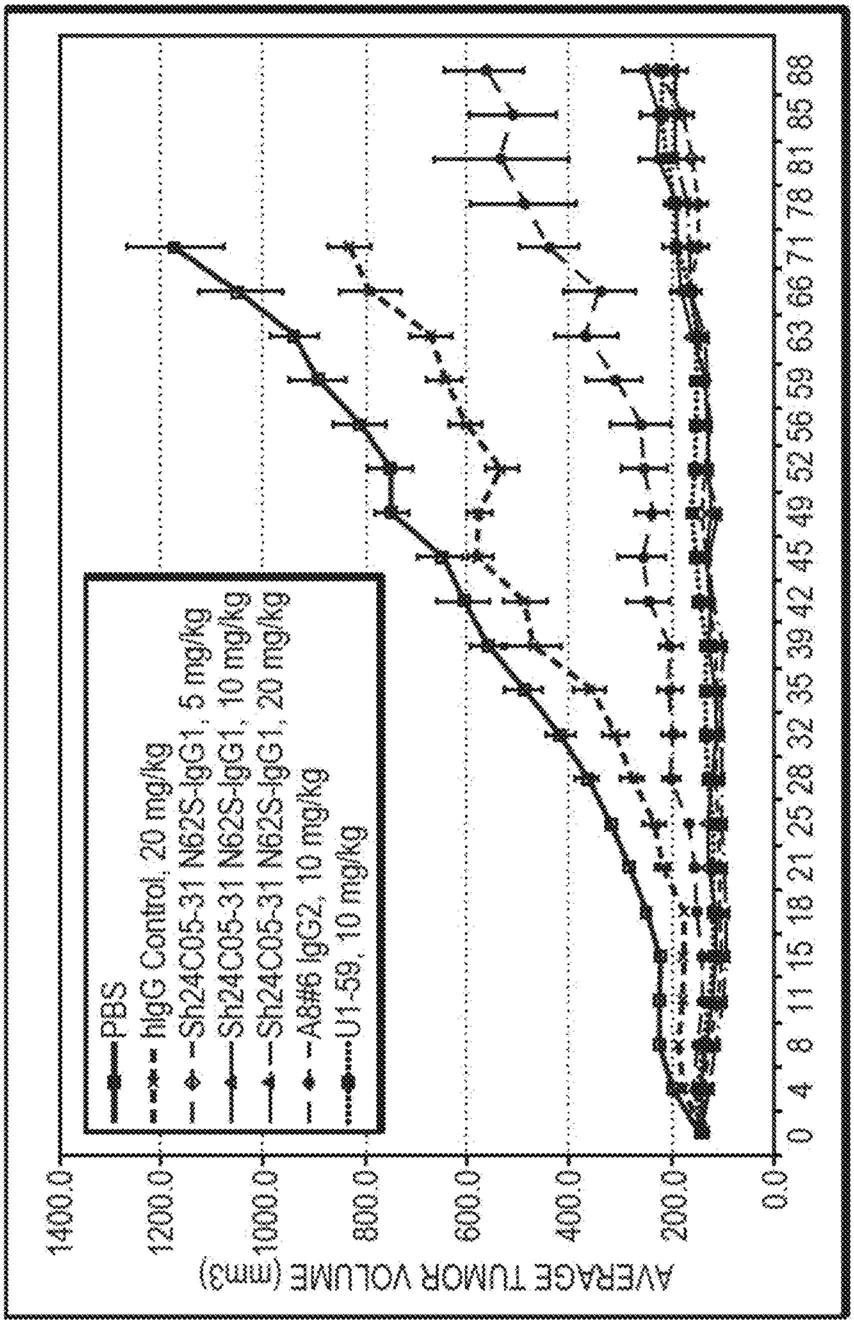
FIG. 24 is a graph summarizing the results from an experiment to measure tumor inhibitory activity of a human IgG, murine or anti-ErbB3 monoclonal antibodies in a MDA-MB-453 breast cancer xenograft model in NOD SCID mice (vehicle control (□), human IgG (x), Sh24C05-31 N62S IgG1 dosed at 5 mg/kg (◇), Sh24C05-31 N62S IgG1 dosed at 10 mg/kg (Δ), Sh24C05-31 N62S IgG1 dosed at 20 mg/kg (▲), Ab #6 IgG2 dosed at 10 mg/kg (●), and U1-59 dosed at 10 mg/kg (■)).

The tested humanized antibodies were active in vivo. All four humanized anti-ErbB3 antibodies had similar efficacy in the BxPC3 model when dosed at 2 mg/kg, ranging from 75-80% tumor growth inhibition ($p<0.001$) (i.e., Sh24C05-25 N62S-IgG1, 75%; Sh24C05-25 N62S-IgG2, 76%; Sh24C05-31 N62S-IgG1, 79%; and Sh24C05-31 N62S-IgG2, 80%) at day 28 of the study (FIG. 22). The murine antibody demonstrated 65% tumor growth inhibition in this study ($p<0.05$). These results suggest similar potency and activity of the four humanized antibodies in this model.

The ability of the humanized monoclonal antibodies U1-53, U1-59, and Ab #6 IgG2 to inhibit tumor growth were also tested in a BxPC3 xenograft model. Using the protocol described above, BxPC3 tumors were generated in CB.17 SCID mice. When tumors reached approximately 200 $mm^3$, the mice were randomized into 11 groups of 10 mice each. One group received PBS and another received huIgG control. Each of the other nine groups received one of the humanized antibodies (i.e., Sh24C05-31 N62S-IgG1, U1-53, U1-59, or Ab #6 IgG2). The antibodies were dosed either at 0.5 mg/kg, 1 mg/kg, or 5 mg/kg body weight, twice per week, by intra-peritoneal injection for 7 weeks. Tumor volumes and mouse body weights were recorded twice per week. Tumor growth inhibition was analyzed using ANOVA and is expressed as percent inhibition compared to the PBS control.

Tumor growth inhibition data determined at day 29 following treatment with one of the humanized antibodies (i.e., Sh24C05-31 N62S-IgG1, U1-59, or Ab #6 IgG2) is shown in Table 20.

TABLE 20

| Treatment | | | Tumor Growth Inhibition | ANOVA Analysis (Compared | ANOVA Analysis (Compared |
|---|---|---|---|---|---|
| Gr. | Agent | mg/kg | (%) | to PBS) | to hIgG) |
| 1 | PBS | — | NA | NA | NA |
| 2 | hIgG | 5 | 29.2 | NS | NS |
| 3 | Sh24C05-31 N62S-IgG1 | 0.5 | 63.3 | P < 0.001 | P < 0.01 |
| 4 | Sh24C05-31 N62S-IgG1 | 1 | 75.0 | P < 0.001 | P < 0.001 |
| 5 | Sh24C05-31 N62S-IgG1 | 5 | 76.5 | P < 0.001 | P < 0.001 |
| 6 | Ab#6 IgG2 | 0.5 | 31.5 | P < 0.05 | NS |
| 7 | Ab#6 IgG2 | 1 | 2.1 | NS | NS |
| 8 | Ab#6 IgG2 | 5 | 40.6 | P < 0.001 | NS |
| 9 | U1-59 | 0.5 | 32.6 | P < 0.01 | NS |
| 10 | U1-59 | 1 | 52.9 | P < 0.001 | NS |
| 11 | U1-59 | 5 | 60.3 | P < 0.001 | P < 0.05 |

The results demonstrate that Sh24C05-31 N62S-IgG1 showed the greatest tumor growth inhibition by day 29 (76.5%, p<0.001) at a dose of 5 mg/kg in the BxPC3 pancreatic xenograft model. The U1-59 and Ab #6 IgG2 antibodies demonstrated approximately 60% and 41% tumor growth inhibition at a dose of 5 mg/kg in the BxPC3 model, respectively (P<0.001).

The results also demonstrate that Sh24C05-31 N62S-IgG1 showed the greatest tumor growth inhibition by day 29 at a dose of 0.5 mg/kg (63.3%, p<0.001) and at a dose of 1 mg/kg (75.0%, p<0.001) in the BxPC3 pancreatic xenograft model. The U1-59 and AB #6 IgG2 antibodies demonstrate approximately 33% (p<0.01) and 31% (p<0.05) tumor growth inhibition at a dose of 0.5 mg/kg in the BxPC3 model, respectively. The U1-59 and AB #6 IgG2 antibodies demonstrated approximately 53% (p<0.001) and 2% (not significant) tumor growth inhibition at a dose of 1.0 mg/kg in the BxPC3 model, respectively.

Example 17—Inhibition of Calu-3 Tumor Xenograft Growth

The ability of the humanized monoclonal antibodies produced in Example 12 to inhibit tumor growth was tested in a Calu-3 non-small cell lung cancer xenograft model. The ability of the humanized monoclonal antibodies U1-59 and Ab #6 IgG2, as described in Example 12, to inhibit tumor growth were also tested in the same model.

Human Non-Small Cell Lung Cancer Calu-3 cells were grown in culture in 37° C. in an atmosphere containing 5% CO2, using EMEM medium containing 10% fetal bovine serum. Calu-3 cells were inoculated subcutaneously into the flank of 8-week old female NCR nude mice (Taconic Labs) with $10\times10^6$ cells per mouse in 50% matrigel (BD Biosciences, Cat No. 356237). Tumor measurements were taken twice weekly using vernier calipers. Tumor volume was calculated using the formula: width×width×length/2.

When tumors reached approximately 200 $mm^3$, the mice were randomized into 11 groups of 10 mice each. One group received PBS and another received muIgG control. Each of the other nine groups received one of the humanized antibodies (i.e., Sh24C05-31 N62S-IgG1, U1-59, or Ab #6 IgG2) at a dose of either 5 mg/kg, 10 mg/kg or 20 mg/kg body weight, twice per week, by intra-peritoneal injection for 4 weeks. Tumor volumes and mouse body weights were recorded twice per week. Tumor growth inhibition was analyzed using ANOVA and is expressed as percent inhibition compared to the PBS control.

Tumor growth inhibition data determined at day 26 following treatment with one of the humanized antibodies (i.e., Sh24C05-31 N62S-IgG1, U1-59, or Ab #6 IgG2) is shown in Table 21.

TABLE 21

| Treatment | | | Tumor Growth Inhibition | ANOVA Analysis (Compared | ANOVA Analysis (Compared |
|---|---|---|---|---|---|
| Gr. | Agent | mg/kg | (%) | to PBS) | to hIgG) |
| 1 | PBS | — | NA | NA | NA |
| 2 | muIgG | 20 | −1.2 | NS | NA |
| 3 | Sh24C05-31 N62S-IgG1 | 5 | 62.3 | P < 0.001 | P < 0.001 |
| 4 | Sh24C05-31 N62S-IgG1 | 10 | 62.0 | P < 0.001 | P < 0.001 |
| 5 | Sh24C05-31 N62S-IgG1 | 20 | 69.0 | P < 0.001 | P < 0.001 |
| 6 | Ab#6 IgG2 | 5 | 24.7 | NS | NS |
| 7 | Ab#6 IgG2 | 10 | 35.9 | P < 0.01 | P < 0.01 |
| 8 | Ab#6 IgG2 | 20 | 48.4 | P < 0.001 | P < 0.001 |
| 9 | U1-59 | 5 | 47.8 | P < 0.001 | P < 0.001 |
| 10 | U1-59 | 10 | 56.7 | P < 0.001 | P < 0.001 |
| 11 | U1-59 | 20 | 57.7 | P < 0.001 | P < 0.001 |

The results using the Calu-3 non-small cell lung cancer xenograft model demonstrate that Sh24C05-31 N62S-IgG1 showed the greatest tumor growth inhibition by day 26 at all doses tested (i.e., 5 mg/kg, 10 mg/kg, and 20 mg/kg of body weight).

For example, at the 10 mg/kg dose, Sh24C05-31 N62S-IgG1 showed the greatest tumor growth inhibition by day 26 (62%, P<0.001) when compared to Ab #6 IgG2 (36%, NS) or U1-59 (57%, P<0.001). At the 20 mg/kg dose, Sh24C05-31 N62S-IgG1 also showed the greatest tumor growth inhibition by day 26 (69%, P<0.001) when compared to Ab #6 IgG2 (48%, P<0.001) or U1-59 (58%, P<0.001).

Example 18—Inhibition of MDA-MB-453 Tumor Xenograft Growth

The ability of the humanized monoclonal antibodies produced in Example 12 to inhibit tumor growth were tested in a MDA-MB-453 breast xenograft model (which is a HER2 positive breast model). The ability of the humanized monoclonal antibodies U1-59 and Ab #6 IgG2, as described in Example 12, to inhibit tumor growth were also tested in the same model.

Human Breast MDA-MB-453 cells were grown in culture in 37° C. in an atmosphere containing 0% CO2, using Leibovitz ATCC medium (Cat No. 30-2008) containing 10% fetal bovine serum. MDA-MB-453 cells were inoculated subcutaneously into the flank of 8-week old female NOD SCID mice (Taconic Labs) with $20\times10^6$ cells per mouse in 50% matrigel (BD Biosciences, Cat No. 356237). Tumor measurements were taken twice weekly using vernier calipers. Tumor volume was calculated using the formula: width×width×length/2.

When tumors reached approximately 200 $mm^3$, the mice were randomized into 7 groups of 10 mice each. One group received PBS and another received huIgG control. Each of the other nine groups received one of the humanized antibodies (i.e., Sh24C05-31 N62S-IgG1, U1-59, or Ab #6 IgG2). Sh24C05-31 N62S-IgG1 was dosed either at 5 mg/kg, 10 mg/kg, or 20 mg/kg body weight, twice per week, by intra-peritoneal injection for more than 10 weeks; U1-59, or Ab #6 were dosed at 10 mg/kg with the same frequency. Tumor volumes and mouse body weights were recorded twice per week. Tumor growth inhibition was analyzed using ANOVA and is expressed as percent inhibition compared to the PBS control.

Tumor growth inhibition data determined at day 71 following treatment with one of the humanized antibodies (i.e., Sh24C05-31 N62S-IgG1, U1-59, or Ab #6 IgG2) is shown in Table 22.

TABLE 22

| Treatment | | | Tumor Growth Inhibition | ANOVA Analysis (Compared | ANOVA Analysis (Compared |
|---|---|---|---|---|---|
| Gr. | Agent | mg/kg | (%) | to PBS) | to hIgG) |
| 1 | PBS | — | NA | NA | NA |
| 2 | hIgG | 20 | 28.87 | p < 0.001 | p < 0.001 |
| 3 | Sh24C05-31 N62S-IgG1 | 5 | 86.57 | p < 0.001 | p < 0.001 |
| 4 | Sh24C05-31 N62S-IgG1 | 10 | 84.09 | p < 0.001 | p < 0.001 |
| 5 | Sh24C05-31 N62S-IgG1 | 20 | 85.26 | p < 0.001 | p < 0.001 |
| 6 | Ab#6 IgG2 | 10 | 62.48 | p < 0.001 | p < 0.001 |
| 7 | U1-59 | 10 | 83.93 | p < 0.001 | p < 0.001 |

The results using the MDA-MB-453 xenograft model demonstrate that Sh24C05-31 N62S-IgG1 showed potent tumor growth inhibition by day 71 at all doses tested (i.e., 5 mg/kg, 10 mg/kg, and 20 mg/kg of body weight).

The results also demonstrate that at the 10 mg/kg dose, Sh24C05-31 N62S-IgG1 showed greater tumor growth inhibition by day 71 (84%, P<0.001) when compared to Ab #6 IgG2 (62%, P<0.001). Sh24C05-31 N62S-IgG1 showed equivalent tumor growth inhibition as U1-59 at the same dose.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated antibody that binds human ErbB3 comprising:

(i) an immunoglobulin heavy chain variable region comprising a $CDR_{H1}$ comprising the amino acid sequence of SEQ ID NO: 41, a $CDR_{H2}$ comprising the amino acid sequence of SEQ ID NO: 42, and a $CDR_{H3}$ comprising the amino acid sequence of SEQ ID NO: 43; and (ii) an immunoglobulin light chain variable region comprising a $CDR_{L1}$ comprising the amino acid sequence of SEQ ID NO: 44, a $CDR_{L2}$ comprising the amino acid sequence of SEQ ID NO: 45, and a $CDR_{L3}$ comprising the amino acid sequence of SEQ ID NO: 46.

2. The antibody of claim 1, wherein the CDR sequences are interposed between human and humanized framework sequences.

3. The antibody of claim 1, wherein the antibody is an antigen-binding fragment.

4. An isolated antibody that binds human ErbB3 comprising an immunoglobulin heavy chain variable region comprising the amino acid sequence of SEQ ID NO: 38 and an immunoglobulin light chain variable region comprising the amino acid sequence of SEQ ID NO: 40.

5. An isolated antibody that binds human ErbB3 comprising an immunoglobulin heavy chain comprising the amino acid sequence of SEQ ID NO. 125 and an immunoglobulin light chain comprising the amino acid sequence of SEQ ID NO. 127.

6. The antibody of claim 4, wherein the antibody is an antigen binding fragment.

7. The antibody of claim 1, wherein the antibody has a $K_D$ of 200 pM or lower as measured by surface plasmon resonance.

8. One or more isolated nucleic acids encoding the antibody of claim 1.

9. An expression vector comprising the one or more nucleic acids of claim 8.

10. A host cell comprising the expression vector of claim 9.

11. The antibody of claim 4, wherein the antibody has a $K_D$ of 200 pM or lower as measured by surface plasmon resonance.

12. The antibody of claim 5, wherein the antibody has a $K_D$ of 200 pM or lower as measured by surface plasmon resonance.

13. A method of inhibiting or reducing proliferation of a tumor cell comprising exposing the cell to an effective amount of the antibody of claim 1 to inhibit or reduce proliferation of the tumor cell, wherein the tumor cell expresses human ErbB3.

14. A method of inhibiting or reducing tumor growth in a mammal, the method comprising exposing a mammal having a tumor to an effective amount of the antibody of claim 1 to inhibit or reduce proliferation of the tumor, wherein the tumor expresses human ErbB3.

15. A method of treating cancer in a mammal, the method comprising administering an effective amount of the antibody of claim 1 to a mammal having cancer, wherein the cancer expresses human ErbB3.

* * * * *